United States Patent
Clark et al.

(10) Patent No.: US 7,371,777 B2
(45) Date of Patent: May 13, 2008

(54) CYCLIC COMPOUND AND PPAR AGONIST

(75) Inventors: Richard Clark, Ibaraki (JP);
Fumiyoshi Matsuura, Ibaraki (JP);
Eita Emori, Ibaraki (JP); Masanobu Shinoda, Ibaraki (JP); Shunji Kasai, Ibaraki (JP); Hideki Yoshitomi, Ibaraki (JP); Kazuto Yamazaki, Ibaraki (JP); Takashi Inoue, Ibaraki (JP); Sadakazu Miyashita, Ibaraki (JP); Taro Hihara, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 287 days.

(21) Appl. No.: 10/486,396

(22) PCT Filed: Aug. 16, 2002

(86) PCT No.: PCT/JP02/08325

§ 371 (c)(1), (2), (4) Date: Feb. 11, 2004

(87) PCT Pub. No.: WO03/016265

PCT Pub. Date: Feb. 27, 2003

(65) Prior Publication Data

US 2005/0014833 A1 Jan. 20, 2005

(30) Foreign Application Priority Data

Aug. 17, 2001 (JP) ............................. 2001-247540

(51) Int. Cl.
*A61K 31/341* (2006.01)
*C07D 307/04* (2006.01)

(52) U.S. Cl. .................... 514/461; 548/146; 548/200; 548/215; 548/247; 546/184; 546/268.1; 546/281.7; 546/284.7; 544/224; 544/336; 544/358; 549/13; 549/20; 549/429; 549/484; 514/365; 514/374

(58) Field of Classification Search ............... 549/429, 549/483, 484, 13, 20; 548/146, 200, 215, 548/247; 546/184, 268.1; 544/224, 358; 514/461, 365
See application file for complete search history.

(56) References Cited

U.S. PATENT DOCUMENTS

| | | | |
|---|---|---|---|
| 6,506,797 B1 | 1/2003 | Nomura et al. | |
| 6,884,821 B1 * | 4/2005 | Shinoda et al. | 514/563 |
| 7,244,861 B2 | 7/2007 | Matsuura et al. | |
| 7,253,178 B2 | 8/2007 | Harada et al. | |
| 2004/0102634 A1 | 5/2004 | Matsuura et al. | |
| 2004/0116708 A1 | 6/2004 | Harada et al. | |
| 2004/0138271 A1 | 7/2004 | Matsuura et al. | |
| 2004/0214888 A1 | 10/2004 | Matsuura et al. | |
| 2005/0014833 A1 | 1/2005 | Clark et al. | |

FOREIGN PATENT DOCUMENTS

DE 3026924 A1 2/1982

(Continued)

OTHER PUBLICATIONS

Jurgen M. Lehmann et al.; The Journal of Biological Chemistry; vol. 270, No. 22, Issue of June 2, pp. 12953-12956, 1995.

(Continued)

*Primary Examiner*—Golam M. M. Shameem
(74) *Attorney, Agent, or Firm*—Birch, Stewart, Kolasch & Birch, LLP

(57) ABSTRACT

The present invention provides a novel compound having an excellent PPAR agonist action. More specifically, it provides a compound represented by the following formula, a salt thereof, an ester thereof or a hydrate of them.

(I)

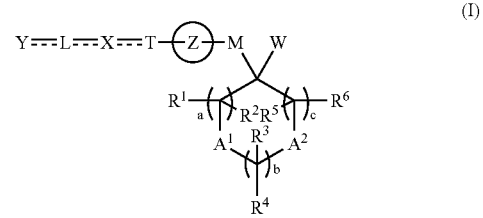

Wherein a, b and c are the same as or different from one another and each represents 0 to 4; $R^1$ to $R^6$ are the same as or different from one another and each represents a hydrogen atom, a hydroxyl group, a cyano group, a halogen atom, etc.; $A^1$ and $A^2$ are the same as or different from each other and each represents a single bond, an oxygen atom, etc.;
L, M and T each represent a single bond, an alkylene group having one to six carbon atoms, etc.;
W represents a carboxyl group;
the partial structure represented by the formula:

‑‑‑‑‑ represents a single bond or a double bond;
X represents a single bond, an oxygen atom, $-NR^{x1}CQ^1O-$, etc.;
Y represents $Y^1-Y^2-$ (wherein $Y^1$ represents a 5 to 14-membered aromatic ring having one to four substituents, etc.; and $Y^2$ represents a single bond or a 5 to 14-membered aromatic ring); and
the ring Z represents a 5 to 14-membered aromatic ring which have one to four substituents selected form the above-mentioned Group A, may have one or more hetero atoms and may be partially saturated.

15 Claims, No Drawings

FOREIGN PATENT DOCUMENTS

| | | | |
|---|---|---|---|
| EP | 0028063 | A1 | 5/1981 |
| EP | 0219308 | A2 | 4/1987 |
| EP | 0 543 662 | A2 | 5/1993 |
| EP | 1026149 | A1 | 8/2000 |
| JP | 57-064639 | A | 4/1982 |
| JP | 9-48771 | A | 2/1997 |
| JP | 11-152269 | A | 6/1999 |
| JP | 2001-55367 | A | 2/2001 |
| JP | 2001-261612 | A | 9/2001 |
| WO | WO-89/03819 | A1 | 5/1989 |
| WO | WO-90/06920 | A1 | 6/1990 |
| WO | WO-94/01420 | A1 | 1/1994 |
| WO | WO-94/13650 | A1 | 6/1994 |
| WO | WO-95/03288 | A1 | 2/1995 |
| WO | WO 99/04815 | A1 | 2/1999 |
| WO | WO 99/16758 | A1 | 4/1999 |
| WO | WO 99/18066 | A1 | 4/1999 |
| WO | WO 99/20275 | A1 | 4/1999 |
| WO | WO-99/65897 | A1 | 12/1999 |
| WO | WO 00/04011 | A1 | 1/2000 |
| WO | WO-00/64876 | A1 | 11/2000 |
| WO | WO 00/64888 | A1 | 11/2000 |
| WO | WO 00/75103 | A1 | 12/2000 |
| WO | WO-01/55086 | A1 | 2/2001 |
| WO | WO-01/21578 | A1 | 3/2001 |
| WO | WO-01/25181 | A1 | 4/2001 |
| WO | WO-01/38325 | A1 | 5/2001 |
| WO | WO-01/55085 | A1 | 8/2001 |
| WO | WO-01/92201 | A1 | 12/2001 |
| WO | WO-02/100812 | A2 | 1/2002 |
| WO | WO-02/079162 | A1 | 10/2002 |
| WO | WO-02/080899 | A1 | 10/2002 |
| WO | WO-02/081428 | A1 | 10/2002 |
| WO | WO 02/083616 | A1 | 10/2002 |
| WO | WO 02/098840 | A1 | 12/2002 |
| WO | WO-03/016265 | A1 | 2/2003 |

OTHER PUBLICATIONS

Timothy M. Willson et al.; Journal of Medicinal Chemistry; vol. 43, No. 4, Feb. 24, 2000, pp. 527-550.

Philip M. Barger et al.; Trends Cardiovasc. Med., vol. 10, No. 6, 2000, pp. 238-245.

Bernard Hulin et al.; Current Pharmaceutical Design, 2, No. 1, pp. 85-102, 1996.

D.R. Buckle et al.; Bioorganic & Medicinal Chemistry Letters, vol. 6, No. 17, pp. 2121-2126, 1996.

Clarie Bastie et al.; The Journal of Biological Chemistry, vol. 274, No. 31, Issue of July 30, pp. 21920-21925, 1999.

Miyachi et al., Bioorganic & Medicinal Chemistry Letters, vol. 12, 2002, pp. 77-80.

"Nuovi Coloranti Per Miste Poliestere/Cotone" Tinctoria, 1996, vol. 93, No. 5, pp. 34-39.

Gibson et al., European Journal of Medicinal Chemistry, vol. 32, No. 10, 1997, pp. 823-831.

Young et al., The Journal of Pharmacology and Experimental Therapeutics, vol. 284, No. 2, 1997, pp. 751-759.

Haigh et al., Bioorganic & Medicinal Chemistry, vol. 7, No. 5, 1999, pp. 821-830.

Lavoie et al., Bioorganic & Medicinal Chemistry Letters, vol. 11, No. 21, pp. 2847-2850.

Li et al., Hcaplus 2006:256663, "Peroxisome proliferators-activated receptors: how their effects on macrophages can lead to the development of a new drug therapy against atherosclerosis", Annual Review of Pharmacology and Toxicology, 2006.

Kurtz, Hcaplus 2006:551484, "New treatment strategies for patients with hypertension and insulin resistance", American Journal of Medicine, 2006.

\* cited by examiner

CYCLIC COMPOUND AND PPAR AGONIST

TECHNICAL FIELD

The present invention relates to a novel carboxylic acid compound, a salt thereof and a hydrate of them. More specifically, it relates to the above-mentioned compound which is useful for prevention or treatment of hyperglycemia, hyperlipemia and inflammatory disease, and to a medicament comprising the compound.

PRIOR ART

Diabetes mellitus refers to a durable hyperglycemic condition attributable to the absolute or relative shortage of intrinsic insulin (blood glucose-depressing hormone produced and secreted from Langerhans islet β cells in the pancreas), and in this disease, metabolic abnormalities caused by this condition appear as various morbid states. Diabetes mellitus is classified roughly into insulin dependent diabetes mellitus (IDDM) that is type 1 diabetes mellitus, for treatment of which insulin administration is absolutely necessary, non insulin dependent diabetes mellitus (NIDDM), that is type 2 diabetes mellitus, and other diabetes mellitus (secondary diabetes mellitus; diabetes mellitus occurs as one symptom of other diseases). In particular, as life-style is modernized, NIDDM is rapidly increased due to overeating and lack of exercise, thus causing a social problem. While IDDM occurs mainly in infants, NIDDM occurs in middle-aged or elderly persons, to account for the majority of diabetes mellitus in Japan. It is said that NIDDM occurs owing to insulin function-suppressing factors (insulin resistance) such as overeating, lack of exercise, obesity and stress, in addition to hereditary factors. Since excessive intake of calories and obesity resulting from lack of exercise are related to diabetes mellitus as described above, the therapy is based on 3 kinds of therapies, that is, dietary therapy, exercise therapy and chemotherapy. However, there are not a few cases where dietary therapy and exercise therapy are hardly to conduct because of an increase in the number of persons of advanced age in this aging society in recent years.

In chemotherapy of NIDDM, sulfonyl urea (SU) medicines such as Tolbutamide, Chlorpropamide and Tolazamide and Biguamide (BG) medicines such as Metformin hydrochloride and Buformin have been used as oral blood glucose depressants, but the morbid state of NIDDM is characterized by insulin deficiency and insulin resistance, and it cannot be said that the SU medicines stimulating insulin secretion from pancreatic β cells are effective therapeutic medicines for patients with NIDDM condition, where the insulin secretion potential is well but adequate blood glucose control is not achieved in target organs due to insulin resistance, thus permitting hyperglycemia. Further, the BG medicines may permit the onset of lactic acid acidosis, so use of such medicines is limited to a certain extent. Further, these chemicals often caused severe hypoglycemia as a side effect. To solve these problems, development of chemicals with a new working mechanism is advancing, and thiazolidine derivatives such as Troglitazone, Pioglitazone and Rosiglitazone are called insulin sensitizers, and these chemicals recently attract attention because they can ameliorate insulin resistance (or enhance the action of insulin) and lower blood glucose without promoting secretion of insulin from the pancreas. It has been revealed that these thiazolidine-type chemicals induce differentiation of adipocytes, and exhibit their action via an intranuclear receptor PPARγ (peroxisome proliferator-activated receptor gamma: a transcriptional factor important for differentiation of adipocytes) (J. Biol. Chem., 270, 12953-12956, 1995). By the differentiation of preadipocytes, immature and small adipocytes with less secretion of TNFα, FFA and leptin are increased thus resulting in amelioration of insulin resistance. Thiazolidine derivatives such as the above Troglitazone, Pioglitazone and Rosiglitazone also act as agonists for PPARγ, to exhibit the effect of ameliorating insulin resistance. Besides PPARγ, PPAR subtypes such as α, β(δ) etc. have been found, any of which regulate expression of genes involved in lipid metabolism. The homology of each subtype among different biological species is higher than the homology of these subtypes in the same species, and with respect to distribution of each subtype in tissues, PPARγ is located substantially in adipose tissues while PPARα occurs mainly in the liver, heart and kidney, and therefore it was considered that each subtype has an independent function. In recent years, it has been revealed that PPARγ mainly mediates lipid anabolism by promoting expression of a group of genes for LPL, acyl-CoA carboxylase, GPDH etc. to convert glucose into lipid and storing the lipid, while PPARα mediates lipid catabolism by regulating expression of a gene group involved in intake of fatty acids into cells and oxidation thereof to decompose lipid. Moreover, researches concerning relationships between particular subtypes of PPAR and various diseases have been widely conducted in recent years (J. Med. Chem., 2000, 43(4), 527-550; Trends Cardiovasc. Med., 2000, 10, p 238-245).

As thiazolidine derivatives acting as PPARγ and a dual agonists, compounds disclosed in e.g. JP-A 9-48771 are known. Further, some compounds are known as insulin sensitizers having a carboxylic acid moiety in their structure (Current Pharmaceutical Design, 2, No. 1, p 85-102, 1996; Bioorganic & Medicinal Chemistry Letters, 6, No. 17, p 2121-2126, 1996; WO200075103; WO9918066; WO9916758).

However, it has been reported that some chemicals acting as PPARγ agonists cause hepatic damage and thus should be carefully used, so chemicals satisfactory in both therapeutic effects and side effects such as toxicity are still not obtained. Further, compounds having a carboxyl group instead of a thiazolidine group are merely presented in literatures and not marketed. Further, there is no report showing that such compounds can be used as PPARγ and α dual agonists, and as a matter of course, their γ, α and β(δ) triple agonist action is not known. However, it is also estimated that the toxicity of PPARγ agonists described above is the unique one derived from the thiazolidine moiety, and if a compound exhibiting the above action with a new structure in place of the above structure can be found, the compound can be expected to solve the problem of toxicity, and is thus very useful. The conventional chemicals are still unsatisfactory in respect of neutral fat (triglyceride (TG)) related closely to arteriosclerosis. Further, the action of PPARβ(δ) to induce differentiation of adipocytes is known (J. Biol. Chem., 274, No. 31, pp. 21920-21925), and by this action, cholesterol levels are reported to be lowered (WO9904815), and if a compound having an agonist action for this subtype can be found, this compound can be expected to exhibit a higher activity than that of the conventional insulin sensitizers and to reduce side effects such as hepatic toxicity. From the foregoing aspects, there is demand for development of excellent chemicals.

DISCLOSURE OF INVENTION

Under these circumstances, the present inventors made intensive investigations for the purpose of providing a medicament effective in prevention or treatment of hyperglycemia, which satisfies these various requirements, and, as a result, they successfully synthesized a novel compound represented by the following formula, a salt thereof, an ester thereof or a hydrate of them and have unexpectedly found that the compound has an excellent anti-hyperglycemia and anti-hyperlipemia action. The present invention has been accomplished based on these findings.

A compound represented by the following formula, a salt thereof, an ester thereof or a hydrate of them.

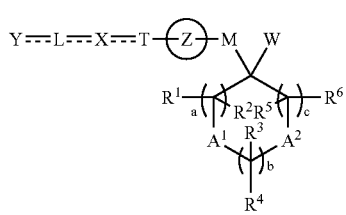

(I)

Wherein a, b and c are the same as or different from one another and each represents 0, 1, 2, 3 or 4; $R^1$, $R^2$, $R^3$, $R^4$, $R^5$ and $R^6$ are the same as or different from one another and each represents 1) a hydrogen atom, 2) a hydroxyl group, 3) a cyano group, 4) a halogen atom, 5) —N($R^7$)$R^8$ (wherein $R^7$ and $R^8$ are the same as or different from each other and each represents a hydrogen atom, a cyano group, a formyl group, or an alkyl group having one to six carbon atoms, a hydroxyalkyl group having one to six carbon atoms, an aminoalkyl group having one to six carbon atoms, a halogeno-alkyl group having one to six carbon atoms, an alkoxyalkyl group having two to twelve carbon atoms, a cycloalkyl group having three to seven carbon atoms, an alkenyl group having two to six carbon atoms, an alkynyl group having two to six carbon atoms, an aryl group having six to twelve carbon atoms, an alkylaryl group having seven to eighteen carbon atoms, an aralkyl group having seven to eighteen carbon atoms, an aliphatic acyl group having two to seven carbon atoms, an aromatic acyl group having seven to nineteen carbon atoms, an aliphatic alkoxycarbonyl group having two to seven carbon atoms or an aromatic alkoxycarbonyl group having seven to nineteen carbon atoms, each of which may have one or more substituents), or 6) an alkyl group having one to six carbon atoms, an alkoxy group having one to six carbon atoms, an alkylthio group having one to six carbon atoms, a hydroxyalkyl group having one to six carbon atoms, a hydroxyalkoxy group having one to six carbon atoms, a hydroxyalkylthio group having one to six carbon atoms, an aminoalkyl group having one to six carbon atoms, an aminoalkoxy group having one to six carbon atoms, an aminoalkylthio group having one to six carbon atoms, a halogeno-alkyl group having one to six carbon atoms, a halogeno-alkoxy group having one to six carbon atoms, a halogeno-alkylthio group having one to six carbon atoms, an alkoxyalkyl group having two to twelve carbon atoms, an alkoxyalkoxy group having two to twelve carbon atoms, an alkoxyalkylthio group having two to twelve carbon atoms, a cycloalkyl group having three to seven carbon atoms, a cycloalkyloxy group having three to seven carbon atoms, a cycloalkylalkyloxy group having four to thirteen carbon atoms, a cycloalkylthio group having three to seven carbon atoms, an alkenyl group having two to six carbon atoms, an alkenyloxy group having two to six carbon atoms, an alkenylthio group having two to six carbon atoms, an alkynyl group having two to six carbon atoms, an alkynyloxy group having two to six carbon atoms, an alkynylthio group having two to six carbon atoms, an aryl group having six to twelve carbon atoms, an aryloxy group having six to twelve carbon atoms, an arylthio group having six to twelve carbon atoms, an alkylaryl group having seven to eighteen carbon atoms, an alkylaryloxy group having seven to eighteen carbon atoms, an alkylarylthio group having seven to eighteen carbon atoms, an aralkyl group having seven to eighteen carbon atoms, an aralkyloxy group having seven to eighteen carbon atoms or an aralkylthio group having seven to eighteen carbon atoms, each of which may have one or more substituents;

$A^1$ and $A^2$ are the same as or different from each other and each represents a single bond, an oxygen atom, a sulfur atom, —SO—, —SO$_2$—, —NR$^{41}$— (wherein $R^{41}$ represents a hydrogen atom, a cyano group, a formyl group, or an alkyl group having one to six carbon atoms, a hydroxyalkyl group having one to six carbon atoms, an aminoalkyl group having one to six carbon atoms, a halogeno-alkyl group having one to six carbon atoms, an alkoxyalkyl group having two to twelve carbon atoms, a cycloalkyl group having three to seven carbon atoms, an alkenyl group having two to six carbon atoms, an alkynyl group having two to six carbon atoms, an aryl group having six to twelve carbon atoms, an alkylaryl group having seven to eighteen carbon atoms, an aralkyl group having seven to eighteen carbon atoms, an aliphatic acyl group having two to seven carbon atoms or an aromatic acyl group having seven to nineteen carbon atoms, each of which may have one or more substituents, or an aliphatic alkoxycarbonyl group having two to seven carbon atoms or an aromatic alkoxycarbonyl group having seven to nineteen carbon atoms), a group represented by the formula:

(wherein $R^{42}$ and $R^{43}$ are the same as or different from each other and each represents a hydrogen atom, a hydroxyl group, a cyano group, a halogen atom, or an alkyl group having one to six carbon atoms, an alkoxy group having one to six carbon atoms, an alkylthio group having one to six carbon atoms, a hydroxyalkyl group having one to six carbon atoms, a hydroxyalkoxy group having one to six carbon atoms, a hydroxyalkylthio group having one to six carbon atoms, an aminoalkyl group having one to six carbon atoms, an aminoalkoxy group having one to six carbon atoms, an aminoalkylthio group having one to six carbon atoms, a halogeno-alkyl group having one to six carbon atoms, a halogeno-alkoxy group having one to six carbon atoms, a halogeno-alkylthio group having one to six carbon atoms, an alkoxyalkyl group having two to twelve carbon atoms, an alkoxyalkoxy group having two to twelve carbon atoms, an alkoxyalkylthio group having two to twelve carbon atoms, a cycloalkyl group having three to seven carbon atoms, a cycloalkyloxy group having three to seven carbon atoms, a cycloalkylalkyloxy group having four to thirteen carbon atoms, a cycloalkylthio group having three to seven carbon atoms, an alkenyl group having two to six carbon atoms, an alkenyloxy group having two to six carbon atoms, an alkenylthio group having two to six carbon atoms, an alkynyl group having two to six carbon atoms, an alkynyloxy group having two to six carbon atoms, an alkynylthio group having two to six carbon atoms, an aryl group having six to twelve carbon atoms, an aryloxy group having six to twelve carbon atoms, an arylthio group having six to twelve carbon atoms, an alkylaryl group having seven to eighteen carbon atoms, an alkylaryloxy group having seven to eighteen carbon atoms, an alkylarylthio group having seven to eighteen carbon atoms, an aralkyl group having seven to eighteen carbon atoms, an aralkyloxy group having seven to eighteen carbon atoms or an aralkylthio group having seven to eighteen carbon atoms, each of which may have one or more substituents), or —N($R^{44}$)$R^{45}$ (wherein $R^{44}$ and $R^{45}$ are the same as or different from each other and each represents a hydrogen atom, a cyano group, a formyl group, or an alkyl group having one to six carbon atoms, a hydroxyalkyl group having one to six carbon atoms, an aminoalkyl group having one to six carbon atoms, a halogeno-alkyl group having one to six carbon atoms, an alkoxyalkyl group having two to twelve carbon atoms, a cycloalkyl group having three to seven carbon atoms, an alkenyl group having two to six carbon atoms, an alkynyl group having two to six carbon atoms, an aryl group having six to twelve carbon atoms, an alkylaryl group having seven to eighteen carbon atoms, an aralkyl group having seven to eighteen carbon atoms, an aliphatic acyl group having two to seven carbon atoms or an aromatic acyl group having seven to nineteen carbon atoms, each of which may have one or more substituents, or an aliphatic alkoxycarbonyl group having two to seven carbon atoms or an aromatic alkoxycarbonyl group having seven to nineteen carbon atoms);

L represents a single bond, or an alkylene group having one to six carbon atoms, an alkenylene group having two to six carbon atoms or an alkynylene group having two to six carbon atoms, each of which may have one or more substituents;

M represents a single bond, or an alkylene group having one to six carbon atoms, an alkenylene group having two to six carbon atoms or an alkynylene group having two to six carbon atoms, each of which may have one or more substituents;

T represents a single bond, or an alkylene group having one to three carbon atoms, an alkenylene group having two or three carbon atoms or an alkynylene group having two or three carbon atoms, each of which may have one or more substituents;

W represents a carboxyl group;

the partial structure represented by the formula:

----- represents a single bond or a double bond;

X represents a single bond, an oxygen atom, —$NR^{x1}CQ^{1}O$— (wherein $Q^{1}$ represents an oxygen atom or a sulfur atom; $R^{X1}$ represents a hydrogen atom, a cyano group, a formyl group, or an alkyl group having one to six carbon atoms, a hydroxyalkyl group having one to six carbon atoms, an aminoalkyl group having one to six carbon atoms, a halogeno-alkyl group having one to six carbon atoms, an alkoxyalkyl group having two to twelve carbon atoms, a cycloalkyl group having three to seven carbon atoms, an alkenyl group having two to six carbon atoms, an alkynyl group having two to six carbon atoms, an aryl group having six to twelve carbon atoms, an alkylaryl group having seven to eighteen carbon atoms, an aralkyl group having seven to eighteen carbon atoms, an aliphatic acyl group having two to seven carbon atoms or an aromatic acyl group having seven to nineteen carbon atoms, each of which may have one or more substituents, or an aliphatic alkoxycarbonyl group having two to seven carbon atoms or an aromatic alkoxycarbonyl group having seven to nineteen carbon atoms), —$OCQ^{1}NR^{X1}$— (wherein $Q^{1}$ and $R^{X1}$ are as defined above), $CQ^{1}NR^{X1}O$— (wherein $Q^{1}$ and $R^{X1}$ are as defined above), —$ONR^{X1}CQ^{1}$— (wherein $Q^{1}$ and $R^{X1}$ are as defined above), —$NR^{X1}CQ^{1}$— (wherein $Q^{1}$ and $R^{X1}$ are as defined above), —$CQ^{1}NR^{X1}$— (wherein $Q^{1}$ and $R^{X1}$ are as defined above), —$NR^{X1a}CQ^{1}NR^{X1b}$— (wherein Q is as defined above; $R^{X1a}$ and $R^{X1b}$ are the same as or different from each other and each represents a hydrogen atom, a cyano group, a formyl group, or an alkyl group having one to six carbon atoms, a hydroxyalkyl group having one to six carbon atoms, an aminoalkyl group having one to six carbon atoms, a halogeno-alkyl group having one to six carbon atoms, an alkoxyalkyl group having two to twelve carbon atoms, a cycloalkyl group having three to seven carbon atoms, an alkenyl group having two to six carbon atoms, an alkynyl group having two to six carbon atoms, an aryl group having six to twelve carbon atoms, an alkylaryl group having seven to eighteen carbon atoms, an aralkyl group having seven to eighteen carbon atoms, an aliphatic acyl group having two to seven carbon atoms or an aromatic acyl group having seven to nineteen carbon atoms, each of which may have one or more substituents, or an aliphatic alkoxycarbonyl group having two to seven carbon atoms or an aromatic alkoxycarbonyl group having seven to nineteen carbon atoms), —$Q^{2}SO_{2}$— (wherein $Q^{2}$ represents an oxygen atom or —$NR^{X10}$— (wherein $R^{X10}$ represents a hydrogen atom, a cyano group, a formyl group, or an alkyl group having one to six carbon atoms, a hydroxyalkyl group having one to six carbon atoms, an aminoalkyl group having one to six carbon atoms, a halogeno-alkyl group having one to six carbon atoms, an alkoxyalkyl group having two to twelve carbon atoms, a cycloalkyl group having three to seven carbon atoms, an alkenyl group having two to six carbon atoms, an alkynyl group having two to six carbon atoms, an aryl group having six to twelve carbon atoms, an alkylaryl group having seven to eighteen carbon atoms, an aralkyl group having seven to eighteen carbon atoms, an aliphatic acyl group having two to seven carbon atoms or an aromatic acyl group having seven to nineteen carbon atoms, each of which may have one or more substituents, or an aliphatic alkoxycarbonyl group having two to seven carbon atoms or an aromatic alkoxycarbonyl group having seven to nineteen carbon atoms)), —$SO_{2}Q^{2}$— (wherein $Q^{2}$ is as defined above), or a group represented by the formula:

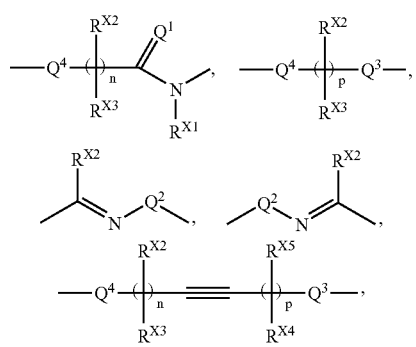

-continued

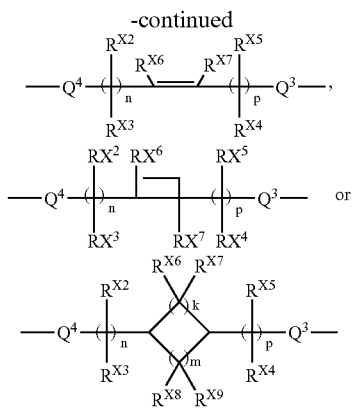

(wherein $Q_1$, $Q_2$ and $R^{X1}$ are as defined above; k represents from 0 to 5; m represents from 1 to 5; n and p are the same as or different from each other and each represents from 1 to 5; $R^{X2}$, $R^{X3}$, $R^{X4}$, $R^{X5}$, $R^{X6}$, $R^{X7}$, $R^{X8}$ and $R^{X9}$ are the same as or different from each other and each represents a hydrogen atom, a hydroxyl group, a cyano group, a halogen atom, or an alkyl group having one to six carbon atoms, an alkoxy group having one to six carbon atoms, an alkylthio group having one to six carbon atoms, a hydroxyalkyl group having one to six carbon atoms, a hydroxyalkoxy group having one to six carbon atoms, a hydroxyalkylthio group having one to six carbon atoms, an aminoalkyl group having one to six carbon atoms, an aminoalkoxy group having one to six carbon atoms, an aminoalkylthio group having one to six carbon atoms, a halogeno-alkyl group having one to six carbon atoms, a halogeno-alkoxy group having one to six carbon atoms, a halogeno-alkylthio group having one to six carbon atoms, an alkoxyalkyl group having two to twelve carbon atoms, an alkoxyalkoxy group having two to twelve carbon atoms, an alkoxyalkylthio group having two to twelve carbon atoms, a cycloalkyl group having three to seven carbon atoms, a cycloalkyloxy group having three to seven carbon atoms, a cycloalkylalkyloxy group having four to thirteen carbon atoms, a cycloalkylthio group having three to seven carbon atoms, an alkenyl group having two to six carbon atoms, an alkenyloxy group having two to six carbon atoms, an alkenylthio group having two to six carbon atoms, an alkynyl group having two to six carbon atoms, an alkynyloxy group having two to six carbon atoms, an alkynylthio group having two to six carbon atoms, an aryl group having six to twelve carbon atoms, an aryloxy group having six to twelve carbon atoms, an arylthio group having six to twelve carbon atoms, an alkylaryl group having seven to eighteen carbon atoms, an alkylaryloxy group having seven to eighteen carbon atoms, an alkylarylthio group having seven to eighteen carbon atoms, an aralkyl group having seven to eighteen carbon atoms, an aralkyloxy group having seven to eighteen carbon atoms or an aralkylthio group having seven to eighteen carbon atoms, each of which may have one or more substituents, or —N($R^{X11}$)$R^{12}$— (wherein $R^{X11}$ and $R^{X12}$ are the same as or different from each other and each represents a hydrogen atom, a cyano group, a formyl group, or an alkyl group having one to six carbon atoms, a hydroxyalkyl group having one to six carbon atoms, an aminoalkyl group having one to six carbon atoms, a halogeno-alkyl group having one to six carbon atoms, an alkoxyalkyl group having two to twelve carbon atoms, a cycloalkyl group having three to seven carbon atoms, an alkenyl group having two to six carbon atoms, an alkynyl group having two to six carbon atoms, an aryl group having six to twelve carbon atoms, an alkylaryl group having seven to eighteen carbon atoms, an aralkyl group having seven to eighteen carbon atoms, an aliphatic acyl group having two to seven carbon atoms or an aromatic acyl group having seven to nineteen carbon atoms, each of which may have one or more substituents, or an aliphatic alkoxycarbonyl group having two to seven carbon atoms or an aromatic alkoxycarbonyl group having seven to nineteen carbon atoms), provided that $R^{X2}$ and $R^{X3}$, and $R^{X4}$ and $R^{X5}$ may together form a ring; and $Q_3$ and $Q_4$ are the same as or different from each other and each represents a single bond, an oxygen atom, (O)S(O) or $NR^{X10}$ (wherein $NR^{X10}$ is as defined above));

Y represents $Y^1$—$Y^2$— (wherein $Y^1$ represents a 5 to 14-membered aromatic ring which has one to four substituents selected from the following Group A and may have one or more hetero atoms; and $Y^2$ represents a single bond or a 5 to 14-membered aromatic ring which has a substituent selected from the following Group A and may have one or more hetero atoms;

Group A: a hydrogen atom, a halogen atom, a hydroxyl group, a sulfamoyl group, or an alkyl group having one to six carbon atoms, a cycloalkyl group having three to seven carbon atoms, an alkoxy group having one to six carbon atoms, a cycloalkyloxy group having three to seven carbon atoms, a hydroxyalkyl group having one to six carbon atoms, a hydroxyalkoxy group having one to six carbon atoms, a halogeno-alkyl group having one to six carbon atoms, an acylamino group having two to seven carbon atoms or a 5 to 14-membered heterocyclic group, each of which may have a substituent, provided that when two or more substituents selected from Group A are present, they may together form a ring); and the ring Z represents a 5 to 14-membered aromatic ring which has one to four substituents selected from the above-mentioned Group A, may have one or more hetero atoms and may be partially saturated.

That is, the present invention relates to (1) a compound represented by the formula (I), a salt thereof, an ester thereof or a hydrate of them; (2) the compound according to (1) wherein c is 0, and $A^2$ is an oxygen atom, a salt thereof, an ester thereof or a hydrate of them; (3) the compound according to (1) or (2) wherein a is 0, b is 1, and $A^1$ is represented by the formula:

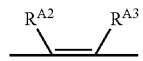

(wherein $R^{A2}$ and $R^{A3}$ each represent the same groups as defined above), a salt thereof, an ester thereof or a hydrate of them; (4) the compound according to (1) or (2) wherein a is 2, b is 1, and $A^1$ is a single bond, a salt thereof, an ester thereof or a hydrate of them; (5) the compound according to any one of (1) to (4) wherein X is —C$Q^1$N$R^{X1}$— (wherein $Q^1$ and $R^{X1}$ each represent the same groups as defined above), a salt thereof, an ester thereof or a hydrate of them; (6) the compound according to any one of (1) to (5) wherein the ring Z is a 5 to 14-membered aromatic ring which has at least an alkoxy group having one to six carbon atoms, which may have one or more hetero atoms and may be partially saturated, a salt thereof, an ester thereof or a hydrate of them; (7) the compound according to any one of (1) to (6) wherein Y is $Y^1$—$Y^2$— (wherein $Y^1$ represents the same group as defined above, and $Y^2$ is a single bond), a salt thereof, an ester thereof or a hydrate of them; (8) the compound according to (7) wherein $Y^1$ is a 5 to 14-membered aromatic ring which has at least an alkoxy group having one to six carbon atoms and may have one or more hetero atoms on the ring, a salt thereof, an ester thereof or a hydrate of them; (9) the compound according to any one of (1) to (8) wherein L is a single bond, a salt thereof, an ester thereof or a hydrate of them; (10) the compound according to any one of (1) to (9) wherein T is an alkylene group having one to six carbon atoms, a salt thereof, an ester thereof or a hydrate of them; (11) the compound according to any one of (1) to (10) wherein the ring Z is represented by the following formula:

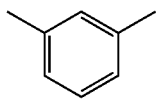

(which may have a hetero atom on the ring), which may have one to four substituents selected from Group A defined in (1), a salt thereof, an ester thereof or a hydrate of them; (12) a medicament comprising a compound represented by the formula (I), a salt thereof, an ester thereof or a hydrate of them; (13) the medicament according to (12), which is a PPAR α and γ dual agonist; (14) the medicament according to (12), which is a PPAR α, β(δ) and γ triple agonist; (15) the medicament according to any one of (12) to (14), which is an insulin sensitizer; (16) the medicament according to any one of (12) to (14), which is an agent for preventing or treating diabetes mellitus; (17) the medicament according to any one of (12) to (14), which is an agent for preventing or treating syndrome X; (18) the medicament according to any one of (12) to (14), which is an agent for preventing or treating diabetic complications; (19) the medicament according to any one of (12) to (14), which is an agent for preventing or treating hyperlipemia; (20) the medicament according to any one of (12) to (14), which is a lipid-lowering agent; (21) the medicament according to any one of (12) to (14), which is an agent for preventing or treating obesity; (22) the medicament according to any one of (12) to (14), which is an agent for treating osteoporosis; (23) the medicament according to any one of (12) to (14), which is an anti-inflammatory agent; (24) the medicament according to any one of (12) to (14), which is an agent for preventing or treating a disease of the digestive organs; (25) the medicament according to (24), wherein the disease of the digestive organs is a disease selected from the group consisting of 1) inflammatory diseases of the digestive organs; 2) proliferative diseases of the digestive organs; and 3) ulcerative diseases of the digestive organs; (26) the medicament according to (25), wherein the inflammatory disease of the digestive organs is a disease selected from the group consisting of 1) ulcerative colitis; 2) Crohn's disease; 3) pancreatitis; and (4) gastritis; (27) the medicament according to (25), wherein the inflammatory disease of the digestive organs is ulcerative colitis; (28) an agent for preventing or treating a disease against which an action of improving insulin resistance is efficacious, which comprises the compound according to any one of (1) to (11) and a pharmacologically acceptable carrier; (29) the medicament according to (25), wherein the proliferative disease of the digestive organs is a disease selected from the group consisting of (1) benign tumor of the digestive organs; (2) digestive polyp; (3) hereditary polyposis syndrome; (4) colon cancer; (5) rectum cancer; and (6) stomach cancer; (30) the medicament according to any one of (12) to (14), which is an agent for preventing or treating (1) stenocardia and myocardial infarction, and sequelae thereof; (2) senile dementia; and/or (3) cerebrovascular dementia, and whose action is improving energy metabolism; (31) the medicament according to any one of (12) to (14), which is an immunomodulatory agent; (32) the medicament according to any one of (12) to (14), which is an agent for treating or preventing cancer; (33) a method of preventing or treating a disease against which an action of improving insulin resistance is efficacious, which comprises administering to a patient a pharmacologically effective amount of the compound according to any one of (1) to (10), a salt thereof, an ester thereof or a hydrate of them; and (34) use of the compound according to any one of (1) to (10), a salt thereof, an ester thereof or a hydrate of them, for producing an agent for preventing or treating a disease against which an action of improving insulin resistance is efficacious.

The present invention provides a method of preventing or treating a disease against which a PPAR α and γ dual agonist or a PPAR α, β(δ) and γ triple agonist is efficacious, which comprises administering to a patient a pharmacologically effective amount of the compound represented by the formula (I), a salt thereof, an ester thereof or a hydrate of them.

The present invention also provides use of the compound represented by the formula (I), a salt thereof, an ester thereof or a hydrate of them, for producing a PPAR α and γ dual agonist or a PPAR α, β(δ) and γ triple agonist.

The meanings of symbols and terms used in the present description will be described, and the present invention will be illustrated in detail below.

The term "dual agonist" as used in the present description means a medicament exhibiting an agonist action concurrently on two receptor subtypes of PPAR α, β(δ) and γ. The term "triple agonist" means a medicament exhibiting an agonist action concurrently on all the receptor subtypes of PPAR α, β(δ) and γ.

In the present description, the structural formulae of compounds may, for the sake of convenience, indicate a certain isomer. However, the present invention includes every possible isomer such as geometric isomer, optical isomer due to an asymmetric carbon, rotational isomer, stereoisomer, tautomer, which can occur in the structures of the compounds, and mixtures of these isomers. Namely, the compounds of the present invention are not limited by the formulae shown for the sake of convenience and can be one of isomers or a mixture thereof. Accordingly, the compounds of the present invention may have an asymmetric carbon in their molecule and may include optically active substances and racemates, but they are not specifically limited and can be any of these substances. In addition, the compounds may exhibit crystal polymorphism, but are not specifically limited and can be of any single crystal form alone or a mixture of these crystal forms. The compounds (I) according to the present invention or salts thereof may be anhydrous or hydrates, but the claims of the present invention include all of them. Metabolites formed as a result of in vivo decomposition of the compounds (I) according to the present invention, and prodrugs of the compounds (I) according to the present invention or salts thereof are also included within the scope of the claims of the present invention.

In the present description, the term "disease against which a PPAR α and γ dual agonist or PPAR α, β(δ) and γ triple agonist is efficacious" means and includes, for example, a "disease against which an action of improving insulin resistance is efficacious".

The term "disease against which an action of improving insulin resistance is efficacious" means and includes, for example, (1) diabetes mellitus, (2) syndrome X, (3) diabetic complications, (4) hyperlipidemia, (5) obesity, (6) osteoporosis, (7) inflammatory diseases, (8) disease of the digestive organs (e.g., (a) inflammatory diseases of the digestive organs such as ulcerative colitis, Crohn's disease, pancreatitis or gastritis; (b) proliferative diseases of the digestive organs such as benign tumor of the digestive organs, digestive polyp, hereditary polyposis syndrome, colon cancer, rectum cancer or stomach cancer; and (c) ulcerous diseases of the digestive organs), (9) stenocardia, (10) myocardial infarction, (11) sequelae of stenocardia or myocardial infarction, (12) senile dementia, (13) cerebrovascular dementia, (14) immunological diseases, and (15) cancer.

The symbols, terms and other definitions as used in the present description will be described, and the present invention will be illustrated in detail below.

In the expression "an alkyl group having one to six carbon atoms which may have one or more substituents", the alkyl group represents a linear or branched alkyl group having one to six carbon atoms, and specific examples thereof include methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group, i-hexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group and 1-ethyl-2-methylpropyl group; preferably methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group and i-hexyl group; more preferably methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group and 1,2-dimethylpropyl group; further preferably methyl group, ethyl group, n-propyl group, i-propyl group, n-butyl group, i-butyl group, sec-butyl group and t-butyl group; and most preferably methyl group, ethyl group, n-propyl group and i-propyl group. Herein, the phrase "which may have a substituent" specifically means that a group may be substituted with a substituent such as a hydroxyl group; a thiol group; a nitro group; a morpholino group; a thiomorpholino group; a halogen atom such as fluorine atom, chlorine atom, bromine atom or iodine atom; a nitrile group; an azide group; a formyl group; an alkyl group such as methyl group, ethyl group, propyl group, isopropyl group or butyl group; an alkenyl group such as vinyl group, allyl group or propenyl group; an alkynyl group such as ethynyl group, butynyl group or propargyl group; an alkoxy group corresponding to a lower alkyl group, such as methoxy group, ethoxy group, propoxy group or butoxy group; a halogeno-alkyl group such as fluoromethyl group, difluoromethyl group, trifluoromethyl group or fluoroethyl group; a hydroxyalkyl group such as hydroxymethyl group, hydroxyethyl group or hydroxypropyl group; a guanidino group; a formimidoyl group; an acetimidoyl group; a carbamoyl group; a thiocarbamoyl group; a carbamoylalkyl group such as carbamoylmethyl group or carbamoylethyl group; an alkylcarbamoyl group such as methylcarbamoyl group or dimethylcarbamoyl group; a carbamide group; an alkanoyl group such as acetyl group; an amino group; an alkylamino group such as methylamino group, ethylamino group or isopropylamino group; a dialkylamino group such as dimethylamino group, methylethylamino group or diethylamino group; an aminoalkyl group such as aminomethyl group, aminoethyl group or aminopropyl group; a carboxyl group; an alkoxycarbonyl group such as methoxycarbonyl group, ethoxycarbonyl group or propoxycarbonyl group; an alkoxycarbonylalkyl group such as methoxycarbonylmethyl group, ethoxycarbonylmethyl group, propoxycarbonylmethyl group, methoxycarbonylethyl group, ethoxycarbonylethyl group or propoxycarbonylethyl group; an alkyloxyalkyl group such as methyloxymethyl group, methyloxyethyl group, ethyloxymethyl group or ethyloxyethyl group; an alkylthioalkyl group such as methylthiomethyl group, methylthioethyl group, ethylthiomethyl group or ethylthioethyl group; an aminoalkylaminoalkyl group such as aminomethylaminomethyl group or aminoethylaminomethyl group; an alkylcarbonyloxy group such as methylcarbonyloxy group, ethylcarbonyloxy group or isopropylcarbonyloxy group; an arylalkoxyalkoxyalkyl group such as benzyloxymethyl oxymethyl group or benzyloxyethyloxyethyl group; a hydroxyalkoxyalkyl group such as hydroxyethyloxymethyl group or hydroxyethyloxyethyl group; an arylalkoxyalkyl group such as benzyloxymethyl group, benzyloxyethyl group or benzyloxypropyl group; a quaternary ammonio group such as trimethylammonio group, methylethylmethylammonio group or triethylammonio group; a cycloalkyl group such as cyclopropyl group, cyclobutyl group, cyclopentyl group or cyclohexyl group; a cycloalkenyl group such as cyclopropenyl group, cyclobutenyl group, cyclopentenyl group or cyclohexenyl group; an aryl group such as phenyl group, pyridinyl group, thienyl group, furyl group or pyrrolyl group; an alkylthio group such as methylthio group, ethylthio group, propylthio group or butylthio group; an arylthio group such as phenylthio group, pyridinylthio group, thienylthio group, furylthio group or pyrrolylthio group; an aryl lower alkyl group such as benzyl group, trityl group or dimethoxytrityl group; a substituted sulfonyl group such as sulfonyl group, mesyl group or p-toluenesulfonyl group; an aryloyl group such as benzoyl group; a halogeno-aryl group such as fluorophenyl group or bromophenyl group; or an oxyalkoxy group such as methylenedioxy group.

The phrase "which may have one or more substituents" means that the mentioned group may have one or more groups arbitrarily selected from these groups, and for example an alkyl group substituted with a hydroxyl group, a thiol group, a nitro group, a morpholino group, a thiomorpholino group, a halogen atom, a nitrile group, an azide group, a formyl group, an amino group, an alkylamino group, a dialkylamino group, a carbamoyl group, a sulfonyl group etc.; an alkenyl group; an alkynyl group; and an alkoxy group also fall under the scope of the invention.

Hereinafter, the phrases "which may have a substituents" and "which may have one or more substituents" shall have the above meanings.

In the expression "an alkoxy group having one to six carbon atoms, which may have one or more substituents", the alkoxy group means a linear or branched alkoxy group having an one to six carbon atoms and represents a group having oxygen atom bound to the end of the alkyl group. Examples thereof include methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-methylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group and 1-ethyl-2-methylpropoxy group; preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group and i-hexyloxy group; more preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group and 1,2-dimethylpropoxy group; further preferably methoxy group, ethoxy group, n-propoxy group, i-propoxy group, n-butoxy group, 1-butoxy group, sec-butoxy group and t-butoxy group; and most preferably methoxy group, ethoxy group, n-propoxy group and i-propoxy group.

In the expression "an alkylthio group having one to six carbon atoms, which may have one or more substituents", the alkylthio group represents a linear or branched alkylthio group having one to six carbon atoms and represents a group having a sulfur atom bound to the end of the alkyl group. Specific examples thereof include methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group, 1,2-dimethylpropylthio group, n-hexylthio group, i-hexylthio group, 1-methylpentylthio group, 2-methylpentylthio group, 3-methylpentylthio group, 1,1-dimethylbutylthio group, 1,2-dimethylbutylthio group, 2,2-dimethylbutylthio group, 1,3-dimethylbutylthio group, 2,3-dimethylbutylthio group, 3,3-dimethylbutylthio group, 1-ethylbutylthio group, 2-ethylbutylthio group, 1,1,2-trimethylpropylthio group, 1,2,2-trimethylpropylthio group, 1-ethyl-1-methylpropylthio group and 1-ethyl-2-methylpropylthio group; preferably methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group, 1,2-dimethylpropylthio group, n-hexylthio group and i-hexylthio group; more preferably methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group and 1,2-dimethylpropylthio group; further preferably methylthio group, ethylthio group, n-propylthio group, i-propylthio group, n-butylthio group, i-butylthio group, sec-butylthio group and t-butylthio group; and most preferably methylthio group, ethylthio group, n-propylthio group and i-propylthio group.

In the expression "a hydroxyalkyl group having one to six carbon atoms, which may have one or more substituents", the hydroxyalkyl group represents a linear or branched alkyl group having one to six carbon atoms substituted at a substitutable position with a hydroxyl group. Specific examples thereof include hydroxymethyl group, 2-hydroxyethyl group and 1-hydroxyethyl group.

In the expression "a hydroxyalkoxy group having one to six carbon atoms, which may have one or more substituents", the hydroxyalkoxy group represents the linear or branched alkoxy group having one to six carbon atoms substituted at a substitutable position with a hydroxy group. Specific examples thereof include hydroxymethoxy group, 2-hydroxyethoxy group and 1-hydroxyethoxy group.

In the expression "a hydroxyalkylthio group having one to six carbon atoms, which may have one or more substituents", the hydroxyalkylthio group represents the linear or branched alkylthio group having one to six carbon atoms substituted at a substitutable position with a hydroxyl group. Specific examples thereof include hydroxymethylthio group, 2-hydroxyethylthio group and 1-hydroxyethylthio group.

In the expression "an aminoalkyl group having one to six carbon atoms, which may have one or more substituents", the aminoalkyl group represents the linear or branched alkyl group having one to six carbon atoms substituted at a substitutable position with an amino group. Specific examples thereof include aminomethyl group, 2-aminoethyl group and 1-aminoethyl group.

In the expression "an aminoalkoxy group having one to six carbon atoms, which may have one or more substituents", the aminoalkoxy group represents the linear or branched alkoxy group having one to six carbon atoms substituted at a substitutable position with an amino group. Specific examples thereof include aminomethoxy group, 2-aminoethoxy group and 1-aminoethoxy group.

In the expression "an aminoalkylthio group having one to six carbon atoms, which may have one or more substituents", the aminoalkylthio group represents the linear or branched alkylthio group having one to six carbon atoms substituted at a substitutable position with an amino group. Specific examples thereof include aminomethylthio group, 2-aminoethylthio group and 1-aminoethylthio group.

In the expression "a halogeno-alkyl group having one to six carbon atoms, which may have one or more substituents", the halogeno-alkyl group represents a group having the linear or branched alkyl group having one to six carbon atoms substituted at substitutable positions with one or more halogen atoms. Herein, the halogen atoms refer to, for example, fluorine atom, chlorine atom, bromine atom and iodine atom. Specific examples thereof include fluoromethyl group, trifluoromethyl group, 2-fluoroethyl group and 1-fluoroethyl group.

In the expression "a halogeno-alkoxy group having one to six carbon atoms, which may have one or more substituents", the halogeno-alkoxy group represents a group having the linear or branched alkoxy group having one to six carbon atoms substituted at substitutable positions with one or more halogen atoms. Specific examples thereof include fluoromethoxy group, trifluoromethoxy group, 2-fluoroethoxy group and 1-fluoroethoxy group.

In the expression "a halogeno-alkylthio group having one to six carbon atoms, which may have one or more substituents", the halogeno-alkylthio group represents a group having the linear or branched alkylthio group having one to six carbon atoms substituted at substitutable positions with one or more halogen atoms. Specific examples thereof include fluoromethylthio group, trifluoromethylthio group, 2-fluoroethylthio group and 1-fluoroethylthio group.

In the expression "an alkoxyalkyl group having two to twelve carbon atoms, which may have one or more substituents", the alkoxyalkyl group represents a group having the linear or branched alkyl group having one to six carbon atoms substituted at a substitutable position with the linear or branched alkoxy group having one to six carbon atoms. Specific examples thereof include methoxymethyl group, ethoxymethyl group, 1-methoxyethyl group, 2-methoxyethyl group, 1-ethoxyethyl group and 2-ethoxyethyl group.

In the expression "an alkoxyalkoxy group having two to twelve carbon atoms, which may have one or more substituents", the alkoxyalkoxy group represents a group having the linear or branched alkoxy group having one to six carbon atoms substituted at a substitutable position with the linear or branched alkoxy group having one to six carbon atoms. Specific examples thereof include methoxymethoxy group, ethoxymethoxy group, 1-methoxyethoxy group, 2-methoxyethoxy group, 1-ethoxyethoxy group and 2-ethoxyethoxy group.

In the expression "an alkoxyalkylthio group having two to twelve carbon atoms, which may have one or more substituents", the alkoxyalkylthio group represents a group having the linear or branched alkylthio group having one to six carbon atoms substituted at a substitutable position with the linear or branched alkoxy group having one to six carbon atoms. Specific examples thereof include methoxymethylthio group, ethoxymethylthio group, 1-methoxyethylthio group, 2-methoxyethylthio group, 1-ethoxyethylthio group and 2-ethoxyethylthio group.

In the expression "a cycloalkyl group having three to seven carbon atoms, which may have one or more substituents", the cycloalkyl group represents a cyclic alkyl group having three to seven carbon atoms, and specific examples thereof include cyclopropyl group, cyclobutyl group, cyclopentyl group, cyclohexyl group and cycloheptyl group.

In the expression "a cycloalkyloxy group having three to seven carbon atoms, which may have one or more substituents", the cycloalkyloxy group represents a group having an oxygen atom bound to the end of the cyclic alkyl group having three to seven carbon atoms, and specific examples thereof include cyclopropyloxy group, cyclobutyloxy group, cyclopentyloxy group, cyclohexyloxy group and cycloheptyloxy group.

In the expression "a cycloalkylthio group having three to seven carbon atoms, which may have one or more substituents", the cycloalkylthio group represents a group having sulfur atom bound to the end of the cycloalkyl group having three to seven carbon atoms, and specific examples thereof include cyclopropylthio group, cyclobutylthio group, cyclopentylthio group, cyclohexylthio group and cycloheptylthio group.

In the expression "an alkenyl group having two to six carbon atoms, which may have one or more substituents", the alkenyl group is a linear or branched alkenyl group having two to six carbon atoms and represents a residue group of a compound having a double bond in the alkyl group containing 2 or more carbon atoms. Specific examples thereof include ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group, 2-butene-2-yl group, 1-methyl-1-propene-1-yl group, 2-methyl-1-propene-1-yl group, 1-methyl-2-propene-1-yl group, 2-methyl-2-propene-1-yl group, 1-methyl-1-butene-1-yl group, 2-methyl-1-butene-1-yl group, 3-methyl-1-butene-1-yl group, 1-methyl-2-butene-1-yl group, 2-methyl-2-butene-1-yl group, 3-methyl-2-butene-1-yl group, 1-methyl-3-butene-1-yl group, 2-methyl-3-butene-1-yl group, 3-methyl-3-butene-1-yl group, 1-ethyl-1-butene-1-yl group, 2-ethyl-1-butene-1-yl group, 3-ethyl-1-butene-1-yl group, 1-ethyl-2-butene-1-yl group, 2-ethyl-2-butene-1-yl group, 3-ethyl-2-butene-1-yl group, 1-ethyl-3-butene-1-yl group, 2-ethyl-3-butene-1-yl group, 3-ethyl-3-butene-1-yl group, 1,1-dimethyl-1-butene-1-yl group, 1,2-dimethyl-1-butene-1-yl group, 1,3-dimethyl-1-butene-1-yl group, 2,2-dimethyl-1-butene-1-yl group, 3,3-dimethyl-1-butene-1-yl group, 1,1-dimethyl-2-butene-1-yl group, 1,2-dimethyl-2-butene-1-yl group, 1,3-dimethyl-2-butene-1-yl group, 2,2-dimethyl-2-butene-1-yl group, 3,3-dimethyl-2-butene-1-yl group, 1,1-dimethyl-3-butene-1-yl group, 1,2-dimethyl-3-butene-1-yl group, 1,3-dimethyl-3-butene-1-yl group, 2,2-dimethyl-3-butene-1-yl group, 3,3-dimethyl-3-butene-1-yl group, 1-pentene-1-yl group, 2-pentene-1-yl group, 3-pentene-1-yl group, 4-pentene-1-yl group, 1-pentene-2-yl group, 2-pentene-2-yl group, 3-pentene-2-yl group, 4-pentene-2-yl group, 1-pentene-3-yl group, 2-pentene-3-yl group, 1-pentene-1-yl group, 2-pentene-1-yl group, 3-pentene-1-yl group, 4-pentene-1-yl group, 1-pentene-2-yl group, 2-pentene-2-yl group, 3-pentene-2-yl group, 4-pentene-2-yl group, 1-pentene-3-yl group, 2-pentene-3-yl group, 1-methyl-1-pentene-1-yl group, 2-methyl-1-pentene-1-yl group, 3-methyl-1-pentene-1-yl group, 4-methyl-1-pentene-1-yl group, 1-methyl-2-pentene-1-yl group, 2-methyl-2-pentene-1-yl group, 3-methyl-2-pentene-1-yl group, 4-methyl-2-pentene-1-yl group, 1-methyl-3-pentene-1-yl group, 2-methyl-3-pentene-1-yl group, 3-methyl-3-pentene-1-yl group, 4-methyl-3-pentene-1-yl group, 1-methyl-4-pentene-1-yl group, 2-methyl-4-pentene-1-yl group, 3-methyl-4-pentene-1-yl group, 4-methyl-4-pentene-1-yl group, 1-methyl-1-pentene-2-yl group, 2-methyl-1-pentene-2-yl group, 3-methyl-1-pentene-2-yl group, 4-methyl-1-pentene-2-yl group, 1-methyl-2-pentene-2-yl group, 2-methyl-2-pentene-2-yl group, 3-methyl-2-pentene-2-yl group, 4-methyl-2-pentene-2-yl group, 1-methyl-3-pentene-2-yl group, 2-methyl-3-pentene-2-yl group, 3-methyl-3-pentene-2-yl group, 4-methyl-3-pentene-2-yl group, 1-methyl-4-pentene-2-yl group, 2-methyl-4-pentene-2-yl group, 3-methyl-4-pentene-2-yl group, 4-methyl-4-pentene-2-yl group, 1-methyl-1-pentene-3-yl group, 2-methyl-1-pentene-3-yl group, 3-methyl-1-pentene-3-yl group, 4-methyl-1-pentene-3-yl group, 1-methyl-2-pentene-3-yl group, 2-methyl-2-pentene-3-yl group, 3-methyl-2-pentene-3-yl group, 4-methyl-2-pentene-3-yl group, 1-hexene-1-yl group, 1-hexen-2-yl group, 1-hexen-3-yl group, 1-hexen-4-yl group, 1-hexen-5-yl group, 1-hexen-6-yl group, 2-hexen-1-yl group, 2-hexen-2-yl group, 2-hexen-3-yl group, 2-hexen-4-yl group, 2-hexen-5-yl group, 2-hexen-6-yl group, 3-hexen-1-yl group, 3-hexen-2-yl group and 3-hexen-3-yl group; preferably ethenyl group, 1-propen-1-yl group, 2-propen-1-yl group, 3-propen-1-yl group, 1-buten-1-yl group, 1-buten-2-yl group, 1-buten-3-yl group, 1-buten-4-yl group, 2-buten-1-yl group, 2-buten-2-yl group, 1-methyl-1-propen-1-yl group, 2-methyl-1-propen-1-yl group, 1-methyl-2-propen-1-yl group, 2-methyl-2-propen-1-yl group, 1-methyl-1-buten-1-yl group, 2-methyl-1-buten-1-yl group, 3-methyl-1-buten-1-yl group, 1-methyl-2-buten-1-yl group, 2-methyl-2-buten-1-yl group, 3-methyl-2-buten-1-yl group, 1-methyl-3-buten-1-yl group, 2-methyl-3-buten-1-yl group, 3-methyl-3-buten-1-yl group, 1-ethyl-1-buten-1-yl group, 2-ethyl-1-buten-1-yl group, 3-ethyl-1-buten-1-yl group, 1-ethyl-2-buten-1-yl group, 2-ethyl-2-buten-1-yl group, 3-ethyl-2-buten-1-yl group, 1-ethyl-3-buten-1-yl group, 2-ethyl-3-buten-1-yl group, 3-ethyl-3-buten-1-yl group, 1,1-dimethyl-1-buten-1-yl group, 1,2-dimethyl-1-buten-1-yl group, 1,3-dimethyl-1-buten-1-yl group, 2,2-dimethyl-1-buten-1-yl group, 3,3-dimethyl-1-buten-1-yl group, 1,1-dimethyl-2-buten-1-yl group, 1,2-dimethyl-2-buten-1-yl group, 1,3-dimethyl-2-buten-1-yl group, 2,2-dimethyl-2-buten-1-yl group, 3,3-dimethyl-2-buten-1-yl group, 1,1-dimethyl-3-buten-1-yl group, 1,2-dimethyl-3-buten-1-yl group, 1,3-dimethyl-3-buten-1-yl group, 2,2-dimethyl-3-propen-1-yloxy group, 1-methyl-2-propen-1-yloxy group, 2-methyl-2-propen-1-yloxy group, 1-methyl-1-buten-1-yloxy group, 2-methyl-1-buten-1-yloxy group, 3-methyl-1-buten-1-yloxy group, 1-methyl-2-buten-1-yloxy group, 2-methyl-2-buten-1-yloxy group, 3-methyl-2-buten-1-yloxy group, 1-methyl-3-buten-1-yloxy group, 2-methyl-3-buten-1-yloxy group, 3-methyl-3-buten-1-yloxy group, 1-ethyl-1-buten-1-yloxy group, 2-ethyl-1-buten-1-yloxy group, 3-ethyl-1-buten-1-yloxy group, 1-ethyl-2-buten-1-yloxy group, 2-ethyl-2-buten-1-yloxy group, 3-ethyl-2-buten-1-yloxy group, 1-ethyl-3-buten-1-yloxy group, 2-ethyl-3-buten-1-yloxy group, 3-ethyl-3-buten-1-yloxy group, 1,1-dimethyl-1-buten-1-yloxy group, 1,2-dimethyl-1-buten-1-yloxy group, 1,3-dimethyl-1-buten-1-yloxy group, 2,2-dimethyl-1-buten-1-yloxy group, 3,3-dimethyl-1-buten-1-yloxy group, 1,1-dimethyl-2-buten-1-yloxy group, 1,2-dimethyl-2-buten-1-yloxy group, 1,3-dimethyl-2-buten-1-yloxy group, 2,2-dimethyl-2-buten-1-yloxy group, 3,3-dimethyl-2-buten-1-yloxy group, 1,1-dimethyl-3-buten-1-yloxy group, 1,2-dimethyl-3-buten-1-yloxy group, 1,3-dimethyl-3-buten-1-yloxy group, 2,2-dimethyl-3-buten-1-yloxy group, 3,3-dimethyl-3-buten-1-yloxy group, 1-penten-1-yloxy group, 2-penten-1-yloxy group, 3-penten-1-yloxy group, 4-penten-1-yloxy group, 1-penten-2-yloxy group, 2-penten-2-yloxy group, 3-penten-2-yloxy group, 4-penten-2-yloxy group, 1-penten-3-yloxy group, 2-penten-3-yloxy group, 1-penten-1-yloxy group, 2-penten-1-yloxy group, 3-penten-1-yloxy group, 4-penten-1-yloxy group, 1-penten-2-yloxy group, 2-penten-2-yloxy group, 3-penten-2-yloxy group, 4-penten-2-yloxy group, 1-penten-3-yloxy group, 2-penten-3-yloxy group, 1-methyl-1-penten-1-yloxy group, 2-methyl-1-penten-1-yloxy group, 3-methyl-1-penten-1-yloxy group, 4-methyl-1-penten-1-yloxy group, 1-methyl-2-penten-1-yloxy group, 2-methyl-2-penten-1-yloxy group, 3-methyl-2-penten-1-yloxy group, 4-methyl-2-penten-1-yloxy group, 1-methyl-3-penten-1-yloxy group, 2-methyl-3-penten-1-yloxy group, 3-methyl-3-penten-1-yloxy group, 4-methyl-3-penten-1-yloxy group, 1-methyl-4-penten-1-yloxy group, 2-methyl-4-penten-1-yloxy group, 3-methyl-4-penten-1-yloxy group, 4-methyl-4-penten-1-yloxy group, 1-methyl-1-penten-2-yloxy group, 2-methyl-1-penten-2-yloxy group, 3-methyl-1-penten-2-yloxy group, 4-methyl-1-penten-2-yloxy group, 1-methyl-2-penten-2-yloxy group, 2-methyl-2-penten-2-yloxy group, 3-methyl-2-penten-2-yloxy group, 4-methyl-2-penten-2-yloxy group, 1-methyl-3-penten-2-yloxy group, 2-methyl-3-penten-2-yloxy group, 3-methyl-3-penten-2-yloxy group, 4-methyl-3-penten-2-yloxy group, 1-methyl-4-penten-2-yloxy group, 2-methyl-4-penten-2-yloxy group, 3-methyl-4-penten-2-yloxy group, 4-methyl-4-penten-2-yloxy group, 1-methyl-1-penten-3-yloxy group, 2-methyl-1-penten-3-yloxy group, 3-methyl-1-penten-3-yloxy group, 4-methyl-1-penten-3-yloxy group, 1-methyl-2-penten-3-yloxy group, 2-methyl-2-penten-3-yloxy group, 3-methyl-2-penten-3-yloxy group, 4-methyl-2-penten-3-yloxy group, 1-hexen-1-yloxy group, 1-hexen-2-yloxy group, 1-hexen-3-yloxy group, 1-hexen-4-yloxy group, 1-hexen-5-yloxy group, 1-hexen-6-yloxy group, 2-hexen-1-yloxy group, 2-hexen-2-yloxy group, 2-hexen-3-yloxy group, 2-hexen-4-yloxy group, 2-hexen-5-yloxy group, 2-hexen-6-yloxy group, 3-hexen-1-yloxy group, 3-hexen-2-yloxy group and 3-hexen-3-yloxy group; preferably ethenyloxy group, 1-propen-1-yloxy group, 2-propen-1-yloxy group, 3-propen-1-yloxy group, 1-buten-1-yloxy group, 1-buten-2-yloxy group, 1-buten-3-yloxy group, 1-buten-4-yloxy group, 2-buten-1-yloxy group, 2-buten-2-yloxy group, 1-methyl-1-propen-1-yloxy group, 2-methyl-1-propen-1-yloxy group, 1-methyl-2-propen-1-yloxy group, 2-methyl-2-propen-1-yloxy group, 1-methyl-1-buten-1-yloxy group, 2-methyl-1-buten-1-yloxy group, 3-methyl-1-buten-1-yloxy group, 1-methyl-2-buten-1-yloxy group, 2-methyl-2-buten-1-yloxy group, 3-methyl-2-buten-1-yloxy group, 1-methyl-3-buten-1-yloxy group, 2-methyl-3-buten-1-yloxy group, 3-methyl-3-buten-1-yloxy group, 1-ethyl-1-buten-1-yloxy group, 2-ethyl-1-buten-1-yloxy group, 3-ethyl-1-buten-1-yloxy group, 1-ethyl-2-buten-1-yloxy group, 2-ethyl-2-buten-1-yloxy group, 3-ethyl-2-buten-1-yloxy group, 1-ethyl-3-buten-1-yloxy group, 2-ethyl-3-buten-1-yloxy group, 3-ethyl-3-buten-1-yloxy group, 1,1-dimethyl-1-buten-1-yloxy group, 1,2-dimethyl-1-buten-1-yloxy group, 1,3-dimethyl-1-buten-1-yloxy group, 2,2-dimethyl-1-buten-1-yloxy group, 3,3-dimethyl-1-buten-1-yloxy group, 1,1-dimethyl-2-buten-1-yloxy group, 1,2-dimethyl-2-buten-1-yloxy group, 1,3-dimethyl-2-buten-1-yloxy group, 2,2-dimethyl-2-buten-1-yloxy group, 3,3-dimethyl-2-buten-1-yloxy group, 1,1-dimethyl-3-buten-1-yloxy group, 1,2-dimethyl-3-buten-1-yloxy group, 1,3-dimethyl-3-buten-1-yloxy group, 2,2-dimethyl-3-buten-1-yloxy group and 3,3-dimethyl-3-buten-1-yloxy group; more preferably ethenyloxy group, 1-propen-1-yloxy group, 2-propen-1-yloxy group, 3-propen-1-yloxy group, 1-buten-1-yloxy group, 1-buten-2-yloxy group, 1-buten-3-yloxy group, 1-buten-4-yloxy group, 2-buten-1-yloxy group, 2-buten-2-yloxy group, 1-methyl-1-propen-1-yloxy group, 2-methyl-1-propen-1-yloxy group, 1-methyl-2-propen-1-yloxy group, 2-methyl-2-propen-1-yloxy group, 1-methyl-1-buten-1-yloxy group, 2-methyl-1-buten-1-yloxy group, 3-methyl-1-buten-1-yloxy group, 1-methyl-2-buten-1-yloxy group, 2-methyl-2-buten-1-yloxy group, 3-methyl-2-buten-1-yloxy group, 1-methyl-3-buten-1-yloxy group, 2-methyl-3-buten-1-yloxy group and 3-methyl-3-buten-1-yloxy group; further preferably ethenyloxy group, 1-propen-1-yloxy group, 2-propen-1-yloxy group, 3-propen-1-yloxy group, 1-buten-1-yloxy group, 1-buten-2-yloxy group, 1-buten-3-yloxy group, 1-buten-4-yloxy group, 2-buten-1-yloxy group and 2-buten-2-yloxy group; and most preferably ethenyloxy group, 1-propen-1-yloxy group, 2-propen-1-yloxy group and 3-propen-1-yloxy group.

In the expression "an alkenylthio group having two to six carbon atoms, which may have one or more substituents", the alkenylthio group represents a group having a sulfur atom bound to the end of the linear or branched alkenyl group having two to six carbon atoms. Specific examples thereof include ethenylthio group, 1-propen-1-ylthio group, 2-propen-1-ylthio group, 3-propen-1-ylthio group, 1-buten-1-ylthio group, 1-buten-2-ylthio group, 1-buten-3-ylthio group, 1-buten-4-ylthio group, 2-buten-1-ylthio group, 2-buten-2-ylthio group, 1-methyl-1-propen-1-ylthio group, 2-methyl-1-propen-1-ylthio group, 1-methyl-2-propen-1- ylthio group, 2-methyl-2-propen-1-ylthio group, 1-methyl-1-buten-1-ylthio group, 2-methyl-1-buten-1-ylthio group, 3-methyl-1-buten-1-ylthio group, 1-methyl-2-buten-1-ylthio group, 2-methyl-2-buten-1-ylthio group, 3-methyl-2-buten-1-ylthio group, 1-methyl-3-buten-1-ylthio group, 2-methyl-3-buten-1-ylthio group, 3-methyl-3-buten-1-ylthio group, 1-ethyl-1-buten-1-ylthio group, 2-ethyl-1-buten-1-ylthio group, 3-ethyl-1-buten-1-ylthio group, 1-ethyl-2-buten-1-ylthio group, 2-ethyl-2-buten-1-ylthio group, 3-ethyl-2-buten-1-ylthio group, 1-ethyl-3-buten-1-ylthio group, 2-ethyl-3-buten-1-ylthio group, 3-ethyl-3-buten-1-ylthio group, 1,1-dimethyl-1-buten-1-ylthio group, 1,2-dimethyl-1-buten-1-ylthio group, 1,3-dimethyl-1-buten-1-ylthio group, 2,2-dimethyl-1-buten-1-ylthio group, 3,3-dimethyl-1-buten-1-ylthio group, 1,1-dimethyl-2-buten-1-ylthio group, 1,2-dimethyl-2-buten-1-ylthio group, 1,3-dimethyl-2-buten-1-ylthio group, 2,2-dimethyl-2-buten-1-ylthio group, 3,3-dimethyl-2-buten-1-ylthio group, 1,1-dimethyl-3-buten-1-ylthio group, 1,2-dimethyl-3-buten-1-ylthio group, 1,3-dimethyl-3-buten-1-ylthio group, 2,2-dimethyl-3-buten-1-ylthio group, 3,3-dimethyl-3-buten-1-ylthio group, 1-penten-1-ylthio group, 2-penten-1-ylthio group, 3-penten-1-ylthio group, 4-penten-1-ylthio group, 1-penten-2-ylthio group, 2-penten-2-ylthio group, 3-penten-2-ylthio group, 4-penten-2-ylthio group, 1-penten-3-ylthio group, 2-penten-3-ylthio group, 1-penten-1-ylthio group, 2-penten-1-ylthio group, 3-penten-1-ylthio group, 4-penten-1-ylthio group, 1-penten-2-ylthio group, 2-penten-2-ylthio group, 3-penten-2-ylthio group, 4-penten-2-ylthio group, 1-penten-3-ylthio group, 2-penten-3-ylthio group, 1-methyl-1-penten-1-ylthio group, 2-methyl-1-penten-1-ylthio group, 3-methyl-1-penten-1-ylthio group, 4-methyl-1-penten-1-ylthio group, 1-methyl-2-penten-1-ylthio group, 2-methyl-2-penten-1-ylthio group, 3-methyl-2-penten-1-ylthio group, 4-methyl-2-penten-1-ylthio group, 1-methyl-3-penten-1-ylthio group, 2-methyl-3-penten-1-ylthio group, 3-methyl-3-penten-1-ylthio group, 4-methyl-3-penten-1-ylthio group, 1-methyl-4-penten-1-ylthio group, 2-methyl-4-penten-1-ylthio group, 3-methyl-4-penten-1-ylthio group, 4-methyl-4-penten-1-ylthio group, 1-methyl-1-penten-2-ylthio group, 2-methyl-1-penten-2-ylthio group, 3-methyl-1-penten-2-ylthio group, 4-methyl-1-penten-2-ylthio group, 1-methyl-2-penten-2-ylthio group, 2-methyl-2-penten-2-ylthio group, 3-methyl-2-penten-2-ylthio group, 4-methyl-2-penten-2-ylthio group, 1-methyl-3-penten-2-ylthio group, 2-methyl-3-penten-2-ylthio group, 3-methyl-3-penten-2-ylthio group, 4-methyl-3-penten-2-ylthio group, 1-methyl-4-penten-2-ylthio group, 2-methyl-4-penten-2-ylthio group, 3-methyl-4-penten-2-ylthio group, 4-methyl-4-penten-2-ylthio group, 1-methyl-1-penten-3-ylthio group, 2-methyl-1-penten-3-ylthio group, 3-methyl-1-penten-3-ylthio group, 4-methyl-1-penten-3-ylthio group, 1-methyl-2-penten-3-ylthio group, 2-methyl-2-penten-3-ylthio group, 3-methyl-2-penten-3-ylthio group, 4-methyl-2-penten-3-ylthio group, 1-hexen-1-ylthio group, 1-hexen-2-ylthio group, 1-hexen-3-ylthio group, 1-hexen-4-ylthio group, 1-hexen-5-ylthio group, 1-hexen-6-ylthio group, 2-hexen-1-ylthio group, 2-hexen-2-ylthio group, 2-hexen-3-ylthio group, 2-hexen-4-ylthio group, 2-hexen-5-ylthio group, 2-hexen-6-ylthio group, 3-hexen-1-ylthio group, 3-hexen-2-ylthio group and 3-hexen-3-ylthio group; preferably ethenylthio group, 1-propen-1-ylthio group, 2-propen-1-ylthio group, 3-propen-1-ylthio group, 1-buten-1-ylthio group, 1-buten-2-ylthio group, 1-buten-3-ylthio group, 1-buten-4-ylthio group, 2-buten-1-ylthio group, 2-buten-2-ylthio group, 1-methyl-1-propen-1-ylthio group, 2-methyl-1-propen-1-ylthio group, 1-methyl-2-propen-1-ylthio group, 2-methyl-2-propen-1-ylthio group, 1-methyl-1-buten-1-ylthio group, 2-methyl-1-buten-1-ylthio group, 3-methyl-1-buten-1-ylthio group, 1-methyl-2-buten-1-ylthio group, 2-methyl-2-buten-1-ylthio group, 3-methyl-2-buten-1-ylthio group, 1-methyl-3-buten-1-ylthio group, 2-methyl-3-buten-1-ylthio group, 3-methyl-buten-1-ylthio group, 1-ethyl-1-buten-1-ylthio group, 2-ethyl-1-buten-1-ylthio group, 3-ethyl-1-buten-1-ylthio group, 1-ethyl-2-buten-1-ylthio group, 2-ethyl-2-buten-1-ylthio group, 3-ethyl-2-buten-1-ylthio group, 1-ethyl-3-buten-1-ylthio group, 2-ethyl-3-buten-1-ylthio group, 3-ethyl-3-buten-1-ylthio group, 1,1-dimethyl-1-buten-1-ylthio group, 1,2-dimethyl-1-buten-1-ylthio group, 1,3-dimethyl-1-buten-1-ylthio group, 2,2-dimethyl-1-buten-1-ylthio group, 3,3-dimethyl-1-buten-1-ylthio group, 1,1-dimethyl-2-buten-1-ylthio group, 1,2-dimethyl-2-buten-1-ylthio group, 1,3-dimethyl-2-buten-1-ylthio group, 2,2-dimethyl-2-buten-1-ylthio group, 3,3-dimethyl-2-buten-1-ylthio group, 1,1-dimethyl-3-buten-1-ylthio group, 1,2-dimethyl-3-buten-1-ylthio group, 1,3-dimethyl-3-buten-1-ylthio group, 2,2-dimethyl-3-buten-1-ylthio group and 3,3-dimethyl-3-buten-1-ylthio group; more preferably ethenylthio group, 1-propen-1-ylthio group, 2-propen-1-ylthio group, 3-propen-1-ylthio group, 1-buten-1-ylthio group, 1-buten-2-ylthio group, 1-buten-3-ylthio group, 1-buten-4-ylthio group, 2-buten-1-ylthio group, 2-buten-2-ylthio group, 1-methyl-1-propen-1-ylthio group, 2-methyl-1-propen-1-ylthio group, 1-methyl-2-propen-1-ylthio group, 2-methyl-2-propen-1-ylthio group, 1-methyl-1-buten-1-ylthio group, 2-methyl-1-buten-1-ylthio group, 3-methyl-1-buten-1-ylthio group, 1-methyl-2-buten-1-ylthio group, 2-methyl-2-buten-1-ylthio group, 3-methyl-2-buten-1-ylthio group, 1-methyl-3-buten-1-ylthio group, 2-methyl-3-buten-1-ylthio group and 3-methyl-3-buten-1-ylthio group; further preferably ethenylthio group, 1-propen-1-ylthio group, 2-propen-1-ylthio group, 3-propen-1-ylthio group, 1-buten-1-ylthio group, 1-buten-2-ylthio group, 1-buten-3-ylthio group, 1-buten-4-ylthio group, 2-buten-1-ylthio group and 2-buten-2-ylthio group; and most preferably ethenylthio group, 1-propen-1-ylthio group, 2-propen-1-ylthio group and 3-propen-1-ylthio group.

In the expression "an alkynyl group having two to six carbon atoms, which may have one or more substituents", the alkynyl group is a linear or branched alkynyl group having two to six carbon atoms and represents a residue group of a compound having a triple bond in the alkyl group containing 2 or more carbon atoms. Specific examples thereof include ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 2-butyn-2-yl group, 1-methyl-1-propyn-1-yl group, 2-methyl-1-propyn-1-yl group, 1-methyl-2-propyn-1-yl group, 2-methyl-2-propyn-1-yl group, 1-methyl-1-butyn-1-yl group, 2-methyl-1-butyn-1-yl group, 3-methyl-1-butyn-1-yl group, 1-methyl-2-butyn-1-yl group, 2-methyl-2-butyn-1-yl group, 3-methyl-2-butyn-1-yl group, 1-methyl-3-butyn-1-yl group, 2-methyl-3-butyn-1-yl group, 3-methyl-3-butyn-1-yl group, 1-ethyl-1-butyn-1-yl group, 2-ethyl-1-butyn-1-yl group, 3-ethyl-1-butyn-1-yl group, 1-ethyl-2-butyn-1-yl group, 2-ethyl-2-butyn-1-yl group, 3-ethyl-2-butyn-1-yl group, 1-ethyl-3-butyn-1-yl group, 2-ethyl-3-butyn-1-yl group, 3-ethyl-3-butyn-1-yl group, 1,1-dimethyl-1-butyn-1-yl group, 1,2-dimethyl-1-butyn-1-yl group, 1,3-dimethyl-1-butyn-1-yl group, 2,2-dimethyl-1-butyn-1-yl group, 3,3-dimethyl-1-butyn-1-yl group, 1,1-dimethyl-2-butyn-1-yl group, 1,2-dimethyl-2-butyn-1-yl group, 1,3-dimethyl-2-butyn-1-yl group, 2,2-dimethyl-2-butyn-1-yl group, 3,3-dimethyl-2-butyn-1-yl group, 1,1-dimethyl-3- butyn-1-yl group, 1,2-dimethyl-3-butyn-1-yl group, 1,3-dimethyl-3-butyn-1-yl group, 2,2-dimethyl-3-butyn-1-yl group, 3,3-dimethyl-3-butyn-1-yl group, 1-pentyn-1-yl group, 2-pentyn-1-yl group, 3-pentyn-1-yl group, 4-pentyn-1-yl group, 1-pentyn-2-yl group, 2-pentyn-2-yl group, 3-pentyn-2-yl group, 4-pentyn-2-yl group, 1-pentyn-3-yl group, 2-pentyn-3-yl group, 1-pentyn-1-yl group, 2-pentyn-1-yl group, 3-pentyn-1-yl group, 4-pentyn-1-yl group, 1-pentyn-2-yl group, 2-pentyn-2-yl group, 3-pentyn-2-yl group, 4-pentyn-2-yl group, 1-pentyn-3-yl group, 2-pentyn-3-yl group, 1-methyl-1-pentyn-1-yl group, 2-methyl-1-pentyn-1-yl group, 3-methyl-1-pentyn-1-yl group, 4-methyl-1-pentyn-1-yl group, 1-methyl-2-pentyn-1-yl group, 2-methyl-2-pentyn-1-yl group, 3-methyl-2-pentyn-1-yl group, 4-methyl-2-pentyn-1-yl group, 1-methyl-3-pentyn-1-yl group, 2-methyl-3-pentyn-1-yl group, 3-methyl-3-pentyn-1-yl group, 4-methyl-3-pentyn-1-yl group, 1-methyl-4-pentyn-1-yl group, 2-methyl-4-pentyn-1-yl group, 3-methyl-4-pentyn-1-yl group, 4-methyl-4-pentyn-1-yl group, 1-methyl-1-pentyn-2-yl group, 2-methyl-1-pentyn-2-yl group, 3-methyl-1-pentyn-2-yl group, 4-methyl-1-pentyn-2-yl group, 1-methyl-2-pentyn-2-yl group, 2-methyl-2-pentyn-2-yl group, 3-methyl-2-pentyn-2-yl group, 4-methyl-2-pentyn-2-yl group, 1-methyl-3-pentyn-2-yl group, 2-methyl-3-pentyn-2-yl group, 3-methyl-3-pentyn-2-yl group, 4-methyl-3-pentyn-2-yl group, 1-methyl-4-pentyn-2-yl group, 2-methyl-4-pentyn-2-yl group, 3-methyl-4-pentyn-2-yl group, 4-methyl-4-pentyn-2-yl group, 1-methyl-1-pentyn-3-yl group, 2-methyl-1-pentyn-3-yl group, 3-methyl-1-pentyn-3-yl group, 4-methyl-1-pentyn-3-yl group, 1-methyl-2-pentyn-3-yl group, 2-methyl-2-pentyn-3-yl group, 3-methyl-2-pentyn-3-yl group, 4-methyl-2-pentyn-3-yl group, 1-hexyn-1-yl group, 1-hexyn-2-yl group, 1-hexyn-3-yl group, 1-hexyn-4-yl group, 1-hexyn-5-yl group, 1-hexyn-6-yl group, 2-hexyn-1-yl group, 2-hexyn-2-yl group, 2-hexyn-3-yl group, 2-hexyn-4-yl group, 2-hexyn-5-yl group, 2-hexyn-6-yl group, 3-hexyn-1-yl group, 3-hexyn-2-yl group and 3-hexyn-3-yl group. Preferred examples include ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 2-butyn-2-yl group, 1-methyl-1-propyn-1-yl group, 2-methyl-1-propyn-1-yl group, 1-methyl-2-propyn-1-yl group, 2-methyl-2-propyn-1-yl group, 1-methyl-1-butyn-1-yl group, 2-methyl-1-butyn-1-yl group, 3-methyl-1-butyn-1-yl group, 1-methyl-2-butyn-1-yl group, 2-methyl-2-butyn-1-yl group, 3-methyl-2-butyn-1-yl group, 1-methyl-3-butyn-1-yl group, 2-methyl-3-butyn-1-yl group, 3-methyl-3-butyn-1-yl group, 1-ethyl-1-butyn-1-yl group, 2-ethyl-1-butyn-1-yl group, 3-ethyl-1-butyn-1-yl group, 1-ethyl-2-butyn-1-yl group, 2-ethyl-2-butyn-1-yl group, 3-ethyl-2-butyn-1-yl group, 1-ethyl-3-butyn-1-yl group, 2-ethyl-3-butyn-1-yl group, 3-ethyl-3-butyn-1-yl group, 1,1-dimethyl-1-butyn-1-yl group, 1,2-dimethyl-1-butyn-1-yl group, 1,3-dimethyl-1-butyn-1-yl group, 2,2-dimethyl-1-butyn-1-yl group, 3,3-dimethyl-1-butyn-1-yl group, 1,1-dimethyl-2-butyn-1-yl group, 1,2-dimethyl-2-butyn-1-yl group, 1,3-dimethyl-2-butyn-1-yl group, 2,2-dimethyl-2-butyn-1-yl group, 3,3-dimethyl-2-butyn-1-yl group, 1,1-dimethyl-3-butyn-1-yl group, 1,2-dimethyl-3-butyn-1-yl group, 1,3-dimethyl-3-butyn-1-yl group, 2,2-dimethyl-3-butyn-1-yl group and 3,3-dimethyl-3-butyn-1-yl group; more preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 2-butyn-2-yl group, 1-methyl-1-propyn-1-yl group, 2-methyl-1-propyn-1-yl group, 1-methyl-2-propyn-1-yl group, 2-methyl-2-propyn-1-yl group, 1-methyl-1-butyn-1-yl group, 2-methyl-1-butyn-1-yl group, 3-methyl-1-butyn-1-yl group, 1-methyl-2-butyn-1-yl group, 2-methyl-2-butyn-1-yl group, 3-methyl-2-butyn-1-yl group, 1-methyl-3-butyn-1-yl group, 2-methyl-3-butyn-1-yl group and 3-methyl-3-butyn-1-yl group; further preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group and 2-butyn-2-yl group; and most preferably ethynyl group, 1-propyn-1-yl group, 2-propyn-1-yl group and 3-propyn-1-yl group.

In the expression "an alkynyloxy group having two to six carbon atoms, which may have one or more substituents", the alkynyloxy group represents a group having an oxygen atom bound to the end of the linear or branched alkynyl group having two to six carbon atoms. Specific examples thereof include ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 2-butyn-2-yloxy group, 1-methyl-1-propyn-1-yloxy group, 2-methyl-1-propyn-1-yloxy group, 1-methyl-2-propyn-1-yloxy group, 2-methyl-2-propyn-1-yloxy group, 1-methyl-1-butyn-1-yloxy group, 2-methyl-1-butyn-1-yloxy group, 3-methyl-1-butyn-1-yloxy group, 1-methyl-2-butyn-1-yloxy group, 2-methyl-2-butyn-1-yloxy group, 3-methyl-2-butyn-1-yloxy group, 1-methyl-3-butyn-1-yloxy group, 2-methyl-3-butyn-1-yloxy group, 3-methyl-3-butyn-1-yloxy group, 1-ethyl-1-butyn-1-yloxy group, 2-ethyl-1-butyn-1-yloxy group, 3-ethyl-1-butyn-1-yloxy group, 1-ethyl-2-butyn-1-yloxy group, 2-ethyl-2-butyn-1-yloxy group, 3-ethyl-2-butyn-1-yloxy group, 1-ethyl-3-butyn-1-yloxy group, 2-ethyl-3-butyn-1-yloxy group, 3-ethyl-3-butyn-1-yloxy group, 1,1-dimethyl-1-butyn-1-yloxy group, 1,2-dimethyl-1-butyn-1-yloxy group, 1,3-dimethyl-1-butyn-1-yloxy group, 2,2-dimethyl-1-butyn-1-yloxy group, 3,3-dimethyl-1-butyn-1-yloxy group, 1,1-dimethyl-2-butyn-1-yloxy group, 1,2-dimethyl-2-butyn-1-yloxy group, 1,3-dimethyl-2-butyn-1-yloxy group, 2,2-dimethyl-2-butyn-1-yloxy group, 3,3-dimethyl-2-butyn-1-yloxy group, 1,1-dimethyl-3-butyn-1-yloxy group, 1,2-dimethyl-3-butyn-1-yloxy group, 1,3-dimethyl-3-butyn-1-yloxy group, 2,2-dimethyl-3-butyn-1-yloxy group, 3,3-dimethyl-3-butyn-1-yloxy group, 1-pentyn-1-yloxy group, 2-pentyn-1-yloxy group, 3-pentyn-1-yloxy group, 4-pentyn-1-yloxy group, 1-pentyn-2-yloxy group, 2-pentyn-2-yloxy group, 3-pentyn-2-yloxy group, 4-pentyn-2-yloxy group, 1-pentyn-3-yloxy group, 2-pentyn-3-yloxy group, 1-pentyn-1-yloxy group, 2-pentyn-1-yloxy group, 3-pentyn-1-yloxy group, 4-pentyn-1-yloxy group, 1-pentyn-2-yloxy group, 2-pentyn-2-yloxy group, 3-pentyn-2-yloxy group, 4-pentyn-2-yloxy group, 1-pentyn-3-yloxy group, 2-pentyn-3-yloxy group, 1-methyl-1-pentyn-1-yloxy group, 2-methyl-1-pentyn-1-yloxy group, 3-methyl-1-pentyn-1-yloxy group, 4-methyl-1-pentyn-1-yloxy group, 1-methyl-2-pentyn-1-yloxy group, 2-methyl-2-pentyn-1-yloxy group, 3-methyl-2-pentyn-1-yloxy group, 4-methyl-2-pentyn-1-yloxy group, 1-methyl-3-pentyn-1-yloxy group, 2-methyl-3-pentyn-1-yloxy group, 3-methyl-3-pentyn-1-yloxy group, 4-methyl-3-pentyn-1-yloxy group, 1-methyl-4-pentyn-1-yloxy group, 2-methyl-4-pentyn-1-yloxy group, 3-methyl-4-pentyn-1-yloxy group, 4-methyl-4-pentyn-1-yloxy group, 1-methyl-1-pentyn-2-yloxy group, 2-methyl-1-pentyn-2-yloxy group, 3-methyl-1-pentyn-2-yloxy group, 4-methyl-1-pentyn-2-yloxy group, 1-methyl-2-pentyn-2-yloxy group, 2-methyl-2-pentyn-2-yloxy group, 3-methyl-2-pentyn-2-yloxy group, 4-methyl-2-pentyn-2-yloxy group, 1-methyl-3-pentyn-2-yloxy group, 2-methyl-3-pentyn-2-yloxy group, 3-methyl-3-pentyn-2-yloxy group, 4-methyl-3-pentyn-2-yloxy group, 1-methyl-4-pentyn-2-yloxy group, 2-methyl-4-pentyn-2-yloxy group, 3-methyl-4-pentyn-2-yloxy group, 4-methyl-4-pentyn-2-yloxy group, 1-methyl-1-pentyn-3-yloxy group, 2-methyl-1-pentyn-3-yloxy group, 3-methyl-1-pentyn-3-yloxy group, 4-methyl-1-pentyn-3-yloxy group, 1-methyl-2-pentyn-3-yloxy group, 2-methyl-2-pentyn-3-yloxy group, 3-methyl-2-pentyn-3-yloxy group, 4-methyl-2-pentyn-3-yloxy group, 1-hexyn-1-yloxy group, 1-hexyn-2-yloxy group, 1-hexyn-3-yloxy group, 1-hexyn-4-yloxy group/1-hexyn-5-yloxy group, 1-hexyn-6-yloxy group, 2-hexyn-1-yloxy group, 2-hexyn-2-yloxy group, 2-hexyn-3-yloxy group, 2-hexyn-4-yloxy group, 2-hexyn-5-yloxy group, 2-hexyn-6-yloxy group, 3-hexyn-1-yloxy group, 3-hexyn-2-yloxy group and 3-hexyn-3-yloxy group; preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 2-butyn-2-yloxy group, 1-methyl-1-propyn-1-yloxy group, 2-methyl-1-propyn-1-yloxy group, 1-methyl-2-propyn-1-yloxy group, 2-methyl-2-propyn-1-yloxy group, 1-methyl-1-butyn-1-yloxy group, 2-methyl-1-butyn-1-yloxy group, 3-methyl-1-butyn-1-yloxy group, 1-methyl-2-butyn-1-yloxy group, 2-methyl-2-butyn-1-yloxy group, 3-methyl-2-butyn-1-yloxy group, 1-methyl-3-butyn-1-yloxy group, 2-methyl-3-butyn-1-yloxy group, 3-methyl-3-butyn-1-yloxy group, 1-ethyl-1-butyn-1-yloxy group, 2-ethyl-1-butyn-1-yloxy group, 3-ethyl-1-butyn-1-yloxy group, 1-ethyl-2-butyn-1-yloxy group, 2-ethyl-2-butyn-1-yloxy group, 3-ethyl-2-butyn-1-yloxy group, 1-ethyl-3-butyn-1-yloxy group, 2-ethyl-3-butyn-1-yloxy group, 3-ethyl-3-butyn-1-yloxy group, 1,1-dimethyl-1-butyn-1-yloxy group, 1,2-dimethyl-1-butyn-1-yloxy group, 1,3-dimethyl-1-butyn-1-yloxy group, 2,2-dimethyl-1-butyn-1-yloxy group, 3,3-dimethyl-1-butyn-1-yloxy group, 1,1-dimethyl-2-butyn-1-yloxy group, 1,2-dimethyl-2-butyn-1-yloxy group, 1,3-dimethyl-2-butyn-1-yloxy group, 2,2-dimethyl-2-butyn-1-yloxy group, 3,3-dimethyl-2-butyn-1-yloxy group, 1,1-dimethyl-3-butyn-1-yloxy group, 1,2-dimethyl-3-butyn-1-yloxy group, 1,3-dimethyl-3-butyn-1-yloxy group, 2,2-dimethyl-3-butyn-1-yloxy group and 3,3-dimethyl-3-butyn-1-yloxy group; more preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 2-butyn-2-yloxy group, 1-methyl-1-propyn-1-yloxy group, 2-methyl-1-propyn-1-yloxy group, 1-methyl-2-propyn-1-yloxy group, 2-methyl-2-propyn-1-yloxy group, 1-methyl-1-butyn-1-yloxy group, 2-methyl-1-butyn-1-yloxy group, 3-methyl-1-butyn-1-yloxy group, 1-methyl-2-butyn-1-yloxy group, 2-methyl-2-butyn-1-yloxy group, 3-methyl-2-butyn-1-yloxy group, 1-methyl-3-butyn-1-yloxy group, 2-methyl-3-butyn-1-yloxy group and 3-methyl-3-butyn-1-yloxy group; further preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group and 2-butyn-2-yloxy group; and most preferably ethynyloxy group, 1-propyn-1-yloxy group, 2-propyn-1-yloxy group and 3-propyn-1-yloxy group.

In the expression "an alkynylthio group having two to six carbon atoms, which may have one or more substituents", the alkynylthio group represents a group having a sulfur atom bound to the end of the linear or branched alkynyl group having two to six carbon atoms. Specific examples thereof include ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 2-butyn-2-ylthio group, 1-methyl-1-propyn-1-ylthio group, 2-methyl-1-propyn-1-ylthio group, 1-methyl-2-propyn-1-ylthio group, 2-methyl-2-propyn-1-ylthio group, 1-methyl-1-butyn-1-ylthio group, 2-methyl-1-butyn-1-ylthio group, 3-methyl-1-butyn-1-ylthio group, 1-methyl-2-butyn-1-ylthio group, 2-methyl-2-butyn-1-ylthio group, 3-methyl-2-butyn-1-ylthio group, 1-methyl-3-butyn-1-ylthio group, 2-methyl-3-butyn-1-ylthio group, 3-methyl-3-butyn-1-ylthio group, 1-ethyl-1-butyn-1-ylthio group, 2-ethyl-1-butyn-1-ylthio group, 3-ethyl-1-butyn-1-ylthio group, 1-ethyl-2-butyn-1-ylthio group, 2-ethyl-2-butyn-1-ylthio group, 3-ethyl-2-butyn-1-ylthio group, 1-ethyl-3-butyn-1-ylthio group, 2-ethyl-3-butyn-1-ylthio group, 3-ethyl-3-butyn-1-ylthio group, 1,1-dimethyl-1-butyn-1-ylthio group, 1,2-dimethyl-1-butyn-1-ylthio group, 1,3-dimethyl-1-butyn-1-ylthio group, 2,2-dimethyl-1-butyn-1-ylthio group, 3,3-dimethyl-1-butyn-1-ylthio group, 1,1-dimethyl-2-butyn-1-ylthio group, 1,2-dimethyl-2-butyn-1-ylthio group, 1,3-dimethyl-2-butyn-1-ylthio group, 2,2-dimethyl-2-butyn-1-ylthio group, 3,3-dimethyl-2-butyn-1-ylthio group, 1,1-dimethyl-3-butyn-1-ylthio group, 1,2-dimethyl-3-butyn-1-ylthio group, 1,3-dimethyl-3-butyn-1-ylthio group, 2,2-dimethyl-3-butyn-1-ylthio group, 3,3-dimethyl-3-butyn-1-ylthio group, 1-pentyn-1-ylthio group, 2-pentyn-1-ylthio group, 3-pentyn-1-ylthio group, 4-pentyn-1-ylthio group, 1-pentyn-2-ylthio group, 2-pentyn-2-ylthio group, 3-pentyn-2-ylthio group, 4-pentyn-2-ylthio group, 1-pentyn-3-ylthio group, 2-pentyn-3-ylthio group, 1-pentyn-1-ylthio group, 2-pentyn-1-ylthio group, 3-pentyn-1-ylthio group, 4-pentyn-1-ylthio group, 1-pentyn-2-ylthio group, 2-pentyn-2-ylthio group, 3-pentyn-2-ylthio group, 4-pentyn-2-ylthio group, 1-pentyn-3-ylthio group, 2-pentyn-3-ylthio group, 1-methyl-1-pentyn-1-ylthio group, 2-methyl-1-pentyn-1-ylthio group, 3-methyl-1-pentyn-1-ylthio group, 4-methyl-1-pentyn-1-ylthio group, 1-methyl-2-pentyn-1-ylthio group, 2-methyl-2-pentyn-1-ylthio group, 3-methyl-2-pentyn-1-ylthio group, 4-methyl-2-pentyn-1-ylthio group, 1-methyl-3-pentyn-1-ylthio group, 2-methyl-3-pentyn-1-ylthio group, 3-methyl-3-pentyn-1-ylthio group, 4-methyl-3-pentyn-1-ylthio group, 1-methyl-4-pentyn-1-ylthio group, 2-methyl-4-pentyn-1-ylthio group, 3-methyl-4-pentyn-1-ylthio group, 4-methyl-4-pentyn-1-ylthio group, 1-methyl-1-pentyn-2-ylthio group, 2-methyl-1-pentyn-2-ylthio group, 3-methyl-1-pentyn-2-ylthio group, 4-methyl-1-pentyn-2-ylthio group, 1-methyl-2-pentyn-2-ylthio group, 2-methyl-2-pentyn-2-ylthio group, 3-methyl-2-pentyn-2-ylthio group, 4-methyl-2-pentyn-2-ylthio group, 1-methyl-3-pentyn-2-ylthio group, 2-methyl-3-pentyn-2-ylthio group, 3-methyl-3-pentyn-2-ylthio group, 4-methyl-3-pentyn-2-ylthio group, 1-methyl-4-pentyn-2-ylthio group, 2-methyl-4-pentyn-2-ylthio group, 3-methyl-4-pentyn-2-ylthio group, 4-methyl-4-pentyn-2-ylthio group, 1-methyl-1-pentyn-3-ylthio group, 2-methyl-1-pentyn-3-ylthio group, 3-methyl-1-pentyn-3-ylthio group, 4-methyl-1-pentyn-3-ylthio group, 1-methyl-2-pentyn-3-ylthio group, 2-methyl-2-pentyn-3-ylthio group, 3-methyl-2-pentyn-3-ylthio group, 4-methyl-2-pentyn-3-ylthio group, 1-hexyn-1-ylthio group, 1-hexyn-2-ylthio group, 1-hexyn-3-ylthio group, 1-hexyn-4-ylthio group, 1-hexyn-5-ylthio group, 1-hexyn-6-ylthio group, 2-hexyn-1-ylthio group, 2-hexyn-2-ylthio group, 2-hexyn-3-ylthio group, 2-hexyn-4-ylthio group, 2-hexyn-5-ylthio group, 2-hexyn-6-ylthio group, 3-hexyn-1-ylthio group, 3-hexyn-2-ylthio group and 3-hexyn-3-ylthio group; preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 2-butyn-2-ylthio group, 1-methyl-1-propyn-1-ylthio group, 2-methyl-1-propyn-1-ylthio group, 1-methyl-2-propyn-1-ylthio group, 2-methyl-2-propyn-1-ylthio group, 1-methyl-1-butyn-1-ylthio group, 2-methyl-1-butyn-1-ylthio group, 3-methyl-1-butyn-1-ylthio group, 1-methyl-2-butyn-1-ylthio group, 2-methyl-2-butyn-1-ylthio group, 3-methyl-2-butyn-1-ylthio group, 1-methyl-3-butyn-1-ylthio group, 2-methyl-3-butyn-1-ylthio group, 3-methyl-3-butyn-1-ylthio group, 1-ethyl-1-butyn-1-ylthio group, 2-ethyl-1-butyn-1-ylthio group, 3-ethyl-1-butyn-1-ylthio group, 1-ethyl-2-butyn-1-ylthio group, 2-ethyl-2-butyn-1-ylthio group, 3-ethyl-2-butyn-1-ylthio group, 1-ethyl-3-butyn-1-ylthio group, 2-ethyl-3-butyn-1-ylthio group, 3-ethyl-3-butyn-1-ylthio group, 1,1-dimethyl-1-butyn-1-ylthio group, 1,2-dimethyl-1-butyn-1-ylthio group, 1,3-dimethyl-1-butyn-1-ylthio group, 2,2-dimethyl-1-butyn-1-ylthio group, 3,3-dimethyl-1-butyn-1-ylthio group, 1,1-dimethyl-2-butyn-1-ylthio group, 1,2-dimethyl-2-butyn-1-ylthio group, 1,3-dimethyl-2-butyn-1-ylthio group, 2,2-dimethyl-2-butyn-1-ylthio group, 3,3-dimethyl-2-butyn-1-ylthio group, 1,1-dimethyl-3-butyn-1-ylthio group, 1,2-dimethyl-3-butyn-1-ylthio group, 1,3-dimethyl-3-butyn-1-ylthio group, 2,2-dimethyl-3-butyn-1-ylthio group and 3,3-dimethyl-3-butyn-1-ylthio group; more preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 2-butyn-2-ylthio group, 1-methyl-1-propyn-1-ylthio group, 2-methyl-1-propyn-1-ylthio group, 1-methyl-2-propyn-1-ylthio group, 2-methyl-2-propyn-1-ylthio group, 1-methyl-1-butyn-1-ylthio group, 2-methyl-1-butyn-1-ylthio group, 3-methyl-1-butyn-1-ylthio group, 1-methyl-2-butyn-1-ylthio group, 2-methyl-2-butyn-1-ylthio group, 3-methyl-2-butyn-1-ylthio group, 1-methyl-3-butyn-1-ylthio group, 2-methyl-3-butyn-1-ylthio group and 3-methyl-3-butyn-1-ylthio group; further preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group and 2-butyn-2-ylthio group; and most preferably ethynylthio group, 1-propyn-1-ylthio group, 2-propyn-1-ylthio group and 3-propyn-1-ylthio group.

In the expression "an aryl group having six to twelve carbon atoms, which may have one or more substituents", the aryl group represents an aromatic cyclic group, and specific examples thereof include phenyl group, 1-naphthyl group, 2-naphthyl group, as-indacenyl group, s-indacenyl group and acenaphthylenyl group; preferably phenyl group, 1-naphthyl group and 2-naphthyl group; and more preferably phenyl group.

In the expression "an aryloxy group having six to twelve carbon atoms, which may have one or more substituents", the aryloxy group represents a group having an oxygen atom bound to the end of the aryl group having six to twelve carbon atoms, and specific examples thereof include phenyloxy group, 1-naphthyloxy group, 2-naphthyloxy group, as-indacenyloxy group, s-indacenyloxy group and acenaphthylenyloxy group; preferably phenyloxy group, 1-naphthyloxy group and 2-naphthyloxy group; and more preferably phenyloxy group.

In the expression "an arylthio group having six to twelve carbon atoms, which may have one or more substituents", the arylthio group represents a group having a sulfur atom bound to the end of the aryl group having six to twelve carbon atoms, and specific examples thereof include phenylthio group, 1-naphthylthio group, 2-naphthylthio group, as-indacenylthio group, s-indacenylthio group and acenaphthylenylthio group; preferably phenylthio group, 1-naphthylthio group and 2-naphthylthio group; and more preferably phenylthio group.

In the expression "an alkylaryl group having seven to eighteen carbon atoms, which may have one or more substituents", the alkylaryl group represents a group having the aryl group having six to twelve carbon atoms substituted at a substitutable position with the alkyl group having one to six carbon atoms, and specific examples thereof include tolyl group, xylyl group, cumenyl group, mesityl group and cymenyl group; preferably tolyl group, xylyl group, cumenyl group, mesityl group, cymenyl group and styryl group; more preferably tolyl group, xylyl group, cumenyl group and mesityl group; and further preferably tolyl group, xylyl group and cumenyl group.

In the expression "an alkylaryloxy group having seven to eighteen carbon atoms, which may have one or more substituents", the alkylaryloxy group represents a group having an oxygen atom bound to the end of the alkylaryl group having seven to eighteen carbon atoms, and specific examples thereof include o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, 2,3-cymenyl-1-oxy group, 2,4-cymenyl-1-oxy group and 2,5-cymenyl-1-oxy group; preferably o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, 2,3-cymenyl-1-oxy group, 2,4-cymenyl-1-oxy group and 2,5-cymenyl-1-oxy group; more preferably o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group and mesityloxy group; further preferably o-tolyloxy group, m-tolyloxy group, p-tolyloxy group, 2,3-xylyl-1-oxy group, 2,4-xylyl-1-oxy group, 2,5-xylyl-1-oxy group and mesityloxy group; and most preferably o-tolyloxy group, m-tolyloxy group and p-tolyloxy group.

In the expression "an alkylarylthio group having seven to eighteen carbon atoms, which may have one or more substituents", the alkylarylthio group represents a group having a sulfur atom bound to the end of the alkylaryl group having seven to eighteen carbon atoms, and specific examples thereof include o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, 2,3-cymenyl-1-thio group, 2,4-cymenyl-1-thio group and 2,5-cymenyl-1-thio group; preferably o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, 2,3-cymenyl-1-thio group, 2,4-cymenyl-1-thio group and 2,5-cymenyl-1-thio group; more preferably o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group and mesitylthio group; further preferably o-tolylthio group, m-tolylthio group, p-tolylthio group, 2,3-xylyl-1-thio group, 2,4-xylyl-1-thio group, 2,5-xylyl-1-thio group and mesitylthio group; and most preferably o-tolylthio group, m-tolylthio group and p-tolylthio group.

In the expression "an aralkyl group having seven to eighteen carbon atoms, which may have one or more substituents", the aralkyl group represents a group having the alkyl group having one to six carbon atoms substituted at a substitutable position with the aryl group having six to twelve carbon atoms, and specific examples thereof include benzyl group, phenethyl group, 3-phenylpropyl group, 4-phenylbutyl group, 5-phenylpentyl group, 6-phenylhexyl group, 1-naphthylmethyl group, 2-naphthylmethyl group, 1-naphthylethyl group, 2-naphthylethyl group, 1-naphthylpropyl group and 2-naphthylpropyl group; preferably benzyl group, phenethyl group, 3-phenylpropyl group, 4-phenylbutyl group, 5-phenylpentyl group, 6-phenylhexyl group, 1-naphthylmethyl group, 2-naphthylmethyl group, 1-naphthylethyl group, 2-naphthylethyl group, 1-naphthylpropyl group and 2-naphthylpropyl group; more preferably benzyl group, phenethyl group, 3-phenylpropyl group, 4-phenylbutyl group, 5-phenylpentyl group, 6-phenylhexyl group, 1-naphthylmethyl group and 2-naphthylmethyl group; further preferably benzyl group, phenethyl group, 3-phenylpropyl group and 4-phenylbutyl group; and most preferably benzyl group and phenethyl group.

In the expression "an aralkyloxy group having seven to eighteen carbon atoms, which may have one or more substituents", the aralkyloxy group represents a group having an oxygen atom bound to the aralkyl group having seven to eighteen carbon atoms. Specific examples thereof include benzyloxy group, phenethyloxy group, 3-phenylpropyloxy group, 4-phenylbutyloxy group, 5-phenylpentyloxy group, 6-phenylhexyloxy group, 1-naphthylmethyloxy group, 2-naphthylmethyloxy group, 1-naphthylethyloxy group, 2-naphthylethyloxy group, 1-naphthylpropyloxy group and 2-naphthylpropyloxy group; preferably benzyloxy group, phenethyloxy group, 3-phenylpropyloxy group, 4-phenylbutyloxy group, 5-phenylpentyloxy group, 6-phenylhexyloxy group, 1-naphthylmethyloxy group, 2-naphthylmethyloxy group, 1-naphthylethyloxy group, 2-naphthylethyloxy group, 1-naphthylpropyloxy group and 2-naphthylpropyloxy group; more preferably benzyloxy group, phenethyloxy group, 3-phenylpropyloxy group, 4-phenylbutyloxy group, 5-phenylpentyloxy group, 6-phenylhexyloxy group, 1-naphthylmethyloxy group and 2-naphthylmethyloxy group; further preferably benzyloxy group, phenethyloxy group, 3-phenylpropyloxy group and 4-phenylbutyloxy group; and most preferably benzyloxy group and phenethyloxy group.

In the expression "an aralkylthio group having seven to eighteen carbon atoms, which may have one or more substituents", the aralkylthio group represents a group having a sulfur atom bound to the end of the aralkyl group having seven to eighteen carbon atoms. Specific examples thereof include benzylthio group, phenethylthio group, 3-phenylpropylthio group, 4-phenylbutylthio group, 5-phenylpentylthio group, 6-phenylhexylthio group, 1-naphthylmethylthio group, 2-naphthylmethylthio group, 1-naphthylethylthio group, 2-naphthylethylthio group, 1-naphthylpropylthio group and 2-naphthylpropylthio group; preferably benzylthio group, phenethylthio group, 3-phenylpropylthio group, 4-phenylbutylthio group, 5-phenylpentylthio group, 6-phenylhexylthio group, 1-naphthylmethylthio group, 2-naphthylmethylthio group, 1-naphthylethylthio group, 2-naphthylethylthio group, 1-naphthylpropylthio group and 2-naphthylpropylthio group; more preferably benzylthio group, phenethylthio group, 3-phenylpropylthio group, 4-phenylbutylthio group, 5-phenylpentylthio group, 6-phenylhexylthio group, 1-naphthylmethylthio group and 2-naphthylmethylthio group; further preferably benzylthio group, phenethylthio group, 3-phenylpropylthio group, 4-phenylbutylthio group; and most preferably benzylthio group and phenethylthio group.

In the expression "a cycloalkylalkyloxy group having four to thirteen carbon atoms, which may have one or more substituents", the cycloalkylalkyloxy group represents a group having the linear or branched alkoxy group having one to six carbon atoms wherein a substitutable position is substituted with the cyclic alkyl group having three to seven carbon atoms. Specific examples thereof include cyclopropylmethoxy group, cyclobutylmethoxy group, cyclopentylmethoxy group, cyclohexylmethoxy group, cycloheptylmethoxy group, 1-cyclopropylethoxy group, 2-cyclopropylethoxy group, 1-cyclopropyl-n-propoxy group, 2-cyclopropyl-n-propoxy group, 3-cyclopropyl-n-propoxy group, cyclopropyl-i-propoxy group, cyclopropyl-n-butoxy group, cyclopropyl-i-butoxy group, cyclopropyl-sec-butoxy group, cyclopropyl-t-butoxy group, cyclopropyl-n-pentyloxy group, cyclopropyl-i-pentyloxy group, cyclopropyl-sec-pentyloxy group, cyclopropyl-t-pentyloxy group and cyclopropylneopentyloxy group; more preferably cyclopropylmethoxy group, cyclopropylethoxy group, cyclopropyl-n-propoxy group, cyclopropyl-i-propoxy group, cyclopropyl-n-butoxy group, cyclopropyl-i-butoxy group, cyclopropyl-sec-butoxy group, cyclopropyl-t-butoxy group, cyclopropyl-n-pentyloxy group, cyclopropyl-i-pentyloxy group, cyclopropyl-sec-pentyloxy group, cyclopropyl-t-pentyloxy group and cyclopropylneopentyloxy group; and most preferably cyclopropylmethoxy group, cyclopropylethoxy group, cyclopropyl-n-propoxy group and cyclopropyl-i-propoxy group.

Specific examples of the term "a hetero atom" as used herein include, for example, oxygen atom, sulfur atom, nitrogen atom, phosphorus, arsenic, antimony, silicon, germanium, tin, lead, boron and mercury; preferably oxygen atom, sulfur atom, nitrogen atom and phosphorus, of which oxygen atom, sulfur atom and nitrogen atom are more preferred. Hereinafter, when expressed as "which may have a hetero atom", the hetero atom is as defined above.

When $Y^1$, $Y^2$ and the ring Z represent "a 5 to 14-membered aromatic ring which may have one or more hetero atoms", specific examples of the aromatic ring not having hetero atoms include phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-naphthyl group, 1-naphthylmethyl group, 2-naphthylmethyl group, 1-naphthylethyl group, 2-naphthylethyl group, as-indacenyl group, s-indacenyl group and acenaphthylenyl group; preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-naphthyl group, 1-naphthylmethyl group, 2-naphthylmethyl group, 1-naphthylethyl group, 2-naphthylethyl group, as-indacenyl group, s-indacenyl group and acenaphthylenyl group; more preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-naphthyl group, 1-naphthylmethyl group and 2-naphthylmethyl group; further preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group and cinnamylidene group; further more preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group and phenethyl group; and most preferably phenyl group, o-tolyl group, m-tolyl group, p-tolyl group, 2,3-xylyl group, 2,4-xylyl group, 2,5-xylyl group and benzyl group. Specific examples of the aromatic ring having a hetero atom include furyl group, thienyl group, pyrrolyl group, pyridyl group, quinolyl group, isoquinolyl group, cinnolyl group, quinazolyl group, quinoxalyl group, indolyl group, indazolyl group, oxazolyl group, isoxazolyl group, thiazolyl group, isothiazolyl group, imidazolyl group, pyrazolyl group, furazanyl group, pyridazinyl group, pyrimidyl group and pyrazyl group.

In the expression "a 5 to 14-membered aromatic ring which may be partially saturated", the aromatic group means a 9 to 14-membered aromatic group wherein two or three rings are condensed, with one or two rings being non-aromatic. Specific examples thereof include dihydrobenzofuranyl group, phthalanyl group, chromanyl group, chromenyl group, chromanonyl group, chromenonyl group, isochromanyl group, tetrahydronaphthalenyl group, dihydrobenzothiophenyl group, indolinyl group, isatinyl group, indanyl group, indanonyl group, tetranonyl group, coumarinyl group, naphthoquinonyl group and anthraquinonyl group; preferably dihydrobenzofuranyl group, phthalanyl group, chromanyl group, chromenyl group, chromanonyl group, chromenonyl group, tetrahydronaphthalenyl group and indanyl group; and further preferably dihydrobenzofuranyl group, chromanyl group and chromenyl group.

In the expression "a 5 to 14-membered heterocyclic group" in Group A, the heterocyclic group represents a cyclic functional group having a hetero atom which is non-aromatic and which may be saturated or unsaturated. Specific examples thereof include piperidine, piperazine, pyrrolidine, imidazolidine, morpholine, oxirane and dioxane, of which piperidine and piperazine are preferred.

When L represents a single bond, the compounds of the present invention are exemplified by compounds having the group X bound via a single bond to the group Y, represented by the following formula:

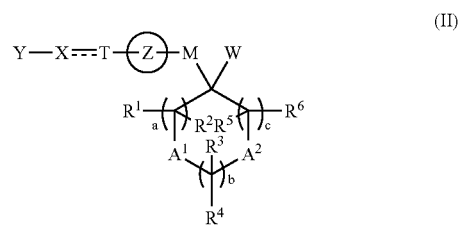

(wherein each symbol represents as defined above), a salt thereof, an ester thereof or a hydrate of them.

When M represents a single bond, the compounds of the present invention are exemplified by compounds represented by the following formula:

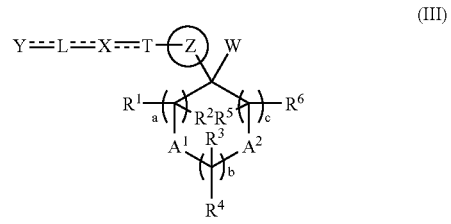

(wherein each symbol represents as defined above), a salt thereof, an ester thereof or a hydrate of them.

When T represents a single bond, the compounds of the present invention are exemplified by compounds represented by the following formula:

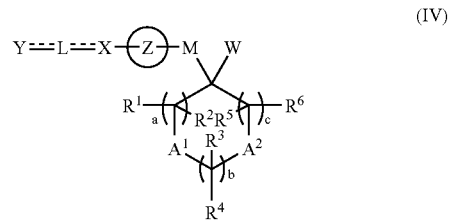

(wherein each symbol represents as defined above), a salt thereof, an ester thereof or a hydrate of them. When X represents a single bond, the compounds of the present invention are exemplified by compounds represented by the following formula:

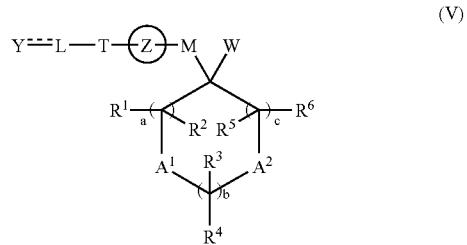

(wherein each symbol represents as defined above), a salt thereof, an ester thereof or a hydrate of them.

When L, T and M each represents an alkylene group having one to six carbon atoms, which may have one or more substituents, the alkylene group represents a divalent group derived from the alkyl group having one to six carbon atoms by removing one hydrogen atom therefrom. Specific examples thereof include methylene group, ethylene group, 1-methylethylene group, 2-methylethylene group, 1-ethylethylene group, 2-ethylethylene group, 1,1-dimethylethylene group, 1,2-dimethylethylene group, propylene group, 1-methylpropylene group, 2-methylpropylene group, 3-methylpropylene group, 1-ethylpropylene group, 2-ethylpropylene group, 3-ethylpropylene group, 1,1-dimethylpropylene group, 1,2-dimethylpropylene group, 1,3-dimethylpropylene group, 1,1-diethylpropylene group, 1,2-diethylpropylene group, 1,3-diethylpropylene group, trimethylene group, 1-methyltrimethylene group, 1-ethyltrimethylene group, 2-methyltrimethylene group, 1,1-dimethyltrimethylene group, tetramethylene group, pentamethylene group and hexamethylene group; preferably methylene group, ethylene group, 2-methylethylene group, 2-ethylethylene group, propylene group, 1,1-dimethylethylene group, 1,2-dimethylethylene group, trimethylene group, 1-methyltrimethylene group, 1-ethyltrimethylene group, 2-methyltrimethylene group, 1,1-dimethyltrimethylene group, tetramethylene group, pentamethylene group and hexamethylene group; more preferably methylene group, ethylene group, 2-methylethylene group, propylene group, 2-ethylethylene group, 1,1-dimethylethylene group, 1,2-dimethylethylene group, trimethylene group, 1-methyltrimethylene group, 1-ethyltrimethylene group, 2-methyltrimethylene group and 1,1-dimethyltrimethylene group; further preferably methylene group, ethylene group, 2-methylethylene group, propylene group, 2-ethylethylene group, 1,1-dimethylethylene group, 1,2-dimethylethylene group and trimethylene group; and most preferably methylene group, ethylene group, methylethylene group and propylene group. Similarly, when T represents an alkylene group having one to three carbon atoms, which may have one or more substituents, the alkylene group represents a divalent group derived from the alkyl group having one to three carbon atoms by removing one hydrogen atom therefrom. Specific examples thereof include the alkylene groups having one to three carbon atoms; preferably methylene group, ethylene group and propylene group; further preferably methylene group and ethylene group; and most preferably methylene group.

When L, T and M each represents an alkenylene group having two to six carbon atoms, which may have one or more substituents, the alkenylene group represents a divalent group derived from the alkenyl group having two to six carbon atoms by removing one hydrogen atom therefrom. Specific examples thereof include vinylene group, 1-methylvinylene group, 2-methylvinylene group, 1-ethylvinylene group, 2-ethylvinylene group, propenylene group, 1-methylpropenylene group, 2-methylpropenylene group, 3-methylpropenylene group, 1-ethylpropenylene group, 2-ethylpropenylene group, 3-ethylpropenylene group, butenylene group, pentenylene group and hexenylene group; preferably vinylene group, 1-methylvinylene group, 2-methylvinylene group, 1-ethylvinylene group, 2-ethylvinylene group, propenylene group, 1-methylpropenylene group, 2-methylpropenylene group, 3-methylpropenylene group, 1-ethylpropenylene group, 2-ethylpropenylene group, 3-ethylpropenylene group, butenylene group and pentenylene group; more preferably vinylene group, 1-methylvinylene group, 2-methylvinylene group, 1-ethylvinylene group, 2-ethylvinylene group, propenylene group, 1-methylpropenylene group, 2-methylpropenylene group, 3-methylpropenylene group, 1-ethylpropenylene group, 2-ethylpropenylene group and 3-ethylpropenylene group; further preferably vinylene group, 1-methylvinylene group, 2-methylvinylene group, 1-ethylvinylene group and 2-ethylvinylene group; and most preferably vinylene group.

When L and T each represents an alkynylene group having two to six carbon atoms, which may have one or more substituents, the alkynylene group represents a divalent group derived from the alkynyl group having two to six carbon atoms by removing one hydrogen atom therefrom. Specific examples thereof include ethynylene group, propynylene group, butynylene group, pentynylene group and hexynylene group; preferably ethynylene group, propynylene group, butynylene group and pentynylene group; more preferably ethynylene group, propynylene group and butynylene group; further preferably butynylene group and propynylene group; and most preferably propynylene group.

Similarly, when M represents an alkynylene group having two to six carbon atoms, which may have one or more substituents, the alkynylene group represents a divalent group derived from the alkynyl group having two to six carbon atoms by removing one hydrogen atom therefrom. Specific examples thereof include the aforementioned alkynylene groups having two to six carbon atoms; preferably ethynylene group and propynylene group; and further preferably ethynylene group.

In the expression "an aliphatic acyl group having two to seven carbon atoms, which may have one or more substituents", the aliphatic acyl group represents the alkyl group having one to six carbon atoms, the alkenyl group having two to six carbon atoms or the alkynyl group having two to six carbon atoms, and each of which has a carbonyl group bound to its end. Specific examples thereof include acetyl group, propionyl group, butyryl group, isobutyryl group, valeryl group, isovaleryl group, pivaloyl group, hexanoyl group, octanoyl group, acryloyl group, methacryloyl group and crotonyl group; preferably acetyl group, propionyl group, butyryl group, isobutyryl group, valeryl group, isovaleryl group, pivaloyl group, hexanoyl group, octanoyl group, acryloyl group, methacryloyl group and crotonyl group; more preferably acetyl group, propionyl group, butyryl group, isobutyryl group, valeryl group, isovaleryl group, pivaloyl group, hexanoyl group and octanoyl group; further preferably acetyl group, propionyl group, butyryl group and isobutyryl group; and most preferably acetyl group and propionyl group.

In the expression "an aromatic acyl group having seven to nineteen carbon atoms, which may have one or more substituents", the aromatic acyl group represents the aryl group having five to twelve carbon atoms, wherein a carbonyl group or a group being derived from the aliphatic acyl group having two to seven carbon atoms by removing one hydrogen atom therefrom is bound to its end. Specific examples thereof include benzoyl group, o-toluoyl group, m-toluoyl group, p-toluoyl group, cinnamoyl group, 1-naphthoyl group and 2-naphthoyl group; preferably benzoyl group, o-toluoyl group, m-toluoyl group, p-toluoyl group, cinnamoyl group, 1-naphthoyl group and 2-naphthoyl group; more preferably benzoyl group, o-toluoyl group, m-toluoyl group, p-toluoyl group, cinnamoyl group; further preferably benzoyl group and cinnamoyl group; and most preferably benzoyl group.

In the expression "an aliphatic alkoxycarbonyl group having two to seven carbon atoms, which may have one or more substituents", the aliphatic alkoxycarbonyl group represents the alkoxy group having one to six carbon atoms, the alkenyloxy group having two to six carbon atoms or the alkynyloxy group having two to six carbon atoms, wherein a carbonyl group is bound to its end. Specific examples thereof include methoxycarbonyl group, ethoxycarbonyl group, propyloxycarbonyl group, butoxycarbonyl group, isobutoxycarbonyl group, t-butoxycarbonyl group, pentyloxycarbonyl group, hexyloxycarbonyl group, octyloxycarbonyl group, allyloxycarbonyl group, methallyloxycarbonyl group and crotyloxycarbonyl group; preferably methoxycarbonyl group, ethoxycarbonyl group, propyloxycarbonyl group, butoxycarbonyl group, isobutoxycarbonyl group, t-butoxycarbonyl group, pentyloxycarbonyl group, hexyloxycarbonyl group, octyloxycarbonyl group and allyloxycarbonyl group; more preferably methoxycarbonyl group, ethoxycarbonyl group, propyloxycarbonyl group, butoxycarbonyl group, isobutoxycarbonyl group, t-butoxycarbonyl group, pentyloxycarbonyl group, hexyloxycarbonyl group and octyloxycarbonyl group; further preferably methoxycarbonyl group, ethoxycarbonyl group, propyloxycarbonyl group, butoxycarbonyl group, isobutoxycarbonyl group; and most preferably methoxycarbonyl group, ethoxycarbonyl group and propyloxycarbonyl group.

In the expression "an aromatic alkoxycarbonyl group having seven to nineteen carbon atoms, which may have one or more substituents", the aromatic alkoxycarbonyl group represents the aryl group having five to twelve carbon atoms, wherein a carbonyl group or a group being derived from the aliphatic acyl group having two to seven carbon atoms by removing one hydrogen atom therefrom is bound to its end. Specific examples thereof include phenoxycarbonyl group, o-tolyloxycarbonyl group, m-tolyloxycarbonyl group, p-tolyloxycarbonyl group, 1-naphthyloxycarbonyl group and 2-naphthyloxycarbonyl group; preferably phenoxycarbonyl group, o-tolyloxycarbonyl group, m-tolyloxycarbonyl group, p-tolyloxycarbonyl group, 1-naphthyloxycarbonyl group; more preferably phenoxycarbonyl group, o-tolyloxycarbonyl group and m-tolyloxycarbonyl group; further preferably phenoxycarbonyl group and o-tolyloxycarbonyl group; and most preferably phenoxycarbonyl group.

In the expression "aliphatic acylamino group having two to seven carbon atoms, which may have one or more substituents", the acylamino group represents a group wherein one hydrogen atom of an amino group is substituted with the above-mentioned aliphatic acyl group having two to seven carbon atoms. Specific examples thereof include acetylamino group, propionylamino group, butyrylamino group, isobutyrylamino group, valerylamino group, isovalerylamino group, pivaloylamino group, hexanoylamino group, octanoylamino group, acryloylamino group, methacryloylamino group and crotonylamino group; preferably acetylamino group, propionylamino group, butyrylamino group, isobutyrylamino group, valerylamino group, isovalerylamino group, pivaloylamino group, hexanoylamino group, octanoylamino group, acryloylamino group, methacryloylamino group and crotonylamino group; more preferably acetylamino group, propionylamino group, butyrylamino group, isobutyrylamino group, valerylamino group, isovalerylamino group, pivaloylamino group, hexanoylamino group and octanoylamino group; further preferably acetylamino group, propionylamino group, butyrylamino group and isobutyrylamino group; and most preferably acetylamino group and propionylamino group. The partial structure represented by the formula:

$$\overline{\overline{\phantom{===}}}$$

represents a single bond or a double bond. Accordingly, the compounds of the present invention represented by the following formula (I):

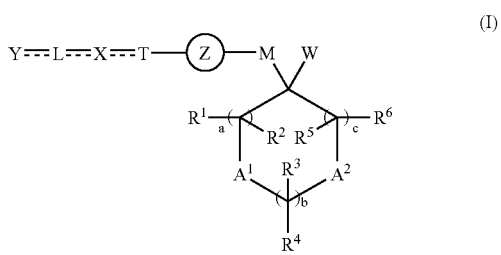

(wherein each symbol has the same meaning as defined above) include compounds represented by the following formulae:

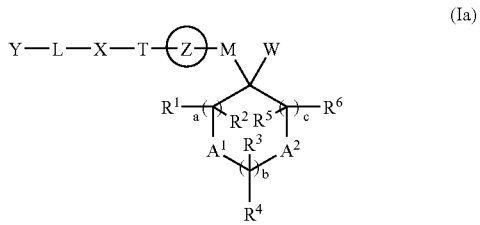

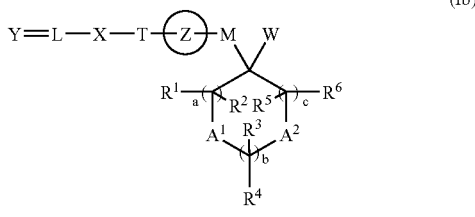

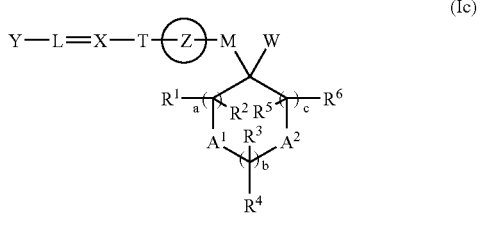

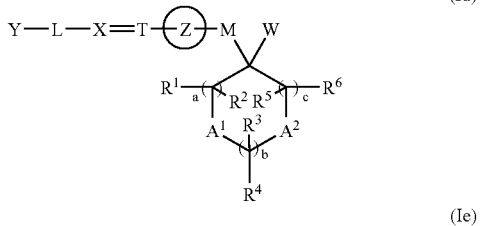

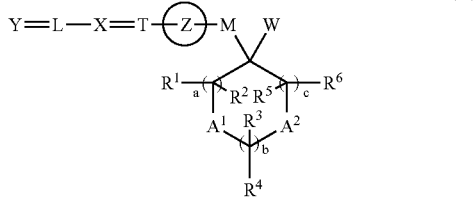

(If)

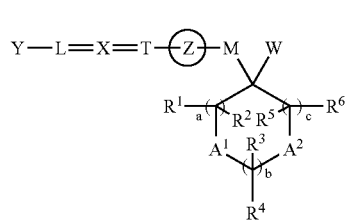

(Ig)

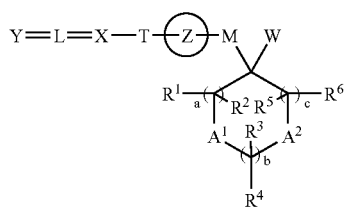

(Ih)

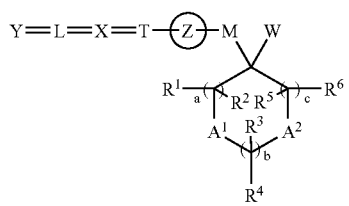

(wherein each symbol has the same meaning as defined above), a salt thereof, an ester thereof or a hydrate of them.

The group represented by the formula:

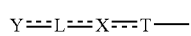

(wherein each symbol has the same meaning as defined above) and the group represented by the formula:

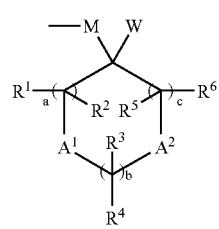

(wherein each symbol has the same meaning as defined above) are combined with each other via two to eight atoms on the ring Z. In the case where such wording is used, the phrase "combined with each other via two to eight atoms on the ring Z" represents the following cases. When the ring Z is a benzene and two atoms are involved in binding, the formula is as follows:

(wherein each symbol has the same meaning as defined above). When the ring Z is an anthracene and eight atoms are involved in binding, the formula is as follows:

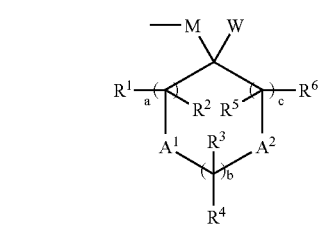

(wherein each symbol has the same meaning as defined above). Accordingly, one represented by the ring Z, the group represented by the formula:

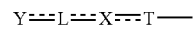

(wherein each symbol has the same meaning as defined above), and the group represented by the formula:

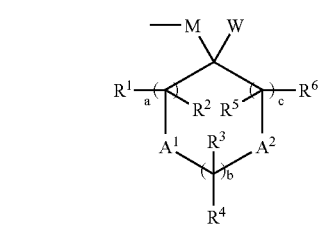

(wherein each symbol has the same meaning as defined above) may be combined at any positions. Preferred compounds are represented by the formulae

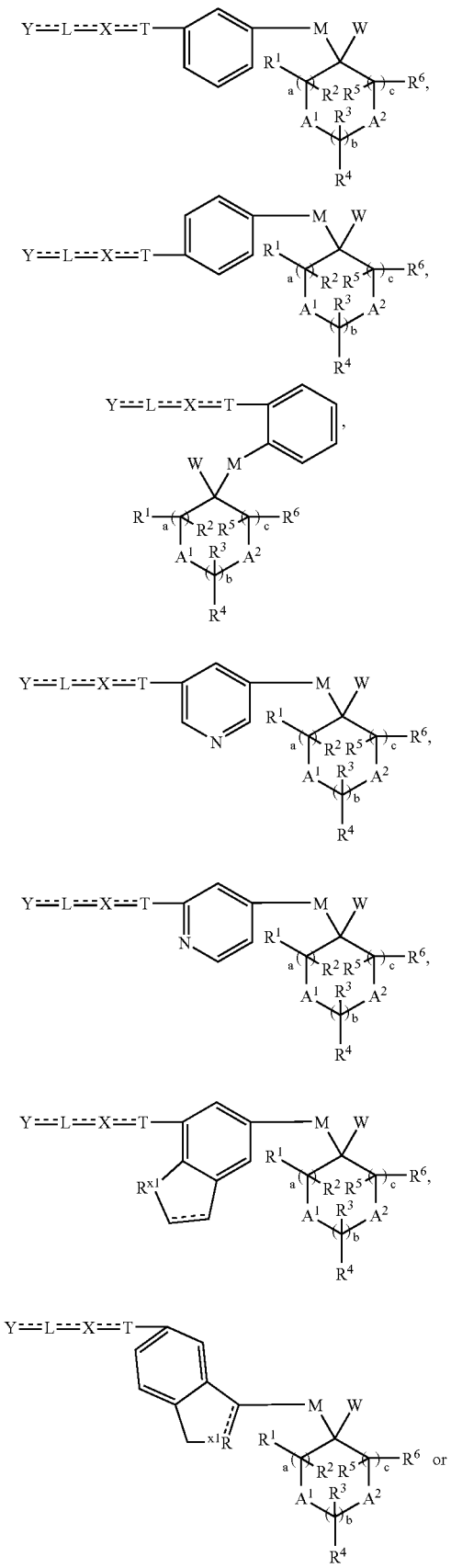

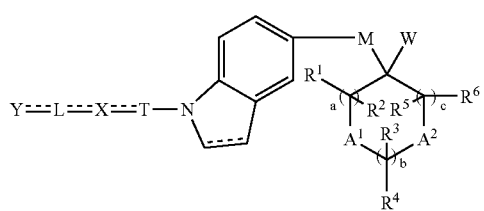

(wherein each symbol has the same meaning as defined above, and the aromatic ring may further have one to four substituents), and more preferably represented by the formulae:

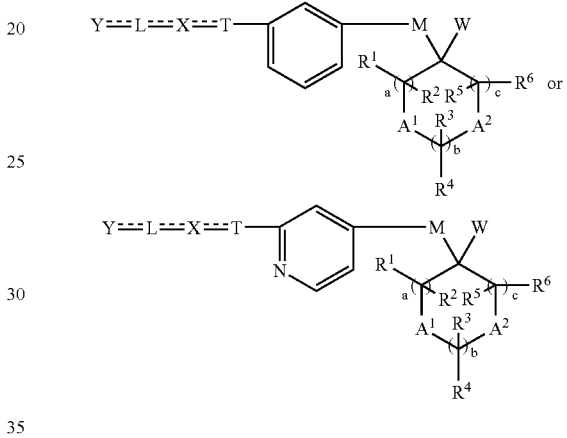

(wherein each symbol has the same meaning as defined above, and the aromatic ring may further have one to four substituents).

The definition of an arbitrary variable substituent in the compound of the present invention is independent from the definition of the same symbol in another position of the compound. Namely, when two or more $R^1$s are present in one molecule, each $R^1$ has a definition independent from each other.

"Salts" as used in the present invention are not specifically limited with respect to the kind and are preferably pharmacologically acceptable salts. Examples thereof include addition salts of inorganic acids, such as hydrochlorides, hydrobromides, sulfates, nitrates or phosphates; addition salts of organic aliphatic carboxylic acids, such as acetates, succinates, fumarates, maleates, tartrates, citrates, lactates or stearates; addition salts of organic aromatic carboxylic acids, such as benzoates; addition salts of organic aliphatic sulfonic acids, such as methanesulfonates; addition salts of organic aromatic sulfonic acids, such as p-toluenesulfonates; addition salts of amines, such as diethylamine salts, diethanolamine salts, meglumine salts or N,N'-dibenzylethylenediamine salts; addition salts of alkali metals, such as sodium salts and potassium salts; addition salts of alkaline earth metals, such as magnesium salts and calcium salts; addition salts of amino acids, such arginine salts, lysine salts, ornithine salts, aspartates and glutamates; as well as aluminium salts and ammonium salts.

The term "ester" used in the present invention means and includes esters of a carboxyl group of W in the formula (I). Such esters are not specifically limited, as long as they are generally used in organic syntheses and include physiologically acceptable ester groups that are hydrolyzable under physiological conditions. Specific examples thereof include alkyl groups having one to six carbon atoms, aryl groups having six to twelve carbon atoms, aralkyl groups having seven to twenty carbon atoms such as a benzyl group, heteroarylalkyl groups having seven to twenty carbon atoms, 4-methoxybenzyl group, alkanoyloxyalkyl groups such as acetoxymethyl group, propionyloxymethyl group or pivaloxymethyl group, alkoxycarbonyloxyalkyl groups such as methoxycarbonyloxymethyl group, ethoxycarbonyloxymethyl group or 2-methoxycarbonyloxyethyl group, and (5-methyl-2-oxo-1,3-dioxo-4-yl)-methyl group.

In the present invention, when the compounds having the formula (I), pharmacologically acceptable salts thereof or pharmacologically acceptable esters thereof form solvates, all such solvates are included in the present invention.

The compounds represented by the formula (I):

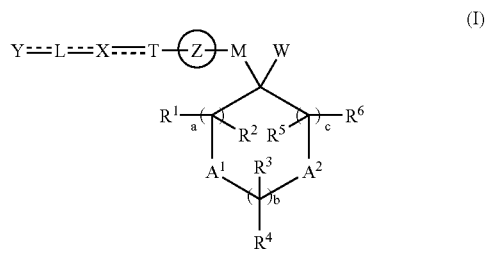

(wherein each symbol represents as defined above) can be synthesized according to a conventional procedure and can be typically produced, for example, by the following process.

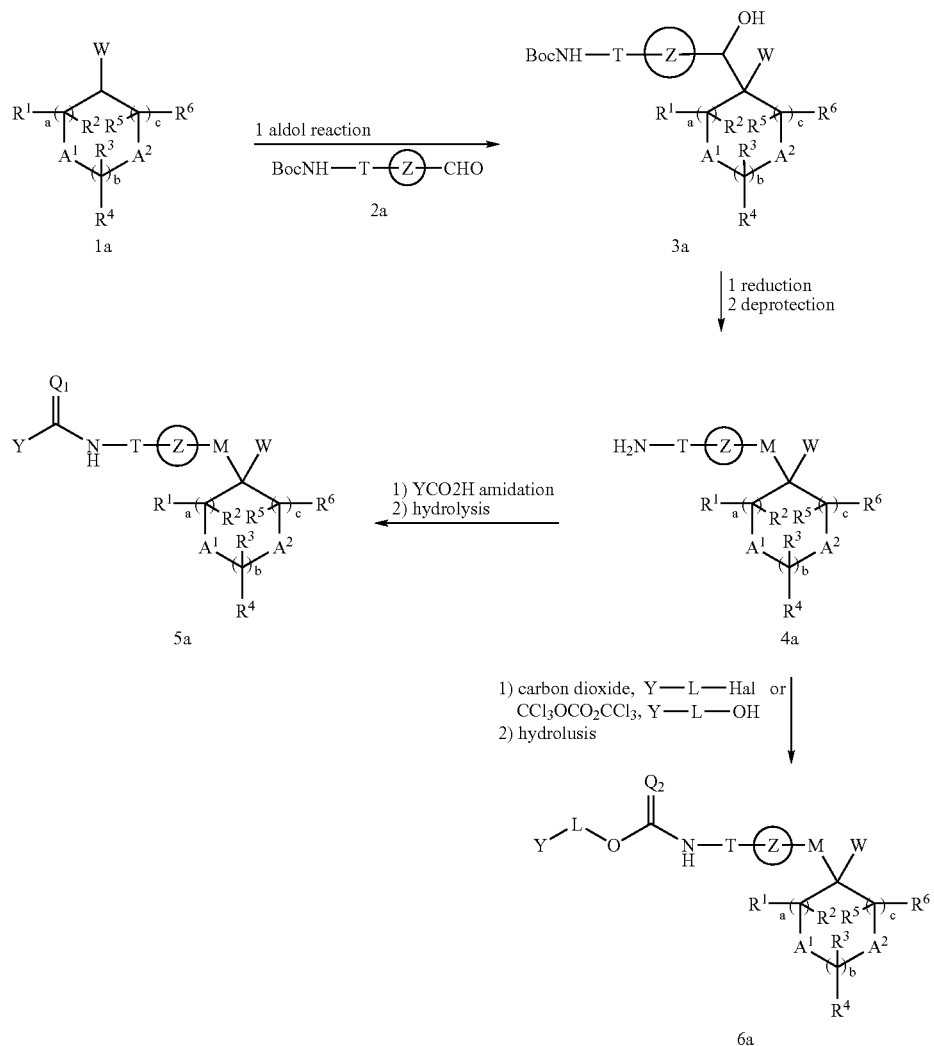

Wherein each symbol represents a group as defined above; and "Hal" represents a halogen atom.

The compound represented by the formula (3a) can be obtained by an aldol reaction between the compound represented by the formula (1a) and the compound represented by the formula (2a). The reaction conditions are not specifically limited. Preferably, the compound represented by the formula (1a) and the compound represented by the formula (2a) are reacted in an organic solvent such as tetrahydrofuran, diethyl ether, hexane or dimethoxyethane in the presence of a base such as lithium diisopropylamide, lithium bis(trimethylsilylamide), sodium bis(trimethylsilylamide) or potassium bis(trimethylsilylamide) at a temperature from −100° C. to 0° C. When the formula (1a) represents a heteroaryl ester or an aryl ester, the compound represented by the formula (1a) and the compound represented by the formula (2a) are preferably allowed to react in ammonia in the presence of a metal such as lithium, sodium, potassium or calcium at a temperature from −100° C. to 0° C. The compound represented by the formula (4a) can be obtained by reducing the compound represented by the formula (3a), followed by deprotection. Of the following reduction conditions when trifluoroacetic acid is used, the compound represented by the formula (4a) may be directly obtained as a result of the reduction reaction. The reaction condition for the reduction is not specifically limited. Preferably, the compound represented by the formula (3a) is reacted in an acidic solvent such as trifluoroacetic acid in the presence of a trialkylsilane such as triethylsilane at a temperature from 0° C. to 50° C.; the compound represented by the formula (3a) is reacted in an acidic solvent such as acetic acid or hydrochloric acid in the presence of a metal such as zinc or tin at a temperature from 20° C. to 120° C.; or the compound represented by the formula (3a) is reacted with carbon disulfide and methyl iodide in an organic solvent such as tetrahydrofuran, N,N-dimethylformamide or dichloromethane in the presence of a base such as sodium hydride at a temperature from 0° C. to 50° C., and the obtained intermediate is reacted in an organic solvent such as toluene, benzene or carbon tetrachloride in the presence of a reducing agent such as tributyltin hydride at a temperature from 20° C. to 150° C. The reaction conditions for the deprotection are not specifically limited, but the deprotection is preferably performed in an organic solvent such as dichloromethane, chloroform, tetrahydrofuran or dioxane treated with an acid such as hydrogen chloride or trifluoroacetic acid at a temperature from 0° C. to 150° C. The compound represented by the formula (5a) can be obtained by amidating the compound represented by the formula (4a), and hydrolyzing the internal ester. The reaction conditions for the amidation are not specifically limited, and the reaction is performed, for example, by treating with a suitable carboxylic acid in a solvent such as N,N-dimethylformamide, N-methylpyrrolidone, dioxane, tetrahydrofuran, toluene, dichloromethane or chloroform in the presence of a condensing agent such as diphenylphosphorylazide, diethylphosphorylcyamide or dicyclohexylcarbodiimide, and a base such as triethylamine, N,N-diisopropylethylamine, tributylamine, sodium hydrogencarbonate or potassium hydrogencarbonate at a temperature from 0° C. to 150° C. The reaction conditions for the hydrolysis are not specifically limited, and the hydrolysis is performed, for example, by reaction with an aqueous solution such as lithium hydroxide, sodium hydroxide or potassium hydroxide in a solvent such as methanol, ethanol, propanol, dimethyl sulfoxide, N,N-dimethylformamide, N-methylpyrrolidone, dioxane or tetrahydrofuran at a temperature from 0° C. to 150° C. The compound represented by the formula (6a) can be obtained by reacting the compound represented by the formula (4a) with carbon dioxide and Y—L-Hal or with triphosgene and Y—L—OH to form a carbamate, and hydrolyzing the internal ester. The reaction conditions for synthesizing the carbamate are not specifically limited, and the reaction may be performed according to the literature (J. Org. Chem. 2000, 66, 1035.). The carbamate can also be obtained by reacting the compound represented by the formula (4a) with triphosgene in an organic solvent such as dichloromethane or tetrahydrofuran and the treating with Y—L—OH. The reaction conditions for the hydrolysis follow the production example for formula (5a) in Production Example A.

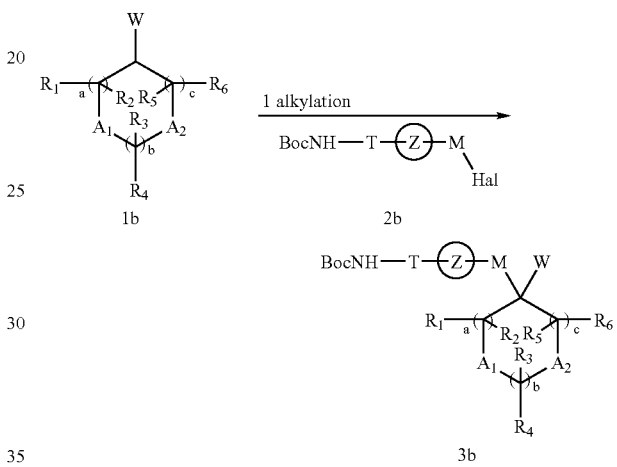

General Synthesis Process B

Wherein each symbol represents a group as defined above; and "Hal" represents a halogen atom.

The compound represented by the formula (3b) can be obtained by an alkylation reaction between the compound represented by the formula (1b) and the compound represented by the formula (2b). The reaction conditions are not specifically limited. Preferably, the compound represented by the formula (1b) and the compound represented by the formula (2b) are reacted in an organic solvent such as tetrahydrofuran, diethyl ether, hexane or dimethoxyethane in the presence of a base such as lithium diisopropylamide, lithium bis(trimethylsilylamide), sodium bis(trimethylsilylamide) or potassium bis(trimethylsilylamide) at a temperature from −100° C. to 0° C.; or the compound represented by the formula (1b) and the compound represented by the formula (2b) are reacted in an organic solvent such as N,N-dimethylformamide or tetrahydrofuran in the presence of sodium hydride at a temperature from 0° C. to 50° C. When the compound represented by the formula (1b) represents a heteroaryl ester or an aryl ester, the compound represented by the formula (1b) and the compound represented by the formula (2b) are preferably reacted in ammonia in the presence of a metal such as lithium, sodium, potassium or calcium at a temperature from −100° C. to 0° C.

General Synthesis Process C

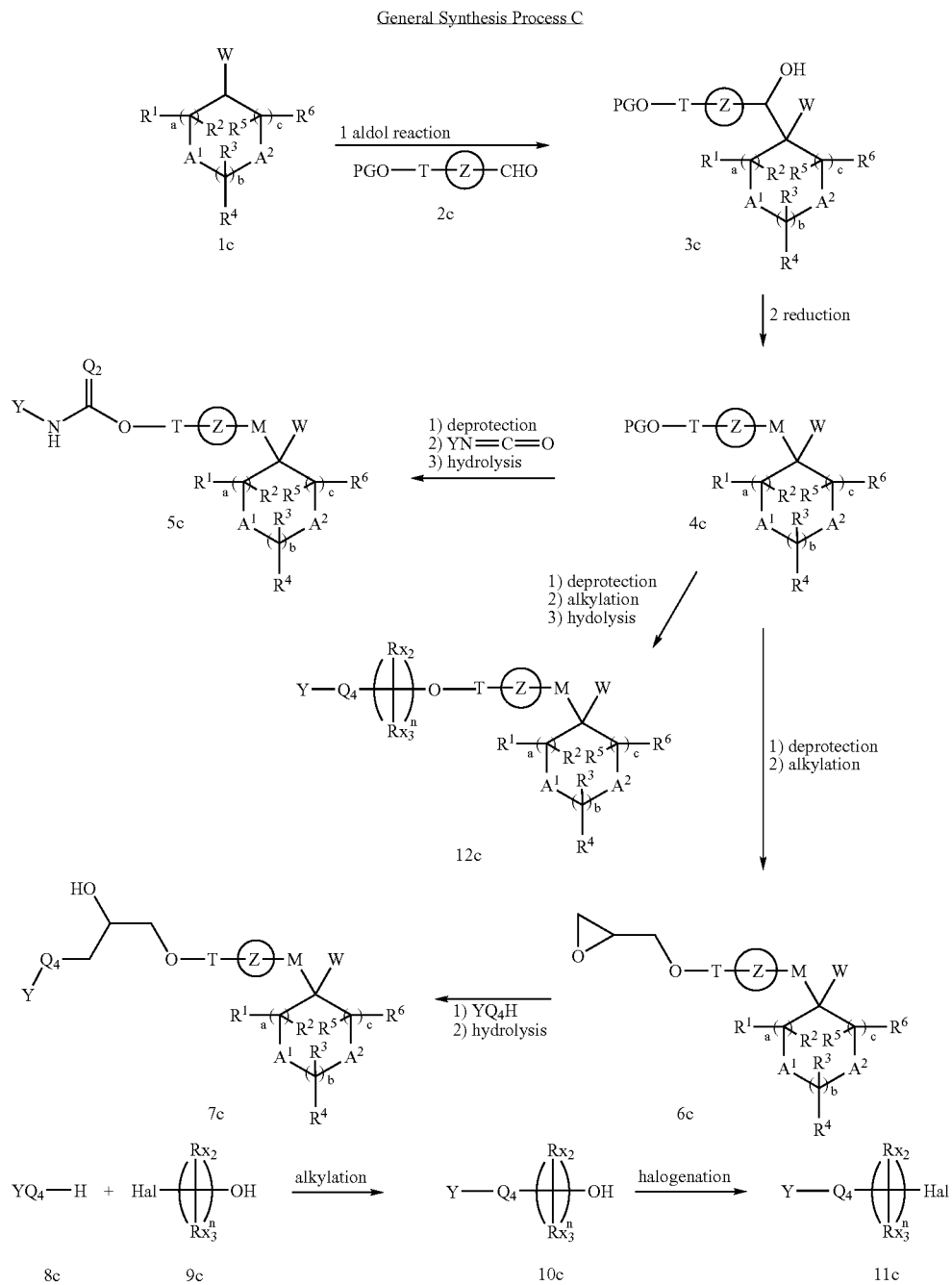

wherein each symbol represents a group as defined above; "Hal" represents a halogen atom; and "PG" represents a protecting group for an alcohol functional group.

The compound represented by the formula (3c) can be obtained by an aldol reaction between the compound represented by the formula (1c) and the compound represented by the formula (2c). The aldol reaction conditions follow those of the production example for formula (3a) in Production Example A. The compound represented by the formula (4c) can be obtained by reducing the compound represented by the formula (3c). The reaction conditions for the reduction follow the production example for formula (4a) in Production Example A. The compound represented by the formula (5c) can be obtained by deprotecting the compound represented by the formula (4c), and subjecting the reduced compound to carbamoylation and hydrolysis of the internal ester. The reaction conditions for the deprotection are not specifically limited. Preferably, the compound represented by the formula (4c) is treated in an alcohol solvent in the presence of an acid such as an acidic resin, hydrochloric acid or sulfuric acid at a temperature from 0° C. to 100° C.; or the compound represented by the formula (4c) is treated in an organic solvent such as dichloromethane in the presence of boron tribromide at a temperature from −100° C. to 0° C. and is then treated in an alcohol with an acid such as hydrochloric acid or sulfuric acid at a temperature from 0° C. to 100° C. The reaction conditions for the carbamoylation are not specifically limited, and the reaction may be performed by treating with a suitable isocyanate in an organic solvent such as tetrahydrofuran, diethyl ether or dichloromethane in the presence of a catalyst such as pyridine at a temperature from 0° C. to 100° C. The reaction conditions for the hydrolysis follow those of the production example for formula (5a) in Production Example A. The compound represented by the formula (6c) can be obtained by deprotecting the compound represented by the formula (4c) and alkylating the resulting compound. The reaction conditions for the deprotection follow those of the production example for formula (5c) in Production Example C. The reaction conditions for the alkylation are not specifically limited, and the alkylation may be performed by treating with a suitable alkylating agent such as epichlorohydrin or glycidyl nosylate in an organic solvent such as N,N-dimethylformamide, N-methylpyrrolidone or 1,3-dimethyl-3,4,5,6-tetrahydro-2(1H)-pyrimidinone in the presence of a base such as potassium carbonate. The compound represented by the formula (7c) can be obtained by reacting the compound represented by the formula (6c) with $YQ^4$—H and hydrolyzing the internal ester. The reaction conditions for $YQ^4$—H alkylation are not specifically limited, but the compound represented by the formula (6c) is preferably treated with $YQ^4$—H in an organic solvent such as tetrahydrofuran, N,N-dimethylformamide, N-methylpyrrolidone or 1,3-dimethyl-3,4,5,6-tetrahydro-2(1H)-pyrimidinone in the presence of a base such as potassium carbonate, sodium carbonate, sodium hydride or triethylamine at a temperature from 0° C. to 100° C. The reaction conditions for the hydrolysis follow those of the production example for formula (5a) in Production Example A. The compound represented by the formula (10c) can be obtained by reacting the compound represented by the formula (8c) with the compound represented by the formula (9c). The reaction conditions are not specifically limited. For example, the reaction is performed in a solvent such as methanol, ethanol, propanol, dimethyl sulfoxide, N,N-dimethylformamide, N-methylpyrrolidone, dioxane, tetrahydrofuran or toluene in the presence of a base such as lithium hydroxide, sodium hydroxide, potassium hydroxide, lithium carbonate, sodium carbonate, potassium carbonate, cesium carbonate, lithium hydride, sodium hydride or potassium hydride at a temperature from 0° C. to 150° C. The compound represented by the formula (11c) can be obtained by halogenating the compound represented by the formula (10c). The reaction condition is not specifically limited, and the reaction can be performed, for example, by treating with phosphorus oxychloride, thionyl chloride, phosphorus trichloride or phosphorus tribromide in a solvent such as dioxane, tetrahydrofuran or dimethoxyethane. The reaction temperature is from 0° C. to 150° C. In addition, triphenylphosphine can be used in combination with, for example, carbon tetrachloride, carbon tetrabromide or N-bromosuccinimide. The compound represented by the formula (12c) can be obtained by reacting the compound represented by the formula (4c) with the compound represented by the formula (11c) and hydrolyzing the intramolecular ester. The reaction conditions for the alkylation follow those of the production example for formula (10c) in Production Example C. The reaction conditions for the hydrolysis follow those of the production example for formula (5a) in Production Example A.

General Synthesis Process D

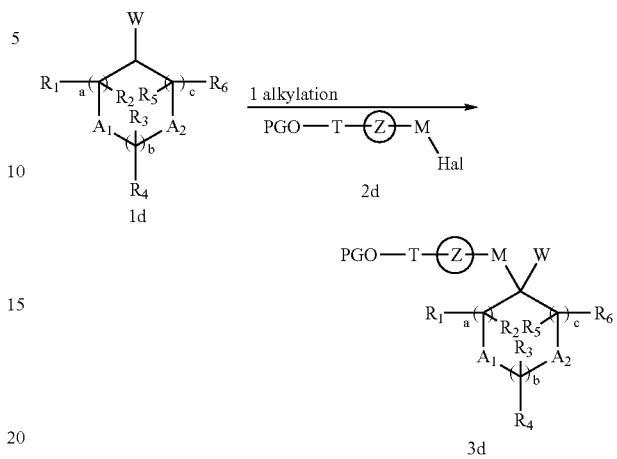

Wherein each symbol represents a group as defined above; "Hal" represents a halogen atom; and "PG" represents a protecting group for alcohol functional group.

The compound represented by the formula (3d) can be obtained by an alkylation reaction between the compound represented by the formula (1d) and the compound represented by the formula (2d). The reaction conditions for the alkylation follow those of the production example for formula (3b) in Production Example B.

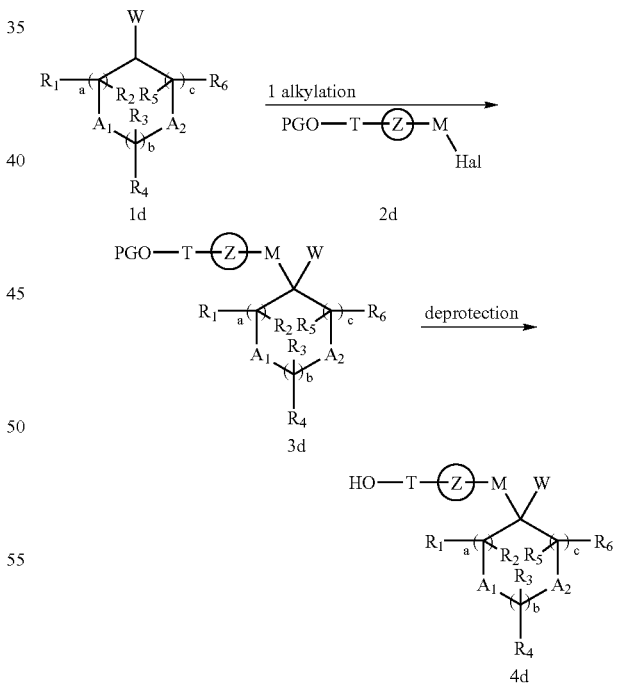

The compound represented by the formula (3d) can be obtained by deprotecting the compound represented by the formula (3c). The reaction conditions for the deprotection preferably follow those of the production example for formula (5c) in Production Example C. However, when Z is a benzene ring; PG is a lower alkyl; and T is a single bond, the reaction is preferably performed by treating with, for example, boron tribromide or boron trichloride in a halogen-containing organic solvent such as dichloroethane at a temperature from −100° C. to 50° C. and heating the resulting compound under reflux in the presence of, for example, sulfuric acid or hydrochloric acid in an alcohol solvent such as methanol or ethanol.

tion can be performed in a solvent such as methanol, ethanol, propanol, dimethyl sulfoxide, N,N-dimethylformamide, N-methylpyrrolidone, dioxane, tetrahydrofuran or toluene in the presence of a metal catalyst such as carbon palladium, platinum oxide or Raney nickel under an atmosphere of hydrogen gas at a temperature from 0° C. to 150° C. The compound represented by the formula (4e) can be obtained

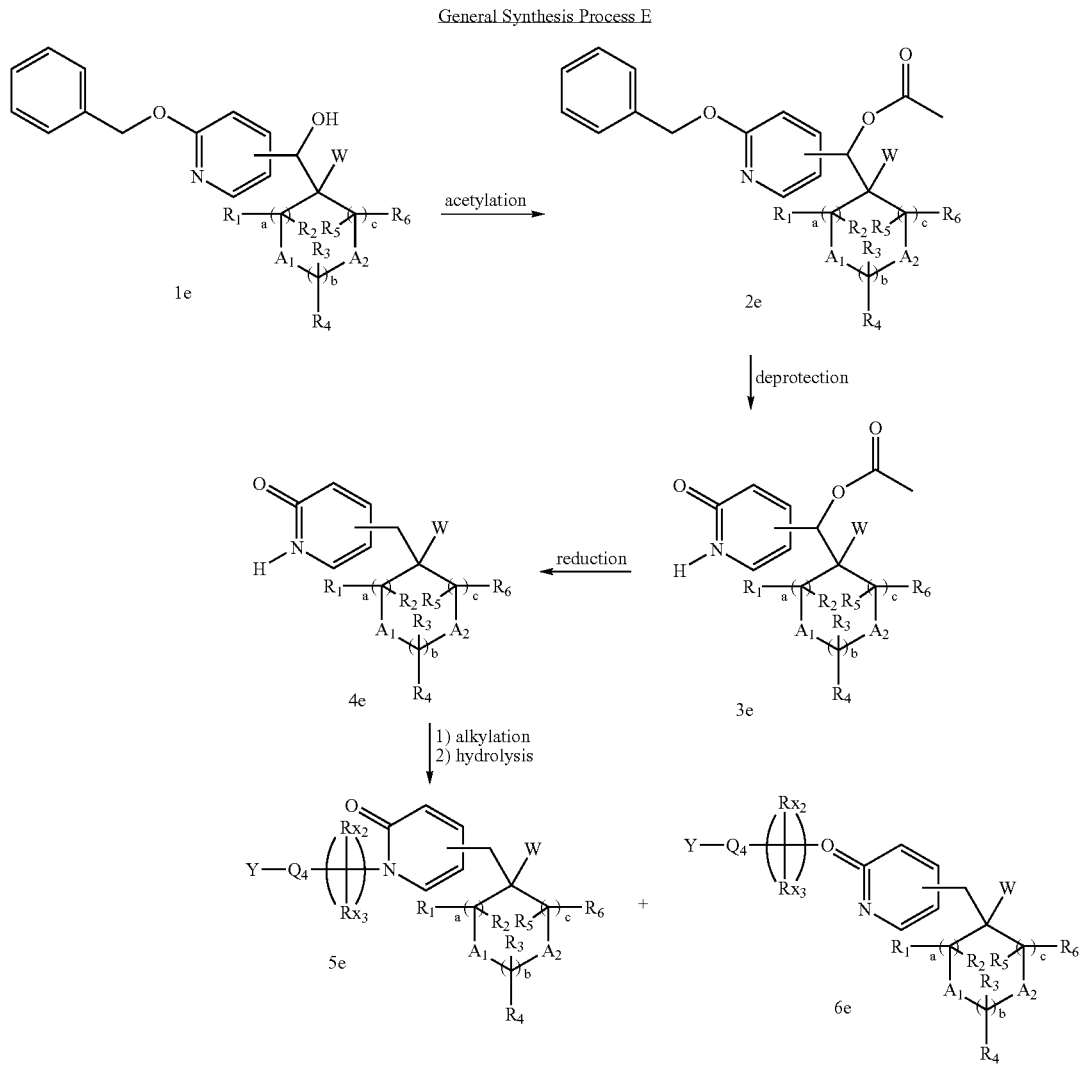

Wherein each symbol represents a group as defined above.

The compound represented by the formula (2e) can be obtained by acetylating the compound represented by the formula (1e). The reaction conditions for the acetylation are not specifically limited. For example, the compound represented by the formula (1e) is treated with an acetylating agent such as acetic anhydride or acetyl chloride in the presence of, or in the absence of, an organic solvent such as dichloromethane, tetrahydrofuran or diethyl ether in the presence of an organic base such as pyridine, triethylamine or 4-dimethylaminopyridine at a temperature from 0° C. to 150° C. The compound represented by the formula (3e) can be obtained by deprotecting the compound represented by the formula (2e). The reaction conditions for the deprotection are not specifically limited. For example, the deprotecby reducing the compound represented by the formula (3e). The reaction conditions for the reduction are not specifically limited. For example, the compound represented by the formula (3e) can be treated in a solvent such as acetic acid or hydrochloric acid in the presence of a metal such as zinc or tin at a temperature from 0° C. to 150° C. The compounds represented by the formula (5e) and the formula (6e) can be obtained by treating the compound represented by the formula (4e) with the compound represented by the formula (11c), and hydrolyzing the internal ester. The reaction conditions for the alkylation follow those of the production example for formula (10c) in Production Example C. The reaction conditions for the hydrolysis follow the production example for formula (5a) in Production Example A.

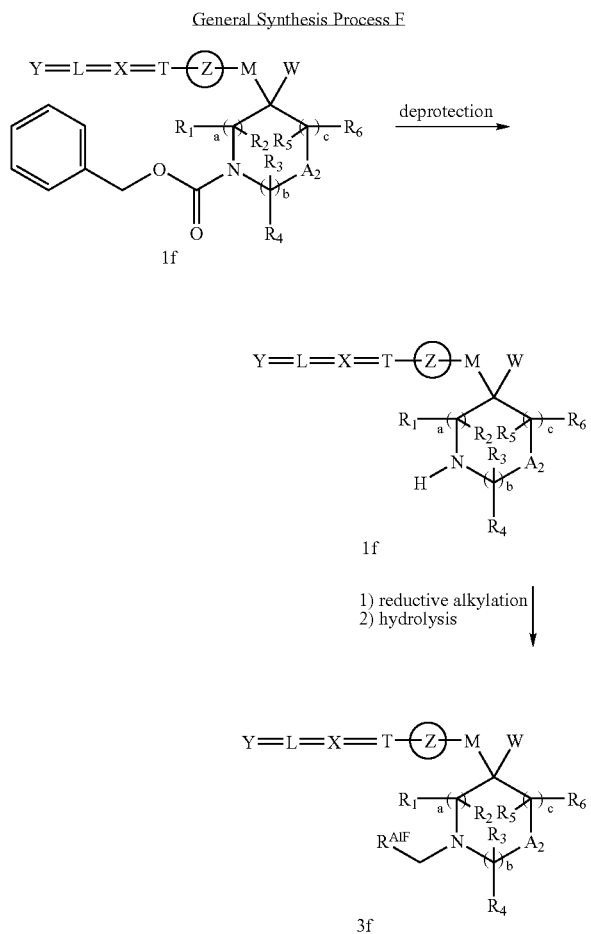

Wherein each symbol represents a group as defined above; $R^{A1F}$ represents an alkyl group having one to six carbon atoms, a hydroxyalkyl group having one to six carbon atoms, an aminoalkyl group having one to six carbon atoms, a halogeno-alkyl group having one to six carbon atoms, an alkoxyalkyl group having two to twelve carbon atoms, a cycloalkyl group having three to seven carbon atoms, an alkenyl group having two to six carbon atoms, an alkynyl group having two to six carbon atoms, an aryl group having six to twelve carbon atoms, an alkylaryl group having seven to eighteen carbon atoms, an aralkyl group having seven to eighteen carbon atoms, an aliphatic acyl group having two to seven carbon atoms, or an aromatic acyl group having seven to nineteen carbon atoms, an aliphatic alkoxycarbonyl group having two to seven carbon atoms or an aromatic alkoxycarbonyl group having seven to nineteen carbon atoms, each of which may have one or more substituents.

The compound represented by the formula (2f) can be obtained by deprotecting the compound represented by the formula (1f). The reaction conditions for the deprotection are not specifically limited. For example, the compound represented by the formula (1f) is preferably treated with a halotrialkylsilane such as iodotrimethylsilane or bromotrimethylsilane in an organic solvent such as dichloromethane or chloroform at a temperature from −100° C. to 50° C. The compound represented by the formula (3f) can be obtained by reductively alkylating the compound represented by the formula (2f), and hydrolyzing the internal ester. The reaction conditions for the reductive alkylation are not specifically limited. Preferably, the compound represented by the formula (2f) is treated with a suitable carbonyl derivative in an organic solvent such as 1,2-dichloroethane or tetrahydrofuran in the presence of sodium triacetoxyborohydride at a temperature from 0° C. to 50° C. The reaction conditions for the hydrolysis follow those of the production example for formula (5a) in Production Example A.

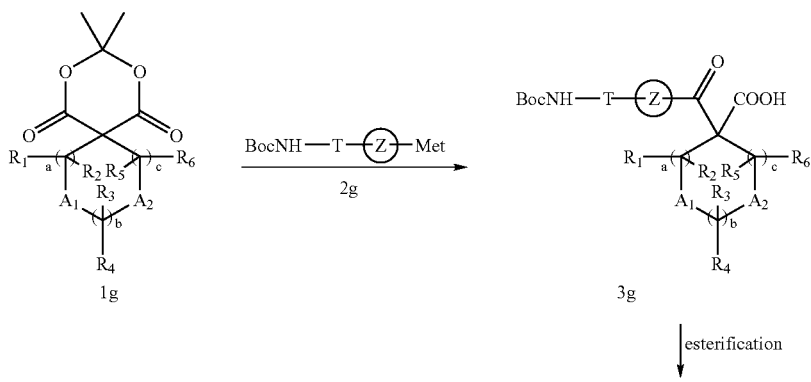

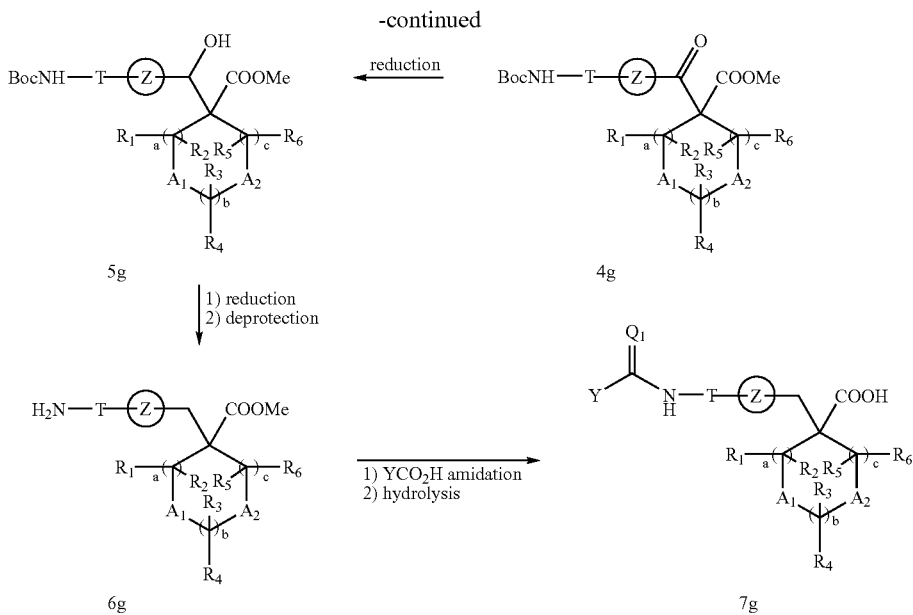

Wherein each symbol represents a group as defined above; and "Met" represents a metal cation.

The compound represented by the formula (3g) can be obtained by an acylation reaction between the compound represented by the formula (1g) and the compound represented by the formula (2g). The reaction conditions for the acylation are not specifically limited, and the reaction can be performed by treating the compound represented by the formula (1g) with the organometallic derivative (2g), which has been obtained by a metal-halogen exchange, in an organic solvent such as tetrahydrofuran, diethyl ether or dimethoxyethane at a temperature from −100° C. to 20° C. The metal for use herein is preferably lithium, magnesium or zinc. The compound represented by the formula (4g) can be obtained by esterifying the compound represented by the formula (3g). The reaction conditions for the esterification are not specifically limited, and the reaction can be performed by treating the compound represented by the formula (3g) with trimethylsilyl diazomethane in an organic solvent mixture containing an alcohol solvent such as methanol or ethanol at a temperature from 0° C. to 50° C. Alternatively, the reaction can be performed by treating the compound represented by the formula (3g) with methyl iodide in an organic solvent such as tetrahydrofuran or N,N-dimethylformamide in the presence of a base such as potassium carbonate, sodium carbonate or sodium hydride at a temperature from 0° C. to 50° C. The compound represented by the formula (5g) can be obtained by reducing the compound represented by the formula (4g). The reaction conditions for the reduction are not specifically limited, and the reaction can be performed by treating the compound represented by the formula (4g) in an organic solvent mixture containing an alcohol solvent such as methanol or ethanol, in the presence of sodium borohydride at a temperature from 0° C. to 80° C. The compound represented by the formula (6g) can be obtained by reducing the compound represented by the formula (5g), and further deprotecting the reduced compound. The reaction conditions for the reduction and deprotection follow those of the production example for formula (4a) in Production Example A. The compound represented by the formula (7g) can be obtained by amidating the compound represented by the formula (6g), and then hydrolyzing the internal ester. The reaction conditions for the amidation and hydrolysis follow those of the production example for formula (5a) in Production Example A.

General Synthesis Process H

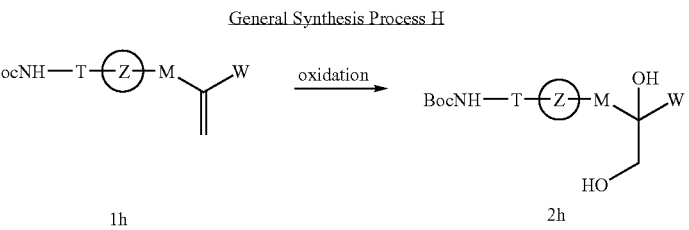

methoxymethylation

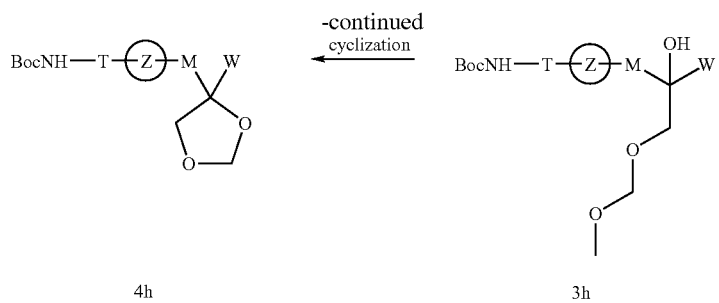

4h   3h

Wherein each symbol represents a group as defined above.

The compound represented by the formula (2h) can be obtained by oxidizing the compound represented by the formula (1h). The reaction conditions for the oxidation are not specifically limited, and the reaction can be performed by treating the compound represented by the formula (1h) in a solvent mixture containing water, acetone and butanol in the presence of osmium (VIII) oxide at a temperature from 0° C. to 80° C. The compound represented by the formula (3h) can be obtained by methoxymethylating the compound represented by the formula (2h). The reaction conditions for the methoxymethylation are not specifically limited, and the reaction can be performed by treating the compound represented by the formula (2h) in a solvent of dimethoxymethane in the presence of a trialkylsilyl trifluoromethanesulfonate such as trimethylsilyl trifluoromethanesulfonate at a temperature from −100° C. to 20° C. The compound represented by the formula (4h) can be obtained by cyclization of the compound represented by the formula (3h). The reaction conditions for the cyclization are not specifically limited, and the reaction can be performed by reacting the compound represented by the formula (3h) in a solvent such as dichloromethane or chloroform, in the presence of a trialkylsilyl trifluoromethanesulfonate such as trimethylsilyl trifluoromethanesulfonate at a temperature from −100° C. to 20° C.

General Synthesis Process I

1i

3i

Wherein each symbol represents a group as defined above.

The compound represented by the formula (3I) can be obtained by treating the compound represented by the formula (1i) with the compound represented by the formula (2i). The reaction conditions for the amidomethylation are not specifically limited. Preferably, the compound represented by the formula (1i) is treated with the compound represented by the formula (2i) in an organic solvent such as dimethoxyethane, toluene, dichloromethane or 1,4-dioxane in the presence of an acid such as sulfuric acid or methanesulfonic acid at a temperature from −50° C. to 50° C.

General Synthesis Process J

1j

2j

3j

4j

Wherein each symbol represents a group as defined above; and "Hal" represents a halogen atom.

The compound represented by the formula (2j) can be obtained by formylating the compound represented by the formula (1j). The reaction conditions are not specifically limited. Preferably, the compound represented by the formula (1j) is treated with an alkyllithium compound such as n-butyllithium or t-butyllithium, and is then treated with a formylating agent such as N,N-dimethylformamide or N-formylmorpholine in an organic solvent such as tetrahydrofuran, diethyl ether, dioxane or dimethoxyethane at a temperature from −100° C. to 0° C.

The compound represented by the formula (3j) can be obtained by reducing the compound represented by the formula (2j). The reaction conditions are not specifically limited, and the reaction can be performed by treating the compound represented by the formula (2j) with, for example, sodium borohydride or lithium borohydride in an organic solvent such as ethanol, methanol or tetrahydrofuran at a temperature from 0° C. to 80° C.

The compound represented by the formula (4j) can be obtained by halogenating the compound represented by the formula (3j). The reaction conditions are not specifically limited, and the compound can be obtained by treating with a halogenating agent such as phosphorus tribromide or triphenylphosphine tetrabromomethane in an organic solvent such as dichloromethane, tetrahydrofuran or dimethoxyethane at a temperature from 0° C. to 80° C.

tetrahydrofuran, toluene or dichloromethane in the presence of a catalyst such as pyridine or an organotin derivative at a temperature from 0° C. to 100° C. The reaction conditions for the hydrolysis can follow those of the production example for formula (5a) in Production Example A. When the end product is an asymmetric carboxylic acid, each

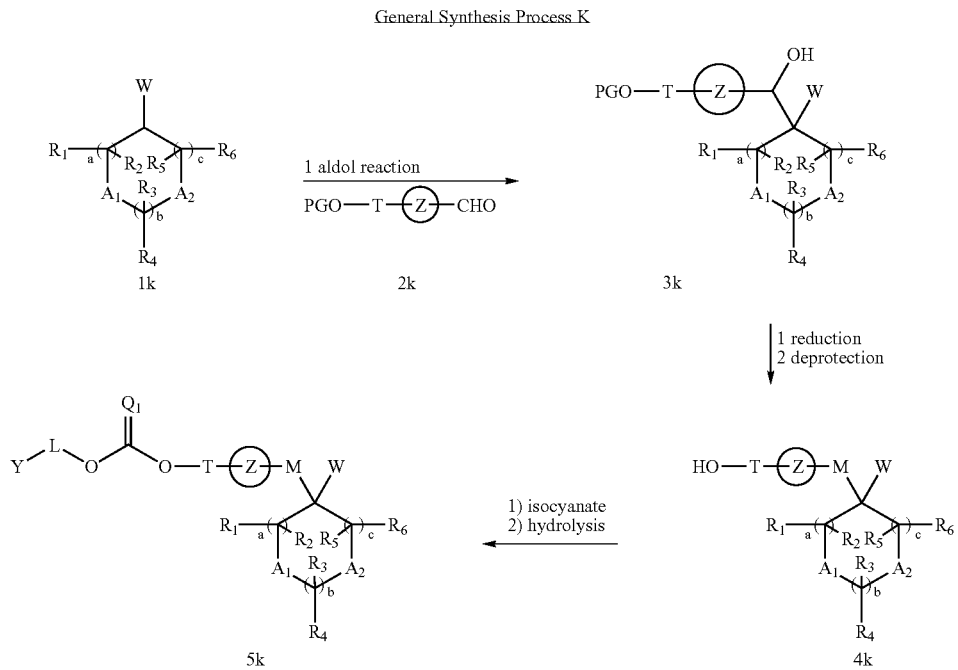

Wherein each symbol represents a group as defined above.

The compound represented by the formula (3k) can be obtained by an aldol reaction between the compound represented by the formula (1k) and the compound represented by the formula (2k). The aldol reaction conditions follow those of the production example for formula (3a) in Production Example A.

The compound represented by the formula (4k) can be obtained by reducing the compound represented by the formula (3k), followed by deprotection. The reaction conditions for the reduction are not specifically limited. Preferably, the compound represented by the formula (3k) is treated with carbon disulfide and methyl iodide in an organic solvent such as tetrahydrofuran, N,N-dimethylformamide or dichloromethane in the presence of a base such as sodium hydride at a temperature from 0° C. to 50° C., and the resulting intermediate is treated in an organic solvent such as toluene, benzene or carbon tetrachloride in the presence of a reducing agent such as tributyltin hydride at a temperature from 20° C. to 150° C. The reaction conditions for the deprotection are not specifically limited, and the compound can be obtained by treating with an acid such as an acidic ion-exchange resin, sulfuric acid or hydrochloric acid in an alcohol organic solvent such as methanol or ethanol at a temperature from 0° C. to 150° C.

The compound represented by the formula (5k) can be obtained by treating the compound represented by the formula (4k) with an isocyanate, and then hydrolyzing the internal ester. The conditions for reaction with the isocyanate is not specifically limited. Preferably, an organic ester of isocyanic acid is treated in an organic solvent such as enantiomer can be obtained by amidating a racemate of the carboxylic acid with an enantiomer of an asymmetric amine according to the method of the formula (5a) in Production Example A, resolving the resulting diastereomers, and hydrolyzing each diastereomer in the presence of, for example, sulfuric acid or hydrochloric acid.

Typical examples of the production processes of the compounds (I) according to the present invention have been described above. The material compounds and reagents used in the production of the compounds of the present invention may form salts or hydrates, vary depending on, for example, the starting material and the solvent used and are not specifically limited, as long as they do not adversely affect the reaction. The solvents used herein vary depending on, for example, the starting material and reagent and are not specifically limited, as long as they do not adversely affect the reaction and can dissolve the starting material to some extent. When the compounds (I) according to the present invention are obtained as free compounds, they can be converted into possible salts of the above-mentioned compounds (I) according to a conventional procedure. Various isomers such as geometrical isomers, optical isomers based on an asymmetric carbon, rotational isomers, stereo isomers, and tautomers obtained as the compounds (I) according to the present invention can be purified and isolated according to a conventional separation means including, for example, recrystallization, diastereomeric salt method, enzymatic resolution, and a variety of chromatographic methods such as thin layer chromatography, column chromatography or gas chromatography.

The compound represented by the formula (I) according to the present invention, a salt thereof or a hydrate of them can be used without modification or formulated into pharmaceutical preparations as a mixture with, for example, a known pharmacologically acceptable carrier according to a conventional procedure. Preferred dosage forms are tablets, powders, fine granules, granules, coated tablets, capsules, syrups, troches, inhalants, suppositories, injections, ointments, ophthalmic ointments, eye drops, nasal drops, ear drops, cataplasms, and lotions. In the formulation, generally used fillers, binders, disintegrators, lubricants, coloring agents, and flavoring agents, as well as stabilizers, emulsifiers, absorbefacients, surfactants, pH adjusting agents, antiseptics, and antioxidants can be used according to need. They can be formulated according to a conventional procedure using components generally used as raw materials for pharmaceutical preparations.

Examples of such components include (1) animal and vegetable oils such as soybean oil, tallow or synthetic glyceride; (2) hydrocarbons such as liquid paraffin, squalene or solid paraffin; (3) ester oils such as octyldodecyl myristate or isopropyl myristate; (4) higher alcohols such as cetostearyl alcohol or behenyl alcohol; (5) silicon resin; (6) silicon oil; (7) surfactants such as polyoxyethylene fatty ester, sorbitan fatty ester, glycerin fatty ester, polyoxyethylene sorbitan fatty ester, polyoxyethylene hardened castor oil or polyoxyethylene-polyoxypropylene block copolymer; (8) water-soluble polymers such as hydroethyl cellulose, polyacrylic acid, carboxyvinyl polymer, polyethylene glycol, polyvinyl pyrrolidone or methyl cellulose; (9) lower alcohols such as ethanol or isopropanol; (10) polyvalent alcohols such as glycerin, propylene glycol, dipropylene glycol or sorbitol; (11) sugars such as glucose or sucrose; (12) inorganic powder such as silicic anhydride, aluminum magnesium silicate or aluminum silicate; and (13) purified water. 1) The fillers include, for example, lactose, corn starch, sucrose, glucose, mannitol, sorbitol, crystalline cellulose and silicon dioxide; 2) the binders include, for example, polyvinyl alcohol, polyvinyl ether, methyl cellulose, ethyl cellulose, gum arabic, tragacanth, gelatin, shellac, hydroxypropyl cellulose, hydroxypropylmethyl cellulose, polyvinylpyrrolidone, polypropylene glycol-polyoxyethylene block polymers, meglumine, calcium citrate, dextrin and pectin; 3) the disintegrators include, for example, starch, agar, gelatin powder, crystalline cellulose, calcium carbonate, sodium hydrogencarbonate, calcium citrate, dextrin, pectin and carboxymethylcellulose calcium; 4) the lubricants include, for example, magnesium stearate, talc, polyethylene glycol, silica, and hardened vegetable oils; 5) the coloring agents can be any coloring agents which are approved to add to pharmaceutical preparations; 6) the flavoring agents include, for example, cocoa powder, menthol, aromatic powder (empasm), peppermint oil, camphol (borneol) and cinnamon powder; 7) the antioxidants can be any antioxidants which are approved to add to pharmaceutical preparations, such as ascorbic acid or α-tocopherol.

1) As oral preparations, the compound according to the present invention or a salt thereof is compounded with a filler, and if necessary, a binder, disintegrator, lubricant, coloring agent, flavoring agent, and other components, and the resulting mixture is formulated according to a conventional procedure into, for example, a powder, fine granules, granules, tablet, coated tablet or capsules.

2) The tablets and granules can be appropriately coated with, for example, sugar or gelatin according to necessity.

3) Liquid formulations such as syrups, injection preparations or eye drops can be prepared according to a conventional procedure, by adding a pH adjusting agent, solubilizer, and isotonizing agent, and if necessary, a solubilizing agent, stabilizer, buffer, suspending agent, antioxidant, and other components. The liquid formulations can also be formed into freeze-dried products. The injections can be administered intravenously, subcutaneously and/or intramuscularly. Preferred examples of the suspending agents are methyl cellulose, polysorbate 80, hydroxyethyl cellulose, gum arabic, powdered tragacanth, carboxymethyl cellulose sodium and polyoxyethylene sorbitan monolaurate; preferred examples of the solubilizers are polyoxyethylene hydrogenated caster oil, polysorbate 80, nicotinamide and polyoxyethylene sorbitan monolaurate; preferred examples of the stabilizers are sodium sulfite, sodium metasulfite and ether; preferred examples of the preservatives are methyl p-hydroxybenzoate, ethyl p-hydroxybenzoate, sorbic acid, phenol, cresol and chlorocresol.

4) External preparations can be produced according to a conventional procedure not specifically limited. Base materials for use herein can be any raw materials generally used in, for example, pharmaceutical preparations (medicaments), quasi drugs and cosmetics. Such raw materials include, for example, animal and vegetable oils, mineral oils, ester oils, waxes, higher alcohols, fatty acids, silicone oils, surfactants, phospholipids, alcohols, polyhydric alcohols, water-soluble polymers, clay minerals, and purified water. Where necessary, any of pH adjusting agents, antioxidants, chelating agents, antiseptics and antimolds, coloring agents, flavors, and others can be added. In addition, components having differentiation-inducing action, blood-flow accelerators, bactericides, anti-inflammatory agents, cell activators, vitamins, amino acids, humectants, keratolytic agents, and other components can be added according to necessity.

Pharmaceutical preparations (medicaments) containing the compound (I) according to the present invention, a salt thereof, an ester thereof or a hydrate of them as an active ingredient are efficacious for treatment and/or prophylaxis in mammals such as humans, mice, rats, guinea pigs, rabbits, dogs, horses, and monkeys, and especially for treatment and/or prophylaxis in humans. The dose of the medicament according to the present invention varies depending on the degree of symptom, age, sex, body weight, administration mode, type of the salt, difference in sensibility to the drug, concrete type of the disease and other factors. Generally, in oral administration to a human, the medicament may be administered at a daily dose of about 30 μg to about 10 g, preferably about 100 μg to about 10 g, and more preferably about 100 μg to about 5g for an adult in one to several divided doses. In injection administration, it may be administered at a daily dose of about 30 μg to about 10 g for an adult in one to several divided doses.

The present invention can provide the compounds represented by the formula (I), salts thereof, esters thereof and hydrates of them. The compounds according to the present invention have an excellent agonist action against PPAR (α, β(δ), γ) and further have a dual agonist action against PPAR α and γ and a triple agonist action against PPAR α, β(δ) and γ. The compounds according to the present invention are useful for treating and/or preventing various diseases based on an action of improving insulin resistance, and for treating and/or preventing diseases relating to blood lipids and inflammatory diseases. They are useful in treating and/or preventing, for example, (1) diabetes mellitus, (2) syndrome X, (3) diabetic complications, (4) hyperlipidemia, (5) obesity, (6) osteoporosis, (7) inflammatory diseases, (8) a disease of the digestive organs (e.g., (a) inflammatory diseases of the digestive organs such as ulcerative colitis, Crohn's disease, pancreatitis or gastritis; (b) proliferative diseases of the digestive organs such as benign tumor of the digestive organs, digestive polyp, hereditary polyposis syndrome, colon cancer, rectum cancer or stomach cancer; and (c) ulcerous diseases of the digestive organs), (9) stenocardia, (10) myocardial infarction, (11) sequelae of stenocardia or myocardial infarction, (12) senile dementia, (13) cerebrovascular dementia, (13) immunological diseases, and (14) cancer.

EXAMPLES

The following production examples, examples, and experiment examples are illustrative, and the compounds according to the present invention are under no circumstances restricted by the following examples. Those skilled in the art can modify not only the following examples but also the claims according to the present description in various ways to exploit to the full of the present invention, and such modifications and variations are also included within the scope of the appended claims relating to the present description.

Reference Example 1

Methyl 2-[(3-{[(t-butoxycarbonyl)amino]methyl}-4-methoxyphenyl)(hydroxy)methyl]tetrahydro-2-furancarboxylate

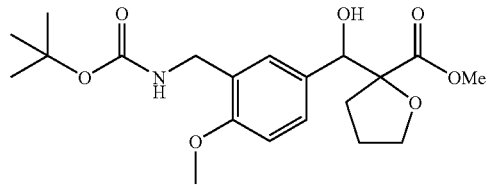

A solution of 2.60 g of methyl tetrahydro-2-furancarboxylate in 10 ml of tetrahydrofuran was added dropwise to 20 ml of sodium bis(trimethyldisilylamide) (1 M solution in tetrahydrofuran) cooled to −75° C. under an atmosphere of nitrogen gas, and the reaction mixture was stirred for 30 minutes. A solution of 2.65 g of t-butyl N-(5-formyl-2-methoxybenzyl)carbamate in 20 ml of tetrahydrofuran was added dropwise, and the mixture was stirred further for 1 hour. 200 ml of saturated aqueous ammonium chloride was added, and the mixture was extracted with 200 ml of ethyl acetate. The organic layer washed with 100 ml of brine, dried over magnesium sulfate and then concentrated. The residue was purified by silica gel column chromatography, to give 1.934 g of the title compound as a colorless powder.

$^1$H-NMR(CDCl$_3$): 1.44(s, 9H), 1.73-1.88(m, 2H), 1.94-2.02 and 2.16-2.23(ddd, J=7.3, 8.1, 13.0 Hz and J=6.0, 9, 12.4 Hz, 1H), 2.05-2.12 and 2.29-2.36(ddd, J=5.5, 7.4, 13.0 Hz and J=7.1, 8.5, 12.4 Hz, 1H), 2.92 and 2.94 (d, J=7.1 Hz and 7.1 Hz, 1H), 3.63 and 3.76(s, 3H), 3.82 and 3.83(s, 3H), 3.81-3.99(m, 2H), 4.28(br. s, 2H), 4.91 and 4.93(d, J=7.1 Hz and 7.1 Hz, 1H), 4.99(br.s, 1H), 6.79 and 6.81(d, J=8.1 Hz and 8.1 Hz, 1H), 7.25-7.31 (m, 2H)

Reference Example 2

Methyl 2-[3-(ammoniomethyl)-4-methoxybenzyl]tetrahydro-2-furancarboxylate chloride

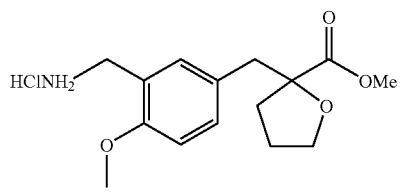

To a solution of 1.934 g of methyl 2-[(3-{[(t-butoxycarbonyl)amino]methyl}-4-methoxyphenyl)(hydroxy)-methyl]tetrahydro-2-furancarboxylate in 50 ml of trifluoroacetic acid was added 8 ml of trimethylsilane at 0° C., and the mixture was stirred at room temperature for 60 hours. The reaction mixture was concentrated, and 20 ml of hydrochloric acid (1N) and 10 ml of diisopropyl ether were added. The aqueous layer was adjusted to pH 12 with sodium hydroxide (5N) and extracted with 20 ml of ethyl acetate for two times. The organic layers were combined, 5 ml of hydrogen chloride (4N solution in ethyl acetate) was added, and the mixture was concentrated. To the residue was added 40 ml of ethyl acetate and the mixture was concentrated again, to give 1.590 g of the title compound as a waxy colorless solid.

$^1$H-NMR(CDCl$_3$): 1.69-1.841(m, 2H), 1.87-1.95(ddd, J=7.3, 7.6, 12.6 Hz, 1H), 2.19-2.15(ddd, J=6.5, 7.1, 12.6 Hz, 1H), 2.85(d, J=13.8 Hz, 1H), 3.10(d, J=13.8 Hz, 1H), 3.66(s, 3H), 3.77-3.92 (m, 2H), 3.83 (s, 3H), 4.01-4.13(br. s, 2H), 6.78(d, J=7.9 Hz, 1H), 7.15(dd, J=1.9, 7.9 Hz, 1H), 7.20(d, J=1.9 Hz, 1H), 8.18(br. s, 3H)

MS m/e (ESI) 280.01 (MH+)

Reference Example 3

(3-{[(t-Butoxycarbonyl)amino]methyl}-4-methoxybenzoyl)-1-cyclopropanecarboxylic acid

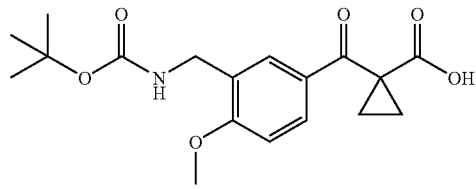

Under an atmosphere of nitrogen gas, a solution of 3.16 g of t-butyl N-(5-bromo-2-methoxybenzyl) carbamate in 40 ml of tetrahydrofuran was cooled to −75° C. n-Butyllithium (1.6 M solution in hexane) was added while keeping the internal temperature at −70° C. or below, and the mixture was stirred for 30 minutes. After addition of a solution of 1.96 g of 6,6-dimethyl-5,7-dioxaspiro[2.5]octane-4,8-dione in 10 ml of tetrahydrofuran, the mixture was stirred for 2 hours. 50 ml of 5% aqueous ammonium chloride was added, and the mixture was adjusted to pH 2 with concentrated hydrochloric acid and then extracted with 300 ml of ethyl acetate. The organic layer washed with 50 ml of brine, dried over magnesium sulfate and concentrated. The residue was purified by silica gel column chromatography, to give 1.069 g of the title compound as a colorless powder.

$^1$H-NMR(CDCl$_3$): 1.44(s, 9H), 1.53(m, 2H), 1.65(m, 2H), 3.91(s, 3H), 4.31 (d, J=6.1 Hz, 2H), 5.03 (br t, J=6.1 Hz, 1H), 6.89 (d, J=8.5 Hz, 1H), 7.85 (br. s, 1H), 7.90 (dd, J=2.4, 8.5 Hz, 1H)

MS m/e (ESI) 372.0 (MNa+)

Reference Example 4

Methyl 1-(3-{[(t-butoxycarbonyl)amino]methyl}-4-methoxybenzoyl)-1-cyclopropanecarboxylate

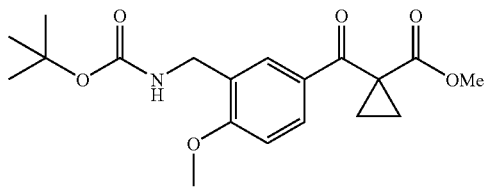

Under a solution of 1.069 g of 1-(3-{[(t-butoxycarbonyl)amino]methyl}-4-methoxybenzoyl)-1-cyclopropanecarboxylic acid in 10 ml of methanol was added 8 ml of trimethylsilyldiazomethane (2N solution in hexane). After stirring for 30 minutes, the solution was treated with acetic acid until its color faded, and then concentrated. The residue was purified by silica gel column chromatography, to give 0.974 g of the title compound as a colorless oil.

$^1$H-NMR(CDCl$_3$): 1.46(s, 9H), 1.54-1.62(m, 4H), 3.61(s, 3H), 3.82(s, 3H), 4.34 (d, J=6.0 Hz, 2H), 4.97 (br t, J=6.0 Hz, 1H), 6.87 (d, J=8.2 Hz, 1H), 7.85-7.88 (m, 2H)

Reference Example 5

Methyl 1-[(3-{[(t-butoxycarbonyl)amino]methyl}-4-methoxyphenyl)(hydroxy)methyl]-1-cyclopropanecarboxylate

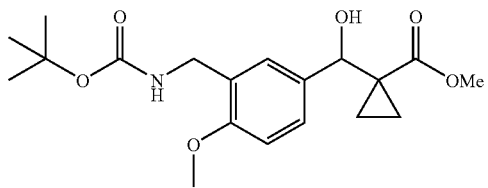

To a solution of 0.974 g of methyl 1-(3-{[(t-butoxycarbonyl)amino]methyl}-4-methoxybenzoyl)-1-cyclopropanecarboxylate in 30 ml of ethanol and 10 ml of tetrahydrofuran was added 0.112 g of sodium borohydride, and the mixture was stirred at room temperature for 15 hours. 50 ml of water, 100 ml of ethyl acetate and 5 ml of hydrochloric acid (2N) were added, and the organic layer was dried over magnesium sulfate and concentrated. The residue was purified by silica gel column chromatography, to give 0.483 g of the title compound as a colorless oil.

$^1$H-NMR(CDCl$_3$): 0.72-0.78(ddd, J=4.4, 6.7, 11.0 Hz, 1H), 0.91-0.95(ddd, J=4.4, 6.9, 9.6 Hz, 1H), 1.17-1.22(ddd, J=4.3, 6.7, 9.6 Hz, 1H), 1.28-1.33(ddd, J=4.3, 6.9, 11.0 Hz, 1H), 1.43(s, 9H), 3.39(br.s, 1H), 3.65(s, 3H), 3.82(s, 3H), 4.28(d, J=6.6 Hz, 2H), 4.88(br.s, 1H), 4.99(br.s, 1H), 6.80(d, J=6.9 Hz, 1H), 7.24-7.25(m, 1H)

Reference Example 6

Methyl 1-[3-(ammoniomethyl)-4-methoxybenzyl-1-cyclopropanecarboxylate chloride

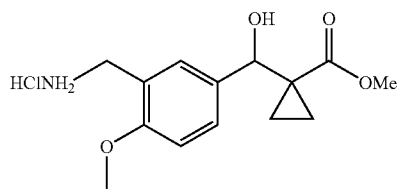

The title compound (0.283 g) was obtained as a colorless solid according to the method of Reference Example 2 from 0.483 g of methyl 1-[(3-{[(t-butoxycarbonyl)amino]methyl}-4-methoxyphenyl)(hydroxy)-methyl]-1-cyclopropanecarboxylate.

$^1$H-NMR(CDCl$_3$): 0.81(q, J=3.7 Hz, 2H), 1.26(q, J=3.7 Hz, 2H), 2.88(s, 2H), 3.60(s, 3H), 3.83(s, 3H), 4.09 (s, 2H), 6.80 (d, J=8.5 Hz, 1H), 7.18(d, J=1.6 Hz, 1H), 7.23(dd, J=1.6, 8.5 Hz, 1H)

Reference Example 7

Methyl 2-[(3-{[(t-butoxycarbonyl)amino]methyl}-phenyl)-(hydroxy)methyl]tetrahydro-2-furancarboxylate

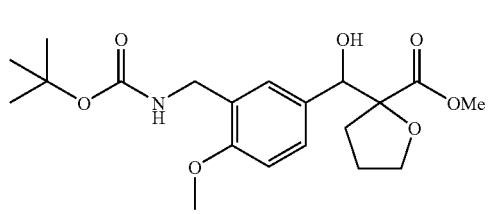

The title compound (2.77 g) was obtained as a colorless waxy solid according to the method of Reference Example 1 from 2.35 g of N-(5-formyl-2-methoxybenzyl)-carbamate.

$^1$H-NMR(CDCl$_3$): 1.46 (s, 9H), 1.73-1.90 (m, 2H), 1.94-2.38 (m, 4H), 3.05 (d, J=6.0 Hz, 1H), 3.64 and 3.76 (s, 3H), 3.80-3.99 (m, 2H), 4.30 (br. s, 2H), 4.83 (br. s, 1H), 4.98 (d, J=6.0 Hz, 1H), 7.19-7.33 (m, 4H)

Reference Example 8

Methyl 2-((3-{[(t-butoxycarbonyl)amino]methyl}phenyl)-{[(methylsulfanyl)carbothioyl]oxy}methyl)tetrahydro-2-furancarboxylate

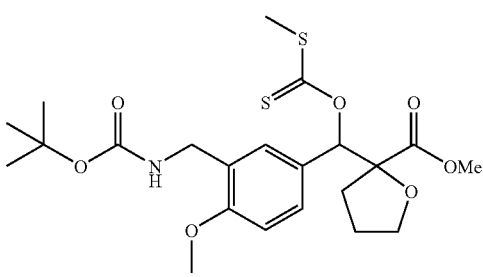

To a solution of 2.48 g of methyl 2-[(3-{[(t-butoxycarbonyl)amino]methyl}-phenyl)(hydroxy)methyl]-tetrahydro-2-furancarboxylate in 100 ml of tetrahydrofuran was added sodium hydride (60% in oil) at 0° C. under an atmosphere of nitrogen gas. After stirring at room temperature for 15 minutes, the mixture was cooled to 0° C., and 0.62 ml of carbon disulfide and 0.64 ml of methyl iodide were added. After stirring at room temperature overnight, 200 ml of ethyl acetate and 50 ml of saturated aqueous ammonium chloride were added. The organic layer was dried over magnesium sulfate and evaporated. The residue was purified by silica gel column chromatography, to give 2.02 g of the title compound as a yellow oil.

$^1$H-NMR (CDCl$_3$): 1.45 (s, 9H), 1.68-1.99 (m, 2H), 2.16-2.34 (m, 2H), 2.41 and 2.56 (s, 3H), 3.67 and 3.78 (s, 3H), 93-4.03 (m, 2H), 4.27-4.34 (m, 2H), 4.77-4.90 (br. s, 1H), 6.79 and 6.94 (s, 1H), 7.19-7.38 (m, 2H)

Reference Example 9

Methyl 2-(3-{[(t-butoxycarbonyl)amino]methyl}benzyl)-tetrahydro-2-furancarboxylate

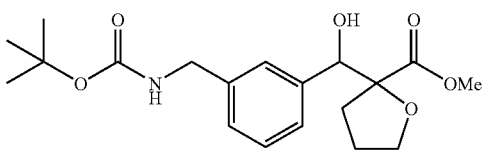

To a solution of methyl 2-((3-{[(t-butoxycarbonyl)amino]methyl}phenyl){[(methylsulfanyl)carbothioyl]oxy}methyl)tetrahydro-2-furancarboxylate in 30 ml of toluene were added 1.55 g of tri-n-butyltin chloride and 0.03 g of 2,2-diazobis(isobutyronitrile) under an atmosphere of nitrogen gas, and the mixture was heated under reflux for 23 hours. After cooling to room temperature, 100 ml of saturated aqueous potassium fluoride was added. After stirring for 30 minutes, the mixture was extracted with 200 ml of ethyl acetate. The organic layer was dried over magnesium sulfate and evaporated. The residue was purified by silica gel column chromatography, to give 1.26 g of the title compound as a colorless oil.

$^1$H-NMR(CDCl$_3$): 1.46(s, 9H), 1.64-1.73 (m, 1H), 1.74-1.85 (m, 2H), 1.85-1.94 (ddd, J=7.1, 8.1, 12.6 Hz, 1H), 2.23-2.31 (ddd, J=5.7, 7.9, 12.6 Hz, 1H), 2.96 (d, J=13.9 Hz, 1H), 3.20 (d, J=13.9 Hz, 1H), 3.79 (s, 3H), 3.85-3.95 (m, 2H), 4.28 (d, J=5.9 Hz, 2H), 4.81 (br.s, 1H), 7.13-7.25 (m, 4H)

Reference Example 10

Methyl 2-[3-(ammoniomethyl)benzyl]tetrahydro-2-furancarboxylate chloride

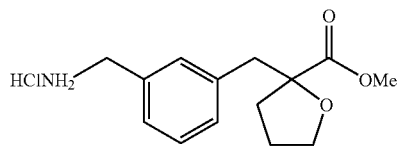

To a solution of 1.26 g of methyl 2-(3-{[(t-butoxycarbonyl)amino]methyl}benzyl)tetrahydro-2-furancarboxylate in 20 ml of dichloromethane was added 20 ml of trifluoroacetic acid, and the mixture was stirred at room temperature for 16 hours. The reaction mixture was evaporated, and the residue was dissolved in 30 ml of ethyl acetate. 2 ml of hydrogen chloride (4N solution in ethyl acetate) was added and the mixture was concentrated again, to give 0.84 g of the title compound as a brown oil.

$^1$H-NMR(CDCl$_3$): 1.75-1.96 (m, 2H), 2.05-2.26 (m, 2H), 2.91 (d, J=13.4 Hz, 1H), 3.17 (d, J=13.4 Hz, 1H), 3.68 (s, 3H), 3.73-3.80 (m, 1H), 3.89-3.96 (m, 1H), 4.03-4.10 (br.s, 2H), 7.10-7.25 (m, 4H)

Reference Example 11

Methyl 2-[[2-(benzyloxy)-4-pyridyl](hydroxy)methyl]tetrahydro-2-furancarboxylate

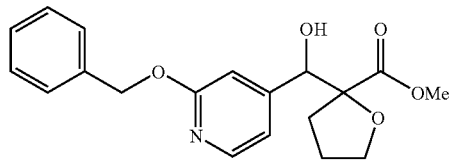

The title compound (4.23 g) was obtained as a white solid according to the method of Reference Example 1, from 2.62 g of 2-(benzyloxy)isonicotinaldehyde.

$^1$H-NMR(CDCl$_3$): 1.56-1.74(m, 1H), 1.80-1.95(m, 1H), 2.07-2.36(m, 2H), 3.15 and 3.23(d, J=5.5 Hz, 1H), 3.68 and 3.75(s, 3H), 3.87-4.03(m, 2H), 4.88 and 4.95(d, J=5.5 Hz, 1H), 5.35(s, 2H), 6.83-6.95(m, 2H), 7.31-7.48(m, 5H), 8.10-8.14(m, 1H)

Reference Example 12

Methyl 2-{(acetyloxy)[2-(benzyloxy)-4-pyridyl]methyl}-tetrahydro-2-furancarboxylate

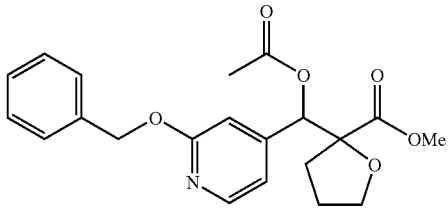

To a solution of 4.23 g of methyl 2-[[2-(benzyloxy)-4-pyridyl](hydroxy)methyl]tetrahydro-2-furancarboxylate in 20 ml of dichloromethane were added 5 ml of acetic anhydride, 5 ml of pyridine and 0.43 g of 4-dimethylaminopyridine, and the mixture was stirred at room temperature for 15 hours. 300 ml of ethyl acetate and 100 ml of hydrochloric acid (2N) were added thereto. The organic layer was sequentially washed with 100 ml of water, 100 ml of saturated aqueous sodium hydrogencarbonate and 100 ml of brine, dried over magnesium sulfate and evaporated, to give 4.52 g of the title compound as a colorless oil.

$^1$H-NMR(CDCl$_3$): 1.69-1.81(m, 1H), 1.84-1.96(m, 1H), 2.05-2.11(m, 1H), 2.07 and 2.13(s, 3H), 2.26-2.33(m, 1H), 3.72 and 3.77(s, 3H), 3.90-4.02(m, 2H), 5.35(m, 2H), 5.98 and 6.12(s, 1H), 6.82 and 6.88(s, 1H), 6.90 and 7.00(d, J=4.8 Hz, 1H), 7.30-7.44(m, 5H), 8.11 and 8.17 (d, J=4.8 Hz, 1H)

Reference Example 13

Methyl 2-[(acetyloxy)(2-oxo-1,2-dihydro-4-pyridinyl)-methyl]tetrahydro-2-furancarboxylate

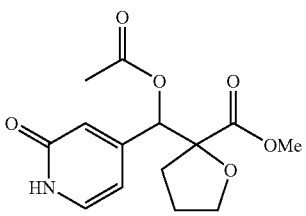

To a solution of 4.52 g of methyl 2-[[2-(benzyloxy)-4-pyridyl](hydroxy)methyl]tetrahydro-2-furancarboxylate in 20 ml of methanol was added 0.45 g of 10% palladium hydroxide/carbon, and the mixture was stirred under an atmosphere of hydrogen gas for 86 hours. The reaction mixture was filtrated and evaporated, to give 3.69 g of the title compound as a colorless waxy solid.

$^1$H-NMR(CDCl$_3$): 1.74-2.37(m, 4H), 2.10 and 2.14(s, 3H), 3.74 and 3.78 (s, 3H), 3.78-4.10(m, 2H), 5.84 and 6.01(s, 3H), 6.36 and 6.44(d, J=5.0 Hz, 1H), 6.54 and 6.62(s, 3H), 7.07 and 7.11(d, J=5.0 Hz, 1H)

Reference Example 14

Methyl 2-[(2-oxo-1,2-dihydro-4-pyridinyl)methyl]tetrahydro-2-furancarboxylate

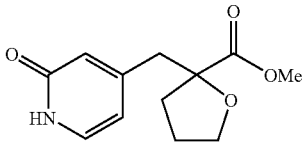

To a solution of 3.69 g of methyl 2-[(acetyloxy)(2-oxo-1,2-dihydro-4-pyridinyl)methyl]tetrahydro-2-furancarboxylate in 30 ml of acetic acid was added 8.17 g of zinc, and the mixture was heated under reflux for 24 hours. This procedure was repeated twice. The reaction mixture was cooled, filtered through Celite, and the Celite and the filtrate were washed with ethanol. The combined organic layers were evaporated, and the residue was purified by silica gel column chromatography, to give 1.31 g of the title compound as a colorless oil.

$^1$H-NMR(CDCl$_3$): 1.73-2.03(m, 3H), 2.23-2.35(m, 1H), 2.83(d, J=13.0 Hz, 1H), 3.08 (d, J=13.0 Hz, 1H), 3.72(s, 3H), 3.90-4.05(m, 2H), 6.33 (d, J=6.0 Hz, 1H), 6.42 (s, 1H), 7.24 (d, J=6.0 Hz, 1H)

Reference Example 15

Ethyl 2-hydroxy-2-(4-methoxybenzyl)-3-(methoxymethoxy)-propanoate

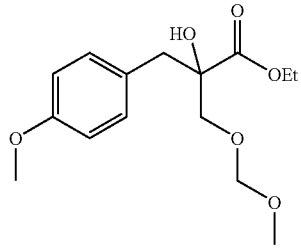

A solution of 1.06 g of ethyl 2,3-dihydroxy-2-(4-methoxybenzyl)propanoate in 20 ml of dimethoxymethanol was cooled to 0° C. under an atmosphere of nitrogen gas. 0.94 g of 2,6-lutidine and 1.59 ml of 1,1,1-trimethylsilyl tri-fluoromethanesulfonate were sequentially added, and the mixture was stirred for 1 hour. 100 ml of ethyl acetate and 50 ml of water were added, and the organic layer was washed with 50 ml of brine, dried over magnesium sulfate and evaporated. The residue was purified by silica gel column chromatography, to give 1.00 g of the title compound as a colorless oil.

$^1$H-NMR(CDCl$_3$): 1.27 (t, J=7.1 Hz, 3H), 2.87 (d, J=13.2 Hz, 1H), 2.96 (d, J=13.2 Hz, 1H), 3.35 (s, 3H), 3.57 (d, J=12.5 Hz, 1H), 3.78 (s, 3H), 3.96 (d, J=12.5 Hz, 1H), 4.19 (q, J=7.1 Hz, 1H), 4.20 (q, J=7.1 Hz, 1H), 4.63(d, J=6.6 Hz, 1H), 4.65 (d, J=6.6 Hz, 1H), 6.80 (d, J=8.0 Hz, 2H), 7.14 (d, J=8.0 Hz, 2H)

Reference Example 16

Ethyl 4-(4-methoxybenzyl)-1,3-dioxiran-4-carboxylate

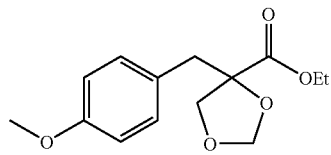

A solution of 1.00 g of ethyl 2-hydroxy-2-(4-methoxybenzyl)-3-(methoxymethoxy)propanoate in 20 ml of dichloromethane was cooled to 0° C. under an atmosphere of nitrogen gas, 0.43 g of 2,6-lutidine and 0.73 ml of 1,1,1-trimethylsilyl trifluoromethanesulfonate were sequentially added, and the mixture was stirred at room temperature for 15 hours. 200 ml of ethyl acetate and 100 ml of water were added, and the organic layer was sequentially washed with 100 ml of 5% aqueous sulfuric acid, 100 ml of saturated aqueous sodium hydrogen carbonate and 100 ml of brine, dried over magnesium sulfate and evaporated. The residue was purified by silica gel column chromatography, to give 0.37 g of the title compound as a colorless oil.

$^1$H-NMR (CDCl$_3$): 1.19(t, J=6.8 Hz, 3H), 3.01(d, J=14.1 Hz, 1H), 3.19(d, J=14.1 Hz, 1H), 3.7(s, 3H), 3.80(d, J=8.5 Hz, 1H), 4.15(q, J=6.8 Hz, 1H), 4.16(q, J=6.8 Hz, 1H), 4.20 (d, J=8.5 Hz, 1H), 5.03 (s, 1H), 5.06 (s, 1H), 6.81 (d, J=8.0 Hz, 2H), 7.14 (d, J=8.0 Hz, 2H)

Reference Example 17

Ethyl 4-(3-{[(2,4-dichlorobenzoyl)amino]methyl}-4-methoxybenzyl)-1,3-dioxiran-4-carboxylate

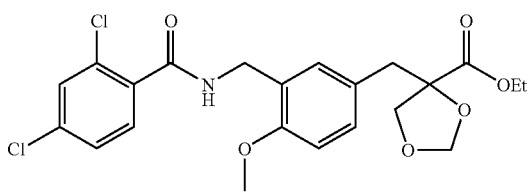

0.187 g of ethyl 4-(4-methoxybenzyl)-1,3-dioxiran-4-carboxylate was dissolved in 2 ml of toluene and 3 ml of dimethoxyethane, and the mixture was cooled to 0° C. Then, 0.163 g of N1-hydroxymethyl-2,4-dichlorobenzamide and 0.77 ml of sulfuric acid were sequentially added to the solution. After stirring at 0° C. for 4 hours, the reaction mixture was poured onto 100 ml of ethyl acetate, and 50 ml of saturated aqueous sodium hydrogen carbonate was added. The organic layer was then washed with 50 ml of brine, dried over magnesium sulfate, and evaporated. The residue was purified by silica gel column chromatography, to give 0.170 g of the title compound as a colorless oil.

$^1$H-NMR(CDCl$_3$): 1.20 (t, J=7.1 Hz, 3H), 2.99 (d, J=14.2 Hz, 1H), 3.20 (d, J=14.2 Hz, 1H), 3.80 (d, J=8.1 Hz, 1H), 3.83 (s, 3H), 4.15 (q, J=7.1 Hz, 1H), 4.16 (q, J=7.1 Hz, 1H), 4.18 (d, J=8.1 Hz, 1H), 4.57 (dd, J=5.7, 14.6 Hz, 1H), 4.61 (dd, J=5.7, 14.6 Hz, 1H), 5.02 (s, 1H), 5.07 (s, 1H), 6.78 (br. t, J=5.7 Hz, 1H), 6.80 (d, J=8.3 Hz, 1H), 7.17 (dd, J=2.0, 8.3 Hz, 1H), 7.21 (d, J=2.0 Hz, 1H), 7.29 (dd, J=2.2, 8.8 Hz, 1H), 7.40 (d, J=2.2 Hz, 1H), 7.64 (d, J=8. Hz, 1H)

Reference Example 18

Ethyl 2-[(3-{[(t-butoxycarbonyl)amino]methyl}-4-methoxyphenyl)(hydroxy)methyl]-2,5-dihydro-2-furancarboxylate

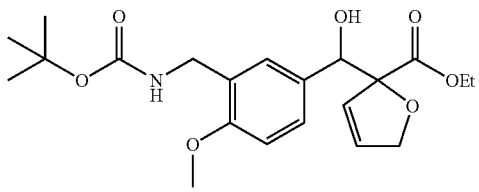

0.057 g of lithium was added to 120 ml of liquid ammonia and 30 ml of tetrahydrofuran at −78° C. under an atmosphere of nitrogen gas. After stirring for 15 minutes, a solution of 0.462 g of ethyl furan-2-carboxylate in 20 ml tetrahydrofuran was added dropwise. After stirring for 30 minutes, 3-methyl-1,3-pentadiene was added drop by drop until the deep blue color faded. A solution of 0.397 g of t-butyl N-(5-formyl-2-methoxybenzyl)carbamate in 15 ml of tetrahydrofuran was added dropwise to the yellow reaction mixture. After stirring at −78° C. for 2 hours, 30 ml of saturated aqueous ammonium chloride was added, and ammonia was evaporated under a flow of nitrogen gas. 200 ml of ethyl acetate and 100 ml of water were added, and the organic layer washed with 100 ml of brine, dried over magnesium sulfate and evaporated. The residue was purified by silica gel column chromatography, to give 0.407 g of the title compound as a white solid.

$^1$H-NMR(CDCl$_3$): 1.14 and 1.17 (t, J=7.4 Hz, 3H), 1.33 (s, 9H), 2.92 and 2.95 (d, J=6.2 Hz, 1H), 3.68 and 3.69 (s, 3H), 4.12 and 4.13 (q, J=7.4 Hz, 2H), 4.16 (d, J=5.4 Hz, 1H), 4.30 and 4.42 (dd, J=1.9, 13.6 Hz, 1H), 4.61 and 4.66 (dd, J=1.9, 13.6 Hz, 1H), 4.85 (br. t, J=5.4 Hz, 1H), 4.88 and 4.93 (d, J=6.2 Hz, 1H), 5.62 and 5.81 (td, J=1.9, 6.3 Hz, 1H), 5.72 and 5.95 (d, J=6.3 Hz, 1H), 6.68 (d, J=8.5 Hz, 1H), 7.10-7.20 (m, 2H)

Reference Example 19

Ethyl 2-[3-(ammoniomethyl)-4-methoxybenzyl]-2,5-dihydro-2-furancarboxylate chloride

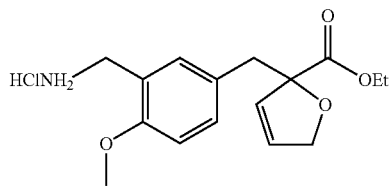

The title compound (0.255 g) was obtained as a brown oil according to the method of Reference Example 2 from 0.407 g of methyl 2-[(3-{[(t-butoxycarbonyl)amino]methyl}-4-methoxyphenyl)(hydroxy)methyl]-2,5-dihydro-2-furancarboxylate.

$^1$H-NMR(CD$_3$OD): 1.22 (t, J=7.0 Hz, 3H), 2.99 (d, J=14.2 Hz, 1H), 3.15 (d, J=14.2 Hz, 1H), 3.85 (s, 3H), 3.97

(br.d, J=13.5 Hz, 1H), 4.05 (br.d, J=13.5 Hz, 1H), 4.12 (q, J=7.0 Hz, 1H), 4.51 (ddd, J=1.5, 2.3, 13.0 Hz, 1H), 4.68 (ddd, J=1.5, 2.3, 13.0 Hz, 1H), 5.84 (td, J=2.3, 6.1 Hz, 1H), 5.95 (td, J=1.5, 6.1 Hz, 1H), 6.86 (d, J=8.1 Hz, 1H), 7.17 (d, J=2.3 Hz, 1H), 7.20 (dd, J=2.3, 8.1 Hz, 1H)

Reference Example 20 t-Butyl N-[5-(hydroxymethyl)-2-methoxybenzyl]carbamate

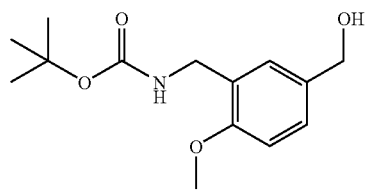

1.8 g of t-butyl N-(5-formyl-2-methoxybenzyl)carbamate was dissolved in 12 ml of ethanol and 6 ml of tetrahydrofuran, and 0.15 g of sodium borohydride was added. After stirring at room temperature overnight, water was added and the mixture was extracted with ethyl acetate. The extract was dried over anhydrous magnesium sulfate, and the solvent was removed. The residue was purified by silica gel column chromatography, to give 1.65 g of the title compound from the 1:1 hexane-ethyl acetate fraction.

$^1$H-NMR(CDCl$_3$): 1.45 (s, 9H) 3.85 (s, 3H) 4.30 (d, J=6.0 Hz, 2H) 4.61 (br, 2H) 5.02 (br, 1H) 6.84 (d, J=8.8 Hz, 1H) 7.25-7.27 (m, 1H)

Reference Example 21 t-Butyl N-[5-(bromomethyl)-2-methoxybenzyl]carbamate

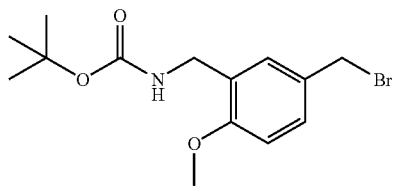

1.65 g of t-butyl N-[5-(hydroxymethyl)-2-methoxybenzyl]carbamate was dissolved in 20 ml of dimethoxyethane, 0.53 ml of phosphorus tribromide was added under ice-cooling, and the mixture was stirred at room temperature for 2 hours. The reaction mixture was diluted with ether and washed with water. The organic layer was washed with brine, dried over anhydrous magnesium sulfate, and the solvent was evaporated. The residue was subjected to silica gel column chromatography, to give 1.76 g of the title compound from the 3:1 hexane-ethyl acetate fraction.

$^1$H-NMR(CDCl$_3$): 1.45 (s, 9H) 3.84 (s, 3H) 4.28 (d, J=6.0 Hz, 2H) 4.49 (s, 2H) 5.00 (br, 1H) 6.81 (d, J=8.8 Hz, 1H) 7.27-7.29 (m, 2H)

Reference Example 22

Ethyl 2-(3-{[(t-butoxycarbonyl)amino]methyl}-4-methoxybenzyl)-1,3-dithian-2-carboxylate

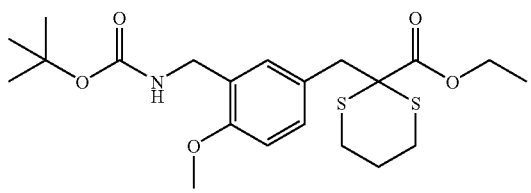

1.76 g of t-butyl N-[5-(bromomethyl)-2-methoxybenzyl] carbamate and 0.76 ml of ethyl 1,3-dithian-2-carboxylate were dissolved in anhydrous N,N-dimethylformamide. A solution of 220 mg of 60% sodium hydride in 18 ml of toluene was added under ice-cooling, and the mixture was stirred overnight. The reaction mixture was diluted with ethyl acetate and washed with water. The organic layer was dried over anhydrous magnesium sulfate, and the solvent was evaporated. The residue was purified by silica gel column chromatography, to give 1.70 g of the title compound from the 3:1 hexane-ethyl acetate fraction.

$^1$H-NMR(CDCl$_3$): 1.35 (t, J=7.2 Hz, 3H) 1.44 (s, 9H) 1.77-1.88 (m, 1H) 2.07-2.14 (m, 1H) 2.64-2.70 (m, 2H) 3.17-3.20 (m, 2H) 3.30 (s, 2H) 3.80 (s, 3H) 4.25 (q, J=7.2 Hz, 2H) 4.28 (br, 2H) 4.95 (br, 1H) 6.75 (d, J=8.4 Hz, 1H) 7.17-7.20 (m, 2H)

Reference Example 23

Methyl 2-[(3-{[(t-butoxycarbonyl)amino]methyl}-4-ethoxyphenyl)(hydroxy)methyl]tetrahydro-2-furancarboxylate

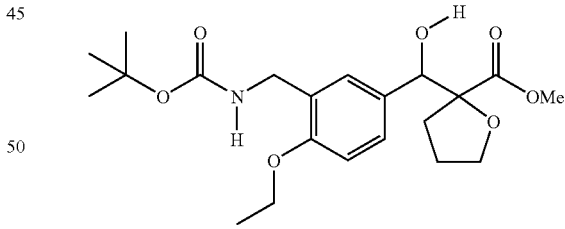

The title compound was obtained according to the method of Reference Example 1 from methyl tetrahydro-2-furancarboxylate and t-butyl N-(5-formyl-2-ethoxybenzyl)carbamate.

$^1$H-NMR(CDCl$_3$): 1.43 (t, J=7.3 Hz, 3H), 1.44(s, 9H), 1.63-1.75(m, 1H), 1.75-1.88 (m, 1H), 2.15-2.23 (ddd, J=5.6, 7.0, 13.4 Hz, 1H), 2.28-2.36 (ddd, J=7.8, 9.1, 13.0 Hz, 1H), 2.90 (d, J=7.0 Hz, 1H), 3.63 (s, 3H), 3.81-3.99 (m, 2H), 4.04 (q, J=7.3 Hz, 2H) 4.28 (d, J=6.1 Hz, 2H), 4.91 (d, J=7.0 Hz, 1H), 4.99 (t, J=6.1 Hz, 1H), 6.78 (d, J=8.1 Hz, 1H), 7.24-7.30 (m, 2H)

Reference Example 24

Methyl 2-[3-(ammoniomethyl)-4-ethoxybenzyl]tetrahydro-2-furancarboxylate chloride

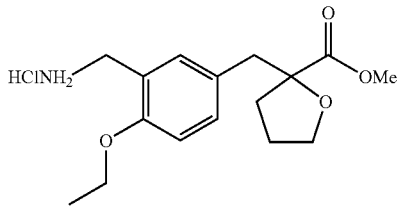

The title compound was obtained according to the method of Reference Example 2 from methyl 2-[(3-{[(t-butoxycarbonyl)amino]methyl}-4-ethoxyphenyl)(hydroxy)methyl]tetrahydro-2-furancarboxylate.

$^1$H-NMR(CDCl$_3$): 1.43 (t, J=6.88 Hz, 3H), 1.65-1.81 (m, 2H), 1.87-1.95 (ddd, J=7.1, 8.0, 12.7 Hz, 1H), 2.19-2.15 (ddd, J=6.1, 7.7, 12.7 Hz, 1H), 2.86 (d, J=14.0 Hz, 1H), 3.09 (d, J=14.0 Hz, 1H), 3.66 (s, 3H), 3.77-3.92 (m, 2H), 4.01-4.13 (br. s, 2H), 4.07 (q, J=6.8 Hz, 2H), 6.76 (d, J=8.6 Hz, 1H), 7.13 (dd, J=1.9, 8.6 Hz, 1H), 7.22 (d, J=1.9 Hz, 1H), 8.18 (br.s, 3H)

Reference Example 25

Methyl 2-(3-methoxybenzyl)-tetrahydro-2-furancarboxylate

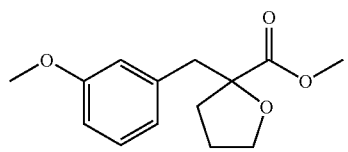

To a solution of 4.44 g of diisopropylamine in 20 ml of tetrahydrofuran were sequentially added 26 ml of 1.6 M solution of n-butyllithium in hexane, 5.30 g of methyl tetrahydro-2-furancarboxylate in 20 ml of tetrahydrofuran and 8.85 g of 1-bromomethyl-3-methoxybenzene in 25 ml of tetrahydrofuran at −70° C. under an atmosphere of nitrogen gas. After warming to room temperature, 100 ml of 1N hydrochloric acid and 200 ml of ethyl acetate were added. The organic layer was dried over anhydrous magnesium sulfate, and the solvent was evaporated. The residue was purified by silica gel column chromatography, to give 6.01 g of the title compound from the 4:1 hexane-ethyl acetate fraction.

$^1$H-NMR(CDCl$_3$): 1.71-1.76 (m, 1H), 1.75-1.86 (m, 1H), 1.88-1.96 (td, J=8.3, 13.1 Hz, 1H), 2.23-2.39 (ddd, J=5.6, 7.8, 13.1 Hz, 1H), 2.96 (d, J=13.7 Hz, 1H) 3.19 (d, J=13.7 Hz, 1H), 3.70 (s, 3H), 3.78 (s, 3H), 3.85-3.95 (m, 2H), 6.74-6.82 (m, 3H), 7.16 (t, J=7.8 Hz, 1H)

Reference Example 26

2-(3-Hydroxybenzyl)-tetrahydro-2-furancarboxylic acid

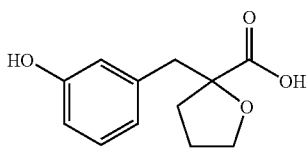

To a solution of 2.50 g of methyl 2-(3-methoxybenzyl)-tetrahydro-2-furancarboxylate in 50 ml of dichloromethane was added 22 ml of a 1 M solution of boron tribromide in dichloromethane at −70° C. under an atmosphere of nitrogen gas. After warming to 0° C., the mixture was cooled again to −70° C., and 20 ml of methanol was added. 200 ml of dichloromethane and 100 ml of water were further added. The organic layer was dried over anhydrous magnesium sulfate, and the solvent was evaporated, to give 2.20 g of the title compound.

$^1$H-NMR(CD$_3$OD): 1.70-1.79 (m, 2H), 2.01-2.10 (m, 2H), 2.84 (d, J=13.8 Hz, 1H), 2.99 (d, J=13.8 Hz, 1H), 3.38-3.49 (m, 2H), 6.63 (d, J=8.0 Hz, 1H), 6.70 (s, 1H), 6.71 (d, J=8.0 Hz, 1H) 7.06 (t, J=8.0 Hz, 1H)

Reference Example 27

Methyl 2-(3-hydroxybenzyl)-tetrahydro-2-furancarboxylate

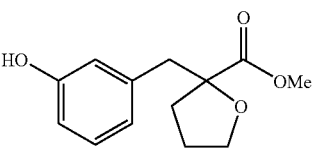

To a solution of 2.20 g of 2-(3-hydroxybenzyl)-tetrahydro-2-furancarboxylate in 50 ml of methanol was added 0.5 ml of sulfuric acid, and the mixture was heated under reflux for 18 hours. The solvent was evaporated, and the residue was dissolved in 200 ml of ethyl acetate. The organic layer washed twice with 50 ml of water, and dried over anhydrous magnesium sulfate. The solvent was evaporated, and the residue was purified by silica gel column chromatography, to give 2.20 g of the title compound from the 7:3 hexane-ethyl acetate fraction.

$^1$H-NMR(CDCl$_3$): 1.64-1.75 (m, 1H), 1.77-1.87 (m, 1H), 1.89-1.97 (td, J=8.0, 12.8 Hz, 1H), 2.24-2.30 (ddd, J=5.8, 9.5, 12.8 Hz, 1H), 2.94 (d, J=14.1 Hz, 1H), 3.16 (d, J=14.1 Hz, 1H), 3.70 (s, 3H), 3.88-3.97 (m, 2H), 6.70 (dd, J=2.2, 7.7 Hz, 1H), 6.75 (d, J=2.22 Hz, 1H), 6.79 (d, J=7.7 Hz, 1H), 7.13 (t, J=7.7 Hz, 1H)

Reference Example 28

Methyl 2-(3-(S)oxiranylmethoxybenzyl)-tetrahydro-2-furancarboxylate

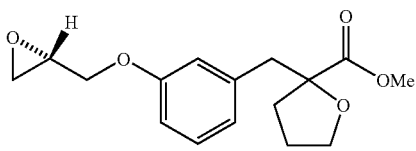

A mixture of 1.10 g of methyl 2-(3-hydroxybenzyl)-tetrahydro-2-furancarboxylate, 1.45 g of (S) glycidyl nosylate, 0.14 g of cesium fluoride and 0.77 g of potassium carbonate in 16 ml of N,N-dimethylformamide was stirred at room temperature for 16 hours, and then 200 ml of ethyl acetate and 100 ml of water were added. The organic layer was sequentially washed with 50 ml of water and 50 ml of brine, and dried over anhydrous magnesium sulfate. The solvent was evaporated, and the residue was purified by silica gel column chromatography, to give 0.95 g of the title compound from the 7:3 hexane-ethyl acetate fraction.

$^1$H-NMR(CDCl$_3$): 1.62-1.72 (m, 1H), 1.76-1.86 (m, 1H), 1.88-1.95 (td, J=7.9, 13.0 Hz, 1H), 2.22-2.29 (ddd, J=6.2, 9.0, 13.0 Hz, 1H), 2.95 (d, J=13.9 Hz, 1H), 3.18 (d, J=13.9 Hz, 1H), 3.69 (s, 3H), 3.85-3.97 (m, 4H), 4.15-4.22 (ddd, J=3.5, 5.1, 10.5 Hz, 1H), 6.78 (d, J=7.9 Hz, 1H), 6.83 (s, 1H), 6.84 (d, J=7.9 Hz, 1H), 7.17 (t, J=7.9 Hz, 1H)

Reference Example 29

Methyl 2-(3-(R)oxiranylmethoxybenzyl)-tetrahydro-2-furancarboxylate

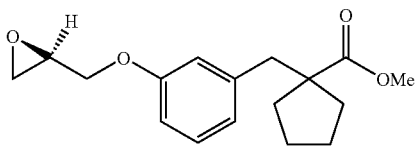

The title compound was obtained according to the method of Reference Example 27 from methyl 2-(3-hydroxybenzyl)-tetrahydro-2-furancarboxylate and (R)-glycidyl nosylate.

$^1$H-NMR(CDCl$_3$): 1.62-1.72 (m, 1H), 1.76-1.86 (m, 1H), 1.88-1.95 (td, J=7.9, 13.0 Hz, 1H), 2.22-2.29 (ddd, J=6.2, 9.0, 13.0 Hz, 1H), 2.95 (d, J=13.9 Hz, 1H), 3.18 (d, J=13.9 Hz, 1H), 3.69 (s, 3H), 3.85-3.97 (m, 4H), 4.15-4.22 (ddd, J=3.5, 5.1, 10.5 Hz, 1H), 6.78 (d, J=7.9 Hz, 1H), 6.83 (s, 1H), 6.84 (d, J=7.9 Hz, 1H), 7.17 (t, J=7.9 Hz, 1H)

Reference Example 30 t-Butyl N-[3-(bromomethyl)benzyl]carbamate

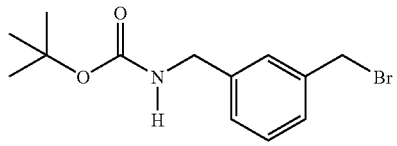

The title compound was obtained according to the method of Reference Example 21 from t-butyl N-[3-(hydroxymethyl)-benzyl]carbamate.

$^1$H-NMR(CDCl$_3$): 1.45 (s, 9H), 4.28 (d, J=6.0 Hz, 2H), 4.49 (s, 2H), 5.00 (br, 1H), 7.19-7.22 (m, 1H), 7.30-7.36 (m, 3H)

Reference Example 31

Isopropyl 2-[(3-{[(t-butoxycarbonyl)amino]methyl}-phenyl)]-methyl]-2,5-dihydro-2-furancarboxylate

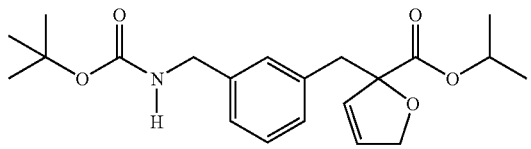

0.146 g of lithium was added to 240 ml of liquid ammonia and 60 ml of tetrahydrofuran at −78° C. under an atmosphere of nitrogen gas. After stirring for 15 minutes, a solution of 1.297 g of isopropyl furan-2-carboxylate in 60 ml of tetrahydrofuran was added dropwise. After stirring for 15 minutes, 3-methyl-1,3-pentadiene was added drop by drop until the deep blue color faded. To the yellow reaction mixture was added dropwise a solution of 1.246 g of t-butyl N-[3-(bromomethyl)benzyl]carbamate in 60 ml of tetrahydrofuran. After stirring at −78° C. for 2 hours, 30 ml of saturated aqueous ammonium chloride was added, and ammonia was evaporated under a flow of nitrogen gas. 200 ml of ethyl acetate and 100 ml of water were added, and the organic layer washed with 100 ml of brine, dried over magnesium sulfate and evaporated. The residue was purified by silica gel column chromatography, to give 0.921 g of the title compound as a white solid.

$^1$H-NMR(CDCl$_3$): 1.12 (t, J=6.3 Hz, 3H), 1.14 (t, J=6.3 Hz, 3H), 1.44 (s, 9H), 3.07 (d, J=13.6 Hz, 1H), 3.21 (d, J=13.6 Hz, 1H), 4.27 (br.d, J=5.4 Hz, 1H), 4.46 (td, J=1.8, 13.6 Hz, 1H), 4.70 (td, J=1.8, 13.6 Hz, 1H), 4.79 (br.s, 1H), 5.01 (sept, J=6.3 Hz, 1H), 5.82 (td, J=1, 8, 6.4 Hz, 1H), 5.87 (td, J=1.8, 6.4 Hz, 1H), 7.12-7.16 (m, 2H), 7.21 (t, J=7.6 Hz, 1H)

Reference Example 32

Isopropyl 2-[3-(ammoniomethyl)-benzyl]-2,5-dihydro-2-furancarboxylate chloride

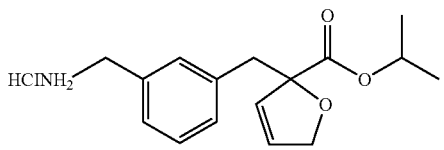

The title compound was obtained according to the method of Reference Example 2 from isopropyl 2-[(3-{[(t-butoxycarbonyl)amino]methyl}-phenyl)]methyl]-2,5-dihydro-2-furancarboxylate.

$^1$H-NMR(CDCl$_1$): 1.22 (d, J=6.3 Hz, 6H), 1.25 (d, J=6.3 Hz, 6H), 3.00 (d, J=13.7 Hz, 1H), 3.15 (d, J=13.7 Hz, 1H), 4.08 (br.s, 2H), 4.44 (d, J=12.8 Hz, 1H), 4.50 (d, J=12.8 Hz, 1H), 5.00 (sept, J=6.3 Hz, 1H), 5.80 (d, J=6.4 Hz, 1H), 5.86 (d, J=6.4 Hz, 1H), 7.12 (d, J=7.5 Hz, 1H), 7.22 (t, J=7.5 Hz, 1H), 7.34 (d, J=7.5 Hz, 1H), 7.43 (s, 1H), 8.56 (br.s, 3H)

Reference Example 33 t-Butyl N-[4-(bromomethyl)benzyl]carbamate

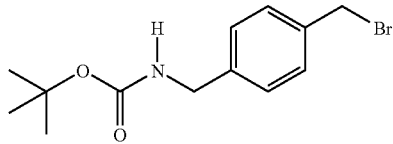

The title compound was obtained according to the method of Reference Example 21 from t-butyl N-[4-(hydroxymethyl)-benzyl]carbamate.

$^1$H-NMR(CDCl$_3$): 1.45 (s, 9H), 4.31 (d, J=5.9 Hz, 2H), 4.49 (s, 2H), 4.84 (br, 1H), 7.24 (d, J=8.0 Hz, 2H), 7.33 (d, J=8.0 Hz, 1H)

Reference Example 34

Methyl 2-[4-(t-butoxycarbonylaminomethyl)-benzyl]-tetrahydro-2-furancarboxylate

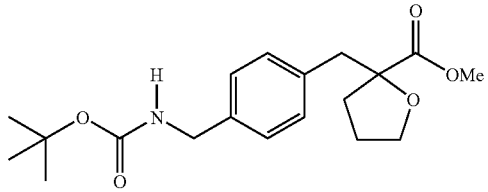

To a solution of diisopropylamine in 10 ml of tetrahydrofuran was added 5.5 ml of 1.6 M solution of n-butyllithium in hexane at −78° C. under an atmosphere of nitrogen gas. After stirring for 30 minutes, a solution of 1.17 g of methyl tetrahydro-2-furancarboxylate in 10 ml of tetrahydrofuran was added dropwise. After stirring for further 30 minutes, a solution of 1.20 g of t-butyl N-[4-(bromomethyl)benzyl]carbamate in 20 ml of tetrahydrofuran was added dropwise, and the mixture was stirred at −78° C. for 3 hours. 50 ml of saturated aqueous ammonium chloride, 200 ml of ethyl acetate and 100 ml of water were added, and the organic layer was dried over anhydrous magnesium sulfate and evaporated. The residue was purified by silica gel column chromatography, to give 0.961 g of the title compound.

$^1$H-NMR(CDCl$_3$): 1.75-1.94 (m, 3H), 2.03-2.10 (m, 1H), 2.96 (d, J=13.6 Hz, 1H), 3.19 (d, J=13.6 Hz, 1H), 3.68 (s, 3H), 3.84-3.95 (m, 2H), 4.27(d, J=4.5 Hz, 2H), 4.77 (br. s, 1H), 7.17-7.21 (m, 4H)

Reference Example 35

Methyl 2-[4-(ammoniomethyl)-benzyl]tetrahydro-2-furancarboxylate chloride

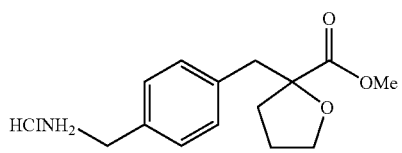

The title compound was obtained according to the method of Reference Example 2 from methyl 2-[4-(t-butoxycarbonylaminomethyl)-benzyl]-tetrahydro-2-furancarboxylate.

$^1$H-NMR(CDCl$_3$): 1.71-1.82 (m, 2H), 1.87-1.95 (td, J=7.8, 11.1 Hz, 1H), 2.17-2.25 (m, 1H), 2.87 (d, J=13.6 Hz, 1H), 3.18 (d, J=13.6 Hz, 1H), 3.62 (q, J=7.8 Hz, 1H), 3.68 (s, 3H), 3.72-3.78 (m, 1H), 4.05 (br. s, 2H), 7.15 (d, J=7.8 Hz, 2H), 7.44 (d, J=7.8 Hz, 2H), 8.22 (br. s, 3H)

Reference Example 36

Methyl 2-{[3-(t-butyldimethylsilanyloxymethyl)-4-ethoxyphenyl]hydroxymethyl}tetrahydro-2-furancarboxylate

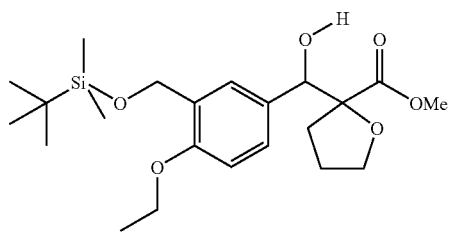

The title compound was obtained according to the method of Reference Example 1 from 3-(t-butyldimethylsilanyloxymethyl)-4-ethoxybenzaldehyde and methyl tetrahydro-2-furancarboxylate.

$^1$H-NMR(CDCl$_3$): 0.08 (s, 6H), 0.95 (s, 9H), 1.23 and 1.37 (t, J=7.0 Hz, 3H), 1.73-1.85(m, 2H), 1.93-2.10 2.15-2.20 and 2.29-2.37 (m, total 2H), 2.73 and 2.82 (d, J=7.0 Hz and 7.0 Hz, 1H), 3.60 and 3.74 (s, 3H), 3.79-4.00 (m, 4H), 4.70 and 4.71 (s, 2H), 4.91 and 4.93 (d, J=7.0 Hz, 1H), 6.74 (m, 2H), 7.33 (s, 1H)

Reference Example 37

Methyl 2-{[3-(t-butyldimethylsilanyloxymethyl)-4-ethoxyphenyl]methylsulfanylcarboxyoxymethyl}tetrahydro-2-furancarboxylate

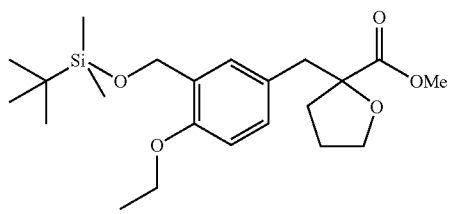

The title compound was obtained according to the method of Reference Example 8 from methyl 2-{[3-(t-butyldimethylsilanyloxymethyl)-4-ethoxyphenyl]-hydroxymethyl}tetrahydro-2-furancarboxylate.

$^1$H-NMR(CDCl$_3$): 0.08 (s, 6H), 0.95(s, 9H), 1.23 and 1.37 (t, J=7.0 Hz, 3H), 1.73-1.95(m, 2H), 2.15-2.32 (m, total 2H), 2.50 and 2.57 (s, 3H), 3.65 and 3.76(s, 3H), 3.60 and 3.74 (s, 3H), 3.96-4.02 (m, 4H), 4.70 and 4.72 (s, 2H), 4.99(br.s, 1H), 6.78 and 6.95 (s, 1H), 6.66-6.75 (m, 2H), 7.47 and 7.54 (s, 1H)

Reference Example 38

Methyl 2-[3-(t-butyldimethylsilanyloxymethyl)-4-ethoxybenzyl]tetrahydro-2-furancarboxylate

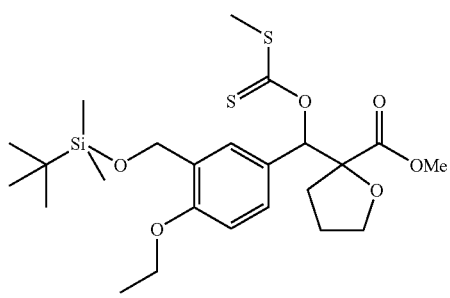

The title compound was obtained according to the method of Reference Example 9 from methyl 2-{[3-(t-butyldimethylsilanyloxymethyl)-4-ethoxyphenyl]methylsulfanylcarboxyoxymethyl}tetrahydro-2-furancarboxylate.

$^1$H-NMR(CDCl$_3$): 0.08 (s, 6H), 0.94 (s, 9H), 1.36 (t, J=7.0 Hz, 3H), 1.60-1.69 (m, 1H), 1.73-1.81 (m, 1H), 1.85-1.93 (ddd, J=7.2, 9.0, 12.6 Hz, 1H), 2.18-2.25 (ddd, J=5.7, 8.0, 12.6 Hz, 1H), 2.92 (d, J=13.9 Hz, 1H), 3.12 (d, J=13.9 Hz, 1H), 3.67 (s, 3H), 3.81-3.90 (m, 2H), 3.98 (q, J=7.0 Hz, 2H), 4.69 (s, 2H), 6.68 (d, J=8.0 Hz, 1H), 7.04 (d, J=8.0 Hz, 1H), 7.26 (s, 1H)

Reference Example 39

Methyl 2-(4-ethoxy-3-hydroxymethylbenzyl)tetrahydro-2-furancarboxylate

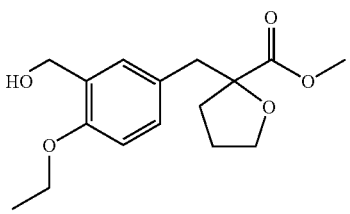

A solution of 0.409 g of methyl 2-[3-(t-butyldimethylsilanyloxymethyl)-4-ethoxybenzyl]tetrahydro-2-furancarboxylate in 20 ml of methanol was treated with 0.400 g of Dowex 50X ion-exchange resin for 6 hours, then the reaction mixture was filtrated and evaporated. The residue was purified by silica gel column chromatography, to give 0.320 g of the title compound.

$^1$H-NMR(CDCl$_3$): 1.43 (t, J=7.0 Hz, 3H), 1.65-1.74 (m, 1H), 1.77-1.85 (m, 1H), 1.87-1.94 (td, J=8.3, 13.2 Hz, 1H), 2.23-2.31 (ddd, J=6.6, 8.0, 13.2 Hz, 1H), 2.43 (br.s, 1H), 2.93 (d, J=13.9 Hz, 1H), 3.15 (d, J=13.9 Hz, 1H), 3.68 (s, 3H), 3.85-3.95 (m, 2H), 4.07 (q, J=7.0 Hz, 2H), 4.64 (d, J=13.2 Hz, 1H), 4.68 (d, J=13.2 Hz, 1H), 6.76 (d, J=8.0 Hz, 1H), 7.01 (s, 1H), 7.04 (d, J=8.0 Hz, 1H)

Reference Example 40

N-Hydroxymethyl-4-propoxybenzamide

4-Propoxybenzamide, 2.02 g of barium hydroxide and 90 ml of 35% aqueous formaldehyde were heated to 80° C. When the solution had become almost transparent, it was filtrated hot. This solution was stored at 0° C. for two days, and 100 ml of water was added. The precipitated crystals were collected and dried, to give 17.0 g of the title compound.

$^1$H-NMR(CDCl$_3$): 1.04 (t, J=6.8 Hz, 3H), 1.83 (sext, J=6.8 Hz, 2H), 3.43 (t, 6.0 Hz, 1H), 3.96 (t, J=6.8 Hz, 2H), 4.94 (t, J=6.60 Hz, 2H), 6.94 (d, J=8.2 Hz, 2H), 7.00 (br.s, 1H), 7.75 (d, J=8.2 Hz, 2H)

Reference Example 41

Methyl 2-[(4-ethoxyphenyl)hydroxymethyl]tetrahydro-2-furancarboxylate

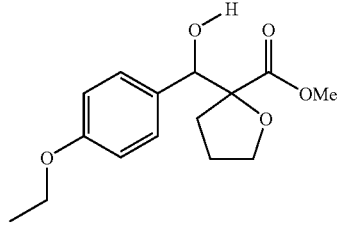

The title compound was obtained according to the method of Reference Example 1 from 4-ethoxybenzaldehyde and methyl tetrahydro-2-furancarboxylate.

$^1$H-NMR (CDCl$_3$): 1.23 and 1.37 (t, J=7.0 Hz, 3H), 1.64-1.85(m, 2H), 1.90-2.14, 2.17-2.26 and 2.29-2.37 (m, total 2H), 2.90 and 2.94 (d, J=7.0 Hz and 7.0 Hz, 1H), 3.61 and 3.76 (s, 3H), 3.79-4.06 (m, 4H), 4.94 and 4.96 (d, J=7.0 Hz, 1H), 6.72 and 6.74 (d, J=8.0 Hz, 2H), 7.31 and 7.33 (d, J=8.0 Hz, 2H)

Reference Example 42

Methyl (4-ethoxybenzyl)-tetrahydro-2-furancarboxylate

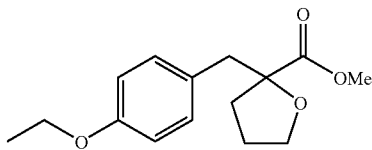

The title compound was obtained according to the method of Reference Example 2 from methyl 2-[(4-ethoxyphenyl)hydroxymethyl]tetrahydro-2-furancarboxylate.

$^1$H-NMR(CDCl$_3$): 1.39 (t, J=7.0 Hz, 3H), 1.62-1.71(m, 1H), 1.75-1.86 (m, 1H), 1.88-1.96 (td, J=8.3, 12.8 Hz, 1H), 2.22-2.29 (ddd, J=5.8, 7.4, 12.8 Hz, 1H), 2.92 (d, J=14.1 Hz, 1H), 3.13 (d, J=14.1 Hz, 1H), 3.68 (s, 3H), 3.85-3.95 (m, 2H), 4.00 (q, J=7.0 Hz, 2H), 6.79 (d, J=8.0 Hz, 2H), 7.12 (d, J=8.0 Hz, 2H)

Reference Example 43

Methyl 2-(3-{[(4-propoxybenzoyl)amino]methyl}-4-ethoxybenzyl)tetrahydro-2-furancarboxylate

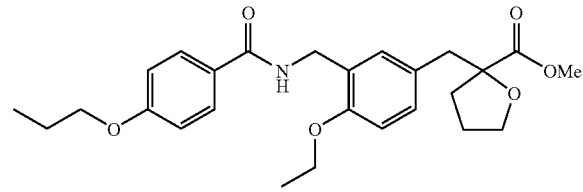

The title compound was obtained according to the method of Reference Example 17 from N-hydroxymethyl-4-propoxybenzamide and methyl (4-ethoxybenzyl)-tetrahydro-2-furancarboxylate.

$^1$H-NMR(CDCl$_3$): 1.13 (t, J=7.6 Hz, 3H), 1.43 (t, J=7.1 Hz, 3H), 1.68-1.93 (m, 5H), 2.21-2.28 (ddd, J=5.9, 7.6, 13.0 Hz, 1H), 2.89 (d, J=14.2 Hz, 1H), 3.13 (d, J=14.2 Hz, 1H), 3.67 (s, 3H), 3.88-3.96 (m, 4H), 4.07 (q, J=7.1 Hz, 2H), 4.58 (dd, J=5.7, 12.9 Hz, 1H), 4.62 (dd, J=5.7, 12.9 Hz, 1H), 6.61 (t, J=5.7 Hz, 1H), 6.77 (d, J=8.5 Hz, 1H), 6.90 (d, J=9.1 Hz, 2H), 7.11 (dd, J=2.4, 8.5 Hz, 1H), 7.17 (d, J=2.4 Hz, 1H), 7.70 (d, J=9.1 Hz, 2H)

Reference Example 44

(4-Ethoxybenzyl)-tetrahydro-2-furancarboxylic acid

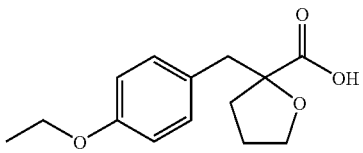

To a solution of 10.85 g methyl (4-ethoxybenzyl)-tetrahydro-2-furancarboxylate in 200 ml of ethanol was added 50 ml of 5N sodium hydroxide solution, and the mixture was stirred at room temperature overnight. The solvent was evaporated, and the residue was dissolved in 500 ml of ethyl acetate and 100 ml of 5N hydrochloric acid. The organic layer was dried over anhydrous magnesium sulfate, and the solvent was evaporated. The residue was washed with diisopropyl ether, to give 8.74 g of the title compound.

$^1$H-NMR(CDCl$_3$): 1.40 (t, J=7.3 Hz, 3H), 1.74-1.90 (m, 2H), 1.98-2.06 (td, J=8.0, 13.2 Hz, 1H), 2.33-2.40 (ddd, J=5.2, 8.0, 13.2 Hz, 1H), 2.88 (d, J=14.2 Hz, 1H), 3.17 (d, J=14.2 Hz, 1H), 3.83-3.89 (q, J=8.0 Hz, 1H), 3.97-4.03 (m, 1H), 4.00 (d, J=7.3 Hz, 2H), 6.80 (d, J=8.0 Hz, 2H), 7.27 (d, J=8.0 Hz, 2H)

Reference Example 45

Methyl 2-(3-{[(4-propoxybenzoyl)amino]methyl}-4-ethoxybenzyl)tetrahydro-2-furancarboxylate

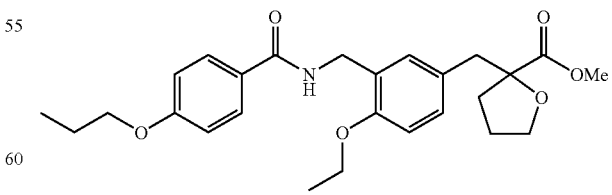

The title compound was obtained according to the method of Reference Example 17 from N-hydroxymethyl-4-propoxybenzamide and methyl (4-ethoxybenzyl)-tetrahydro-2-furancarboxylate.

Reference Example 46

2-(S)-2-(3-{[(4-Propoxybenzoyl)amino]methyl}-4-ethoxybenzyl)tetrahydro-2-furancarboxylic acid 1-(R)-(2-hydroxy-1-phenylethyl)-amide and 2-(R)-2-(3-{[(4-propoxybenzoyl)amino]methyl}-4-ethoxybenzyl)tetrahydro-2-furancarboxylic acid 1-(R)-(2-hydroxy-1-phenylethyl)-amide

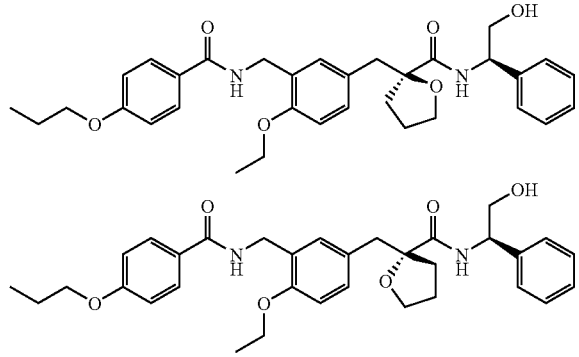

To a solution of 4.69 g of 2-(3-{[(4-propoxybenzoyl)-amino]methyl}-4-ethoxybenzyl)tetrahydro-2-furancarboxylate in 50 ml of N,N-dimethylformamide were sequentially added 1.63 g of (R) 2-amino-2-phenylethanol, 1.63 ml of triethylamine and 1.78 ml of diethyl cyanophosphonate at 0° C., and the mixture was stirred at room temperature for 15 hours. 500 ml of ethyl acetate and 300 ml of water were added, and the organic layer was sequentially washed with 200 ml of water and 200 ml of brine, and dried over anhydrous magnesium sulfate. The solvent was evaporated, and the residue was purified by silica gel column chromatography, to give 2.47 g of the (S),(R)-diastereoisomer from the 1:1 hexane-ethyl acetate fraction, and 2.96 g of the (R),(R)-diastereoisomer from the 1:4 hexane-ethyl acetate fraction.

$^1$H-NMR(CDCl$_3$): 1.04 (t, J=7.3 Hz, 3H), 1.43 (t, J=6.9 Hz, 3H), 1.75-1.96 (m, 5H), 2.34-2.41 (m, 1H), 2.80 (d, J=13.9 Hz, 1H), 3.10-3.17 (dd, 6.0, 7.8 Hz, 1H), 3.22 (d, J=13.9 Hz, 1H), 3.37-3.43 (ddd, J=7.5, 7.8, 12.0 Hz, 1H), 3.43-3.50 (ddd, J=6.0, 7.5, 12.0 Hz, 1H), 3.86-3.97 (m, 2H), 3.94 (t, J=6.0 Hz, 2H), 4.07 (q, J=6.9 Hz, 3H), 4.63 (t, J=5.7 Hz, 2H), 4.79-4.85 (dt, J=3.6, 7.5 Hz, 1H), 6.81 (d, J=8.2 Hz, 1H), 6.90 (d, J=8.5 Hz, 2H), 7.01 (t, J=5.7 Hz, 1H), 7.08 (dd, J=1.7, 8.5 Hz, 2H), 7.12 (dd, J=2.3, 8.2 Hz, 1H), 7.23-7.30 (m, 5H), 7.76 (d, J=8.5 Hz, 2H)

$^1$H-NMR(CDCl$_3$): 1.04 (t, J=7.4 Hz, 3H), 1.46 (t, J=7.0 Hz, 3H), 1.77-1.98 (m, 5H), 2.37-2.44(m, 1H), 2.51 (br., s), 2.80 (d, J=14.2 Hz, 1H), 3.15 (d, J=14.2 Hz, 1H), 3.78 (br.s, 2H), 3.90-3.98 (m, 2H), 3.95 (t, J=6.4 Hz, 2H), 4.04 (q, J=7.0 Hz, 2H), 4.42-4.47 (dd, J=5.8, 14.5 Hz, 1H), 4.54-4.61 (dd, J=5.8, 14.5 Hz, 1H), 4.83-4.88 (td, J=5.8, 7.4 Hz, 1H), 6.37 (t, J=5.7 Hz, 1H), 6.67 (d, J=8.3 Hz, 1H), 6.83-6.83 (m, 2H), 6.89 (d, J=8.7 Hz, 2H), 7.03 (dd, J=2.4, 8.3 Hz, 1H), 7.15-7.20 (m, 4H), 7.23 (d, J=7.4 Hz, 1H), 7.65 (d, J=8.7 Hz, 2H)

Example 1

2-(3-{[(2-Chloro-4-propoxybenzoyl)amino]methyl}-4-methoxybenzyl)tetrahydro-2-furancarboxylic acid

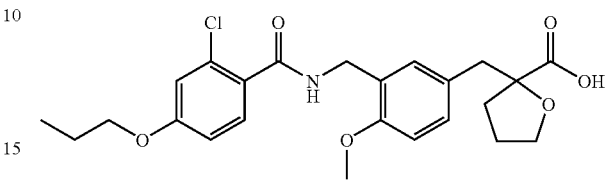

To a solution of 0.091 g of methyl 2-[3-(ammoniomethyl)-4-methoxybenzyl]tetrahydro-2-furancarboxylate chloride and 0.074 g of 2-chloro-4-propoxybenzoic acid in 2.5 ml of N,N-dimethylformamide were added 0.119 µl of triethylamine and 0.119 µl of diethyl cyanophosphonate, and the mixture was stirred at room temperature for 4 hours. 10 ml of water and 10 ml of ethyl acetate were added, and the organic layer was evaporated. The residue was dissolved in 2.5 ml of ethanol, 0.3 ml of 5N sodium hydroxide was added, and the mixture was stirred at room temperature for 14 hours. The reaction mixture was concentrated, and 5 ml of ethyl acetate, 2.5 ml of water and 0.5 ml of 5N hydrochloric acid were added. The organic layer was concentrated, and the residue was purified by HPLC, to give 0.081 g of the title compound as a white solid.

$^1$H-NMR(CDCl$_3$): 1.06(t, J=6.9 Hz, 3H), 1.76-1.88(m, 4H), 2.01(td, J=7.8, 13.2 Hz, 1H), 2.36(ddd, J=5.3, 7.6, 2 Hz, 1H), 2.89(d, J=14.3 Hz, 1H), 3.16(d, J=14.3 Hz, 1H), 3.84(s, 3H), 3.87-3.93(m, 1H), 3.92(t, J=6.7 Hz, 2H), 3.99 (ddd, J=5.9, 7.1, 8.2 Hz, 1H), 4.58(dd, J=5.7, 14.3 Hz, 1H), 4.63(dd, J=5.7, 3 Hz, 1H), 6.78(d, J=8.2 Hz, 1H), 6.83(dd, J=2.7, 8.2 Hz, 1H), 6.88(d, J=2.7 Hz, 1H), 6.98(br.s, 1H), 7.13(dd, J=2.2, 8.1 Hz, 1H), 7.27(d, J=2.2 Hz, 1H), 7.73(d, J=8.1 Hz, 1H)

MS m/e (ESI) 462.21 (MH+)

Example 2

2-(3-{[(2,4-Dichlorobenzoyl)amino]methyl}-4-methoxybenzyl)tetrahydro-2-furancarboxylic acid

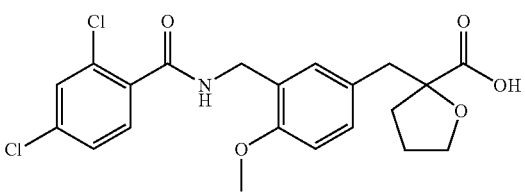

The title compound was obtained according to the method of Example 1 from methyl 2-[3-(ammoniomethyl)-4-methoxybenzyl]tetrahydro-2-furancarboxylate chloride and 2,4-dichlorobenzoic acid.

MS m/e (ESI) 441.12 (MH+)

Example 3

2-(3-{[(2-Fluoro-4-(trifluoromethyl)benzoyl)amino]methyl}-4-methoxybenzyl)tetrahydro-2-furancarboxylic acid

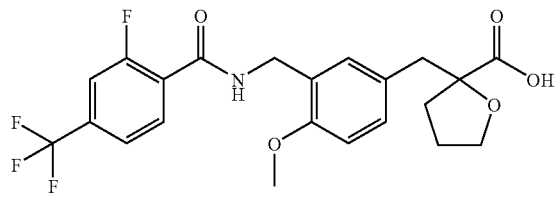

The title compound was obtained according to the method of Example 1 from methyl 2-[3-(ammoniomethyl)-4-methoxybenzyl]tetrahydro-2-furancarboxylate chloride and 2-fluoro-4-(trifluoromethyl)benzoic acid.

MS m/e (ESI) 457.18 (MH+)

Example 4

2-(3-{[(4-Chloro-2-fluorobenzoyl)amino]methyl}-4-methoxybenzyl)tetrahydro-2-furancarboxylic acid

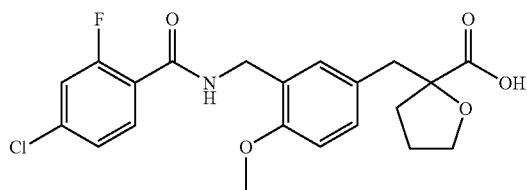

The title compound was obtained according to the method of Example 1 from methyl 2-[3-(ammoniomethyl)-4-methoxybenzyl]tetrahydro-2-furancarboxylate chloride and 4-chloro-2-fluorobenzoic acid.

MS m/e (ESI) 422.16 (MH+)

Example 5

2-(3-{[(2-Chloro-4-cyclopentyloxybenzoyl)amino]methyl}-4-methoxybenzyl)tetrahydro-2-furancarboxylic acid

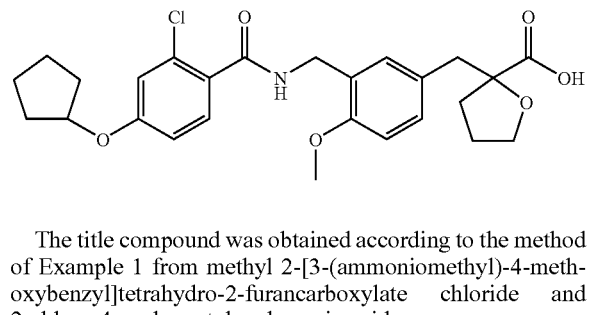

The title compound was obtained according to the method of Example 1 from methyl 2-[3-(ammoniomethyl)-4-methoxybenzyl]tetrahydro-2-furancarboxylate chloride and 2-chloro-4-cyclopentyloxybenzoic acid.

MS m/e (ESI) 488.24 (MH+)

Example 6

2-(3-{[(2-Chloro-4-cyclohexylbenzoyl)amino]methyl}-4-methoxybenzyl)tetrahydro-2-furancarboxylic acid

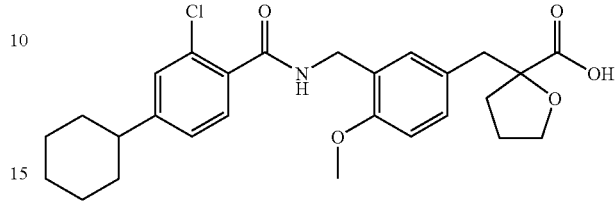

The title compound was obtained according to the method of Example 1 from methyl 2-[3-(ammoniomethyl)-4-methoxybenzyl]tetrahydro-2-furancarboxylate chloride and 2-chloro-4-cyclohexylbenzoic acid.

MS m/e (ESI) 452.31 (MH+)

Example 7

2-[4-Methoxy-3-({[(4-methyl-2-phenyl-1,3-thiazol-5-yl)carbonyl]amino}methyl)benzyl]tetrahydro-2-furancarboxylic acid

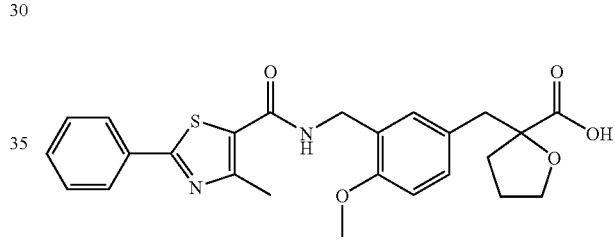

The title compound was obtained according to the method of Example 1 from methyl 2-[3-(ammoniomethyl)-4-methoxybenzyl]tetrahydro-2-furancarboxylate chloride and 4-methyl-2-phenyl-1,3-thiazol-5-carboxylic acid.

MS m/e (ESI) 467.13 (MH+)

Example 8

2-{4-Methoxy-3-[({[4-methyl-2-(4-methylphenyl)-1,3-thiazol-5-yl]carbonyl}amino)methyl]benzyl}tetrahydro-2-furancarboxylic acid

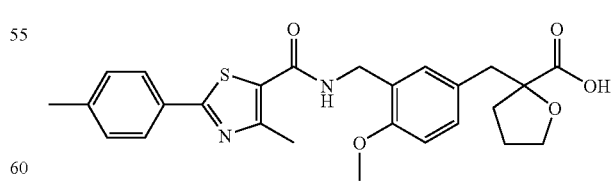

The title compound was obtained according to the method of Example 1 from methyl 2-[3-(ammoniomethyl)-4-methoxybenzyl]tetrahydro-2-furancarboxylate chloride and 4-methyl-2-(4-methylbenzyl)-1,3-thiazol-5-carboxylic acid.

MS m/e (ESI) 481.18 (MH+)

Example 9

2-{3-[({[2-(4-Chlorophenyl)-4-methyl-1,3-thiazol-5-yl]carbonyl}amino)methyl]-4-methoxybenzyl}tetrahydro-2-furancarboxylic acid

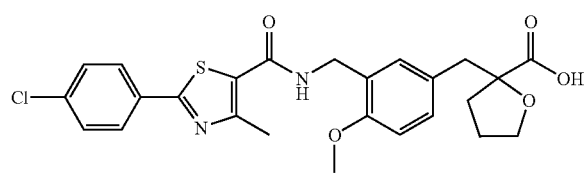

The title compound was obtained according to the method of Example 1 from methyl 2-[3-(ammoniomethyl)-4-methoxybenzyl]tetrahydro-2-furancarboxylate chloride and 2-(4-chlorobenzyl)-4-methyl-1,3-thiazol-5-carboxylic acid.

MS m/e (ESI) 501.15 (MH+)

Example 10

2-[4-Methoxy-3-({[(5-phenyl-3-isoxazolyl)carbonyl]amino}-methyl)benzyl]tetrahydro-2-furancarboxylic acid

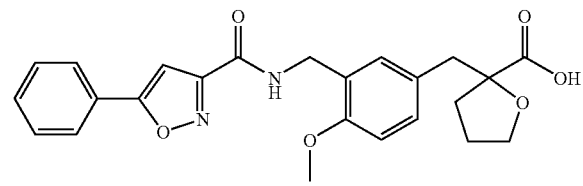

The title compound was obtained according to the method of Example 1 from methyl 2-[3-(ammoniomethyl)-4-methoxybenzyl]tetrahydro-2-furancarboxylate chloride and 5-phenylisoxazole-3-carboxylic acid.

MS m/e (ESI) 437.23 (MH+)

Example 11

1-(3-{[(2,4-Dichlorobenzoyl)amino]methyl}-4-methoxybenzyl)-1-cyclopropanecarboxylic acid

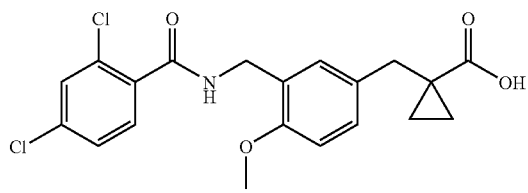

The title compound was obtained according to the method of Example 1 from methyl 1-[3-(ammoniomethyl)-4-methoxybenzyl-1-cyclopropanecarboxylate chloride and 2,4-dichlorobenzoic acid.

MS m/e (ESI) 430.05 (MNa+)

Example 12

1-(3-{[(4-Cyclohexylbenzoyl)amino]methyl}-4-methoxybenzyl)-1-cyclopropanecarboxylic acid

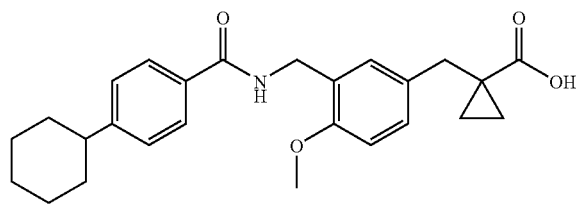

The title compound was obtained according to the method of Example 1 from methyl 1-[3-(ammoniomethyl)-4-methoxybenzyl-1-cyclopropanecarboxylate chloride and 4-cyclohexylbenzoic acid.

MS m/e (ESI) 422.22 (MH+)

Example 13

1-{4-Methoxy-3-[({[4-methyl-2-(4-methylphenyl)-1,3-thiazol-5-yl]carbonyl}amino)methyl]benzyl}-1-cyclopropanecarboxylic acid

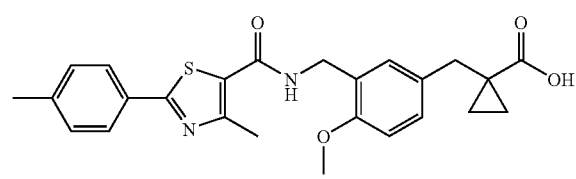

The title compound was obtained according to the method of Example 1 from methyl 1-[3-(ammoniomethyl)-4-methoxybenzyl-1-cyclopropanecarboxylate chloride and 5-methyl-2-(4-methylbenzyl)-1,3-thiazol-4-carboxylic acid.

MS m/e (ESI) 451.16 (MH+)

Example 14

1-[4-Methoxy-3-({[3-(5-methyl-2-phenyl-1,3-oxazol-4-yl)propanoyl]amino}methyl)benzyl]-1-cyclopropanecarboxylic acid

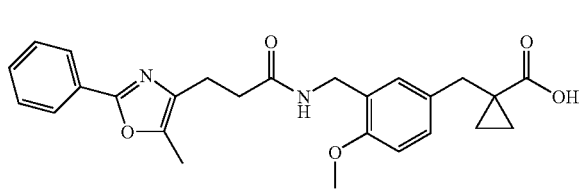

The title compound was obtained according to the method of Example 1 from methyl 1-[3-(ammoniomethyl)-4-methoxybenzyl-1-cyclopropanecarboxylate chloride and 3-(5-methyl-2-phenyl-1,3-oxazol-4-yl)propanoic acid.

MS ale (ESI) 449.19 (MH+)

Example 15

1-[4-Methoxy-3-({[2-({[(E)-1-(3-phenyl)-phenyleth-ylidene]amino}oxy)acetyl]amino}methyl)benzyl]-1-cyclopropanecarboxylic acid

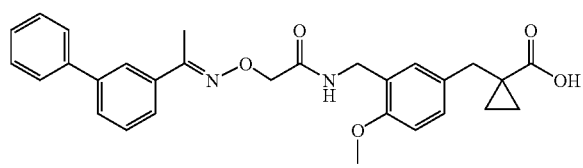

The title compound was obtained according to the method of Example 1 from methyl 1-[3-(ammoniomethyl)-4-methoxybenzyl-1-cyclopropanecarboxylate chloride and 2-({[(E)-1-(3-phenyl)-phenylethylidene]amino}oxy)acetic acid.

MS m/e (ESI) 487.20 (MH+)

Example 16

1-[4-Methoxy-3-({[2-({[(E)-1-(4-pyridin-2-yl)-phenylethylidene]amino}oxy)acetyl]amino}methyl)benzyl]-1-cyclopropanecarboxylic acid

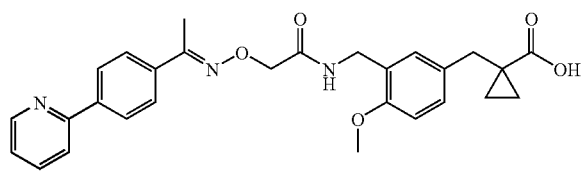

The title compound was obtained according to the method of Example 1 from methyl 1-[3-(ammoniomethyl)-4-methoxybenzyl-1-cyclopropanecarboxylate chloride and 2-({[(E)-1-(4-pyridin-2-yl)-phenylethylidene]amino}oxy)acetic acid.

MS m/e (ESI) 488.19 (MH+)

Example 17

2-(3-{[(2-Chloro-4-propoxybenzoyl)amino]methyl}benzyl)-tetrahydro-2-furancarboxylic acid

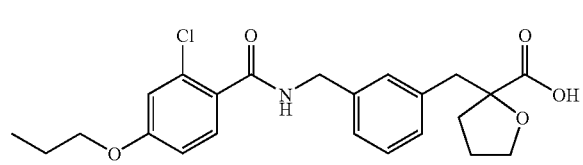

The title compound was obtained according to the method of Example 1 from methyl 2-[3-(ammoniomethyl)-benzyl]tetrahydro-2-furancarboxylate chloride and 2-chloro-4-propoxybenzoic acid.

MS m/e (ESI) 432.08 (MH+)

Example 18

2-(3-{[(2,4-Dichlorobenzoyl)amino]methyl}benzyl)tetrahydro-2-furancarboxylic acid

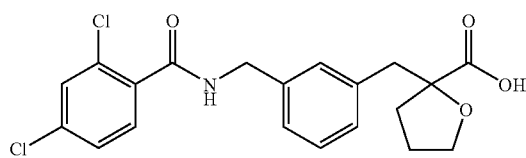

The title compound was obtained according to the method of Example 1 from methyl 2-[3-(ammoniomethyl)-benzyl]tetrahydro-2-furancarboxylate chloride and 2,4-dichlorobenzoic acid.

$^1$H-NMR(CDCl$_3$): 1.75-1.86 (m, 2H), 1.94-2.01 (td, J=7.5, 12.8 Hz, 1H), 2.30-2.37 (ddd, J=6.8, 7.5, 12.8 Hz, 1H), 2.87 (d, J=13.9 Hz, 1H), 3.18 (d, J=13.9 Hz, 1H), 3.81-3.87 (q, J=7.5 Hz, 1H), 3.92-3.96 (dt, J=6.8, 7.5 Hz, 1H), 4.55 (d, J=6.0 Hz, 2H), 6.46-6.53 (br.s, 1H), 7.11 (br.d, J=7.2 Hz, 1H), 7.16-7.21 (m, 3H), 7.25 (dd, J=2.2, 8.4 Hz, 1H), 7.36 (d, J=2.2 Hz, 1H), 7.61 (d, J=8.4 Hz, 1H)

MS m/e (ESI) 432.92 (MNa+)

Example 19

2-(3-{[(2-Fluoro-4-(trifluoromethyl)-benzoyl)amino]methyl}-benzyl)tetrahydro-2-furancarboxylic acid

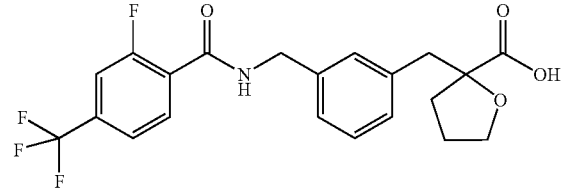

The title compound was obtained according to the method of Example 1 from methyl 2-[3-(ammoniomethyl)-benzyl]tetrahydro-2-furancarboxylate chloride and 2-fluoro-4-(trifluoromethyl)benzoic acid.

MS m/e (ESI) 426.16 (MH+)

Example 20

2-(3-{[(2-Chloro-4-phenylbenzoyl)amino]methyl}benzyl)-tetrahydro-2-furancarboxylic acid

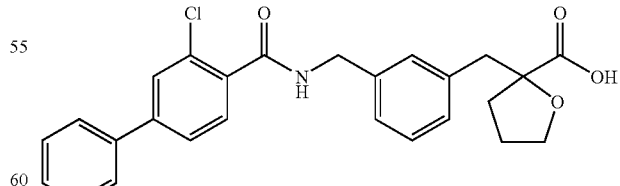

The title compound was obtained according to the method of Example 1 from methyl 2-[3-(ammoniomethyl)benzyl]tetrahydro-2-furancarboxylate chloride and 2-chloro-4-phenylbenzoic acid.

MS m/e (ESI) 472.01 (MNa+)

Example 21

2-(3-{[(4-Cyclohexylbenzoyl)amino]methyl}benzyl)tetrahydro-2-furancarboxylic acid

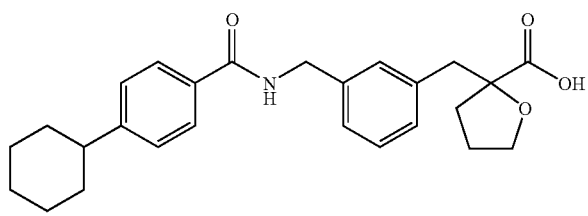

The title compound was obtained according to the method of Example 1 from methyl 2-[3-(ammoniomethyl)-benzyl]tetrahydro-2-furancarboxylate chloride and 4-cyclohexylbenzoic acid.

MS m/e (ESI) 422.14 (MH+)

Example 22

2-(3-{[(2-Chloro-4-ethoxybenzoyl)amino]methyl}benzyl)-tetrahydro-2-furancarboxylic acid

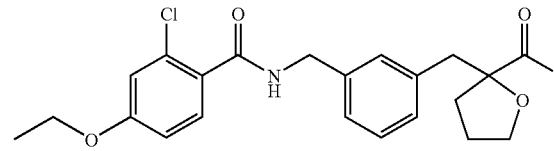

The title compound was obtained according to the method of Example 1 from methyl 2-[3-(ammoniomethyl)-benzyl]tetrahydro-2-furancarboxylate chloride and 2-chloro-4-ethoxybenzoic acid.

MS m/e (ESI) 418.06 (MH+)

Example 23

2-(3-{[(2-Chloro-4-isopropoxybenzoyl)amino]methyl}benzyl)-tetrahydro-2-furancarboxylic acid

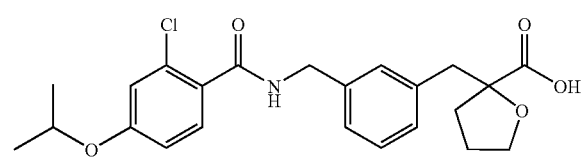

The title compound was obtained according to the method of Example 1 from methyl 2-[3-(ammoniomethyl)-benzyl]tetrahydro-2-furancarboxylate chloride and 2-chloro-4-isopropoxybenzoic acid.

MS m/e (ESI) 432.09 (MH+)

Example 24

2-(3-{[(2-Chloro-4-cyclopentyloxybenzoyl)amino]methyl}-benzyl)tetrahydro-2-furancarboxylic acid

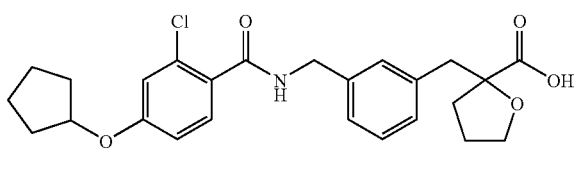

The title compound was obtained according to the method of Example 1 from methyl 2-[3-(ammoniomethyl)-benzyl]tetrahydro-2-furancarboxylate chloride and 2-chloro-4-cyclopentyloxybenzoic acid.

MS m/e (ESI) 458.10 (MH+)

Example 25

2-{3-[({[4-Methyl-2-(4-methylphenyl)-1,3-thiazol-5-yl]carbonyl}amino)methyl]benzyl}tetrahydro-2-furancarboxylic acid

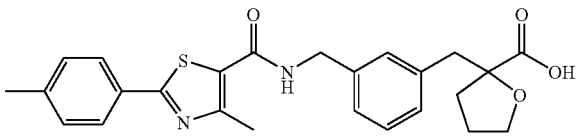

The title compound was obtained according to the method of Example 1 from methyl 2-[3-(ammoniomethyl)-benzyl]tetrahydro-2-furancarboxylate chloride and 4-methyl-2-(4-methylbenzyl)-1,3-thiazol-5-carboxylic acid.

MS m/e (ESI) 451.10 (MH+)

Example 26

2-{3-[({[4-Ethyl-2-(4-methylphenyl)-1,3-thiazol-5-yl]carbonyl}amino)methyl]benzyl}tetrahydro-2-furancarboxylic acid

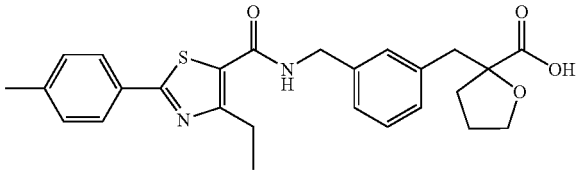

The title compound was obtained according to the method of Example 1 from methyl 2-[3-(ammoniomethyl)-benzyl]tetrahydro-2-furancarboxylate chloride and 4-ethyl(4-methylbenzyl)-1,3-thiazol-4-carboxylic acid.

MS m/e (ESI) 465.13 (MH+)

Example 27

2-{3-[({[2-(4-Chlorophenyl)-4-methyl-1,3-thiazol-5-yl]carbonyl}amino)methyl]benzyl}tetrahydro-2-furancarboxylic acid

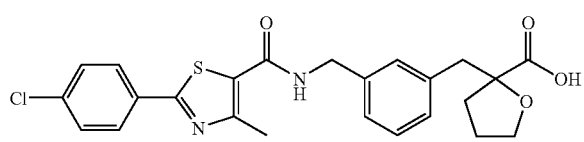

The title compound was obtained according to the method of Example 1 from methyl 2-[3-(ammoniomethyl)-benzyl]tetrahydro-2-furancarboxylate chloride and 2-(4-chlorobenzyl)-4-methyl-1,3-thiazol-5-carboxylic acid.

MS m/e (ESI) 471.05 (MH+)

Example 28

2-{3-[({[2-(2,4-Dichlorophenyl)-4-methyl-1,3-thiazol-5-yl]carbonyl}amino)methyl]benzyl}tetrahydro-2-furancarboxylic acid

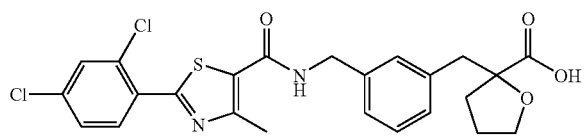

The title compound was obtained according to the method of Example 1 from methyl 2-[3-(ammoniomethyl)-benzyl]tetrahydro-2-furancarboxylate chloride and 2-(2,4-dichlorobenzyl)-4-methyl-1,3-thiazol-5-carboxylic acid.

MS m/e (ESI) 505.02 (MH+)

Example 29

2-(3-{[({[4-(Trifluoromethyl)benzyl]oxy}carbonyl)amino]-methyl}benzyl)tetrahydro-2-furancarboxylic acid

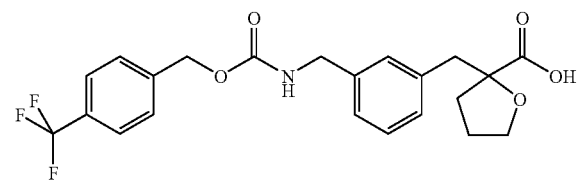

To a solution of 0.020 g of methyl 2-[3-(ammoniomethyl)benzyl]tetrahydro-2-furancarboxylate chloride in 0.5 ml of N,N-dimethylformamide were added 0.064 g of cesium carbonate and 0.046 g of tetrabutylammonium iodide, and dry ice was added thereto little by little over 30 minutes with stirring. 30 μl of 4-trifluoromethylbenzyl bromide was added, and the mixture was stirred for a further 4 hours while adding dry ice. 2 ml of ethyl acetate and 2 ml of water were added, and the organic layer was concentrated. The residue was dissolved in 0.5 ml of ethanol, 0.1 ml of a 5N solution of sodium hydroxide was added, and the mixture was stirred for 14 hours. The reaction mixture was concentrated, and 1 ml of ethyl acetate, 1 ml of water and 0.2 ml of 5N hydrochloric acid were added. The organic layer was concentrated, and the residue was purified by HPLC, to give 0.003 g of the title compound as a white solid.

$^1$H-NMR (CDCl$_3$): 1.70-2.05 (m, 2H), 2.29-2.36 (ddd, J=6.3, 7.6, 13.9 Hz, 1H), 2.36-2.45 (td, J=7.2, 13.9 Hz, 1H), 2.8(d, J=13.5 Hz, 1H), 3.16 (d, J=13.5 Hz, 1H), 3.77-3.95 (m, 2H), 4.30 (d, J=4.9 Hz, 1H), 5.00-5.07 (br. s, 1H), 5.13 (s, 2H), 7.07-7.21 (m, 4H), 7.41 (d, J=8.1 Hz, 2H), 7.54(d, J=8.1 Hz, 2H)

MS m/e (ESI) 460.09 (MNa+)

Example 30

2-(3-{[({[2-(Trifluoromethyl)benzyl]oxy}carbonyl)amino]-methyl}benzyl)tetrahydro-2-furancarboxylic acid

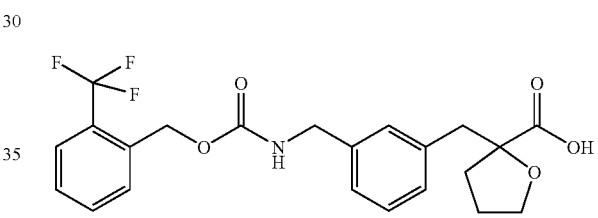

The title compound was obtained according to the method of Example 29 from methyl 2-[3-(ammoniomethyl)-benzyl]tetrahydro-2-furancarboxylate chloride and 2-trifluoromethylbenzyl bromide.

MS m/e (ESI) 460.09 (MNa+)

Example 31

2-(3-{[({[3-(Trifluoromethyl)benzyl]oxy}carbonyl)amino]-methyl}benzyl)tetrahydro-2-furancarboxylic acid

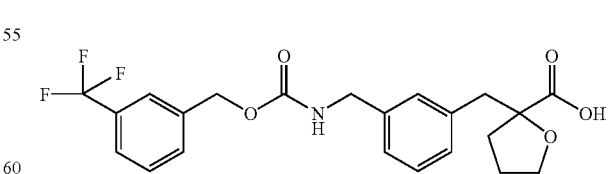

The title compound was obtained according to the method of Example 29 from methyl 2-[3-(ammoniomethyl)-benzyl]tetrahydro-2-furancarboxylate chloride and 3-trifluoromethylbenzyl bromide.

MS m/e (ESI) 460.08 (MNa+)

Example 32

2-(3-{[({[3-Chlorobenzyl]oxy}carbonyl)amino]methyl}benzyl)-tetrahydro-2-furancarboxylic acid

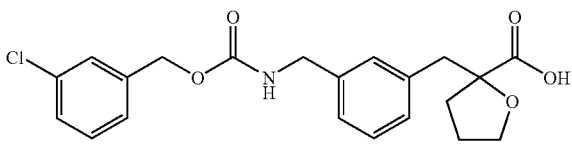

The title compound was obtained according to the method of Example 29 from methyl 2-[3-(ammoniomethyl)-benzyl]tetrahydro-2-furancarboxylate chloride and 3-chlorobenzyl bromide.

MS m/e (ESI) 426.06 (MNa+)

Example 33

2-(3-{[({[4-Chlorobenzyl]oxy}carbonyl)amino]methyl}benzyl)-tetrahydro-2-furancarboxylic acid

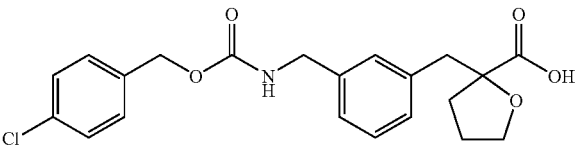

The title compound was obtained according to the method of Example 29 from methyl 2-[3-(ammoniomethyl)-benzyl]tetrahydro-2-furancarboxylate chloride and 4-chlorobenzyl bromide.

MS m/e (ESI) 426.06 (MNa+)

Example 34

2-(3-{[({[2,4-Dichlorobenzyl]oxy}carbonyl)amino]methyl}-benzyl)tetrahydro-2-furancarboxylic acid

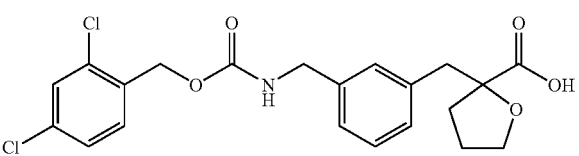

The title compound was obtained according to the method of Example 29 from methyl 2-[3-(ammoniomethyl)-benzyl]tetrahydro-2-furancarboxylate chloride and 2,4-dichlorobenzyl bromide.

MS m/e (ESI) 460.02 (MNa+)

Example 35

2-(3-{[({[2,6-Dichlorobenzyl]oxy}carbonyl)amino]methyl}-benzyl)tetrahydro-2-furancarboxylic acid

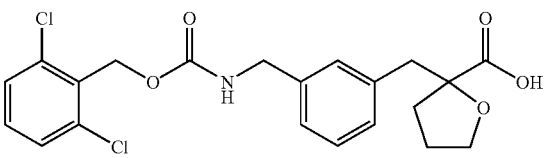

The title compound was obtained according to the method of Example 29 from methyl 2-[3-(ammoniomethyl)-benzyl]tetrahydro-2-furancarboxylate chloride and 2,6-dichlorobenzyl bromide.

MS m/e (ESI) 460.02 (MNa+)

Example 36

2-({2-[2-(4-Isopropylphenoxy)ethoxy]-4-pyridyl}methyl)tetrahydrofuran-2-carboxylic acid and 2-({1-[2-(4-isopropylphenoxy)ethyl]-2-oxo-1,2-dihydro-4-pyridinyl}methyl)tetrahydrofuran-2-carboxylic acid

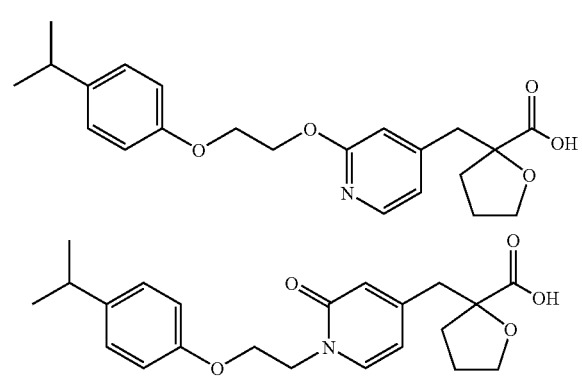

To a solution of 0.020 g of methyl 2-[(2-oxo-1,2-dihydro-4-pyridinyl)methyl]tetrahydro-2-carboxylate in 0.6 ml of N,N-dimethylformamide were added 0.020 g of potassium carbonate and 0.030 g of 1-(2-bromoethoxy)-4-isopropylbenzene, and the mixture was heated at 70° C. for 18 hours. After cooling to room temperature, 2 ml of water and 2 ml of ethyl acetate were added, and the organic layer was concentrated. The residue was dissolved in 0.5 ml of ethanol and 0.5 ml of tetrahydrofuran, 0.2 ml of 5N sodium hydroxide was added, and the mixture was stirred at room temperature for 14 hours. The reaction mixture was concentrated, and 1 ml of ethyl acetate and 1 ml of water were added. The mixture was adjusted to pH 4 with hydrochloric acid (5N), and the organic layer was concentrated. The residue was purified by HPLC, to give respectively 0.0007 mg and 0.0024 g of the title compounds as colorless oils.

MS m/e (ESI): 386.21 (MH+) and 386.22 (MH+)

Example 37

2-({2-[2-(4-t-Butylphenoxy)ethoxy]-4-pyridyl}methyl)tetrahydrofuran-2-carboxylic acid and 2-({1-[2-(4-t-butylphenoxy)ethyl]-2-oxo-1,2-dihydro-4-pyridinyl}methyl)tetrahydrofuran-2-carboxylic acid

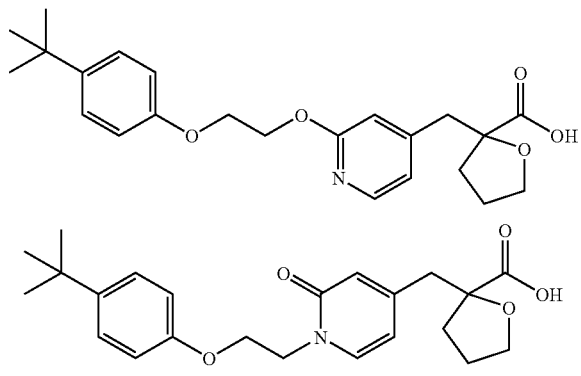

The title compounds were obtained according to the method of Example 36 from methyl 2-[(2-oxo-1,2-dihydro-4-pyridinyl)methyl]tetrahydro-2-carboxylate and 1-(2-bromoethoxy)-4-t-butylbenzene.

MS m/e (ESI): 400.26 (MH+) and 400.25 (MH+)

Example 38

2-({2-[2-(4-Cyclopentylphenoxy)ethoxy]-4-pyridyl}methyl)tetrahydrofuran-2-carboxylic acid and 2-({1-[2-(4-cyclopentylphenoxy)ethyl]-2-oxo-1,2-dihydro-4-pyridinyl}methyl)tetrahydrofuran-2-carboxylic acid

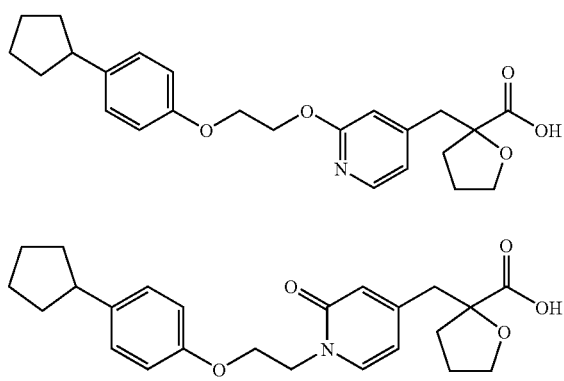

The title compounds were obtained according to the method of Example 36 from methyl 2-[(2-oxo-1,2-dihydro-4-pyridinyl)methyl]tetrahydro-2-furancarboxylate and 1-(2-bromoethoxy)-4-cyclohexylbenzene.

MS m/e (ESI) 412.27 (MH+) and 412.28 (MH+)

Example 39

2-({2-[2-(4-Cyclohexylphenoxy)ethoxy]-4-pyridyl}methyl)tetrahydrofuran-2-carboxylic acid and 2-({1-[2-(4-cyclohexylphenoxy)ethyl]-2-oxo-1,2-dihydro-4-pyridinyl}methyl)tetrahydrofuran-2-carboxylic acid

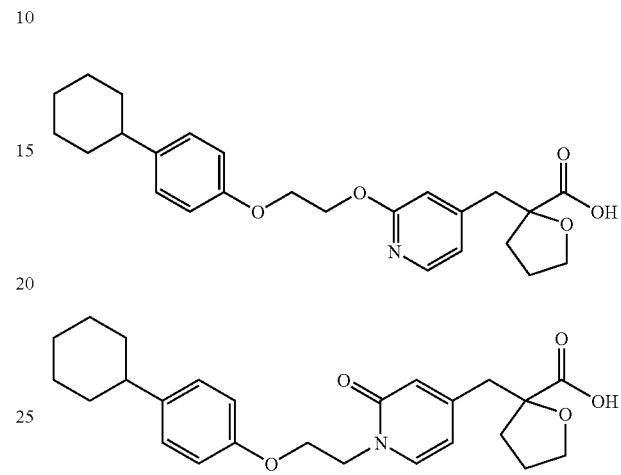

The title compounds were obtained according to the method of Example 36 from methyl 2-[(2-oxo-1,2-dihydro-4-pyridinyl)methyl]tetrahydro-2-furancarboxylate and 1-(2-bromoethoxy)-4-cyclohexylbenzene.

MS m/e (ESI): 426.32 (MH+) and 426.33 (MH+)

Example 40

2-({2-[2-(2,4-Dichlorophenoxy)ethoxy]-4-pyridyl}methyl)tetrahydrofuran-2-carboxylic acid and 2-({1-[2-(2,4-dichlorophenoxy)ethyl]-2-oxo-1,2-dihydro-4-pyridinyl}methyl)tetrahydrofuran-2-carboxylic acid

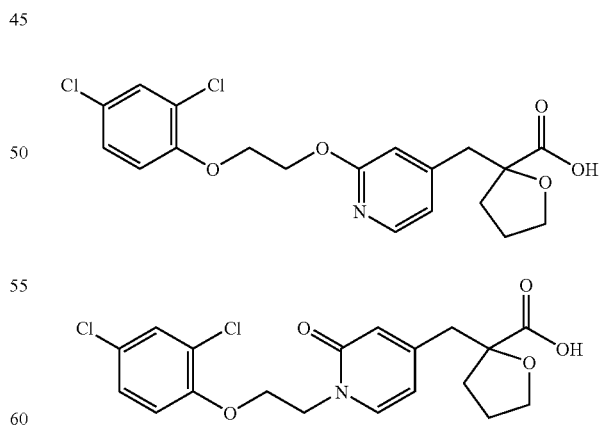

The title compounds were obtained according to the method of Example 36 from methyl 2-[(2-oxo-1,2-dihydro-4-pyridinyl)methyl]tetrahydro-2-furancarboxylate and 1-(2-bromoethoxy)-2,4-dichlorobenzene.

MS m/e (ESI): 412.17 (MH+) and 412.27 (MH+)

Example 41

2-({2-[3-(4-Cyclopentylphenoxy)propoxy]-4-pyridyl}methyl)tetrahydrofuran-2-carboxylic acid and 2-({1-[3-(4-cyclopentylphenoxy)propyl]-2-oxo-1,2-dihydro-4-pyridinyl}methyl)tetrahydrofuran-2-carboxylic acid

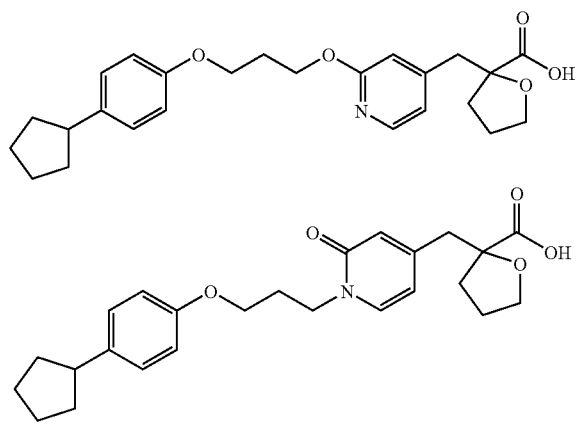

The title compounds were obtained according to the method of Example 36 from methyl 2-[(2-oxo-1,2-dihydro-4-pyridinyl)methyl]tetrahydro-2-furancarboxylate and 1-(2-bromopropoxy)-4-cyclopentylbenzene.

MS m/e (ESI): 440.34 (MH+) and 440.34 (MH+)

Example 42

2-({2-[3-(2,4-Dichlorophenoxy)propoxy]-4-pyridyl}methyl)tetrahydrofuran-2-carboxylic acid and 2-({1-[3-(2,4-dichlorophenoxy)propyl]-2-oxo-1,2-dihydro-4-pyridinyl}methyl)tetrahydrofuran-2-carboxylic acid

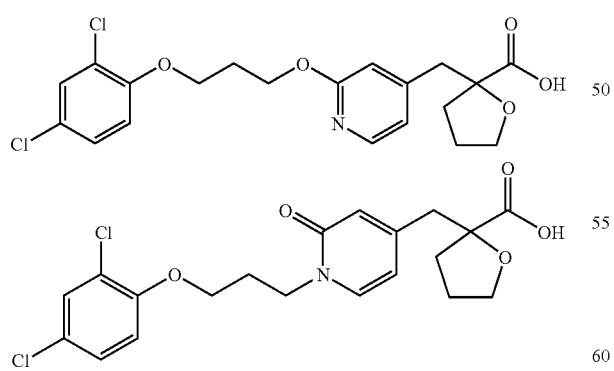

The title compounds were obtained according to the method of Example 36 from methyl 2-[(2-oxo-1,2-dihydro-4-pyridinyl)methyl]tetrahydro-2-furancarboxylate and 1-(2-bromopropoxy)-2,4-dichlorobenzene.

MS m/e (ESI): 426.21 (MH+) and 426.21 (MH+)

Example 43

4-(3-{[(2,4-Dichlorobenzoyl)amino]methyl}-4-methoxybenzyl)-1,3-dioxiran-4-carboxylic acid

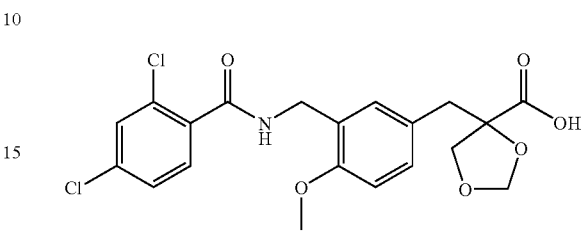

0.170 g of ethyl 4-(3-{[(2,4-dichlorobenzoyl)amino]-methyl}-4-methoxybenzyl)-1,3-dioxiran-4-carboxylate was dissolved in 5 ml of tetrahydrofuran and 5 ml of ethanol. 0.2 ml of 5N sodium hydroxide was added and the mixture was stirred at room temperature for 14 hours. The reaction mixture was evaporated, and the residue was dissolved in 10 ml of water. The mixture was adjusted to pH 4 with hydrochloric acid, and extracted with ethyl acetate. The organic layer was dried over magnesium sulfate and evaporated, to give 0.160 g of the title compound as a white solid.

$^1$H-NMR(CDCl$_3$): 2.96 (d, J=13.9 Hz, 1H), 3.20(d, J=13.9 Hz, 1H), 3.81 (s, 3H), 3.83 (d, J=9.3 Hz, 1H), 4.26 (d, J=9.3 Hz, 1H), 4.51 (dd, J=5.8, 11.1 Hz, 1H), 4.57 (dd, J=5.8, 11.1 Hz, 1H), 5.02 (s, 1H), 5.07 (s, 1H), 6.78 (d, J=8.3 Hz, 1H), 6.85 (br.t, J=5.8 Hz, 1H), 7.15 (dd, J=2.4, 8.3 Hz, 1H), 7.25 (dd, J=2.1, 8.3 Hz, 1H), 7.27 (d, J=2.4 Hz, 1H), 7.37 (d, J=2.1 Hz, 1H), 7.59 (d, J=8.3 Hz, 1H)

MS m/e (ESI) 438.09 ([M–H]–)

Example 44

2-(3-{[(2,4-Dichlorobenzoyl)amino]methyl}-4-methoxybenzyl)-2,5-dihydro-2-furancarboxylic acid

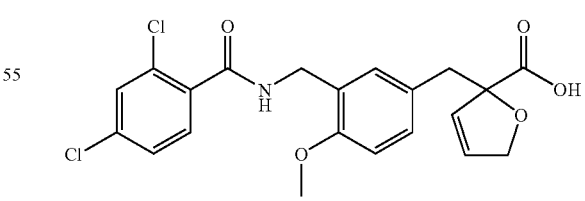

The title compound was obtained according to the method of Example 1 from methyl 2-[3-(ammoniomethyl)-4-methoxybenzyl]-2,5-dihydro-2-furancarboxylate chloride and 2,4-dichlorobenzoic acid.

MS m/e (ESI) 435.98 (MH+)

Example 45

2-(3-{[(2-Fluoro-4-(trifluoromethyl)benzoyl)amino]methyl}-4-methoxybenzyl)-2,5-dihydro-2-furancarboxylic acid

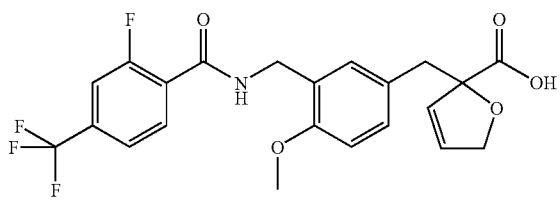

The title compound was obtained according to the method of Example 1 from methyl 2-[3-(ammoniomethyl)-4-methoxybenzyl]-2,5-dihydro-2-furancarboxylate chloride and 2-fluoro-4-(trifluoromethyl)benzoic acid.

MS m/e (ESI) 476.02 (MNa+)

Example 46

2-(3-{[(2-Fluoro-4-methoxybenzoyl)amino]methyl}-4-methoxybenzyl)-2,5-dihydro-2-furancarboxylic acid

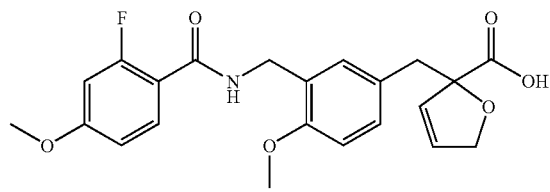

The title compound was obtained according to the method of Example 1 from methyl 2-[3-(ammoniomethyl)-4-methoxybenzyl]-2,5-dihydro-2-furancarboxylate chloride and 2-fluoro-4-methoxybenzoic acid.

MS m/e (ESI) 416.08 (MH+)

Example 47

2-(3-{[(2-Chloro-4-methoxybenzoyl)amino]methyl}-4-methoxybenzyl)-2,5-dihydro-2-furancarboxylic acid

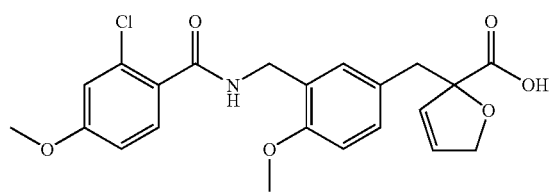

The title compound was obtained according to the method of Example 1 from methyl 2-[3-(ammoniomethyl)-4-methoxybenzyl]-2,5-dihydro-2-furancarboxylate chloride and 2-chloro-4-methoxybenzoic acid.

MS m/e (ESI) 432.05 (MH+)

Example 48

2-(3-{[(2-Chloro-4-ethoxybenzoyl)amino]methyl}-4-methoxybenzyl)-2,5-dihydro-2-furancarboxylic acid

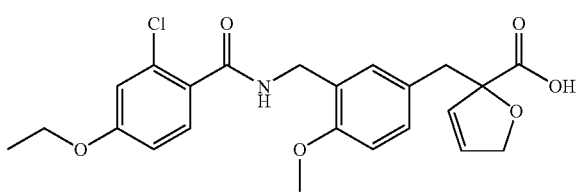

The title compound was obtained according to the method of Example 1 from methyl 2-[3-(ammoniomethyl)-4-methoxybenzyl]-2,5-dihydro-2-furancarboxylate chloride and 2-chloro-4-ethoxybenzoic acid.

MS m/e (ESI) 446.07 (MH+)

Example 49

2-(3-{[(2-Chloro-4-propoxybenzoyl)amino]methyl}-4-methoxybenzyl)-2,5-dihydro-2-furancarboxylic acid

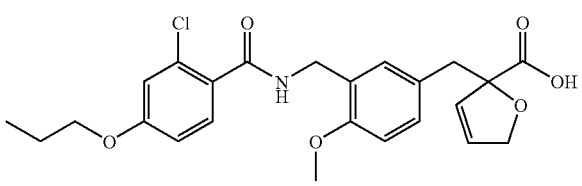

The title compound was obtained according to the method of Example 1 from methyl 2-[3-(ammoniomethyl)-4-methoxybenzyl]-2,5-dihydro-2-furancarboxylate chloride and 2-chloro-4-propoxybenzoic acid.

$^1$H-NMR(CDCl$_3$): 0.95(t, J=7.2 Hz, 3H), 1.68-1.76(sext, J=7.2 Hz, 2H), 2.94(d, J=14.1 Hz, 1H), 3.12(d, J=14.1 Hz, 1H), 3.76(s, 3H), 3.85(t, J=7.2 Hz, 2H), 4.44(d, J=13.1 Hz, 1H), 4.48(dd, J=6.0, 13.6 Hz, 1H), 4.53(dd, J=6.0, 13.6 Hz, 1H), 4.65(d, J=13.1 Hz, 1H), 5.80(s, 2H), 6.70(d, J=8.3 Hz, 1H), 6.74(dd, J=2.1, 8.3 Hz, 1H), 6.80(d, J=2.1 Hz, 1H), 6.94(br.t, J=6.0 Hz, 1H), 7.03(dd, J=2.3, 8.2 Hz, 1H), 7.17(dd, J=2.3 Hz, 1H), 7.64 (d, J=8.3 Hz, 1H)

MS m/e (ESI) 460.08 (MH+)

Example 50

2-(3-{[(2-Chloro-4-isopropoxybenzoyl)amino]methyl}-4-methoxybenzyl)-2,5-dihydro-2-furancarboxylic acid

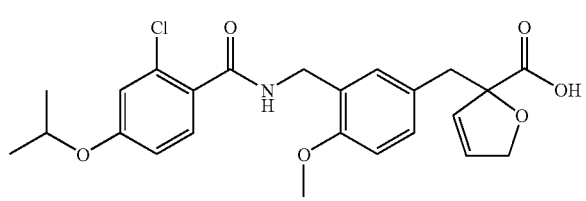

The title compound was obtained according to the method of Example 1 from methyl 2-[3-(ammoniomethyl)-4-methoxybenzyl]-2,5-dihydro-2-furancarboxylate chloride and 2-chloro-4-isopropoxybenzoic acid.
MS m/e (ESI) 460.08 (MH+)

Example 51

2-(3-{[(2-Chloro-4-cyclopentyloxybenzoyl)amino]methyl}-4-methoxybenzyl)-2,5-dihydro-2-furancarboxylic acid

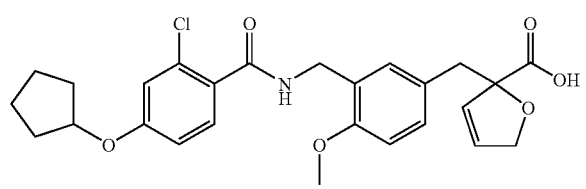

The title compound was obtained according to the method of Example 1 from methyl 2-[3-(ammoniomethyl)-4-methoxybenzyl]-2,5-dihydro-2-furancarboxylate chloride and 2-chloro-4-cyclopentyloxybenzoic acid.
MS m/e (ESI) 486.09 (MH+)

Example 52

2-(3-{[(2-Chloro-4-phenylbenzoyl)amino]methyl}-4-methoxybenzyl)-2,5-dihydro-2-furancarboxylic acid

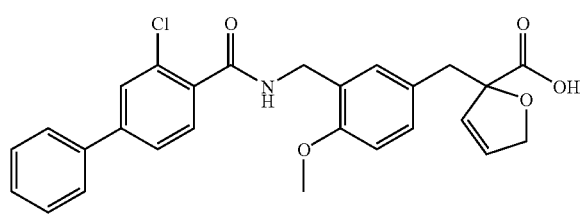

The title compound was obtained according to the method of Example 1 from methyl 2-[3-(ammoniomethyl)-4-methoxybenzyl]-2,5-dihydro-2-furancarboxylate chloride and 2-chloro-4-phenylbenzoic acid.
MS m/e (ESI) 478.06 (MH+)

Example 53

2-(3-{[(4-Cyclohexylbenzoyl)amino]methyl}-4-methoxybenzyl)-2,5-dihydro-2-furancarboxylic acid

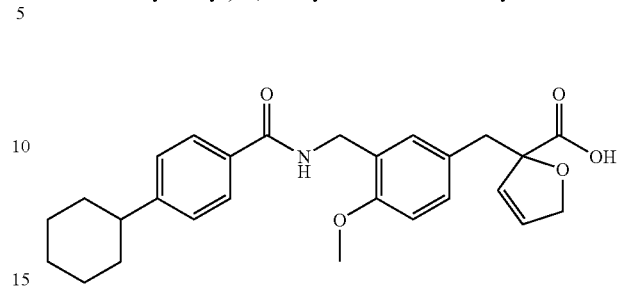

The title compound was obtained according to the method of Example 1 from methyl 2-[3-(ammoniomethyl)-4-methoxybenzyl]-2,5-dihydro-2-furancarboxylate chloride and 4-cyclohexylbenzoic acid.
MS m/e (ESI) 450.16 (MH+)

Example 54

2-(3-{[(4-Isopropylbenzoyl)amino]methyl}-4-methoxybenzyl)-2,5-dihydro-2-furancarboxylic acid

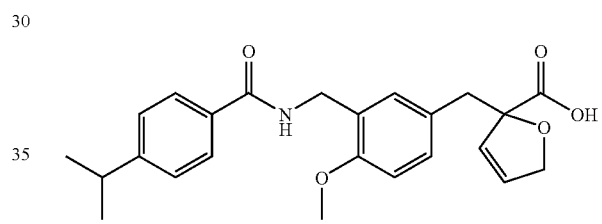

The title compound was obtained according to the method of Example 1 from methyl 2-[3-(ammoniomethyl)-4-methoxybenzyl]-2,5-dihydro-2-furancarboxylate chloride and 4-isopropylbenzoic acid.
MS m/e (ESI) 410.14 (MH+)

Example 55

2-[3-({[2-(2,4-Dichlorophenoxy)acetyl]amino}methyl)-4-methoxybenzyl]-2,5-dihydro-2-furancarboxylic acid

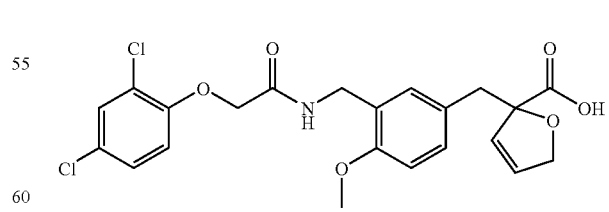

The title compound was obtained according to the method of Example 1 from methyl 2-[3-(ammoniomethyl)-4-methoxybenzyl]-2,5-dihydro-2-furancarboxylate chloride and 2,4-dichlorophenoxyacetic acid.
MS m/e (ESI) 487.99 (MNa+)

Example 56

2-{3-[({[5-(2-Chlorophenyl)-3-isoxazolyl]carbonyl}amino)-methyl]-4-methoxybenzyl}-2,5-dihydro-2-furancarboxylic acid

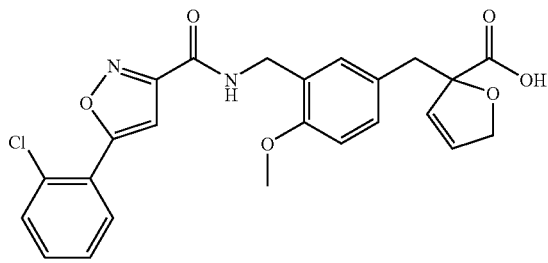

The title compound was obtained according to the method of Example 1 from methyl 2-[3-(ammoniomethyl)-4-methoxybenzyl]-2,5-dihydro-2-furancarboxylate chloride and 5-(2-chlorophenyl)-3-isoxazolecarboxylic acid.

MS m/e (ESI) 491.03 (MNa+)

Example 57

2-{4-Methoxy-3-[({[4-methyl-2-(4-methylphenyl)-1,3-thiazol-5-yl]carbonyl}amino)methyl]benzyl}-2,5-dihydro-2-furancarboxylic acid

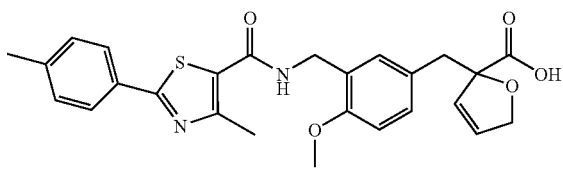

The title compound was obtained according to the method of Example 1 from methyl 2-[3-(ammoniomethyl)-4-methoxybenzyl]-2,5-dihydro-2-furancarboxylate chloride and 4-methyl-2-(4-methylphenyl)-1,3-thiazol-5-carboxylic acid.

MS m/e (ESI) 479.09 (MH+)

Example 58

2-{4-Methoxy-3-[({[4-methyl-2-(3-pyridyl)-1,3-thiazol-5-yl]carbonyl}amino)methyl]benzyl}-2,5-dihydro-2-furancarboxylic acid

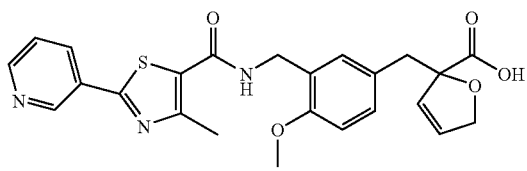

The title compound was obtained according to the method of Example 1 from methyl 2-[3-(ammoniomethyl)-4-methoxybenzyl]-2,5-dihydro-2-furancarboxylate chloride and 4-methyl-2-(3-pyridyl)-1,3-thiazol-5-carboxylic acid.

MS m/e (ESI) 466.07 (MH+)

Example 59

2-{3-[({[2-(4-Chlorophenyl)-4-methyl-1,3-thiazol-5-yl]carbonyl}amino)methyl]-4-methoxybenzyl}-2,5-dihydro-2-furancarboxylic acid

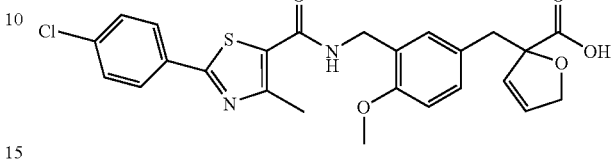

The title compound was obtained according to the method of Example 1 from methyl 2-[3-(ammoniomethyl)-4-methoxybenzyl]-2,5-dihydro-2-furancarboxylate chloride and 4-methyl-2-(4-chlorophenyl)-1,3-thiazol-5-carboxylic acid.

MS m/e (ESI) 499.03 (MH+)

Example 60

2-{3-[({[2-(2,4-Dichlorophenyl)-4-methyl-1,3-thiazol-5-yl]carbonyl}amino)methyl]-4-methoxybenzyl}-2,5-dihydro-2-furancarboxylic acid

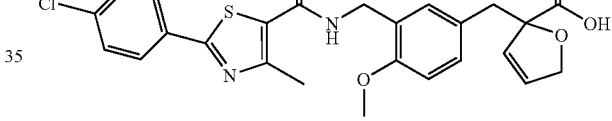

The title compound was obtained according to the method of Example 1 from methyl 2-[3-(ammoniomethyl)-4-methoxybenzyl]-2,5-dihydro-2-furancarboxylate chloride and 4-methyl-2-(2,4-dichlorophenyl)-1,3-thiazol-5-carboxylic acid.

MS m/e (ESI) 533.00 (MH+)

Example 61

2-(3-{[(2,4-Dichlorobenzoyl)amino]methyl}-4-methoxybenzyl)-1,3-dithian-2-carboxylic acid

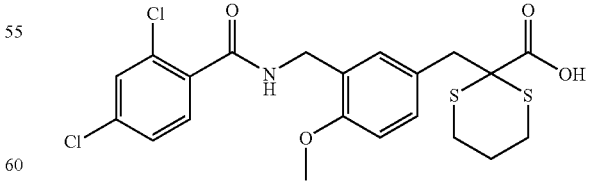

To 50 mg of ethyl 2-(3-{[[(t-butoxycarbonyl)amino]-methyl}-4-methoxybenzyl)-1,3-dithian-2-carboxylate was added 4N HCl in dioxane (2 mL), and the mixture was stirred at room temperature for 2 hours. After concentrating the reaction mixture, the residue was dissolved in 2 mL of N,N-dimethylformamide. To 1 mL of this solution were added 14 mg of 2,4-dichlorobenzoic acid, 12 μL of diethyl cyanophosphonate and 20 μL of triethylamine, and the mixture was stirred at room temperature for 4 hours. The reaction mixture was diluted with water, and extracted with ethyl acetate. After concentrating the organic layer, the residue was dissolved in 1.0 mL of ethanol. 0.3 mL of 2N aqueous sodium hydroxide was added, and the mixture was stirred at room temperature for 1 hour. After neutralizing with 1N hydrochloric acid, the reaction mixture was extracted with ethyl acetate. After evaporating the solvent, the residue was purified by HPLC using a reverse-phase column and a water-acetonitrile-trifluoroacetic acid eluent, to give 8.33 mg of the title compound.

MS m/e (ESI) 486 (MH+)

Example 62

2-[3-({[2-Fluoro-4-(trifluoromethyl)benzoyl]amino}methyl)-4-methoxybenzyl]-1,3-dithian-2-carboxylic acid

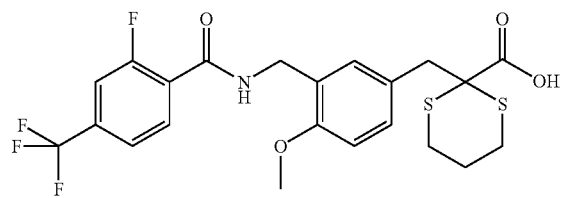

The title compound was obtained according to the method of Example 61 from 2-fluoro-4-(trifluoromethyl)-benzoic acid and ethyl 2-(3-{[(t-butoxycarbonyl)amino]-methyl}-4-methoxybenzyl)-1,3-dithian-2-carboxylate.

MS m/e (ESI) 504 (MH+)

Example 63

2-(3-{[(4-Chloro-2-fluorobenzoyl)amino]methyl}-4-methoxybenzyl)-1,3-dithian-2-carboxylic acid

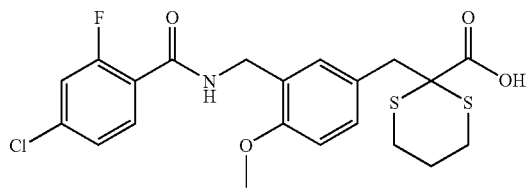

The title compound was obtained according to the method of Example 61 from 4-chloro-2-fluorobenzoic acid and ethyl 2-(3-{[(t-butoxycarbonyl)amino]methyl}-4-methoxybenzyl)-1,3-dithian-2-carboxylate.

MS m/e (ESI) 470 (MH+)

Example 64

2-(3-{[(2-Chloro-4-propoxybenzoyl)amino]methyl}-4-methoxybenzyl)-1,3-dithian-2-carboxylic acid

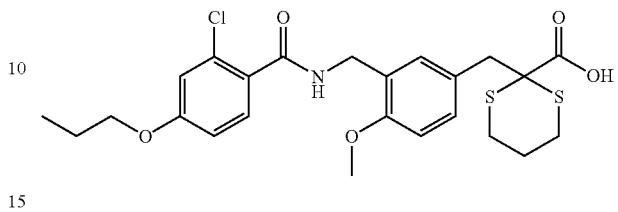

The title compound was obtained according to the method of Example 61 from 2-chloro-4-propoxybenzoic acid and ethyl 2-(3-{[(t-butoxycarbonyl)amino]methyl}-4-methoxybenzyl)-1,3-dithian-2-carboxylate.

MS m/e (ESI) 510 (MH+)

Example 65

2-[3-({[2-Chloro-4-(cyclopentyloxy)benzoyl]amino}methyl)-4-methoxybenzyl]-1,3-dithian-2-carboxylic acid

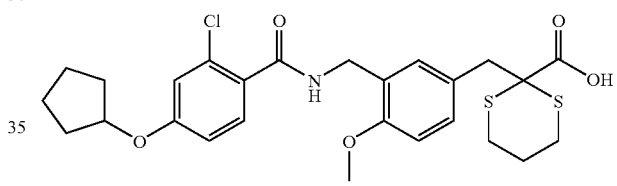

The title compound was obtained according to the method of Example 61 from 2-chloro-4-cyclopentyloxybenzoic acid and ethyl 2-(3-{[(t-butoxycarbonyl)amino]methyl}-4-methoxybenzyl)-1,3-dithian-2-carboxylate.

MS m/e (ESI) 536 (MH+)

Example 66

2-[3-({[2-(2,4-Dichlorophenoxy)acetyl]amino}methyl)-4-methoxybenzyl]-tetrahydro-2-furancarboxylic acid

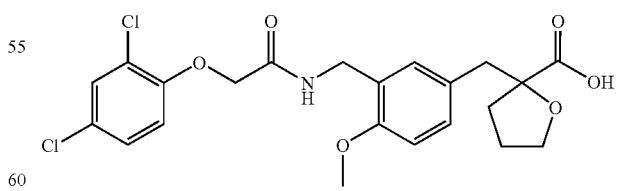

The title compound was obtained according to the method of Example 1 from methyl 2-[3-(ammoniomethyl)-4-methoxybenzyl]-tetrahydro-2-furancarboxylate chloride and 2,4-dichlorophenoxyacetic acid.

MS m/e (ESI) 489.98 (MNa+)

Example 67

2-(3-{[(2-Chloro-4-ethoxybenzoyl)amino]methyl}-4-methoxybenzyl)tetrahydro-2-furancarboxylic acid

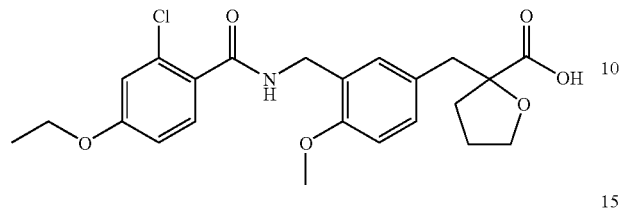

The title compound was obtained according to the method of Example 1 from methyl 2-[3-(ammoniomethyl)-4-methoxybenzyl]tetrahydro-2-furancarboxylate chloride and 2-chloro-4-ethoxybenzoic acid.

MS m/e (ESI) 448.14 (MH$^+$)

Example 68

2-(3-{[(2-Chloro-4-isopropoxybenzoyl)amino]methyl}-4-methoxybenzyl)tetrahydro-2-furancarboxylic acid

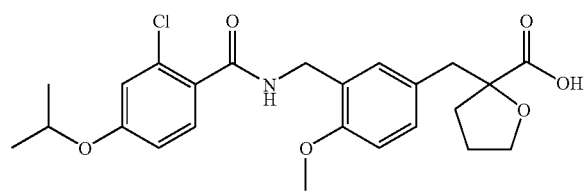

The title compound was obtained according to the method of Example 1 from methyl 2-[3-(ammoniomethyl)-4-methoxybenzyl]tetrahydro-2-furancarboxylate chloride and 2-chloro-4-isopropoxybenzoic acid.

MS m/e (ESI) 462.15 (MH$^+$)

Example 69

2-(3-{[(2,4-Dichlorobenzoyl)amino]methyl}-4-ethoxybenzyl)-tetrahydro-2-furancarboxylic acid

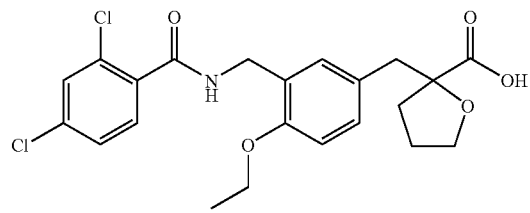

The title compound was obtained according to the method of Example 1 from methyl 2-[3-(ammoniomethyl)-4-ethoxybenzyl]tetrahydro-2-furancarboxylate chloride and 2,4-dichlorobenzoic acid.

MS m/e (ESI) 451.92 (MH$^+$)

Example 70

2-(3-{[(2-Fluoro-4-trifluoromethylbenzoyl)amino]methyl}-4-ethoxybenzyl)tetrahydro-2-furancarboxylic acid

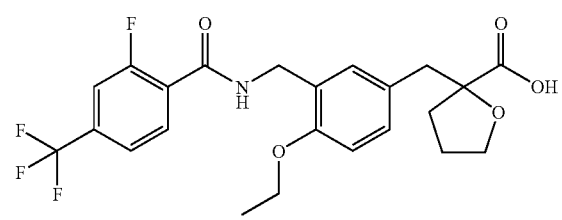

The title compound was obtained according to the method of Example 1 from methyl 2-[3-(ammoniomethyl)-4-ethoxybenzyl]tetrahydro-2-furancarboxylate chloride and 2-fluoro-4-trifluoromethylbenzoic acid.

MS m/e (ESI) 491.98 (MNa$^+$)

Example 71

2-(3-{[(3-Chlorobiphenyl-4-carbonyl)amino]methyl}-4-ethoxybenzyl)tetrahydro-2-furancarboxylic acid

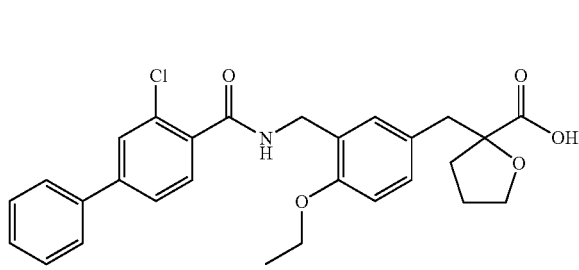

The title compound was obtained according to the method of Example 1 from methyl 2-[3-(ammoniomethyl)-4-ethoxybenzyl]tetrahydro-2-furancarboxylate chloride and 3-chlorobiphenyl-4-carboxylic acid.

MS m/e (ESI) 494.03 (MH$^+$)

Example 72

2-(3-{[(2-Chloro-4-ethoxybenzoyl)amino]methyl}-4-ethoxybenzyl)tetrahydro-2-furancarboxylic acid

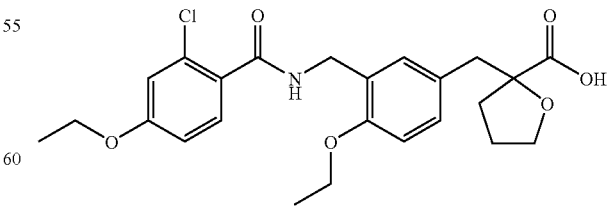

The title compound was obtained according to the method of Example 1 from methyl 2-[3-(ammoniomethyl)-4-ethoxybenzyl]tetrahydro-2-furancarboxylate chloride and 2-chloro-4-ethoxybenzoic acid.

$^1$H-NMR(CDCl$_3$): 1.41 (t, J=7.2 Hz, 3H), 1.42 (t, J=7.2 Hz, 3H), 1.80-1.88 (m, 2H), 1.95-2.05 (td, J=8.1, 12.8 Hz, 1H), 2.34-2.40 (ddd, J=5.6, 7.2, 12.8 Hz, 1H), 2.88 (d, J=13.9 Hz, 1H), 3.18 (d, J=13.9 Hz, 1H), 3.89 (t, J=7.0 Hz, 1H), 3.98 (ddd, J=5.5, 7.0, 8.0 Hz, 1H), 4.03 (q, J=7.2 Hz, 2H), 4.05 (q, J=7.2 Hz, 2H), 4.59 (dd, J=6.0, 14.1 Hz, 1H), 4.64 (dd, J=6.0, 14.1 Hz, 1H), 6.77 (d, J=8.3 Hz, 1H), 6.82 (dd, J=2.5, 8.5 Hz, 1H), 6.94 (d, J=2.5 Hz, 1H), 6.99 (t, J=6.0 Hz, 1H), 7.10 (dd, J=2.5, 8.3 Hz, 1H), 7.26 (d, J=2.5 Hz, 1H), 7.74 (d, J=8.5 Hz, 1H)

MS m/e (ESI) 462.05 (MH$^+$)

Example 73

2-(3-{[(2-Chloro-4-propoxybenzoyl)amino]methyl}-4-ethoxybenzyl)tetrahydro-2-furancarboxylic acid

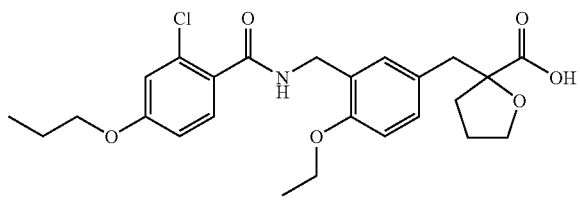

The title compound was obtained according to the method of Example 1 from methyl 2-[3-(ammoniomethyl)-4-ethoxybenzyl]tetrahydro-2-furancarboxylate chloride and 2-chloro-4-propoxybenzoic acid.

$^1$H-NMR(CDCl$_3$): 1.02 (t, J=7.6 Hz, 3H), 1.42 (t, J=7.2 Hz, 3H), 1.75-1.88 (m, 4H), 1.95-2.05 (td, J=8.1, 12.7 Hz, 1H), 2.33-2.39 (ddd, J=5.7, 7.4, 12.7 Hz, 1H), 2.88 (d, J=14.2 Hz, 1H), 3.16 (d, J=14.2 Hz, 1H), 3.89 (q, J=7.2 Hz, 1H), 3.92 (t, J=6.4 Hz, 2H), 3.98(dt, J=6.2, 7.6 Hz, 1H), 4.05 (q, J=7.2 Hz, 2H), 4.59 (dd, J=5.7, 14.2 Hz, 1H), 4.62 (dd, J=5.7, 14.2 Hz, 1H), 6.77 (d, J=8.2 Hz, 1H), 6.83 (dd, J=2.6, 8.8 Hz, 1H), 6.88 (d, J=2.6 Hz, 1H), 7.00 (t, J=5.7 Hz, 1H), 7.10 (dd, J=2.6, 8.2 Hz, 1H), 7.26 (d, J=2.6 Hz, 1H), 7.74 (d, J=8.8 Hz, 1H)

MS m/e (ESI) 476.07 (MH$^+$)

Example 74

2-(3-{[(2-Chloro-4-isopropoxybenzoyl)amino]methyl}-4-ethoxybenzyl)tetrahydro-2-furancarboxylic acid

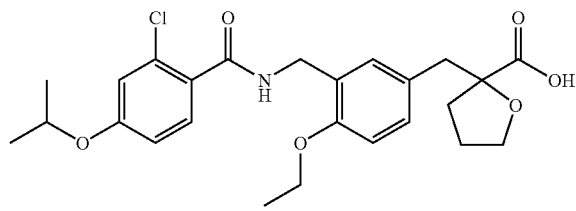

The title compound was obtained according to the method of Example 1 from methyl 2-[3-(ammoniomethyl)-4-ethoxybenzyl]tetrahydro-2-furancarboxylate chloride and 2-chloro-4-isopropoxybenzoic acid.

MS m/e (ESI) 476.08 (MH$^+$)

Example 75

2-(3-{[(2-Chloro-4-cyclopentyloxybenzoyl)amino]methyl}-4-ethoxybenzyl)tetrahydro-2-furancarboxylic acid

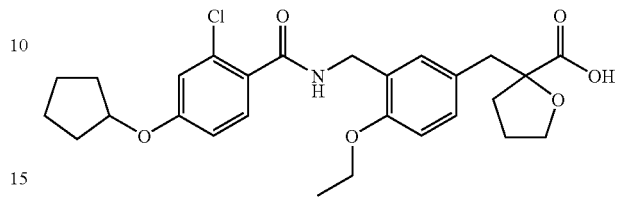

The title compound was obtained according to the method of Example 1 from methyl 2-[3-(ammoniomethyl)-4-ethoxybenzyl]tetrahydro-2-furancarboxylate chloride and 2-chloro-4-cyclopentyloxybenzoic acid.

MS m/e (ESI) 502.10 (MH$^+$)

Example 76

2-{3-[({[2-(4-Chlorophenyl)-4-methyl-1,3-thiazol-5-yl]carbonyl}amino)methyl]-4-ethoxybenzyl}tetrahydro-2-furancarboxylic acid

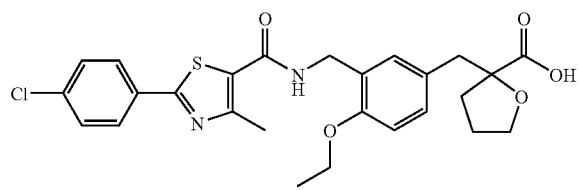

The title compound was obtained according to the method of Example 1 from methyl 2-[3-(ammoniomethyl)-4-ethoxybenzyl]tetrahydro-2-furancarboxylate chloride and 2-(4-chlorobenzyl)-4-methyl-1,3-thiazol-5-carboxylic acid.

MS m/e (ESI) 515.05 (MH$^+$)

Example 77

2-(3-{[(4-Ethoxybenzoyl)amino]methyl}-4-ethoxybenzyl)-tetrahydro-2-furancarboxylic acid

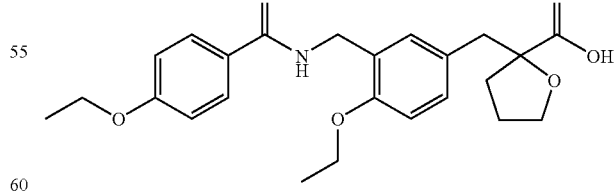

The title compound was obtained according to the method of Example 1 from methyl 2-[3-(ammoniomethyl)-4-ethoxybenzyl]tetrahydro-2-furancarboxylate chloride and 4-ethoxybenzoic acid.

$^1$H-NMR(CDCl$_3$): 1.43 (t, J=6.8 Hz, 3H), 1.45 (t, J=6.8 Hz, 3H), 1.80-1.88 (m, 2H), 1.94-2.05 (td, J=8.0, 12.8 Hz,

1H), 2.34-2.40 (ddd, J=5.6, 6.8, 12.8 Hz, 1H), 2.87 (d, J=13.6 Hz, 1H), 3.15 (d, J=13.6 Hz, 1H), 3.89 (t, J=7.3 Hz, 1H), 3.98 (dt, J=6.0, 7.3 Hz, 1H), 4.06 (q, J=6.8 Hz, 2H), 4.07 (q, J=6.8 Hz, 2H), 4.57 (dd, J=6.0, 14.0 Hz, 1H), 4.62 (dd, J=6.0, 14.0 Hz, 1H), 6.65 (t, J=6.0 Hz, 1H), 6.78 (d, J=8.2 Hz, 1H), 6.89 (d, J=8.8 Hz, 2H), 7.10 (dd, J=2.2, 8.2 Hz, 1H), 7.23 (d, J=2.2 Hz, 1H), 7.70 (d, J=8.8 Hz, 2H)

Example 78

2-(3-{[(4-Propoxybenzoyl)amino]methyl}-4-ethoxybenzyl)-tetrahydro-2-furancarboxylic acid

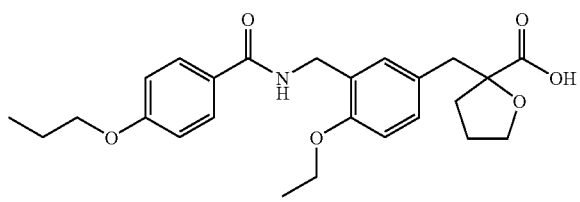

The title compound was obtained according to the method of Example 1 from methyl 2-[3-(ammoniomethyl)-4-ethoxybenzyl]tetrahydro-2-furancarboxylate chloride and 4-propoxybenzoic acid.

$^1$H-NMR(CDCl$_3$): 1.12 (t, J=7.5 Hz, 3H), 1.44 (t, J=7.1 Hz, 3H), 1.77-1.88 (m, 4H), 1.94-2.05 (td, J=7.7, 12.8 Hz, 1H), 2.34-2.40 (ddd, J=5.5, 6.8, 12.8 Hz, 1H), 2.87 (d, J=14.2 Hz, 1H), 3.15 (d, J=14.2 Hz, 1H), 3.89 (q, J=7.6 Hz, 1H), 3.94 (t, J=6.6 Hz, 2H), 3.98 (dt, J=6.0, 7.6 Hz, 1H), 4.07 (q, J=7.1 Hz, 2H), 4.57 (dd, J=5.8, 13.9 Hz, 1H), 4.62 (dd, J=5.8, 13.9 Hz, 1H), 6.68 (t, J=5.8 Hz, 1H), 6.78 (d, J=8.3 Hz, 1H), 6.90 (d, J=8.8 Hz, 2H), 7.10 (dd, J=2.2, 8.3 Hz, 1H), 7.23 (d, J=2.2 Hz, 1H), 7.70 (d, J=8.8 Hz, 2H)

MS m/e (ESI) 442.19 (MH$^+$)

Example 79

2-(3-{[(4-Isopropoxybenzoyl)amino]methyl}-4-ethoxybenzyl)-tetrahydro-2-furancarboxylic acid

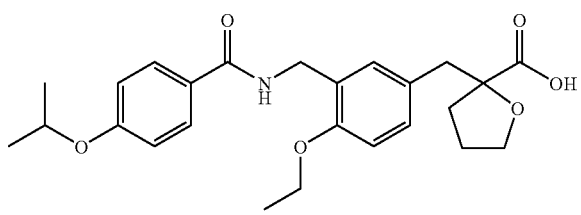

The title compound was obtained according to the method of Example 1 from methyl 2-[3-(ammoniomethyl)-4-ethoxybenzyl]tetrahydro-2-furancarboxylate chloride and 4-isopropoxybenzoic acid.

MS m/e (ESI) 442.20 (MH$^+$)

Example 80

2-(3-{[(4-Butoxybenzoyl)amino]methyl}-4-ethoxybenzyl)-tetrahydro-2-furancarboxylic acid

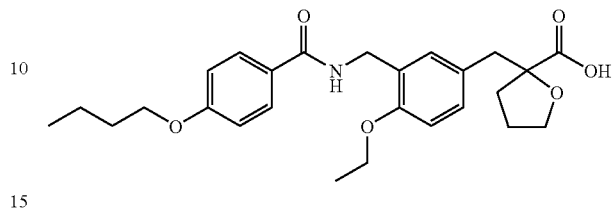

The title compound was obtained according to the method of Example 1 from methyl 2-[3-(ammoniomethyl)-4-ethoxybenzyl]tetrahydro-2-furancarboxylate chloride and 4-butoxybenzoic acid.

MS m/e (ESI) 456.07 (MH$^+$)

Example 81

2-(3-{[(2,4-Dimethoxybenzoyl)amino]methyl}-4-ethoxybenzyl)-tetrahydro-2-furancarboxylic acid

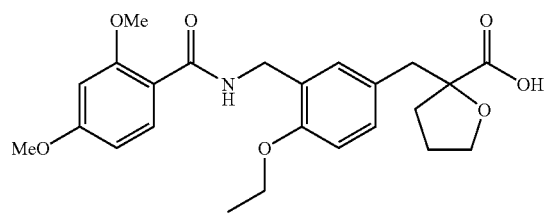

The title compound was obtained according to the method of Example 1 from methyl 2-[3-(ammoniomethyl)-4-ethoxybenzyl]tetrahydro-2-furancarboxylate chloride and 2,4-dimethoxybenzoic acid.

MS m/e (ESI) 444.04 (MH$^+$)

Example 82

2-(3-{[(4-Phenoxybenzoyl)amino]methyl}-4-ethoxybenzyl)-tetrahydro-2-furancarboxylic acid

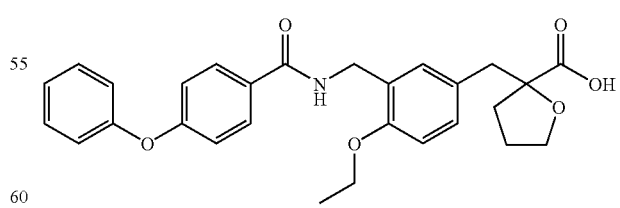

The title compound was obtained according to the method of Example 1 from methyl 2-[3-(ammoniomethyl)-4-ethoxybenzyl]tetrahydro-2-furancarboxylate chloride and 4-phenoxybenzoic acid.

MS m/e (ESI) 475.20 (MH$^+$)

Example 83

2-(3-{[(4-Benzyloxybenzoyl)amino]methyl}-4-ethoxybenzyl)-tetrahydro-2-furancarboxylic acid

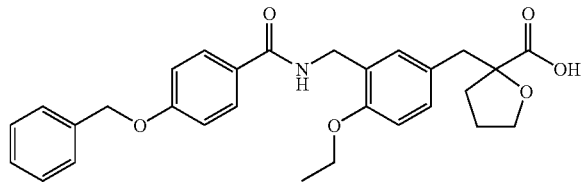

The title compound was obtained according to the method of Example 1 from methyl 2-[3-(ammoniomethyl)-4-ethoxybenzyl]tetrahydro-2-furancarboxylate chloride and 4-benzyloxybenzoic acid.

MS m/e (ESI) 490.10 (MH$^+$)

Example 84

2-(3-{[({[4-Methylbenzyl]oxy}carbonyl)amino]methyl}-4-ethoxybenzyl)tetrahydro-2-furancarboxylic acid

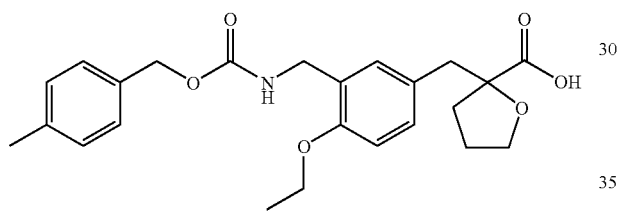

To 0.0058 g of triphosgene in 0.1 ml of dichloromethane were added 0.016 g of methyl 2-[3-(ammoniomethyl)-4-ethoxybenzyl]tetrahydro-2-furancarboxylate chloride in 0.3 ml of dichloromethane, 0.018 μl of pyridine and 0.010 μl of 4-methylbenzyl alcohol at 0° C. After stirring for 15 hours, the reaction mixture was concentrated. The residue was dissolved in 0.5 ml of methanol, and treated with 0.1 ml of 1N aqueous sodium hydroxide for 15 hours. The mixture was acidified with 5N hydrochloric acid, and the solvent was evaporated. The residue was purified by HPLC using a reverse-phase column and a water-acetonitrile-trifluoroacetic acid eluent, to give the title compound.

MS m/e (ESI) 384.13 (MH$^+$—CO$_2$), 428.09 (MH$^+$)

Example 85

2-(3-{[({[4-Isopropylbenzyl]oxy}carbonyl)amino]methyl}-4-ethoxybenzyl)tetrahydro-2-furancarboxylic acid

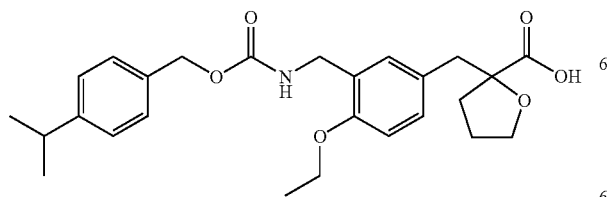

The title compound was obtained according to the method of Example 84 from methyl 2-[3-(ammoniomethyl)-4-ethoxybenzyl]tetrahydro-2-furancarboxylate chloride and 4-isopropylbenzyl alcohol.

MS m/e (ESI) 412.19 (MH$^+$—CO$_2$), 466.13 (MH$^+$)

Example 86

2-(3-{[({[4-Butylbenzyl]oxy}carbonyl)amino]methyl}-4-ethoxybenzyl)tetrahydro-2-furancarboxylic acid

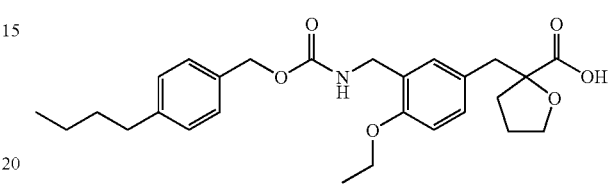

The title compound was obtained according to the method of Example 84 from methyl 2-[3-(ammoniomethyl)-4-ethoxybenzyl]tetrahydro-2-furancarboxylate chloride and 4-butylbenzyl alcohol.

MS m/e (ESI) 426.23 (MH$^+$—CO$_2$), 470.15 (MH$^+$)

Example 87

2-(3-{[({[4-Ethoxybenzyl]oxy}carbonyl)amino]methyl}-4-ethoxybenzyl)tetrahydro-2-furancarboxylic acid

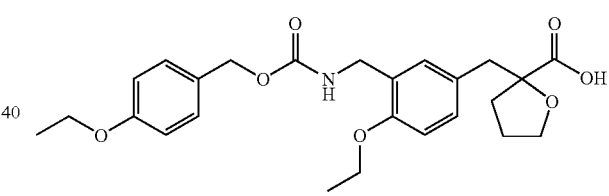

The title compound was obtained according to the method of Example 84 from methyl 2-[3-(ammoniomethyl)-4-ethoxybenzyl]tetrahydro-2-furancarboxylate chloride and 4-ethoxybenzyl alcohol.

MS m/e (ESI) 414.20 (MH$^+$—CO$_2$), 458.11 (MH$^+$)

Example 88

2-(3-{[({[4-Propoxybenzyl]oxy}carbonyl)amino]methyl}-4-ethoxybenzyl)tetrahydro-2-furancarboxylic acid

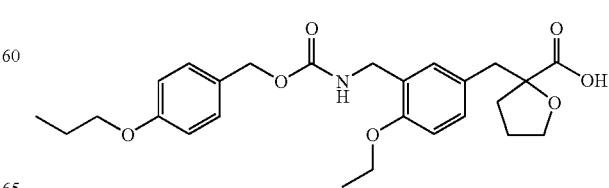

The title compound was obtained according to the method of Example 84 from methyl 2-[3-(ammoniomethyl)-4-ethoxybenzyl]tetrahydro-2-furancarboxylate chloride and 4-propoxybenzyl alcohol.
MS m/e (ESI) 428.24 (MH⁺—CO₂), 472.13 (MH⁺)

Example 89

2-(3-{[({[4-Isopropoxybenzyl]oxy}carbonyl)amino]methyl}-4-ethoxybenzyl)tetrahydro-2-furancarboxylic acid

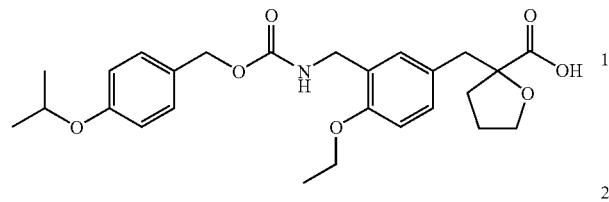

The title compound was obtained according to the method of Example 84 from methyl 2-[3-(ammoniomethyl)-4-ethoxybenzyl]tetrahydro-2-furancarboxylate chloride and 4-isopropoxybenzyl alcohol.
MS m/e (ESI) 428.24 (MH⁺—CO₂), 472.13 (MH⁺)

Example 90

2-(3-{[({[3-Chlorobenzyl]oxy}carbonyl)amino]methyl}-4-ethoxybenzyl)tetrahydro-2-furancarboxylic acid

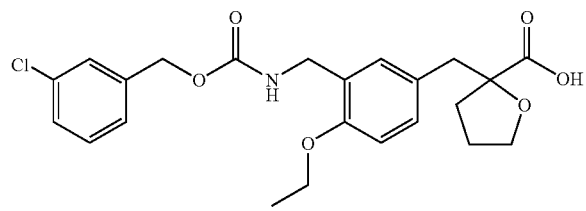

The title compound was obtained according to the method of Example 84 from methyl 2-[3-(ammoniomethyl)-4-ethoxybenzyl]tetrahydro-2-furancarboxylate chloride and 3-chlorobenzyl alcohol.
MS m/e (ESI) 470.15 (MNa⁺)

Example 91

2-(3-{[({[3-Trifluoromethylbenzyl]oxy}carbonyl)amino]-methyl}-4-ethoxybenzyl)tetrahydro-2-furancarboxylic acid

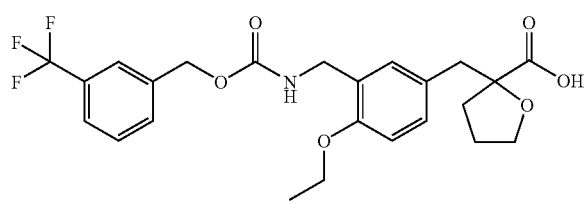

The title compound was obtained according to the method of Example 84 from methyl 2-[3-(ammoniomethyl)-4-ethoxybenzyl]tetrahydro-2-furancarboxylate chloride and 3-trifluoromethylbenzyl alcohol.
MS m/e (ESI) 482.19 (MH⁺)

Example 92

2-(3-{[({[4-Trifluoromethylbenzyl]oxy}carbonyl)amino]-methyl}-4-ethoxybenzyl)tetrahydro-2-furancarboxylic acid

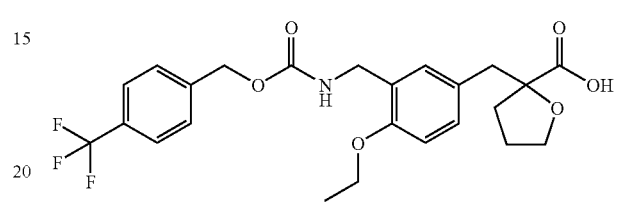

The title compound was obtained according to the method of Example 84 from methyl 2-[3-(ammoniomethyl)-4-ethoxybenzyl]tetrahydro-2-furancarboxylate chloride and 4-trifluoromethylbenzyl alcohol.
MS m/e (ESI) 482.19 (MH⁺)

Example 93

2-(3-{[({[3-Trifluoromethoxybenzyl]oxy}carbonyl)amino]-methyl}-4-ethoxybenzyl)tetrahydro-2-furancarboxylic acid

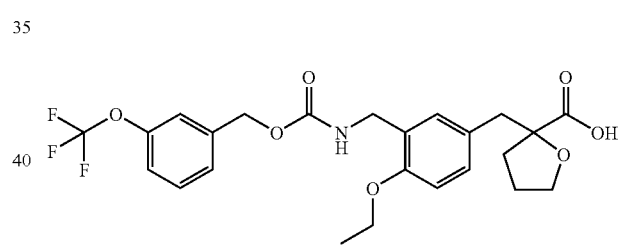

The title compound was obtained according to the method of Example 84 from methyl 2-[3-(ammoniomethyl)-4-ethoxybenzyl]tetrahydro-2-furancarboxylate chloride and 3-trifluoromethoxybenzyl alcohol.
MS m/e (ESI) 498.19 (MH⁺)

Example 94

2-(3-{[({[4-Trifluoromethoxybenzyl]oxy}carbonyl)amino]-methyl}-4-ethoxybenzyl)tetrahydro-2-furancarboxylic acid

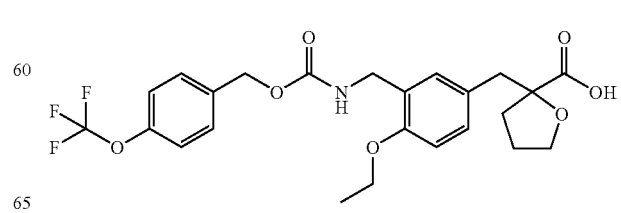

Example 95

2-(3-{[({[2,4-Dichlorobenzyl]oxy}carbonyl)amino]methyl}-4-ethoxybenzyl)tetrahydro-2-furancarboxylic acid

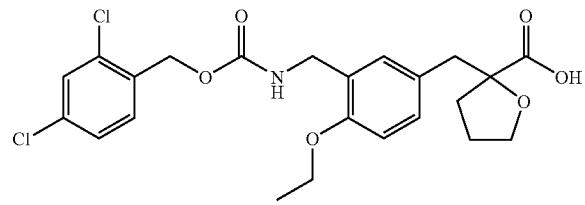

The title compound was obtained according to the method of Example 84 from methyl 2-[3-(ammoniomethyl)-4-ethoxybenzyl]tetrahydro-2-furancarboxylate chloride and 2,4-dichlorobenzyl alcohol.

MS m/e (ESI) 482.13 (MH$^+$)

Example 96

2-(3-{[({[3,4-Dichlorobenzyl]oxy}carbonyl)amino]methyl}-4-ethoxybenzyl)tetrahydro-2-furancarboxylic acid

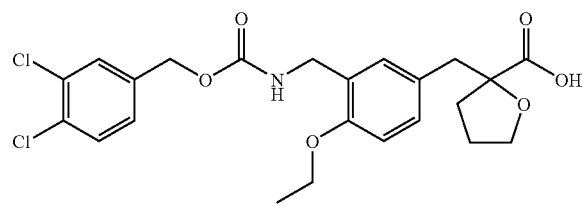

The title compound was obtained according to the method of Example 84 from methyl 2-[3-(ammoniomethyl)-4-ethoxybenzyl]tetrahydro-2-furancarboxylate chloride and 3,4-dichlorobenzyl alcohol.

MS m/e (ESI) 504.12 (MH$^+$)

Example 97

2-(3-{[({[3-Chloro-4-trifluoromethylbenzyl]oxy}carbonyl)amino]methyl}-4-ethoxybenzyl)tetrahydro-2-furancarboxylic acid

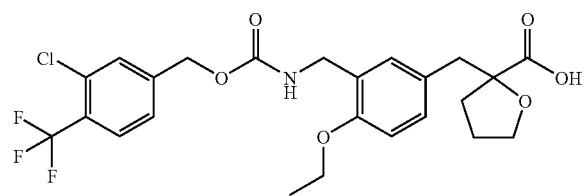

The title compound was obtained according to the method of Example 84 from methyl 2-[3-(ammoniomethyl)-4-ethoxybenzyl]tetrahydro-2-furancarboxylate chloride and 3-chloro-4-trifluoromethylbenzyl alcohol.

MS m/e (ESI) 522.17 (MNa$^+$)

Example 98

2-(3-{[({[2-Chloro-4-propoxybenzyl]oxy}carbonyl)amino]-methyl}-4-ethoxybenzyl)tetrahydro-2-furancarboxylic acid

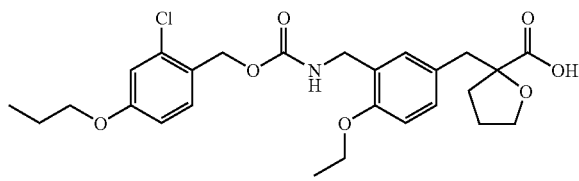

The title compound was obtained according to the method of Example 84 from methyl 2-[3-(ammoniomethyl)-4-ethoxybenzyl]tetrahydro-2-furancarboxylate chloride and 2-chloro-4-propoxybenzyl alcohol.

MS m/e (ESI) 462.22 (MH$^+$—CO$_2$), 506.19 (MH$^+$)

Example 99

2-{3-[(Benzo[1,3]dioxol-5-ylmethoxycarbonylamino)methyl]-4-ethoxybenzyl}tetrahydro-2-furancarboxylic acid

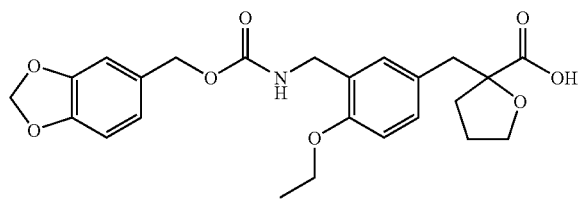

The title compound was obtained according to the method of Example 84 from methyl 2-[3-(ammoniomethyl)4-ethoxybenzyl]tetrahydro-2-furancarboxylate chloride and benzo[1,3]dioxol-5-ylmethanol.

MS m/e (ESI) 415.21 (MH$^+$—CO$_2$), 480.20 (MH$^+$)

Example 100

2-{3-[3-(3-Chlorophenoxy)2(R)-hydroxypropoxy]-benzyl}tetrahydro-2-furancarboxylic acid

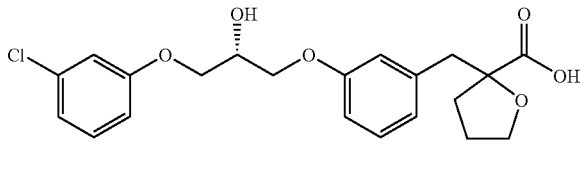

To a solution of 0.020 g of methyl 2-(3-(S)oxiranylmethoxybenzyl)-tetrahydro-2-furancarboxylate in 0.5 ml of N,N-dimethylformamide were added 0.010 g of potassium carbonate and 0.020 g of 3-chlorophenol, and the mixture was heated at 50° C. for 15 hours. The solvent was removed, and the residue was dissolved in 0.5 ml of methanol and treated with 0.1 ml of 1N aqueous sodium hydroxide for 15 hours. The mixture was acidified with 5N hydrochloric acid, and the solvent was evaporated. The residue was purified by HPLC using a reverse-phase column and a water-acetonitrile-trifluoroacetic acid eluent, to give the title compound.

$^1$H-NMR(CDCl$_3$): 1.78-1.92 (m, 2H), 2.00-2.07 (td, J=8.1, 13.1 Hz, 1H), 2.35-2.42 (ddd, J=5.8, 7.9, 13.1 Hz, 1H), 2.92 (d, J=13.9 Hz, 1H), 3.21 (d, J=13.9 Hz, 1H), 3.97-3.93 (q, J=7.2 Hz, 1H), 3.98-4.04 (ddd, J=5.4, 7.2, 8.4 Hz, 1H), 4.08-4.17 (m, 4H), 4.35-4.40 (qd, J=5.4, 7.2 Hz, 1H), 6.81-6.87 (m, 4H), 6.93-6.96 (m, 2H), 7.18-7.23 (m, 2H)

MS m/e (ESI) 363.01 (MH$^+$—CO$_2$), 407.01 (MH$^+$)

Example 101

2-{3-[3-(4-Chlorophenoxy)2(R)-hydroxypropoxy]-benzyl}tetrahydro-2-furancarboxylic acid

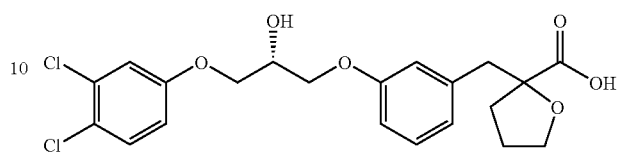

The title compound was obtained according to the method of Example 100 from methyl 2-(3-(S)oxiranylmethoxybenzyl)-tetrahydro-2-furancarboxylate and 4-chlorophenol.

MS m/e (ESI) 361.03 (MH$^+$—CO$_2$), 429.02 (MNa$^+$)

Example 102

2-{3-[3-(4-Fluorophenoxy)2(R)-hydroxypropoxy]-benzyl}-tetrahydro-2-furancarboxylic acid

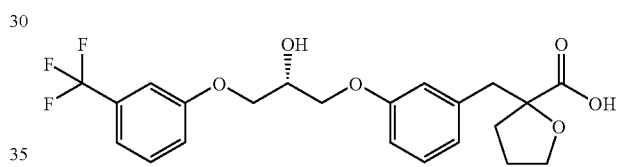

The title compound was obtained according to the method of Example 100 from methyl 2-(3-(S)oxiranylmethoxybenzyl)-tetrahydro-2-furancarboxylate and 4-fluorophenol.

MS m/e (ESI) 345.09 (MH$^+$—CO$_2$), 413.07 (MNa$^+$)

Example 103

2-{3-[3-(2,4-Dichlorophenoxy)2(R)-hydroxypropoxy]-benzyl}tetrahydro-2-furancarboxylic acid

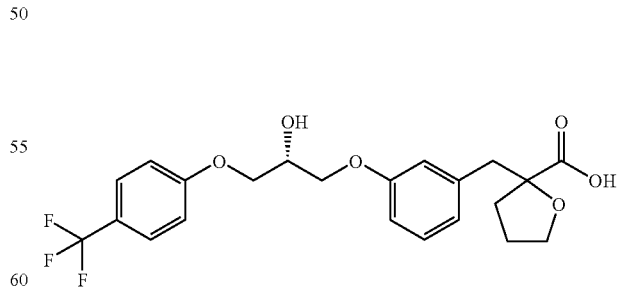

The title compound was obtained according to the method of Example 100 from methyl 2-(3-(S)oxiranylmethoxybenzyl)-tetrahydro-2-furancarboxylate and 2,4-dichlorophenol.

MS m/e (ESI) 463.01 (MNa$^+$)

Example 104

2-{3-[3-(3,4-Dichlorophenoxy)2(R)-hydroxypropoxy]-benzyl}tetrahydro-2-furancarboxylic acid The title compound was obtained according to the method of Example 100 from methyl 2-(3-(S)oxiranylmethoxybenzyl)-tetrahydro-2-furancarboxylate and 3,4-dichlorophenol.

MS m/e (ESI) 463.02 (MNa$^+$)

Example 105

2-{3-[3-(3-Trifluoromethylphenoxy)2(R)-hydroxypropoxy]-benzyl}tetrahydro-2-furancarboxylic acid The title compound was obtained according to the method of Example 100 from methyl 2-(3-(S)oxiranylmethoxybenzyl)-tetrahydro-2-furancarboxylate and 3-trifluoromethylphenol.

MS t/e (ESI) 463.10 (MNa$^+$)

Example 106

2-{3-[3-(4-Trifluoromethylphenoxy)2(R)-hydroxypropoxy]-benzyl}tetrahydro-2-furancarboxylic acid The title compound was obtained according to the method of Example 100 from methyl 2-(3-(S)oxiranylmethoxybenzyl)-tetrahydro-2-furancarboxylate and 4-trifluoromethylphenol.

MS m/e (ESI) 463.10 (MNa$^+$)

Example 107

2-{3-[3-(2-Trifluoromethoxyphenoxy)2(R)-hydroxypropoxy]-benzyl}tetrahydro-2-furancarboxylic acid

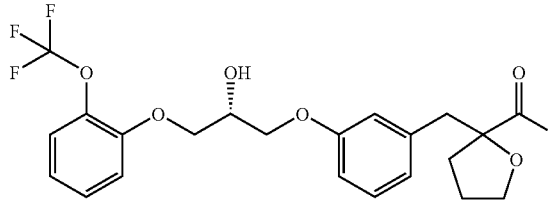

The title compound was obtained according to the method of Example 100 from methyl 2-(3-(S)oxiranylmethoxybenzyl)-tetrahydro-2-furancarboxylate and 2-trifluoromethoxyphenol.

MS m/e (ESI) 479.10 (MNa$^+$)

Example 108

2-{3-[3-(4-Chloro-3-methylphenoxy)2(R)-hydroxypropoxy]-benzyl}tetrahydro-2-furancarboxylic acid

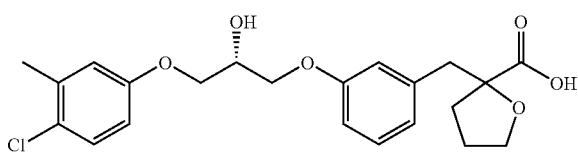

The title compound was obtained according to the method of Example 100 from methyl 2-(3-(S)oxiranylmethoxybenzyl)-tetrahydro-2-furancarboxylate and 4-chloro-3-methylphenol.

MS m/e (ESI) 443.09 (MNa$^+$)

Example 109

2-{3-[3-(4-Ethylphenoxy)2(S)-hydroxypropoxy]-benzyl}tetrahydro-2-furancarboxylic acid

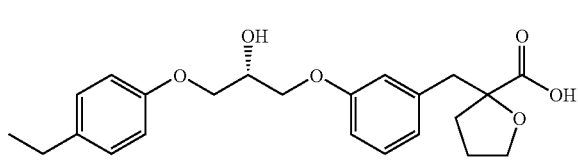

The title compound was obtained according to the method of Example 100 from methyl 2-(3-(S)oxiranylmethoxybenzyl)-tetrahydro-2-furancarboxylate and 4-ethylphenol.

MS m/e (ESI) 423.16 (MNa$^+$)

Example 110

2-{3-[3-(4-t-Butylphenoxy)2(R)-hydroxypropoxy]-benzyl}tetrahydro-2-furancarboxylic acid

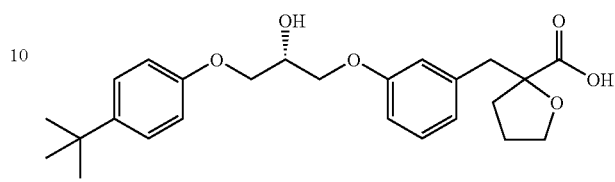

The title compound was obtained according to the method of Example 100 from methyl 2-(3-(S)oxiranylmethoxybenzyl)-tetrahydro-2-furancarboxylate and 4-t-butylphenol.

MS m/e (ESI) 451.19 (MNa$^+$)

Example 111

2-{3-[3-(2-Cyclopentylphenoxy)2(R)-hydroxypropoxy]-benzyl}tetrahydro-2-furancarboxylic acid

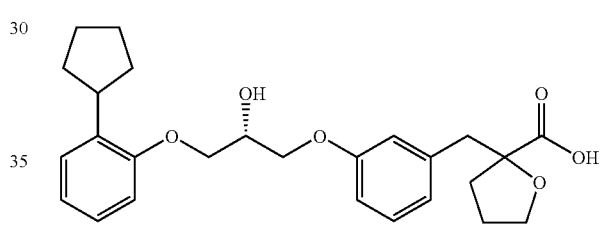

The title compound was obtained according to the method of Example 100 from methyl 2-(3-(S)oxiranylmethoxybenzyl)-tetrahydro-2-furancarboxylate and 2-cyclopentylphenol.

MS m/e (ESI) 463.18 (MNa$^+$)

Example 112

2-{3-[3-(4-Cyclopentylphenoxy)2(R)-hydroxypropoxy]-benzyl}tetrahydro-2-furancarboxylic acid

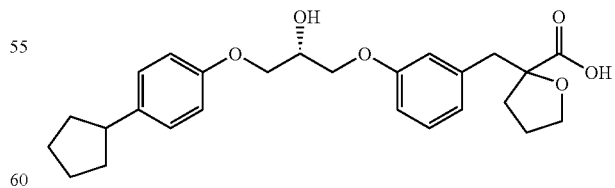

The title compound was obtained according to the method of Example 100 from methyl 2-(3-(S)oxiranylmethoxybenzyl)-tetrahydro-2-furancarboxylate and 4-cyclopentylphenol.

MS m/e (ESI) 441.20 (MH$^+$)

Example 113

2-{3-[3-(Benzo[1,3]dioxol-5-yloxy)2(R)-hydroxypropoxy]-benzyl}tetrahydro-2-furancarboxylic acid

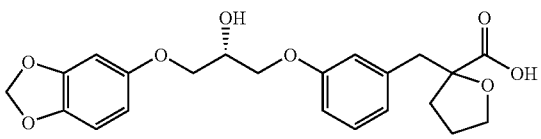

The title compound was obtained according to the method of Example 100 from methyl 2-(3-(S)oxiranylmethoxybenzyl)-tetrahydro-2-furancarboxylate and benzo[1,3]dioxol-5-ol.

$^1$H-NMR(CDCl$_3$): 1.75-1.92 (m, 2H), 2.00-2.07 (td, J=8.1, 13.1 Hz, 1H), 2.35-2.42 (ddd, J=5.9, 7.7, 13.1 Hz, 1H), 2.92 (d, J=14.0 Hz, 1H), 3.22 (d, J=14.0 Hz, 1H), 3.87-3.94 (q, J=7.7 Hz, 1H), 3.98-4.05 (dt, J=5.9, 7.7 Hz, 1H), 4.07-4.17 (m, 4H), 4.34-4.38 (quint, J=5.4 Hz, 1H), 6.36 (dd, J=2.7, 8.5 Hz, 1H), 6.53 (d, J=2.7 Hz, 1H), 6.71 (d, J=8.5 Hz, 1H), 6.81-6.86 (m, 3H), 7.18-7.22 (m, 1H)

MS m/e (ESI) 417.14 (MH$^+$)

Example 114

2-{3-[2(R)-Hydroxy-3-(indan-5-yloxy)propoxy]-benzyl}tetrahydro-2-furancarboxylic acid

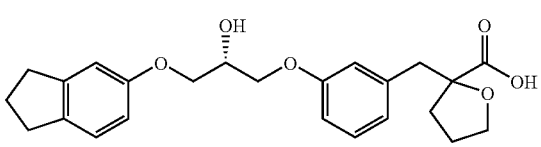

The title compound was obtained according to the method of Example 100 from methyl 2-(3-(S)oxiranylmethoxybenzyl)-tetrahydro-2-furancarboxylate and indan-5-ol.

MS m/e (ESI) 413.18 (MH$^+$)

Example 115

2-(3-{3-[3-(2-Hydroxyethyl)phenoxy]2(S)-hydroxypropoxy}-benzyl)tetrahydro-2-furancarboxylic acid

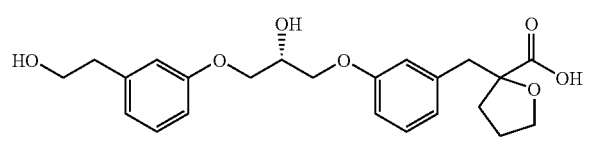

The title compound was obtained according to the method of Example 100 from methyl 2-(3-(S)oxiranylmethoxybenzyl)-tetrahydro-2-furancarboxylate and 3-(2-hydroxyethyl)phenol.

MS m/e (ESI) 439.15 (MNa$^+$)

Example 116

2-(3-{3-[4-(2-Hydroxyethyl)phenoxy]2(S)-hydroxypropoxy}-benzyl)tetrahydro-2-furancarboxylic acid

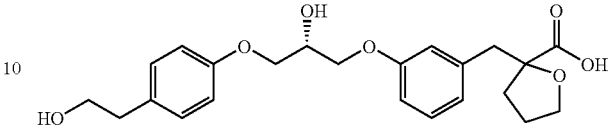

The title compound was obtained according to the method of Example 100 from methyl 2-(3-(S)oxiranylmethoxybenzyl)-tetrahydro-2-furancarboxylate and 4-(2-hydroxyethyl)phenol.

$^1$H-NMR(CDCl$_3$): 1.80-1.92 (m, 2H), 2.00-2.07 (td, J=7.5, 12.7 Hz, 1H), 2.35-2.42 (ddd, J=0.8, 6.2, 12.7 Hz, 1H), 2.84 (t, J=6.2 Hz, 2H), 2.94 (d, J=14.1 Hz, 1H), 3.23 (d, J=14.1 Hz, 1H), 3.84 (t, J=6.2 Hz, 2H), 3.90 (q, J=7.5 Hz, 1H), 4.02 (dt, J=7.0, 7.5 Hz, 1H), 4.09-4.18 (m, 4H), 4.38 (quint, J=5.5 Hz, 1H), 6.81-6.83 (m, 2H), 6.85 (d, J=7.7 Hz, 1H), 6.89 (d, J=8.8 Hz, 2H), 7.15 (d, J=8.8 Hz, 2H), 7.20 (dd, J=7.7, 8.9 Hz, 1H)

MS m/e (ESI) 439.15 (MNa$^+$)

Example 117

2-{3-[3-(4-Hydroxymethyl-2-methoxyphenoxy)2(R)-hydroxypropoxy]-benzyl}tetrahydro-2-furancarboxylic acid

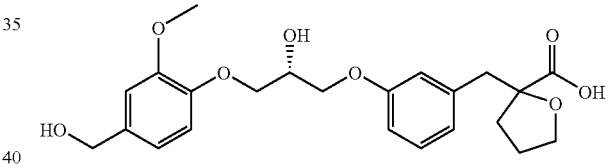

The title compound was obtained according to the method of Example 100 from methyl 2-(3-(S)oxiranylmethoxybenzyl)-tetrahydro-2-furancarboxylate and 4-hydroxymethyl-2-methoxyphenol.

MS m/e (ESI) 455.15 (MH$^+$)

Example 118

2-{3-[3-(5-Hydroxymethyl-2-methoxyphenoxy)2(R)-hydroxypropoxy]-benzyl}tetrahydro-2-furancarboxylic acid

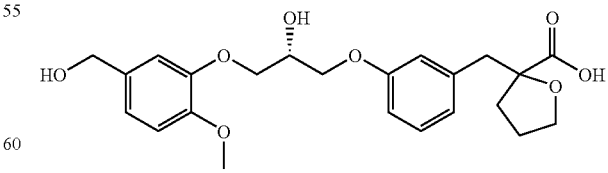

The title compound was obtained according to the method of Example 100 from methyl 2-(3-(S)oxiranylmethoxybenzyl)-tetrahydro-2-furancarboxylate and 5-hydroxymethyl-2-methoxyphenol.

MS m/e (ESI) 455.15 (MH$^+$)

Example 119

2-(3-{3-[2-(2-Hydroxyethoxy)phenoxy]2(R)-hydroxypropoxy}-benzyl)tetrahydro-2-furancarboxylic acid

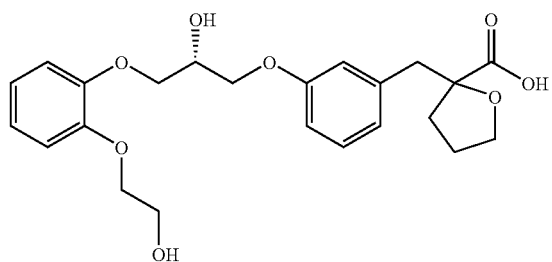

The title compound was obtained according to the method of Example 100 from methyl 2-(3-(S)oxiranylmethoxybenzyl)-tetrahydro-2-furancarboxylate and 2-(2-hydroxyethoxy)phenol.

MS m/e (ESI) 455.15 (MH$^+$)

Example 120

2-{3-[3-(4-Cyanomethylphenoxy)2(R)-hydroxypropoxy]-benzyl}tetrahydro-2-furancarboxylic acid

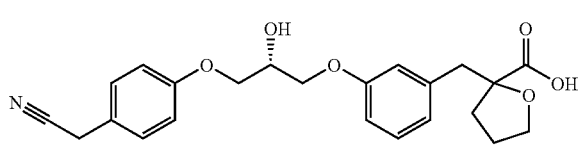

The title compound was obtained according to the method of Example 100 from methyl 2-(3-(S)oxiranylmethoxybenzyl)-tetrahydro-2-furancarboxylate and (4-hydroxyphenyl)acetonitrile.

MS m/e (ESI) 434.17 (MNa$^+$)

Example 121

2-{3-[3-(3-Hydroxymethylphenoxy)2(R)-hydroxypropoxy]-benzyl}tetrahydro-2-furancarboxylic acid

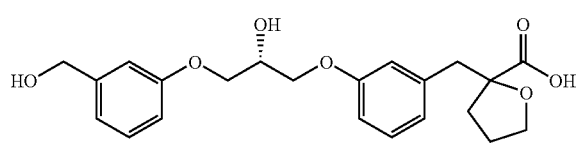

The title compound was obtained according to the method of Example 100 from methyl 2-(3-(S)oxiranylmethoxybenzyl)-tetrahydro-2-furancarboxylate and 3-hydroxymethylphenol.

MS m/e (ESI) 425.12 (MNa$^+$)

Example 122

2-{3-[3-(4-Hydroxymethylphenoxy)2(R)-hydroxypropoxy]-benzyl}tetrahydro-2-furancarboxylic acid

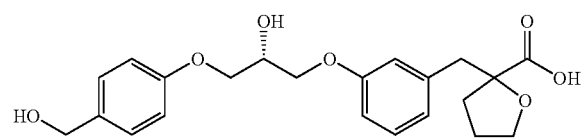

The title compound was obtained according to the method of Example 100 from methyl 2-(3-(S)oxiranylmethoxybenzyl)-tetrahydro-2-furancarboxylate and 4-hydroxymethylphenol.

MS m/e (ESI) 425.12 (MNa$^+$)

Example 123

2-{3-[3-(2-Acetylaminophenoxy)2(R)-hydroxypropoxy]-benzyl}tetrahydro-2-furancarboxylic acid

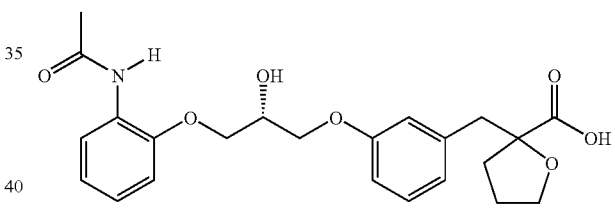

The title compound was obtained according to the method of Example 100 from methyl 2-(3-(S)oxiranylmethoxybenzyl)-tetrahydro-2-furancarboxylate and N-(2-hydroxyphenyl)acetamide.

MS m/e (ESI) 430.16 (MH$^+$)

Example 124

2-{3-[3-(3-Acetylaminophenoxy)2(R)-hydroxypropoxy]-benzyl}tetrahydro-2-furancarboxylic acid

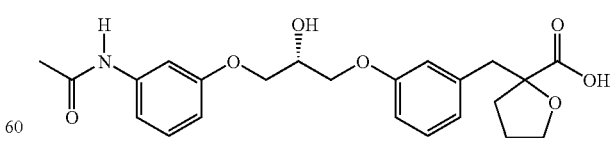

The title compound was obtained according to the method of Example 100 from methyl 2-(3-(S)oxiranylmethoxybenzyl)-tetrahydro-2-furancarboxylate and N-(3-hydroxyphenyl)acetamide.

MS m/e (ESI) 430.16 (MH$^+$)

Example 125

2-{3-[3-(4-Acetylaminophenoxy)2(R)-hydroxypropoxy]-benzyl}tetrahydro-2-furancarboxylic acid

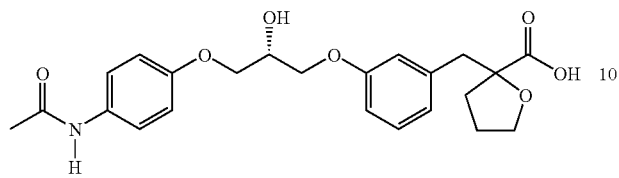

The title compound was obtained according to the method of Example 100 from methyl 2-(3-(S)oxiranylmethoxybenzyl)-tetrahydro-2-furancarboxylate and N-(4-hydroxyphenyl)acetamide.
MS m/e (ESI) 430.16 (MH$^+$)

Example 126

2-{3-[3-(4-Sulfamoylphenoxy)2(R)-hydroxypropoxy]-benzyl}tetrahydro-2-furancarboxylic acid

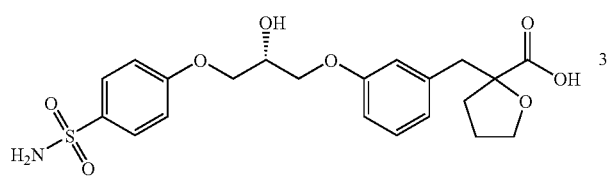

The title compound was obtained according to the method of Example 100 from methyl 2-(3-(S)oxiranylmethoxybenzyl)-tetrahydro-2-furancarboxylate and 4-hydroxybenzene sulfonamide.
MS m/e (ESI) 452.11 (MH$^+$)

Example 127

2-{3-[3-(4-Carboxymethyl-3-methoxyphenoxy)2(R)-hydroxypropoxy]-benzyl}tetrahydro-2-furancarboxylic acid

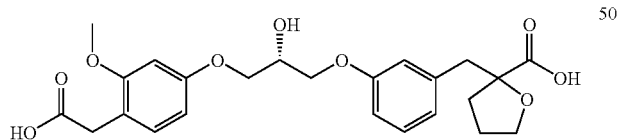

The title compound was obtained according to the method of Example 100 from methyl 2-(3-(S)oxiranylmethoxybenzyl)-tetrahydro-2-furancarboxylate and methyl (4-hydroxy-2-methoxyphenyl)acetate.
$^1$H-NMR(CD$_3$OD): 1.71-1.77 (m, 1H), 1.78-1.83 (m, 1H), 1.88-1.96 (m, 1H), 2.19-2.28 (m, 2H), 2.92 (d, J=13.44 Hz, 1H), 3.14 (d, J=13.4 Hz, 1H), 3.83 (s, 3H), 3.79-3.90 (m, 1H), 3.88 (s, 2H), 4.04-4.16 (m, 4H), 4.20-4.24 (m, 1H), 4.25-4.36 (m, 1H) 6.76-6.88 (m, 5H), 6.91-6.96 (m, 1H), 7.13 (t, J=7.9 Hz, 1H)
MS m/e (ESI) 483.13 (MNa$^+$)

Example 128

2-{3-[3-(2-Piperidin-1-ylphenoxy)2(R)-hydroxypropoxy]-benzyl}tetrahydro-2-furancarboxylic acid

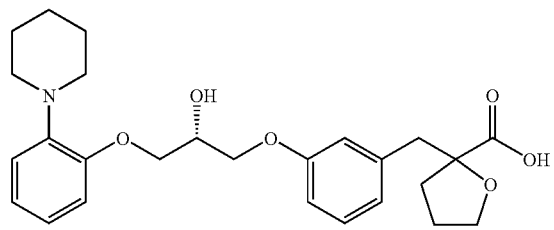

The title compound was obtained according to the method of Example 100 from methyl 2-(3-(S)oxiranylmethoxybenzyl)-tetrahydro-2-furancarboxylate and 2-piperidin-1-ylphenol.
MS m/e (ESI) 456.21 (MH$^+$)

Example 129

2-{3-[3-(2-Oxo-2H-chromen-7-yloxy)2(R)-hydroxypropoxy]-benzyl}tetrahydro-2-furancarboxylic acid

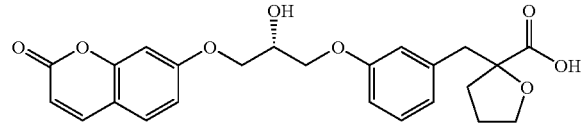

The title compound was obtained according to the method of Example 100 from methyl 2-(3-(S)oxiranylmethoxybenzyl)-tetrahydro-2-furancarboxylate and 7-hydroxychromen-2-one
MS m/e (ESI) 441.12 (MH$^+$)

Example 130

2-(3-{3-[4-(4-Acetylpiperazin-1-yl)phenoxy]-2(R)-hydroxypropoxy}-benzyl)tetrahydro-2-furancarboxylic acid

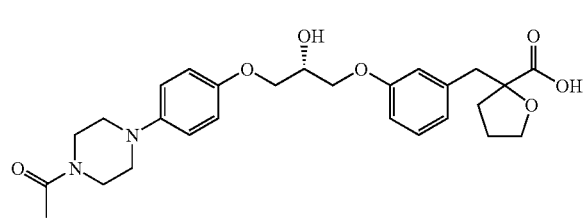

The title compound was obtained according to the method of Example 100 from methyl 2-(3-(S)oxiranylmethoxybenzyl)-tetrahydro-2-furancarboxylate and 1-[4-(4-hydroxyphenyl)-piperazin-1-yl]-ethanone.
MS m/e (ESI) 499.21 (MH$^+$)

Example 131

2-{3-[3-(4-Carboxymethylphenoxy)2(R)-hydroxypropoxy]-benzyl}tetrahydro-2-furancarboxylic acid

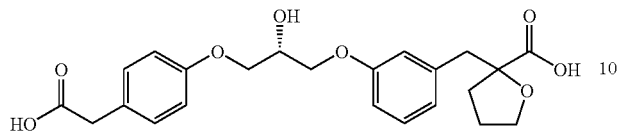

The title compound was obtained according to the method of Example 100 from methyl 2-(3-(S)oxiranylmethoxybenzyl)-tetrahydro-2-furancarboxylate and methyl (4-hydroxyphenyl)acetate.

MS m/e (ESI) 453.12 (MNa$^+$)

Example 132

2-{3-[3-(2-Benzoxazol-2-ylphenoxy)2(R)-hydroxypropoxy]-benzyl}tetrahydro-2-furancarboxylic acid

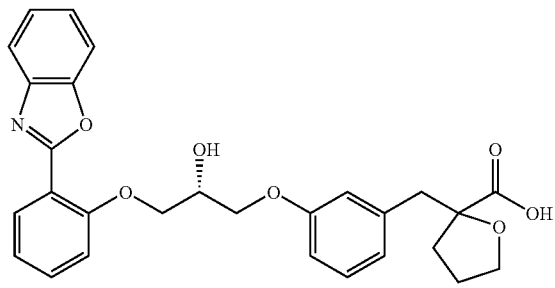

The title compound was obtained according to the method of Example 100 from methyl 2-(3-(S)oxiranylmethoxybenzyl)-tetrahydro-2-furancarboxylate and 2-benzoxazol-2-ylphenol.

MS m/e (ESI) 490.17 (MH$^+$)

Example 133

2-(3-{3-[4-(1-Carboxy-1-methyl-ethyl)-phenoxy]-2(R)-hydroxypropoxy}-benzyl)tetrahydro-2-furancarboxylic acid

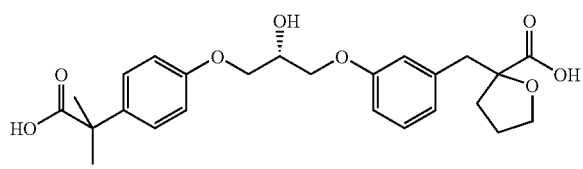

The title compound was obtained according to the method of Example 100 from methyl 2-(3-(S)oxiranylmethoxybenzyl)-tetrahydro-2-furancarboxylate and methyl 2-(4-hydroxyphenyl)-2-methylpropionate.

MS m/e (ESI) 481.20 (MNa$^+$)

Example 134

2-{3-[3-(7-Acetyl-2,3-dihydrobenzofuran-5-yloxy)-2(R)-hydroxypropoxy]-benzyl}tetrahydro-2-furancarboxylic acid

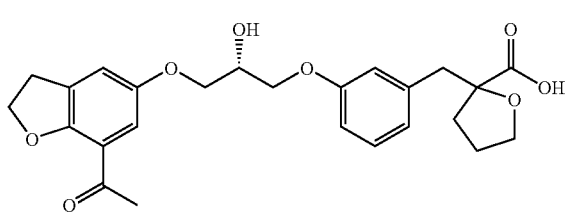

The title compound was obtained according to the method of Example 100 from methyl 2-(3-(S)oxiranylmethoxybenzyl)-tetrahydro-2-furancarboxylate and 1-(5-hydroxy-2,3-dihydrobenzofuran-7-yl)-ethanone.

MS m/e (ESI) 457.16 (MH$^+$)

Example 135

2-{3-[3-(7-Hydroxymethyl-2,3-dihydrobenzofuran-5-yloxy)-2(R)-hydroxypropoxy]-benzyl}tetrahydro-2-furancarboxylic acid

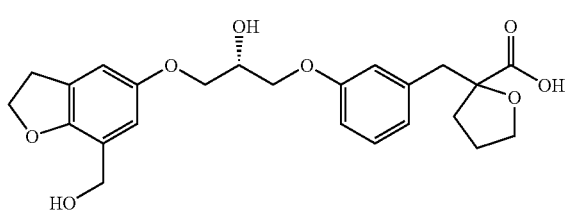

The title compound was obtained according to the method of Example 100 from methyl 2-(3-(S)oxiranylmethoxybenzyl)-tetrahydro-2-furancarboxylate and 7-hydroxymethyl-2,3-dihydrobenzofuran-5-ol.

MS m/e (ESI) 443.13 (MH$^+$)

Example 136

2-{3-[3-(1-Oxoindan-4-oxy)-2(R)-hydroxypropoxy]-benzyl}tetrahydro-2-furancarboxylic acid

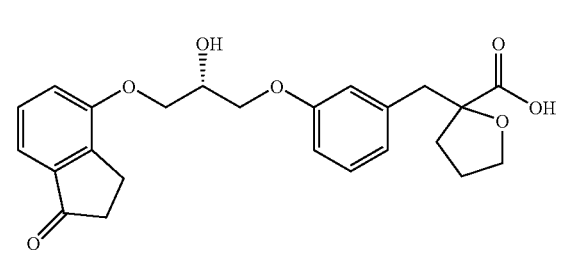

The title compound was obtained according to the method of Example 100 from methyl 2-(3-(S)oxiranylmethoxybenzyl)-tetrahydro-2-furancarboxylate and 4-hydroxyindan-1-one.
MS m/e (ESI) 427.14 (MH⁺)

Example 137

2-(3-{3-[4-(Pyrrolidine-1-carbonyl)-phenoxy]-2(R)-hydroxypropoxy}-benzyl)tetrahydro-2-furancarboxylic acid

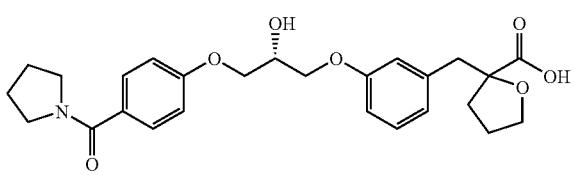

The title compound was obtained according to the method of Example 100 from methyl 2-(3-(S)oxiranylmethoxybenzyl)-tetrahydro-2-furancarboxylate and (4-hydroxyphenyl)-pyrrolidin-1-ylmethanone.
MS m/e (ESI) 470.18 (MH⁺)

Example 138

2-(3-{3-[4-(3-Aziridin-1-yl-3-oxopropenyl)-2-methoxyphenoxy]-2(R)-hydroxypropoxy}-benzyl)tetrahydro-2-furancarboxylic acid

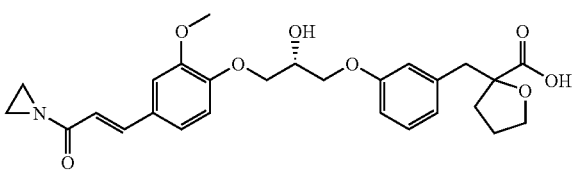

The title compound was obtained according to the method of Example 100 from methyl 2-(3-(S)oxiranylmethoxybenzyl)-tetrahydro-2-furancarboxylate and 1-aziridin-1-yl-3-(4-hydroxy-3-methoxyphenyl)-propenone.
MS m/e (ESI) 498.18 (MH⁺)

Example 139

2-{3-[3-(4-Methyl-2-oxobenzoxazol-3-yl)-2(R)-hydroxypropoxy]-benzyl}tetrahydro-2-furancarboxylic acid

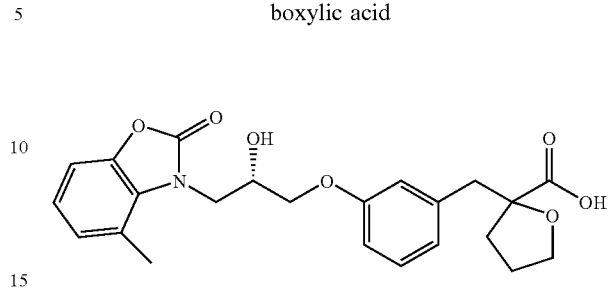

The title compound was obtained according to the method of Example 100 from methyl 2-(3-(S)oxiranylmethoxybenzyl)-tetrahydro-2-furancarboxylate and 1-butyl-3-(2-hydroxy-6-methylphenyl)-urea.
MS m/e (ESI) 428.13 (MH⁺)

Example 140

2-{3-[3-(1-Butylcarbamoyl-1,2,3,4-tetrahydroquinolin-8-yloxy)-2(R)-hydroxypropoxy]-benzyl}tetrahydro-2-furancarboxylic acid

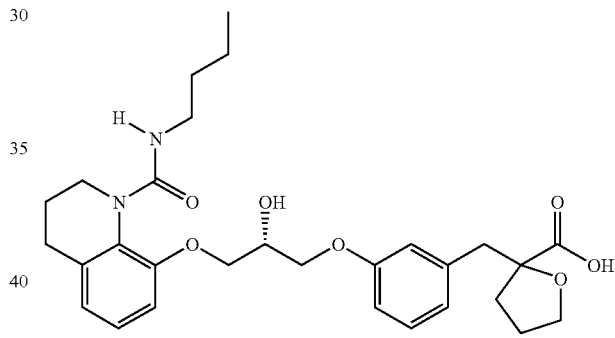

The title compound was obtained according to the method of Example 100 from methyl 2-(3-(S)oxiranylmethoxybenzyl)-tetrahydro-2-furancarboxylate and 8-hydroxy-3,4-dihydro-2H-quinoline-1-carboxylic acid butylamide.
MS m/e (ESI) 527.24 (MH⁺)

Example 141

2-(3-{3-[2-(4-Cyanophenyl)benzoxazol-5-yloxy]-2(R)-hydroxypropoxy}-benzyl)tetrahydro-2-furancarboxylic acid

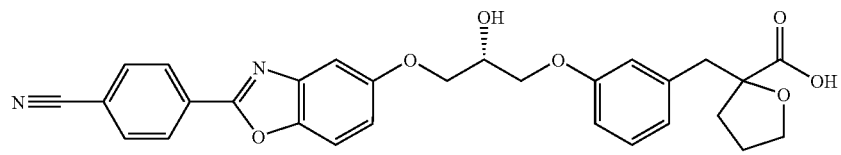

The title compound was obtained according to the method of Example 100 from methyl 2-(3-(S)oxiranylmethoxybenzyl)-tetrahydro-2-furancarboxylate and 4-(5-hydroxybenzoxazol-2-yl)-benzonitrile.
MS m/e (ESI) 515.14 (MH⁺)

Example 142

2-(3-{3-[4-(1-Hydroxy-1-methyl-2-oxopropyl)-phenoxy]-2(R)-hydroxypropoxy}-benzyl)tetrahydro-2-furancarboxylic acid

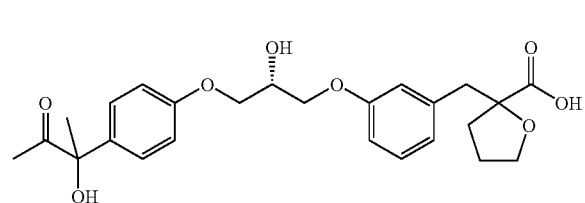

The title compound was obtained according to the method of Example 100 from methyl 2-(3-(S)oxiranylmethoxybenzyl)-tetrahydro-2-furancarboxylate and 3-hydroxy-3-(4-hydroxyphenyl)-butan-2-one.
MS m/e (ESI) 481.14 (MNa⁺)

Example 143

2-(3-{3-[4-(2,2-Dimethylpropyl)-phenoxy]-2(S)-hydroxypropoxy}-benzyl)tetrahydro-2-furancarboxylic acid

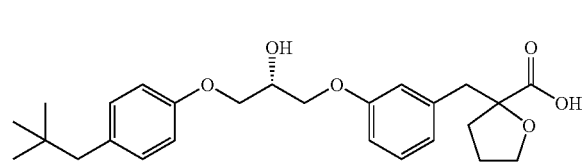

The title compound was obtained according to the method of Example 100 from methyl 2-(3-(S)oxiranylmethoxybenzyl)-tetrahydro-2-furancarboxylate and 4-(2,2-dimethylpropyl)-phenol.
MS m/e (ESI) 443.20 (MH⁺)

Example 144

2-(3-{3-[4-(Pyrazin-2-ylsulfanyl)-phenoxy]-2(R)-hydroxypropoxy}-benzyl)tetrahydro-2-furancarboxylic acid

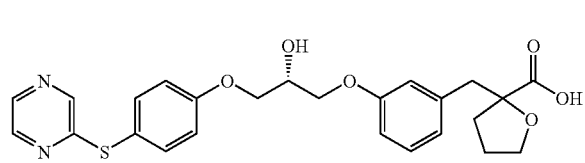

The title compound was obtained according to the method of Example 100 from methyl 2-(3-(S)oxiranylmethoxybenzyl)-tetrahydro-2-furancarboxylate and 4-pyrazin-2-ylsulfanyl)phenol.
MS m/e (ESI) 483.11 (MH⁺)

Example 145

2-(3-{3-[3-(2-Carboxyethyl)-4-methoxyphenoxy]-2(R)-hydroxypropoxy}-benzyl)tetrahydro-2-furancarboxylic acid

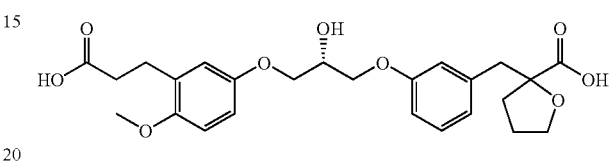

The title compound was obtained according to the method of Example 100 from methyl 2-(3-(S)oxiranylmethoxybenzyl)-tetrahydro-2-furancarboxylate and methyl 3-(5-hydroxy-2-methoxyphenyl)-propionate.
MS m/e (ESI) 497.13 (MNa⁺)

Example 146

2-{3-[3-(2-Oxo-1,2,3,4-tetrahydroquinolin-5-yloxy)-2(R)-hydroxypropoxy]-benzyl}tetrahydro-2-furancarboxylic acid

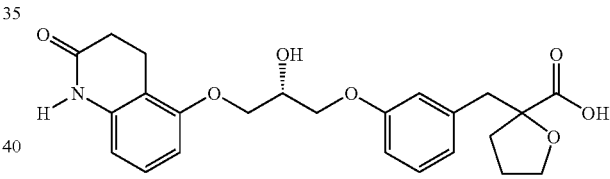

The title compound was obtained according to the method of Example 100 from methyl 2-(3-(S)oxiranylmethoxybenzyl)-tetrahydro-2-furancarboxylate and 5-hydroxy-3,4-dihydro-1H-quinolin-2-one.
MS m/e (ESI) 442.16 (MH⁺)

Example 147

2-{3-[3-(2,4-Dichlorophenoxy)2(S)-hydroxypropoxy]-benzyl}tetrahydro-2-furancarboxylic acid

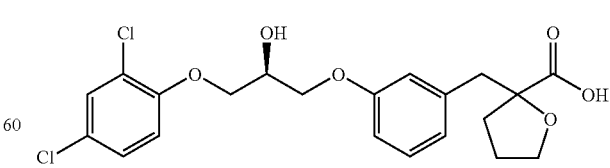

The title compound was obtained according to the method of Example 100 from methyl 2-(3-(R)oxiranylmethoxybenzyl)-tetrahydro-2-furancarboxylate and 2,4-dichlorophenol.
MS m/e (ESI) 463.03 (MNa⁺)

Example 148

2-{3-[3-(4-t-Butylphenoxy)2(S)-hydroxypropoxy]-benzyl}tetrahydro-2-furancarboxylic acid

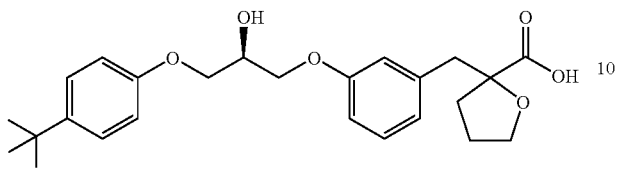

The title compound was obtained according to the method of Example 100 from methyl 2-(3-(R)oxiranylmethoxybenzyl)-tetrahydro-Z-furancarboxylate and 4-t-butylphenol.

MS m/e (ESI) 451.17 (MNa$^+$)

Example 149

2-(3-{[(2,4-Dichlorobenzoyl)amino]methyl}-benzyl)-2,5-dihydro-2-furancarboxylic acid

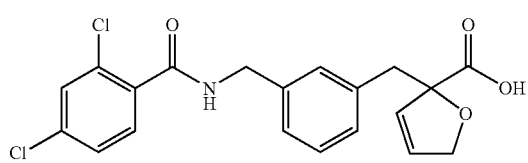

The title compound was obtained according to the method of Example 1 from isopropyl 2-[3-(ammoniomethyl)-benzyl]-2,5-dihydro-2-furancarboxylate chloride and 2,4-dichlorobenzoic acid.

MS m/e (ESI) 405.88 (MH$^+$)

Example 150

2-(3-{[(2-Fluoro-4-(trifluoromethyl)benzoyl)amino]methyl}-benzyl)-2,5-dihydro-2-furancarboxylic acid

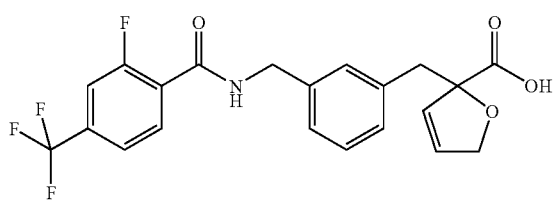

The title compound was obtained according to the method of Example 1 from isopropyl 2-[3-(ammoniomethyl)-benzyl]-2,5-dihydro-2-furancarboxylate chloride and 2-fluoro-4-(trifluoromethyl)benzoic acid.

MS m/e (ESI) 445.92 (MNa$^+$)

Example 151

2-(3-{[(2-Chloro-4-phenylbenzoyl)amino]methyl}-benzyl)-2,5-dihydro-2-furancarboxylic acid

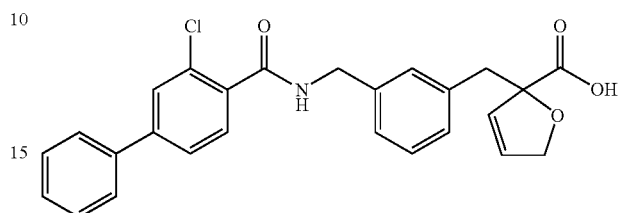

The title compound was obtained according to the method of Example 1 from isopropyl 2-[3-(ammoniomethyl)-benzyl]-2,5-dihydro-2-furancarboxylate chloride and 2-chloro-4-phenylbenzoic acid.

MS m/e (ESI) 447.98 (MH$^+$)

Example 152

2-(3-{[(2-Chloro-4-ethoxybenzoyl)amino]methyl}-benzyl)-2,5-dihydro-2-furancarboxylic acid

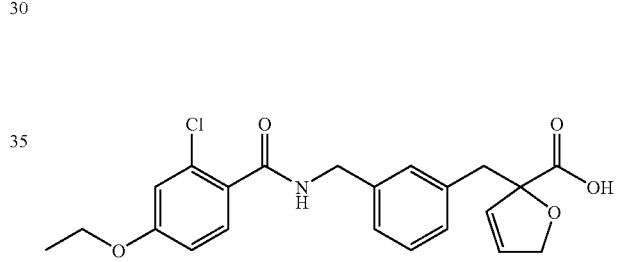

The title compound was obtained according to the method of Example 1 from isopropyl 2-[3-(ammoniomethyl)-benzyl]-2,5-dihydro-2-furancarboxylate chloride and 2-chloro-4-ethoxybenzoic acid.

MS m/e (ESI) 415.98 (MH$^+$)

Example 153

2-(3-{[(2-Chloro-4-propoxybenzoyl)amino]methyl}-benzyl)-2,5-dihydro-2-furancarboxylic acid

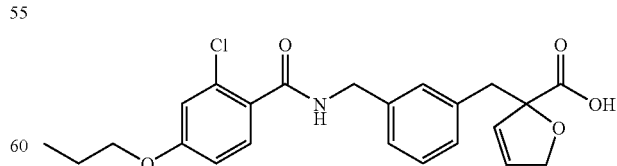

The title compound was obtained according to the method of Example 1 from isopropyl 2-[3-(ammoniomethyl)-benzyl]-2,5-dihydro-2-furancarboxylate chloride and 2-chloro-4-propoxybenzoic acid.

MS m/e (ESI) 430.00 (MH$^+$)

Example 154

2-(3-{[(2-Chloro-4-isopropoxybenzoyl)amino]methyl}-benzyl)-2,5-dihydro-2-furancarboxylic acid

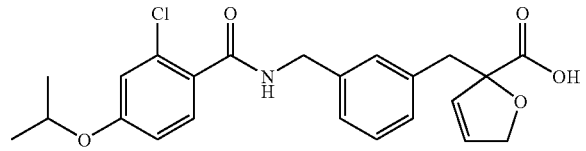

The title compound was obtained according to the method of Example 1 from isopropyl 2-[3-(ammoniomethyl)-benzyl]-2,5-dihydro-2-furancarboxylate chloride and 2-chloro-4-isopropoxybenzoic acid.

MS m/e (ESI) 430.01 (MH$^+$)

Example 155

2-(3-{[(2-Chloro-4-cyclopentyloxybenzoyl)amino]methyl}-benzyl)-2,5-dihydro-2-furancarboxylic acid

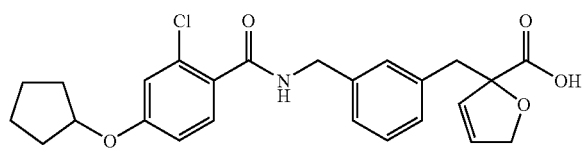

The title compound was obtained according to the method of Example 1 from isopropyl 2-[3-(ammoniomethyl)-benzyl]-2,5-dihydro-2-furancarboxylate chloride and 2-chloro-4-cyclopentyloxybenzoic acid.

MS m/e (ESI) 456.01 (MH$^+$)

Example 156

2-{3-[({[2-(4-Chlorophenyl)-4-methyl-1,3-thiazol-5-yl]carbonyl}amino)methyl]-benzyl}-2,5-dihydro-2-furancarboxylic acid

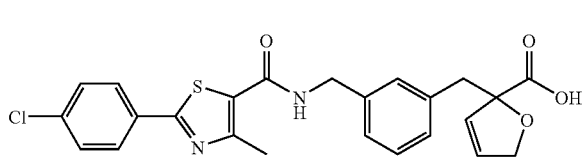

The title compound was obtained according to the method of Example 1 from isopropyl 2-[3-(ammoniomethyl)-benzyl]-2,5-dihydro-2-furancarboxylate chloride and 4-methyl-2-(4-chlorophenyl)-1,3-thiazol-5-carboxylic acid.

MS m/e (ESI) 468.96 (MH$^+$)

Example 157

2-(4-{[(2,4-Dichlorobenzoyl)amino]methyl}benzyl)tetrahydro-2-furancarboxylic acid

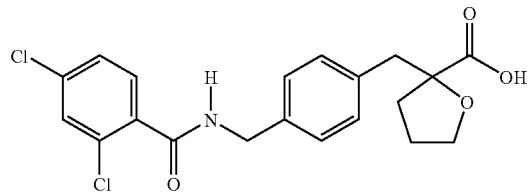

The title compound was obtained according to the method of Example 1 from methyl 2-[4-(ammoniomethyl)-benzyl]tetrahydro-2-furancarboxylate chloride and 2,4-dichlorobenzoic acid.

MS m/e (ESI) 429.98 (MNa$^+$)

Example 158

2-(4-{[(2-Fluoro-4-(trifluoromethyl)-benzoyl)amino]methyl}-benzyl)tetrahydro-2-furancarboxylic acid

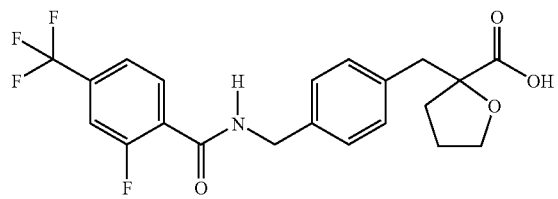

The title compound was obtained according to the method of Example 1 from methyl 2-[4-(ammoniomethyl)benzyl]tetrahydro-2-furancarboxylate chloride and 2-fluoro-4-(trifluoromethyl)benzoic acid.

MS m/e (ESI) 448.00 (MNa$^+$)

Example 159

2-(4-{[(2-Chloro-4-propoxybenzoyl)amino]methyl}benzyl)-tetrahydro-2-furancarboxylic acid

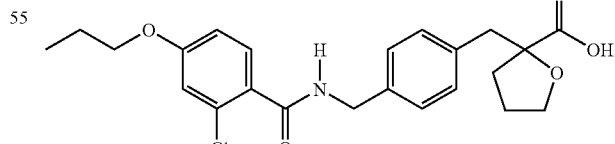

The title compound was obtained according to the method of Example 1 from methyl 2-[4-(ammoniomethyl)-benzyl]tetrahydro-2-furancarboxylate chloride and 2-chloro-4-propoxybenzoic acid.

MS m/e (ESI) 432.07 (MH$^+$)

Example 160

2-(4-{[(2-Chloro-4-isopropoxybenzoyl)amino]methyl}benzyl)-tetrahydro-2-furancarboxylic acid

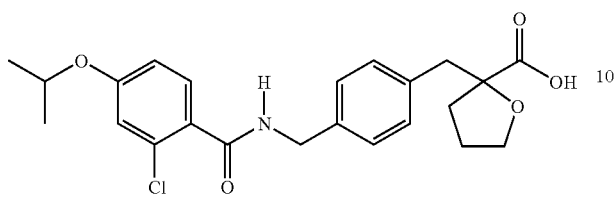

The title compound was obtained according to the method of Example 1 from methyl 2-[4-(ammoniomethyl)-benzyl]tetrahydro-2-furancarboxylate chloride and 2-chloro-4-isopropoxybenzoic acid.

MS m/e (ESI) 432.09 (MH$^+$)

Example 161

2-(4-{[(2-Chloro-4-cyclopentyloxybenzoyl)amino]methyl}-benzyl)tetrahydro-2-furancarboxylic acid

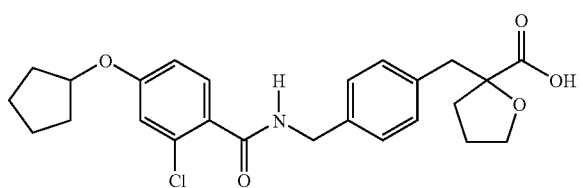

The title compound was obtained according to the method of Example 1 from methyl 2-[4-(ammoniomethyl)-benzyl]tetrahydro-2-furancarboxylate chloride and 2-chloro-4-cyclopentyloxybenzoic acid.

MS m/e (ESI) 458.15 (MH$^+$)

Example 162

2-{4-[({[2-(4-Chlorophenyl)-4-methyl-1,3-thiazol-5-yl]carbonyl}amino)methyl]benzyl}tetrahydro-2-furancarboxylic acid

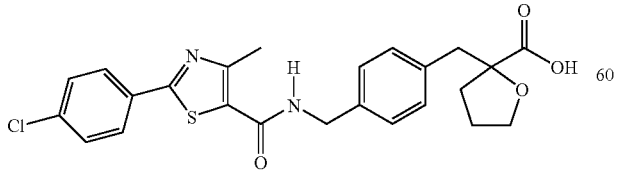

The title compound was obtained according to the method of Example 1 from methyl 2-[4-(ammoniomethyl)-benzyl]tetrahydro-2-furancarboxylate chloride and 2-(4-chlorobenzyl)-4-methyl-1,3-thiazol-5-carboxylic acid.

MS n/e (ESI) 471.08 (MH$^+$)

Example 163

2-[3-(3-Chlorophenylcarbamoyloxymethyl)-4-ethoxybenzyl]-tetrahydro-2-furancarboxylic acid

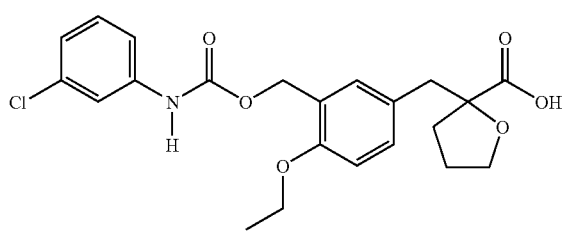

To a solution of 0.012 g of methyl 2-(4-ethoxy-3-hydroxymethylbenzyl)tetrahydro-2-furancarboxylate in 0.2 ml of tetrahydrofuran were added 0.010 ml of pyridine and 0.0066 g of 3-chlorophenylisocyanic acid, and the mixture was stirred at room temperature for 15 hours. 1 ml of ethyl acetate and 0.5 ml of 1 N hydrochloric acid were added, and the organic layer was concentrated. The residue was dissolved in 0.5 ml of tetrahydrofuran, 0.5 ml of ethanol and 0.2 ml of 1 N sodium hydroxide, and the mixture was stirred for 2 hours. 1 ml of ethyl acetate and 0.5 ml of 1 N hydrochloric acid were added, and the organic layer was concentrated. The residue was purified by HPLC using a reverse-phase column and a water-acetonitrile-trifluoroacetic acid elution solvent system, to give the title compound.

MS m/e (ESI) 455.94 (MNa$^+$)

Example 164

2-[3-(4-Chlorophenylcarbamoyloxymethyl)-4-ethoxybenzyl]-tetrahydro-2-furancarboxylic acid

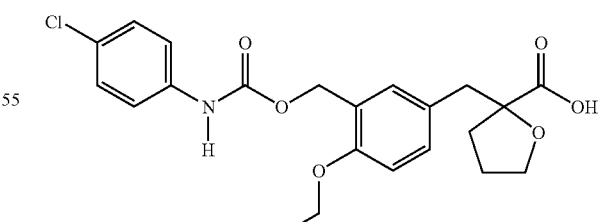

The title compound was obtained according to the method of Example 163 from methyl 2-(4-ethoxy-3-hydroxymethylbenzyl)tetrahydro-2-furancarboxylate and 4-chlorophenylisocyanic acid.

MS m/e (ESI) 455.96 (MNa$^+$)

Example 165

2-[3-(2,4-Dichlorophenylcarbamoyloxymethyl)-4-ethoxybenzyl]-tetrahydro-2-furancarboxylic acid

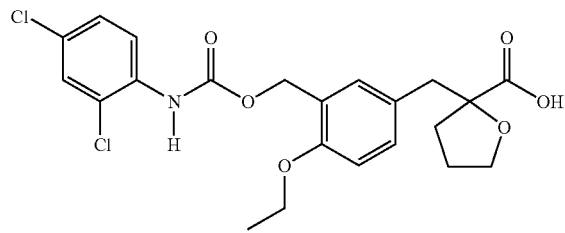

The title compound was obtained according to the method of Example 163 from methyl 2-(4-ethoxy-3-hydroxymethylbenzyl)tetrahydro-2-furancarboxylate and 2,4-dichlorophenylisocyanic acid.

MS m/e (ESI) 489.92 (MNa$^+$)

Example 166

2-[3-(2,4-Difluorophenylcarbamoyloxymethyl)-4-ethoxybenzyl]-tetrahydro-2-furancarboxylic acid

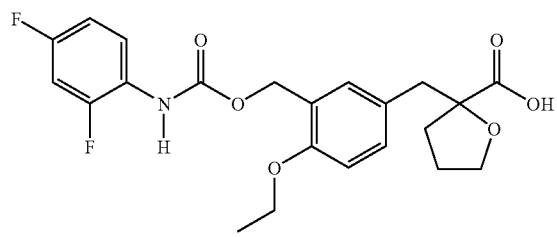

The title compound was obtained according to the method of Example 163 from methyl 2-(4-ethoxy-3-hydroxymethylbenzyl)tetrahydro-2-furancarboxylate and 2,4-difluorophenylisocyanic acid.

MS m/e (ESI) 458.00 (MNa$^+$)

Example 167

2-[3-(3-Trifluoromethylphenylcarbamoyloxymethyl)-4-ethoxybenzyl]-tetrahydro-2-furancarboxylic acid

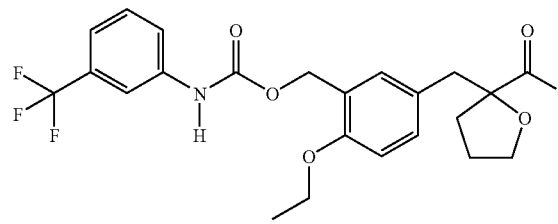

The title compound was obtained according to the method of Example 163 from methyl 2-(4-ethoxy-3-hydroxymethylbenzyl)tetrahydro-2-furancarboxylate and 3-trifluoromethylphenylisocyanic acid.

MS m/e (ESI) 490.02 (MNa$^+$)

Example 168

2-[3-(4-Trifluoromethylphenylcarbamoyloxymethyl)-4-ethoxybenzyl]-tetrahydro-2-furancarboxylic acid

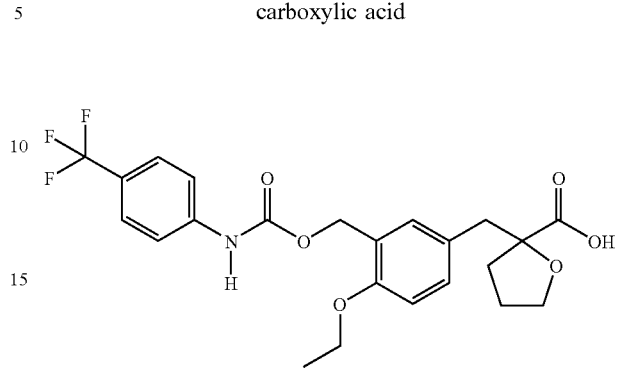

The title compound was obtained according to the method of Example 163 from methyl 2-(4-ethoxy-3-hydroxymethylbenzyl)tetrahydro-2-furancarboxylate and 4-trifluoromethylphenylisocyanic acid.

MS m/e (ESI) 490.03 (MNa$^+$)

Example 169

2-[3-(4-Ethoxyphenylcarbamoyloxymethyl)-4-ethoxybenzyl]-tetrahydro-2-furancarboxylic acid

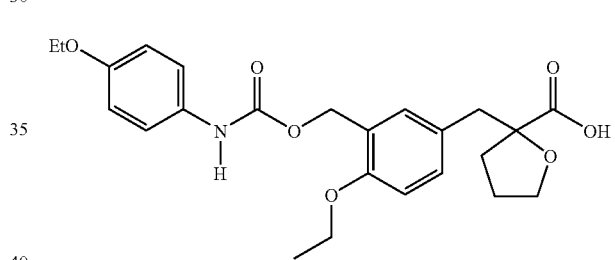

The title compound was obtained according to the method of Example 163 from methyl 2-(4-ethoxy-3-hydroxymethylbenzyl)tetrahydro-2-furancarboxylate and 4-ethoxyphenylisocyanic acid.

MS m/e (ESI) 466.08 (MNa$^+$)

Example 170

2-[3-(Benzo[1,3]dioxol-5-ylcarbamoyloxymethyl)-4-ethoxybenzyl]-tetrahydro-2-furancarboxylic acid

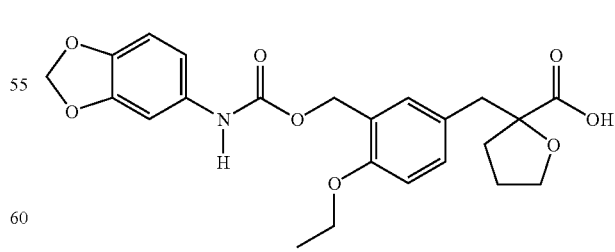

The title compound was obtained according to the method of Example 163 from methyl 2-(4-ethoxy-3-hydroxymethylbenzyl)tetrahydro-2-furancarboxylic acid and benzo[1,3]dioxol-5-ylisocyanic acid.

MS m/e (ESI) 466.04 (MNa$^+$)

Example 171

2(R)-2-(3-{[(2-Chloro-4-propoxybenzoyl)amino]
methyl}-4-ethoxybenzyl)tetrahydro-2-furancarboxylic acid and 2(S)-2-(3-{[(2-chloro-4-propoxybenzoyl)amino]methyl}-4-ethoxybenzyl)tetrahydro-2-furancarboxylic acid

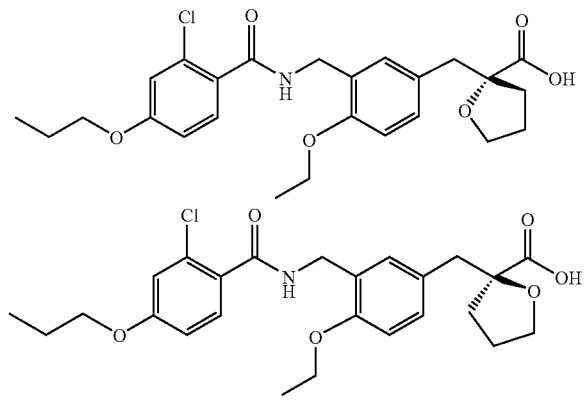

2 ml potions of a solution of 0.327 g of the racemate of 2-(3-{[(2-chloro-4-propoxybenzoyl)amino]methyl}-4-ethoxybenzyl)tetrahydro-2-furancarboxylic acid in a 500:500:1 solvent mixture (6 ml) of propan-2-ol:hexane:trifluoroacetic acid were resolved on a Chiralcel OD Column (eluent: propan-2-ol:hexane:trifluoroacetic acid; 500:500:1), to give 0.147 g of the (R)-enantiomer of the title compound having a retention time of 9 min and 0.159 g of the (S)-enantiomer having a retention time of 18 min.

Example 172

2(R)-2-(3-{[(2-Chloro-4-ethoxybenzoyl)amino]methyl}-4-ethoxybenzyl)tetrahydro-2-furancarboxylic acid and 2(S)-2-(3-{[(2-chloro-4-ethoxybenzoyl)amino]methyl}-4-ethoxybenzyl)tetrahydro-2-furancarboxylic acid

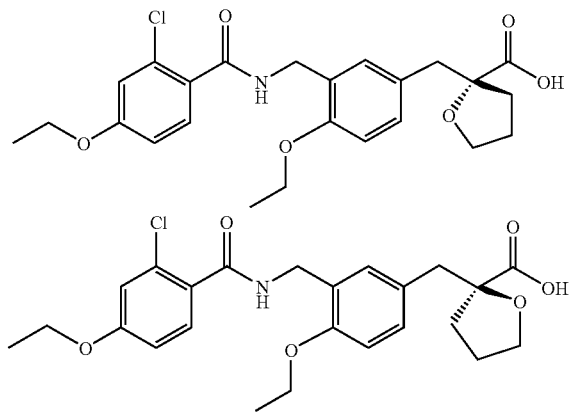

By a similar procedure to Example 171, the (R)-enantiomer and (S)-enantiomer of the title compound were obtained at retention times of 10 min and 17 min, respectively, from the racemate of 2-(3-{[(2-chloro-4-ethoxybenzoyl)amino]methyl}-4-ethoxybenzyl)tetrahydro-2-furancarboxylic acid using a Chiralcel OD Column (eluent: propan-2-ol:hexane:trifluoroacetic acid; 500:500:1).

Example 173

2(R)-2-(3-{[(4-Propoxybenzoyl)amino]methyl}-4-ethoxybenzyl)tetrahydro-2-furancarboxylic acid and 2(S)-2-(3-{[(4-propoxybenzoyl)amino]methyl}-4-ethoxybenzyl)tetrahydro-2-furancarboxylic acid

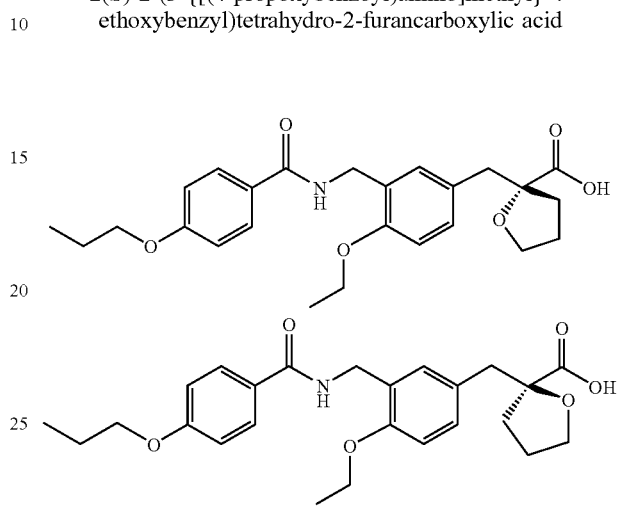

By a similar procedure to Example 171, the (R)-enantiomer and (S)-enantiomer of the title compound were obtained at retention times of 12 min and 18 min, respectively, from the racemate of 2-(3-{[(-4-propoxybenzoyl)amino]methyl}-4-ethoxybenzyl)tetrahydro-2-furancarboxylic acid using a Chiralcel OD Column (eluent: propan-2-ol:hexane:trifluoroacetic acid; 300:700:1).

Example 174

2(R)-2-(3-{[(4-Ethoxybenzoyl)amino]methyl}-4-ethoxybenzyl)tetrahydro-2-furancarboxylic acid and 2(S)-2-(3-{[(4-ethoxybenzoyl)amino]methyl}-4-ethoxybenzyl)tetrahydro-2-furancarboxylic acid

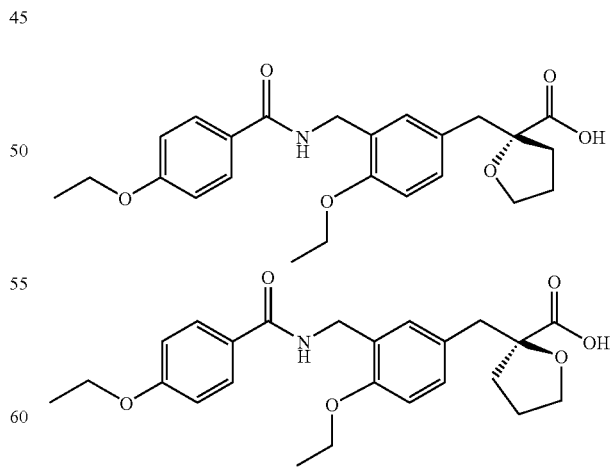

By a similar procedure to Example 171, the (R)-enantiomer and (S)-enantiomer of the title compound were obtained at retention times of 6 min and 9 min, respectively, from the racemate of 2-(3-{[(-4-ethoxybenzoyl)amino]me-

Example 175

2-(3-{[(4-Propoxybenzoyl)amino]methyl}-4-ethoxybenzyl)tetrahydro-2-furancarboxylic acid

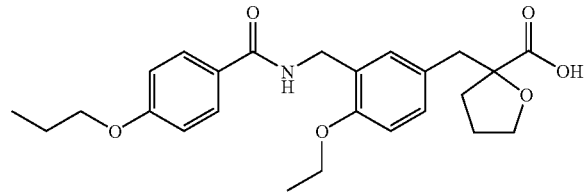

The title compound was obtained according to the method of Reference Example 17 from N-hydroxymethyl-4-propoxybenzamide and (4-ethoxybenzyl)-tetrahydro-2-furancarboxylic acid.

Example 176

2-(3-{[(4-Propoxybenzoyl)amino]methyl}-4-ethoxybenzyl)tetrahydro-2-furancarboxylic acid

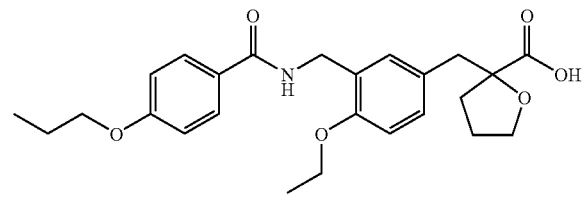

The title compound was obtained according to the method of Reference Example 43 from methyl 2-(3-{[(4-propoxybenzoyl)amino]methyl}-4-ethoxybenzyl)tetrahydro-2-furancarboxylate.

Example 177

2(R)-2-(3-{[(4-Propoxybenzoyl)amino]methyl}-4-ethoxybenzyl)tetrahydro-2-furancarboxylic acid

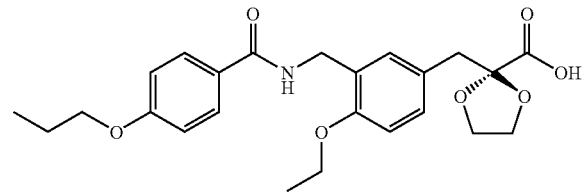

To 2.81 g of 2-(R)-2-(3-{[(4-propoxybenzoyl)amino]-methyl}-4-ethoxybenzyl)tetrahydro-2-furancarboxylic acid 1-(R)-(2-hydroxy-1-phenylethyl)-amide was added 50 ml of 2M sulfuric acid, and the mixture was heated at 100° C. for 24 hours. 250 ml of acetic acid and 100 ml of water were added, and the organic layer was dried over anhydrous magnesium sulfate. The solvent was evaporated, and the residue was purified by silica gel column chromatography, to give 1.71 g of the title compound.

Example 178

2(S)-2-(3-{[(4-Propoxybenzoyl)amino]methyl}-4-ethoxybenzyl)tetrahydro-2-furancarboxylic acid

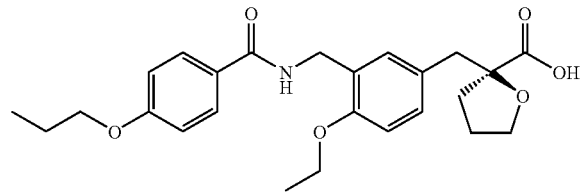

The title compound was obtained according to the method of Example 177 from 2-(S)-2-(3-{[(4-propoxybenzoyl)amino]methyl}-4-ethoxybenzyl)tetrahydro-2-furancarboxylic acid 1-(R)-(2-hydroxy-1-phenylethyl)-amide.

The medicament according to the present invention improves insulin resistance by the agonism of PPAR as described above, and the present invention can be applied not only as an insulin sensitizer but also as various medicaments based on PPAR ($\alpha$, $\beta(\delta)$, $\gamma$) agonism (based on e.g. PPAR $\alpha$ and $\gamma$ dual agonism or PPAR $\alpha$, $\beta(\delta)$ and $\gamma$ triple agonism).

For example, a relationship of PPAR not only with insulin resistance but also with blood lipids, and with inflammatory diseases is known (Current Opinion in Lipidol. 10:245-257, 1999; Jiang, C., et al., PPAR-gamma agonists inhibit production of monocyte inflammatory cytokines, Nature 391: 82-86 (1998); Jackson, S. M., et al., Peroxisome proliferator-activated receptor activators target human endothelial cells to inhibit leukocyte-endothelial cell interaction., Arterioscler. Thromb. Vasc. Biol. 19: 2094-2104 (1999); Su, C. G., et al., A novel therapy for colitis utilizing PPAR-gamma ligands to inhibit the epithelial inflammatory response., J Clin Invest 1999 August; 104(4):383-9; Ricote, M., et al., The peroxisome proliferator-activated receptor-gamma is a negative regulator of macrophage activation., Nature 1998 Jan. 1; 391(6662):79-82), and the medicaments of the present invention can be applied to diseases against which it is reported to be effective in the above literature

Experiment Example 1

Measurement of Blood Glucose Reduction, Blood Triglyceride Reduction and Blood Non-Esterified Fatty Acids Reduction (1) Test Method: A chemical suspended in 0.5% methyl cellulose was orally administered via a sonde into male db/db mice (Nippon Charles River, Yokohama, JP) once a day (30 mg/kg/day). Before treatment and on the 4th and 9th day of treatment, blood was collected from a tail vein after the mice fasting for 1 hour. On Day 10, an oral glucose loading test was conducted; in this test, the mice were fasted overnight from the previous day, and on the following morning, given 2 g/kg glucose. Plasma glucose, triglycerides (TG) and non-esterified fatty acid (NEFA) can be measured using commercial kits, that is, the Glucose C-II Test Wako (trade name) (Wako Pure Chemical Industries, Ltd., Tokyo), Determiner L TG II (trade name) (Kyowa Medex, Tokyo) and NEFA C-Test Wako (trade name) (Wako Pure Chemical Industries, Ltd., Tokyo), respectively. And in this test, the measurements were performed in this way.

(2) Result: The compounds according to the present invention represented by the formula (I), salts thereof, esters thereof, and hydrates of them exhibit excellent blood glucose reduction, blood triglyceride reduction and blood non-esterified fatty acids reduction.

Experiment Example 2

Determination of Transcriptional Activity (1) Test Method: A GAL4-PPAR LBD chimera expression vector was constructed by ligating human PPAR167-468 (PPARa), 138-440 (NUC-1) and 174-475 (PPARg) amino acid regions (LBD: Ligand Binding Domain) to a yeast transcriptional factor GAL4 1-147 amino acid region. As the reporter gene, PLAP (Placental Alkaline Phosphatase) was used, and this was ligated downstream of a TK promoter containing a 5-copy GAL4 DNA binding element to construct a vector. As host cells, CV-1 (ATCC CCL-70) were used. That is, CV-1 cells were spread at a density of $5 \times 10^5$ cells on a 35-mm dish and cultured in 10% FCS/DMEM for 24 hours, and using FuGENE 6 transfection reagent, the cells were co-transfected with the GAL4-PPAR LBD expression vector and GAL4 DBD-TK-PLAP expression vector. Twentyfour hours after this transfection, the cells were spread again on a 96-well plate at a density of $1 \times 10^4$/well and further cultured for 24 hours. After 24 hours, the medium was exchanged with DMEM containing 10% FCS, which was previously treated at 65° C. for inactivating intrinsic alkaline phosphatase, and a test compound was added at an arbitrary concentration. The transcriptional activity was determined in terms of PLAP activity secreted 24 hours after addition of the compound, to calculate $EC_{50}$. The PLAP activity was determined after adding 50 ml assay buffer and 50 ml chemiluminescent substrate to 10 ml culture supernatant and incubating the mixture at room temperature for 1 hour.

(2) Result: The compounds according to the present invention represented by the formula (I), salts thereof, esters thereof, and hydrates of them exhibit an excellent blood glucose- and blood lipid-ameliorating action. The results are shown the table below, indicating that the compounds of the present invention are very useful as anti-diabetic agents, anti-hyperlipemia agents and insulin sensitizers.

TABLE 1

| | Transcriptional activity $EC_{50}$ (μM) | | |
|---|---|---|---|
| | PPARα | PPARβ | PPARγ |
| Ex. 1 | 0.028 | 0.533 | 0.056 |
| Ex. 5 | 0.015 | 1.322 | 0.04 |
| Ex. 6 | 0.011 | 1.206 | 0.078 |
| Ex. 49 | 0.054 | 0.771 | 0.037 |
| Ex. 72 | 0.092 | 0.234 | 0.04 |
| Ex. 73 | 0.013 | 0.038 | 0.005 |

Experiment Example 3

Anti-Inflammatory Action (1) Test Method: Experimental colitis was induced in female ICR mice (10 mice/group, Charles River Japan, Yokohama) by giving 4% dextran sulfate sodium solution in drinking water for 5 days. After 8 days, the mice were grouped into sections from "0" (normal) to "4" (severe) based on diarrhea, hematochezia and weight loss as described by Cooper H S et al., (Laboratory Invest (69), pp. 238-249, 1993) and the average of the values was used as the Disease Activity Index for colitis. Each test compound was suspended in a 0.5% methylcellulose solution and administered to the mice orally once a day via a sonde from the day when the induction of colitis was initiated.

(2) Result: The compounds according to the present invention represented by the formula (I), salts thereof, esters thereof, and hydrates of them exhibit an excellent antiinflammatory action.

The invention claimed is:

1. A compound represented by the following formula, a salt thereof, or an ester thereof:

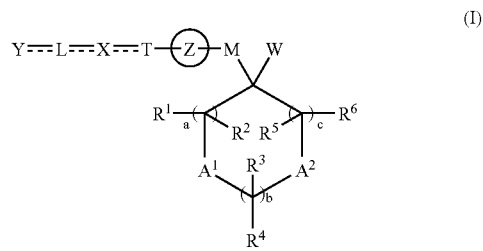

wherein:
a, b and c are the same as or different from one another and each represents 0, 1, 2, 3 or 4;
$R^1$, $R^2$, $R^3$, $R^4$, $R^5$ and $R^6$ are the same as or different from one another and each represents: 1) a hydrogen atom, 2) a hydroxyl group, 3) a cyano group, 4) a halogen atom, or 5) an alkyl group having one to six carbon atoms, an alkoxy group having one to six carbon atoms, an alkylthio group having one to six carbon atoms, a hydroxyalkyl group having one to six carbon atoms, a hydroxyalkoxy group having one to six carbon atoms, a hydroxyalkylthio group having one to six carbon atoms, an aminoalkyl group having one to six carbon atoms, an aminoalkoxy group having one to six carbon atoms, an aminoalkylthio group having one to six carbon atoms, a halogeno-alkyl group having one to six carbon atoms, a halogeno-alkoxy group having one to six carbon atoms, a halogeno-alkylthio group having one to six carbon atoms, an alkoxyalkyl group having two to twelve carbon atoms, an alkoxyalkoxy group having two to twelve carbon atoms, an alkoxyalkylthio group having two to twelve carbon atoms, a cycloalkyl group having three to seven carbon atoms, a cycloalkyloxy group having three to seven carbon atoms, a cycloalkylalkyloxy group having four to thirteen carbon atoms, a cycloalkylthio group having three to seven carbon atoms, an alkenyl group having two to six carbon atoms, an alkenyloxy group having two to six carbon atoms, an alkenylthio group having two to six carbon atoms, an alkynyl group having two to six carbon atoms, an alkynyloxy group having two to six carbon atoms, an alkynylthio group having two to six carbon atoms, an aryl group having six to twelve carbon atoms, an aryloxy group having six to twelve carbon atoms, an arylthio group having six to twelve carbon atoms, an alkylaryl group having seven to eighteen carbon atoms, an alkylaryloxy group having seven to eighteen carbon atoms, an alkylarylthio group having seven to eighteen carbon atoms, an aralkyl group having seven to eighteen carbon atoms, an aralkyloxy group having seven to eighteen carbon atoms or an aralkylthio group having seven to eighteen carbon atoms, each of which optionally has one or more substituents;

$A^1$ and $A^2$ are the same as or different from each other and each represents: a single bond, an oxygen atom, a sulfur atom, or a group represented by the formula:

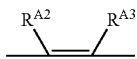

wherein $R^{A2}$ and $R^{A3}$ are the same as or different from each other and each represents a hydrogen atom or an alkyl group having one to six carbon atoms;

L represents a single bond, or an alkylene group having one to six carbon atoms, an alkenylene group having two to six carbon atoms or an alkynylene group having two to six carbon atoms, each of which optionally has one or more substituents;

M represents a single bond, or an alkylene group having one to six carbon atoms, an alkenylene group having two to six carbon atoms or an alkynylene group having two to six carbon atoms, each of which optionally has one or more substituents;

T represents a single bond, or an alkylene group having one to three carbon atoms, an alkenylene group having two or three carbon atoms or an alkynylene group having two or three carbon atoms, each of which optionally has one or more substituents;

W represents a carboxyl group;

the partial structure represented by the formula:

represents a single bond;

X represents —$NR^{X1}CQ^1O$—, wherein $Q^1$ represents an oxygen atom; and $R^{X1}$ represents a hydrogen atom, —$NR^{X1}CQ^1$—, wherein $Q^1$ and $R^{X1}$ are as defined above, —$CQ^1NR^{X1}$—, wherein $Q^1$ and $R^{X1}$ are as defined above, or a group represented by the formula:

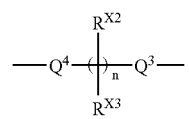

wherein n is 1 to 5; $R^{X2}$ and $R^{X3}$ are the same as or different from each other and each represents a hydrogen atom, a hydroxyl group, a cyano group, a halogen atom, or an alkyl group having one to six carbon atoms, an alkoxy group having one to six carbon atoms, or an alkylthio group having one to six carbon atoms; and $Q_3$ and $Q_4$ are the same as or different from each other and each represents a single bond or an oxygen atom;

Y represents $Y^1$—$Y^2$—, wherein $Y^1$ represents a 5 to 14-membered aromatic ring which has one to four substituents selected from the following Group A, optionally has one or more hetero atoms and is optionally partially saturated; and $Y^2$ represents a single bond or a 5 to 14-membered aromatic ring which has a substituent selected from the following Group A, optionally has one or more hetero atoms and is optionally partially saturated; Group A: a hydrogen atom, a halogen atom, a hydroxyl group, a sulfamoyl group, an alkyl group having one to six carbon atoms, a cycloalkyl group having three to seven carbon atoms, an alkoxy group having one to six carbon atoms, a cycloalkyloxy group having three to seven carbon atoms, a hydroxyalkyl group having one to six carbon atoms, a hydroxyalkoxy group having one to six carbon atoms, a halogeno-alkyl group having one to six carbon atoms, an acylamino group having two to seven carbon atoms, a $C_{6-10}$ aryl group or a 5 to 14-membered heterocyclic group, each of which optionally has a substituent, provided that when two or more substituents selected from Group A are present, they optionally together form a ring; and the ring Z represents a 6-membered aromatic ring which has one to four substituents selected from the above-mentioned Group A, and optionally has one or more hetero atoms.

2. The compound according to claim 1, a salt thereof, or an ester thereof, wherein in the formula (I), c is 0, and $A^2$ is an oxygen atom.

3. The compound according to claim 1 or 2, a salt thereof, or an ester thereof, wherein in the formula (I), a is 0, and b is 1.

4. The compound according to claim 1 or 2, a salt thereof or an ester thereof, wherein in the formula (I), a is 2, b is 1, and $A^1$ is a single bond.

5. The compound according to claim 1, a salt thereof, or an ester thereof, wherein in the formula (I), the ring Z is has one or more hetero atoms and is partially saturated.

6. The compound according to claim 1, a salt thereof, or an ester thereof, wherein in the formula (I), Y is $Y^1$—$Y^2$—, wherein $Y^1$ represents the same group as defined above, and $Y^2$ is a single bond.

7. The compound according to claim 6, a salt thereof, or an ester thereof, wherein $Y^1$ is a 5 to 14-membered aromatic ring which has at least an alkoxy group having one to six carbon atoms and optionally has one or more hetero atoms on the ring.

8. The compound according to claim 1, a salt thereof, or an ester thereof, wherein in the formula (I), L is a single bond.

9. The compound according to claim 1, a salt thereof or an ester thereof wherein in the formula (I), T is an alkylene group having one to six carbon atoms.

10. The compound according to claim 1, a salt thereof, or an ester thereof, wherein in the formula (I), the ring Z is represented by the following formula:

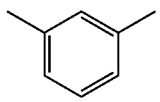

wherein a hetero atom is optionally on the ring, and said Z optionally has one to four substituents selected from Group A defined in claim 1.

11. A pharmaceutical composition comprising:
an effective amount of the compound according to claim 1, a salt thereof or an ester thereof; and
a pharmaceutically acceptable carrier.

12. The compound according to claim 1, a salt thereof or an ester thereof, wherein said compound is the following formula:

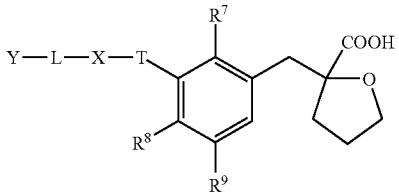

wherein $R^7$, $R^8$ and $R^9$ are the same as or different from one another and each represents a hydrogen atom, a hydroxyl group, a halogen atom or a $C_{1-6}$ alkoxy group;
L represents a single bond or a $C_{1-3}$ alkylene group optionally having one or more substituents;
T represents a single bond, an oxygen atom or a $C_{1-3}$ alkylene group optionally having one or more substituents;
X represents —NHCO—, —CONH—, a $C_{2-3}$ hydroxylalkylenedioxy group or a $C_{3-6}$ haloalkylenedioxy group;
Y represents a benzene ring optionally having one to four substituents selected from the following Group B;
Group B: a hydrogen atom, a halogen atom, a hydroxyl group, a $C_{1-6}$ alkyl group, a $C_{3-7}$ cycloalkyl group, a $C_{1-6}$ alkoxy group, a $C_{3-7}$ cycloalkoxy group, a $C_{1-6}$ hydroxyalkyl group, a $C_{1-6}$ hydroxyalkoxy group, a $C_{1-6}$ haloalkyl group, a $C_{1-6}$ haloalkoxy group and a 5 to 10-membered heterocyclic group, each of which optionally has a substituent.

13. The salt or ester of the compound according to claim 1 represented by the following formula:

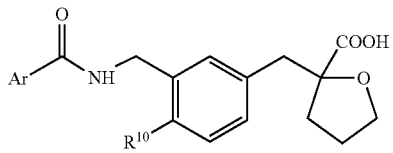

wherein $R^{10}$ represents a $C_{1-6}$ alkoxy group; and Ar represents a 5 to 6-membered aromatic ring optionally having one to four substituents selected from Group A;
Group A: a hydrogen atom, a halogen atom, a hydroxyl group, a $C_{1-6}$ alkyl group, a $C_{3-7}$ cycloalkyl group, a $C_{1-6}$ alkoxy group, a $C_{3-7}$ cycloalkoxy group, a $C_{1-6}$ hydroxyalkyl group, a $C_{1-6}$ hydroxyalkoxy group, a $C_{1-6}$ haloalkyl group, a $C_{1-6}$ haloalkoxy group, a $C_{2-7}$ acylamino group and a 5 to 14-membered heterocyclic group, each of which optionally has a substituent; provided that when two or more substituents selected from Group A are present, they optionally together form a ring.

14. The compound according to claim 1, a salt thereof or an ester thereof, wherein Y is selected from the group consisting of 1-naphthyl group, 2-naphthyl group, furyl group, thienyl group, pyrrolyl group, pyridyl group, quinolyl group, isoquinolyl group, cinnolyl group, quinazolyl group, quinoxalyl group, indolyl group, indazolyl group, oxazolyl group, isoxazolyl group, thiazolyl group, isothiazolyl group, imidazolyl group, pyrazolyl group, furazanyl group, pyridazinyl group, pyrimidyl group, pyrazyl group, dihydrobenzofuranyl group, phthalanyl group, chromanyl group, chromenyl group, chromanonyl group, chromenonyl group, tetrahydronaphthalenyl group or indanyl, each of which optionally has one to four substituents selected from the following Group A;
Group A: a hydrogen atom, a halogen atom, a hydroxyl group, a sulfamoyl group, a $C_{1-6}$ alkyl group, a $C_{3-7}$ cycloalkyl group, a $C_{1-6}$ alkoxy group, a $CO_{3-7}$ cycloalkyloxy group, a $C_{1-6}$ hydroxyalkyl group, a $C_{1-6}$ hydroxyalkoxy group, a $C_{1-6}$ halogeno-alkyl group, a $C_{2-7}$ acylamino group, a $C_{6-10}$ aryl group and a 5 to 14-membered heterocyclic group, each of which optionally has a substituent, provided that when two or more substituents selected from Group A are present, they optionally together form a ring.

15. The compound of claim 12, wherein X represents 2-hydroxy-1,3-propylenedioxy.

* * * * *

UNITED STATES PATENT AND TRADEMARK OFFICE
CERTIFICATE OF CORRECTION

PATENT NO. : 7,371,777 B2 Page 1 of 1
APPLICATION NO. : 10/486396
DATED : May 13, 2008
INVENTOR(S) : Richard Clark et al.

It is certified that error appears in the above-identified patent and that said Letters Patent is hereby corrected as shown below:

Title page, line 73, Assignee:

"Eisai Co., Ltd., Tokyo (JP)"

should read

--Eisai R&D Management Co., Ltd., Tokyo (JP)--

Signed and Sealed this

Fifth Day of May, 2009

JOHN DOLL
*Acting Director of the United States Patent and Trademark Office*